US012653881B2

(12) United States Patent
Duprex et al.

(10) Patent No.: US 12,653,881 B2
(45) Date of Patent: *Jun. 16, 2026

(54) MEASLES VIRUS VACCINE EXPRESSING SARS-COV-2 PROTEIN(S)

(71) Applicant: University of Pittsburgh-Of the Commonwealth System of Higher Education, Pittsburgh, PA (US)

(72) Inventors: William Paul Duprex, Pennsylvania, PA (US); Natasha Tilston-Lunel, Pittsburgh, PA (US); Shamkumar Nambulli, Bridgeville, PA (US); Linda J. Murphy, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 726 days.

This patent is subject to a terminal disclaimer.

(21) Appl. No.: 18/010,294

(22) PCT Filed: Jun. 15, 2021

(86) PCT No.: PCT/US2021/037339
§ 371 (c)(1),
(2) Date: Dec. 14, 2022

(87) PCT Pub. No.: WO2021/257510
PCT Pub. Date: Dec. 23, 2021

(65) Prior Publication Data

US 2023/0272421 A1 Aug. 31, 2023

Related U.S. Application Data

(60) Provisional application No. 63/071,479, filed on Aug. 28, 2020, provisional application No. 63/039,275, filed on Jun. 15, 2020.

(51) Int. Cl.
| | |
|---|---|
| *C07K 14/005* | (2006.01) |
| *A61K 39/00* | (2006.01) |
| *A61K 39/12* | (2006.01) |
| *A61K 39/165* | (2006.01) |
| *A61K 39/215* | (2006.01) |
| *A61P 31/14* | (2006.01) |
| *C07K 16/10* | (2026.01) |
| *C12N 7/00* | (2006.01) |
| *C12N 15/86* | (2006.01) |

(52) U.S. Cl.
CPC .......... *A61K 39/215* (2013.01); *A61K 39/165* (2013.01); *A61P 31/14* (2018.01); *C07K 14/005* (2013.01); *C12N 7/00* (2013.01); *C12N 15/86* (2013.01); *A61K 2039/5256* (2013.01); *A61K 2039/53* (2013.01); *A61K 2039/575* (2013.01); *C12N 2760/18434* (2013.01); *C12N 2760/18443* (2013.01); *C12N 2770/20034* (2013.01)

(58) Field of Classification Search
CPC ........ A61K 2039/5256; A61K 39/2125; A61K 2039/53; A61K 39/12; A61K 39/165
See application file for complete search history.

(56) References Cited

U.S. PATENT DOCUMENTS

| | | | |
|---|---|---|---|
| 11,103,576 | B1 | 8/2021 | Duprex et al. |
| 11,298,417 | B2 | 4/2022 | Duprex et al. |

FOREIGN PATENT DOCUMENTS

| | | |
|---|---|---|
| CN | 111218459 A | 6/2020 |
| EP | 3 865 180 A1 | 2/2020 |
| WO | WO 97/06270 A1 | 2/1997 |
| WO | WO 98/13501 A2 | 4/1998 |
| WO | WO 2009/032954 A1 | 3/2009 |
| WO | WO 2021/160850 A1 | 8/2021 |

OTHER PUBLICATIONS

"An Early Look at Vaccines for COVID-19", *The Native Antigen Company*, published Apr. 14, 2020, retrieved on Sep. 22, 2021 from URL: thenativeantigencompany.com/an-early-look-at-vaccines-for-covid-19/, pp. 1-8.
"UniProtKB—P0DTC2 (SPIKE-SARS2)", published Apr. 22, 2020, retrieved on Nov. 8, 2021 from URL: uniprot.org/uniprot/P0DTC2, pp. 1-4.
Bankamp et al., "Genetic Characterization of Measles Vaccine Strains", *Journal of Infectious Diseases*, 204 Suppl. 1: S533-S548 (2011).
Case et al., "Neutralizing antibody and soluble ACE2 inhibition of a replication-competent VSV-SARS-CoV-2 and a clinical isolate of SARS-CoV-2", *bioRxiv* pp. 1-34 (2020) doi:10.1101/2020.05.18.102038.

(Continued)

*Primary Examiner* — Barry A Chestnut
(74) *Attorney, Agent, or Firm* — Leydig, Voit & Mayer, Ltd.

(57) ABSTRACT

A recombinant measles viral vector comprising a nucleic acid sequence encoding a Severe Acute Respiratory Syndrome Coronavirus 2 (SARS-CoV-2) spike glycoprotein is provided. Polypeptides comprising the SARS-CoV-2 spike glycoprotein also are provided, as well as related nucleic acids, vectors, and compositions. The polypeptides, nucleic acids, vectors, and compositions can be used in methods of preventing, inhibiting, reducing, eliminating, protecting, or delaying the onset of an infection or an infectious clinical condition caused by coronavirus and methods for inducing an immune response against a coronavirus.

20 Claims, 17 Drawing Sheets

Specification includes a Sequence Listing.

(56) References Cited

OTHER PUBLICATIONS

De Swart et al., "Needle-free delivery of measles virus vaccine to the lower respiratory tract of non-human primates elicits optimal immunity and protection", *NPJ Vaccines*, 2(1):22, pp. 1-11 (2017).

Duckert et al., "Prediction of proprotein convertase cleavage sites", *Protein Engineering, Design & Selection*, 17(1):107-112 (2004).

Hartman et al., "SARS-CoV-2 infection of African green monkeys results in mild respiratory disease discernible by PET/CT imaging and prolonged shedding of infectious virus from both respiratory and gastrointestinal tracts", *bioRxiv*, pp. 1-18 (2020) doi.org/10.1101/2020.06.20.137687.

Klimstra et al., "SARS-CoV-2 growth, furin-cleavage-site adaptation and neutralization using serum from acutely infected hospitalized COVID-19 patients", *Journal of General Virology*, 101:1156-1169 (2020) doi: 10.1099/jgv.0.001481.

Liniger et al., "Induction of neutralising antibodies and cellular immune responses against SARS coronavirus by recombinant measles viruses," *Vaccine*, 26: 2164-2174 (2008).

Malczyk et al., "A Highly Immunogenic and Protective Middle East Respiratory Syndrome Coronavirus Vaccine Based on a Recombinant Measles Virus Vaccine Platform", *Journal of Virology*, 89(22): 11654-11667 (2015).

Padron-Regalado, "Vaccines for SARS-CoV-2: Lessons from Other Coronavirus Strains," *Infectious Diseases Therapy*, 9: 255-274 (2020).

Rennick et al., "Live-Attenuated Measles Virus Vaccine Targets Dendritic Cells and Macrophages in Muscle of Nonhuman Primates", *Journal of Virology* 89(4): 2192-2200 (2015) doi:10.1128/jvi.02924-14.

Schneider-Schaulies et al., "Receptor usage and differential downregulation of CD46 by measles virus wild-type and vaccine strains", *PNAS*, 92(9): 3943-3947 (1995).

Sinitsyna et al., "Further-attenuated measles vaccine: Virus passages affect viral surface protein expression, immunogenicity and histopathology pattern in vivo", *Research in Virology*, 141(5): 517-531 (1990).

Takeda et al., "Measles Virus Attenuation Associated with Transcriptional Impediment and a Few Amino Acid Changes in the Polymerase and Accessory Proteins", *Journal of Virology*, 72(11): 8690-8696 (1998).

U.S. Patent and Trademark Office, Invitation to Pay Additional Fees in International Patent Application No. PCT/US21/37339, dated Sep. 24, 2021.

U.S. Patent and Trademark Office, International Search Report in International Patent Application No. PCT/US2021/037339, dated Dec. 8, 2021.

U.S. Patent and Trademark Office, Written Opinion in International Patent Application No. PCT/US2021/037339, dated Dec. 8, 2021.

Wrapp et al., "Cryo-EM structure of the 2019-nCoV spike in the prefusion conformation", Science, 367: 1260-1263 (2020).

rMV<sup>EZ</sup>SARSCoV2-S6 rMV<sup>EZ</sup>SARSCoV2-S6 vaccine dose: $10^{-4}$ $10^{-5}$ days : 1    prime      21    boost      42    sacrificed

|  | 1:20 | 1:40 | 1:80 | 1:160 | 1:320 | 1:640 |
|---|---|---|---|---|---|---|
| rMV^EZSARSCoV-2-S-CO | + | + | +/- | - | - | - |
| rMV^EZSARSCoV2-S-COAA | + | + | + | +/- | - | - |
| rMV^EZSARSCoV2-S6 | + | + | + | +/- | - | - |
| rMV^EZ | - | - | - | - | - | - | vaccine dose: $10^4$ to $10^5$
challenge dose:

$10^4$ to $10^5$     $10^6$ days :   1         21       * 42    46*    53*    56 prime      boost      challenge    PET/CT and sampling*    necropsy

| | measles virus neutralization (pre-challenge) | | | | | | SARS-CoV-2 neutralization (pre-challenge) | | | | | | |
|---|---|---|---|---|---|---|---|---|---|---|---|---|---|
| | 1:20 | 1:40 | 1:80 | 1:160 | 1:320 | 1:640 | 1:20 | 1:40 | 1:80 | 1:160 | 1:320 | 1:640 |
| rMV$^{EZ}$SARS-CoV-2-S-CO | + | + | + | + | - | - | + | + | +/- | + | - | - |
| rMV$^{EZ}$SARS-CoV-2-S-CO | + | + | + | + | - | - | + | + | + | + | + | + |
| rMV$^{EZ}$SARS-CoV-2-S-CO | + | - | - | - | - | - | + | + | - | - | - | - |
| rMV$^{EZ}$ | + | + | + | + | - | - | - | - | - | - | - | - |
| rMV$^{EZ}$ | + | + | + | + | - | - | - | - | - | - | - | - |

Fig. 13A (Cont.)

CD4+CD44+ rMV$^{EZ}$ rMV$^{EZ}$-SARS-CoV-2-CO rMV$^{EZ}$-SARS-CoV-2-S6 rMV$^{EZ}$-SARS-CoV-2-COAA

% IL-13 positive

MEASLES VIRUS VACCINE EXPRESSING SARS-COV-2 PROTEIN(S)

CROSS-REFERENCE TO RELATED APPLICATIONS

This patent application is the U.S. National Stage of International Patent Application No. PCT/US2021/037339, filed Jun. 15, 2021, which claims the benefit of U.S. Provisional Patent Application No. 63/039,275, filed Jun. 15, 2020, and U.S. Provisional Patent Application No. 63/071,479, filed Aug. 28, 2020, each of which is incorporated by reference herein in its entirety.

INCORPORATION-BY-REFERENCE OF MATERIAL SUBMITTED ELECTRONICALLY

Incorporated by reference in its entirety herein is a nucleotide/amino acid sequence listing submitted concurrently herewith and identified as follows: One 337,235 Byte ASCII (Text) file named "766323_ST25.txt." created on Dec. 7, 2022.

BACKGROUND OF THE INVENTION

In December 2019, a novel coronavirus (Severe Acute Respiratory Syndrome Coronavirus 2 or SARS-CoV-2) belonging to the betacoronavirus family emerged. All human betacoronaviruses are unique from one another, however, they do share a certain degree of genetic and structural homology. SARS-CoV-2 genome sequence homology with SARS-CoV and MERS-CoV is 77% and 50%, respectively.

In contrast to the relatively smaller outbreaks of SARS-CoV in 2002 and MERS-CoV in 2012, SARS-CoV-2 is exhibiting an unprecedented scale of infection, resulting in a global pandemic declaration of Coronavirus Infectious Disease (COVID-19) by the World Health Organization (WHO). COVID-19 has a high infection rate and long incubation period. Similar to influenza, COVID-19 has the potential to become a seasonal disease.

Therefore, there is a desire for a COVID-19 vaccine.

BRIEF SUMMARY OF THE INVENTION

An embodiment of the invention provides a recombinant measles viral vector (rMV) (e.g., Edmonston Zagreb (EZ) MV) comprising a nucleic acid sequence encoding a Severe Acute Respiratory Syndrome Coronavirus 2 (SARS-CoV-2) spike (S) glycoprotein.

An embodiment of the invention provides a pharmaceutical composition comprising the recombinant measles viral vector, as well as methods for preventing, inhibiting, reducing, eliminating, protecting, or delaying the onset of an infection or an infectious clinical condition caused by coronavirus in a subject and methods for inducing an immune response against a coronavirus in a subject.

An embodiment of the invention also provides a polypeptide comprising an amino acid sequence selected from the group consisting of the amino acid sequences of SEQ ID NO: 8 (S6), SEQ ID NO: 9 (S-CO), SEQ ID NO: 10 (S-CO-AA), SEQ ID NO: 11 (S), SEQ ID NO: 12 (S-CO-AA-PP), SEQ ID NO: 13 (S-CO-AA-fneg-PP), and SEQ ID NO: 14 (S-CO-AA-fneg), as well as related nucleic acids, recombinant vectors, compositions, and methods.

BRIEF DESCRIPTION OF THE SEVERAL VIEWS OF THE DRAWINGS

FIG. 1A is a schematic representation of parental virus $rMV^{EZ}EGFP(3)$, the cDNA clone of which was used to generate cDNA plasmids for viruses $rMV^{EZ}SARS-CoV-2-S3$, $rMV^{EZ}SARS-CoV-2-S6$, $rMV^{EZ}SARS-CoV-2-S-CO$ and $rMV^{EZ}SARS-CoV-2-S-COAA$. Amino acid differences in the spike between the four viruses are shown, wherein underlined residues differ from wild-type spike sequence. Residues K and H in the cytoplasmic tail region were altered to A and A to disrupt a endoplasmic reticulum (ER) retention signal (KxHxx) sequence in viruses $rMV^{EZ}SARS-CoV-2-S3$, $rMV^{EZ}SARS-CoV-2-S6$ and $rMV^{EZ}SARS-CoV-2-S-COAA$. RBD; receptor binding domain, TM; transmembrane domain. FIG. 1B is a phase image of Vero cell monolayer infected with $rMV^{EZ}SARS-CoV-2-S6$ (shown as a representative image of a primary rescue). FIG. 1C are images of an immunoplaque assay of Vero cell monolayers infected with a 10-fold dilution of rescued $rMV^{EZ}SARS-CoV-2-S6$. Plaques were stained using anti-SARS-CoV-2-S antibody. Dilutions $10^{-6}$ and $10^{-7}$ are shown as representatives.

FIG. 3A is a schematic describing the experiment. Groups of 5 mice were infected with either $rMV^{EZ}SARS-CoV-2-S3$, $rMV^{EZ}SARS-CoV-2-S6$, $rMV^{EZ}SARS-CoV-2-S-CO$, $rMV^{EZ}SARS-CoV-2-S-COAA$, or $rMV^{EZ}EGFP(3)$. Serum was collected on days 21 and 42, and splenocytes were collected on day 42. FIG. 3B is table showing neutralization of SARS-CoV-2 using the harvested mice serum, indicating that SARS-CoV-2 neutralizing antibodies were produced in mice vaccinated with $rMV^{EZ}SARS-CoV-2-S-CO$ and $rMV^{EZ}SARS-CoV-2-S-COAA$ viruses.

FIGS. 11A-B demonstrates an experimental set-up for non-human primates vaccinated (prime and/or boost) with any of the candidates. FIG. 11A is a schematic describing the experiment. Groups of 2 or 3 African green monkeys (AGMs) were vaccinated with $rMV^{EZ}SARS-CoV-2-S-CO$ or $rMV^{EZ}$ and then challenged with SARS-CoV-2. FIG. 11B is a table with neutralization titers of serum against SARS-CoV-2, which were determined as described in Klimstra et al., 2020: PMID: 32821033, and MV as described in de Swart et al., 2017: PMID: 29263877. The results support that primates produce antibodies which neutralize both SARS-CoV-2 and measles virus following vaccination.

DETAILED DESCRIPTION OF THE INVENTION

An embodiment of the invention provides a recombinant measles viral vector that encodes one or more (e.g., two, three, four, or five) SARS-CoV-2 spike glycoproteins, wherein the SARS-CoV-2 spike glycoproteins may be the same or different. The recombinant measles viral vector or a composition thereof can be administered to a subject to prevent, inhibit, reduce, eliminate, protect, or delay the onset of an infection or an infectious clinical condition caused by coronavirus (e.g., SARS-CoV-2) in a subject. The recombinant measles viral vector or a composition thereof also can be administered to a subject to induce an immune response against a coronavirus (e.g., SARS-CoV-2) in a subject.

The recombinant measles viral vector can be any suitable recombinant measles viral vector. For example, the measles viral vector can be an Edmonston wild-type virus or vaccine strains of the Edmonston lineage, such as the AIK-C, Moraten, Rubeovax, Schwarz, or Zagreb strains (Bankamp et al., *J. Infect. Dis.*, 204 Suppl. 1: 5533-5548 (2011)). Alternatively, the measles viral vector can be selected from the group consisting of CAM-70, Changchun-47, Leningrad-4, Shanghai-191 (Bankamp et al., *J. Infect. Dis.*, 204 Suppl. 1: 5533-5548 (2011)), Leningrad-16, Moscow-5 (Sinitsyna et al., *Res. Virol.*, 141(5): 517-31 (1990)), 9301B (Takeda et al., *J Virol.*, 72(11): 8690-8696 (1998)), ATTENUVAX®, and those described in Schneider-Schaulies et al., *PNAS*, 92(2): 3943-7 (1995).

Measles viruses and recombinant measles viral vectors are described in WO 98/13501, which provides the sequence of a DNA copy of the positive strand (antigenomic) message sense RNA of various wild-type of vaccine measles strains, including Edmonston wild-type strain, Moraten strain, and Schwarz strain, and WO 97/06270, which discloses the production of recombinant measles vectors.

Figure 4:
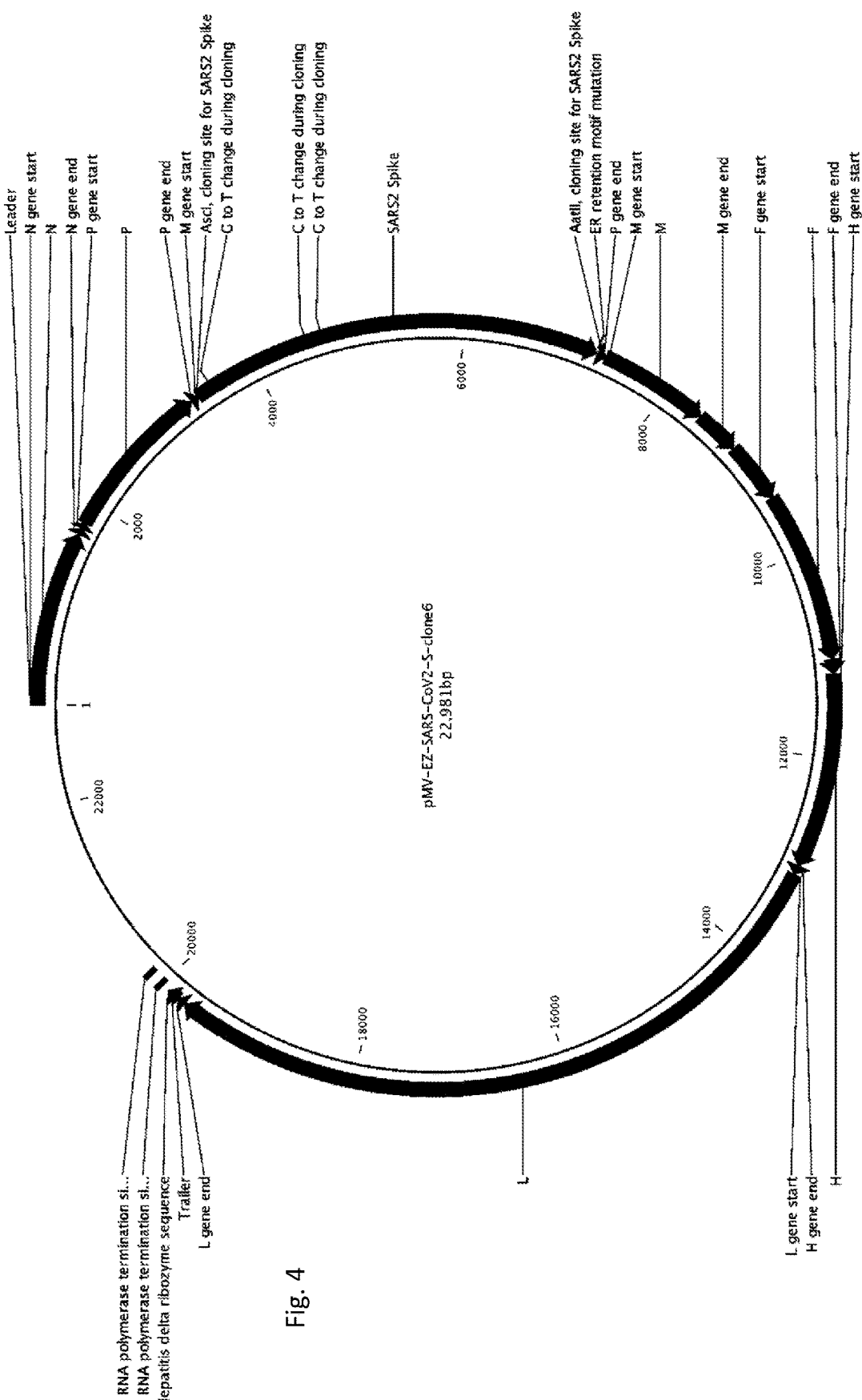
FIG. 4 is a vector map of $rMV^{EZ}SARS-CoV-2-S6$.
Figure 5:
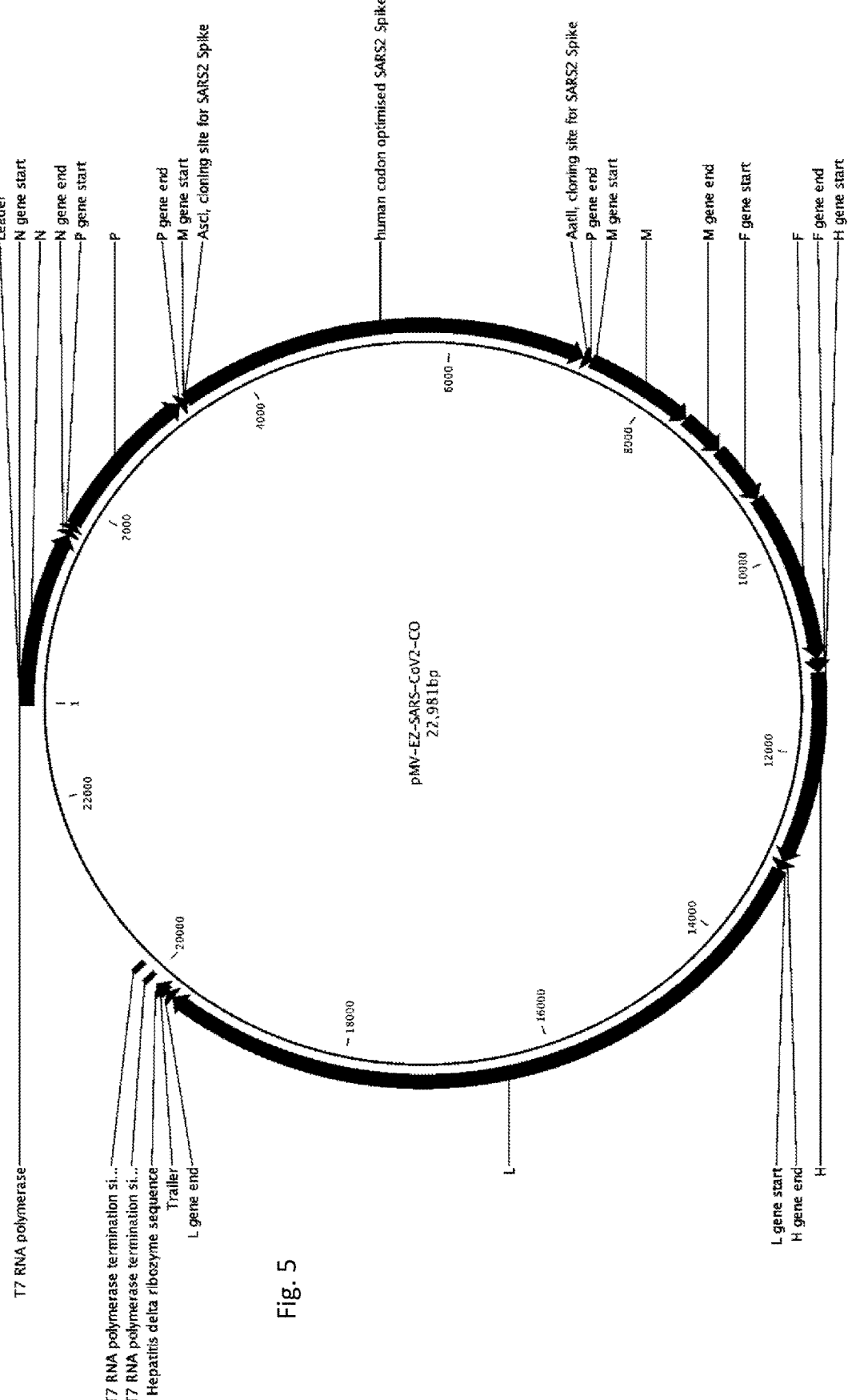
FIG. 5 is a vector map of $rMV^{EZ}SARS-CoV-2-S-CO$.
Figure 6:
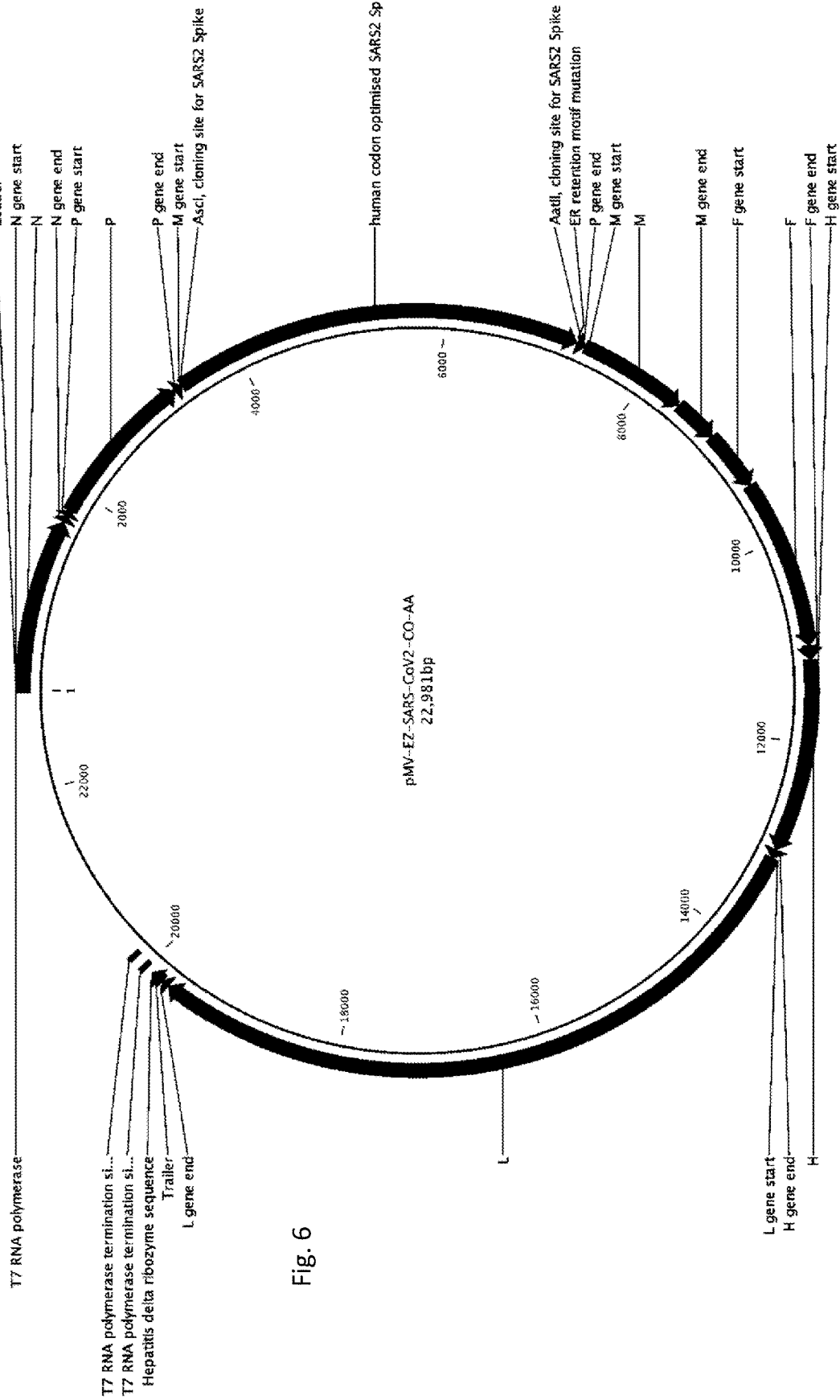
FIG. 6 is a vector map of $rMV^{EZ}SARS-CoV-2-S-COAA$.
Figure 7:
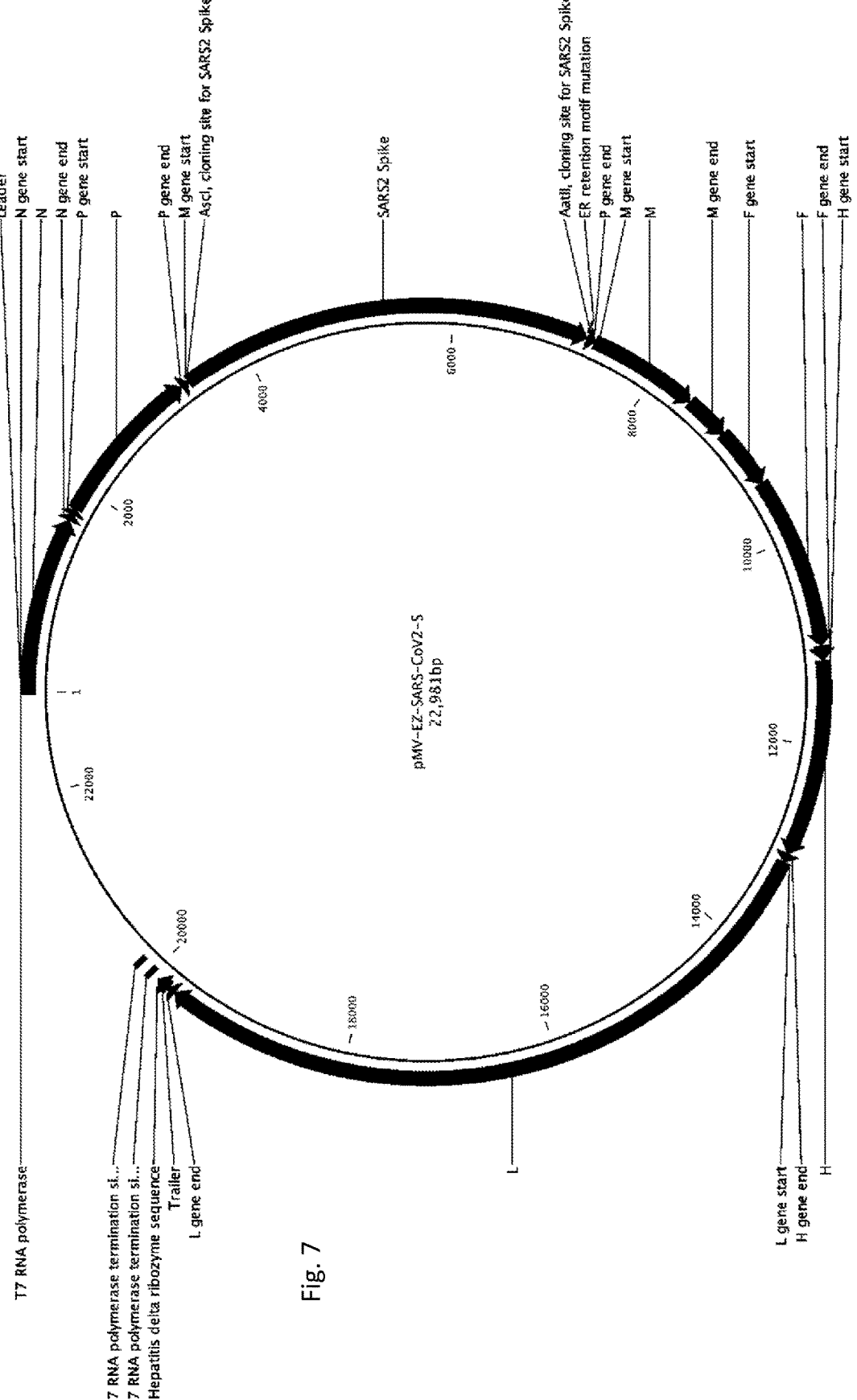
FIG. 7 is a vector map of $rMV^{EZ}SARS-CoV-2-S$.
Figure 8:
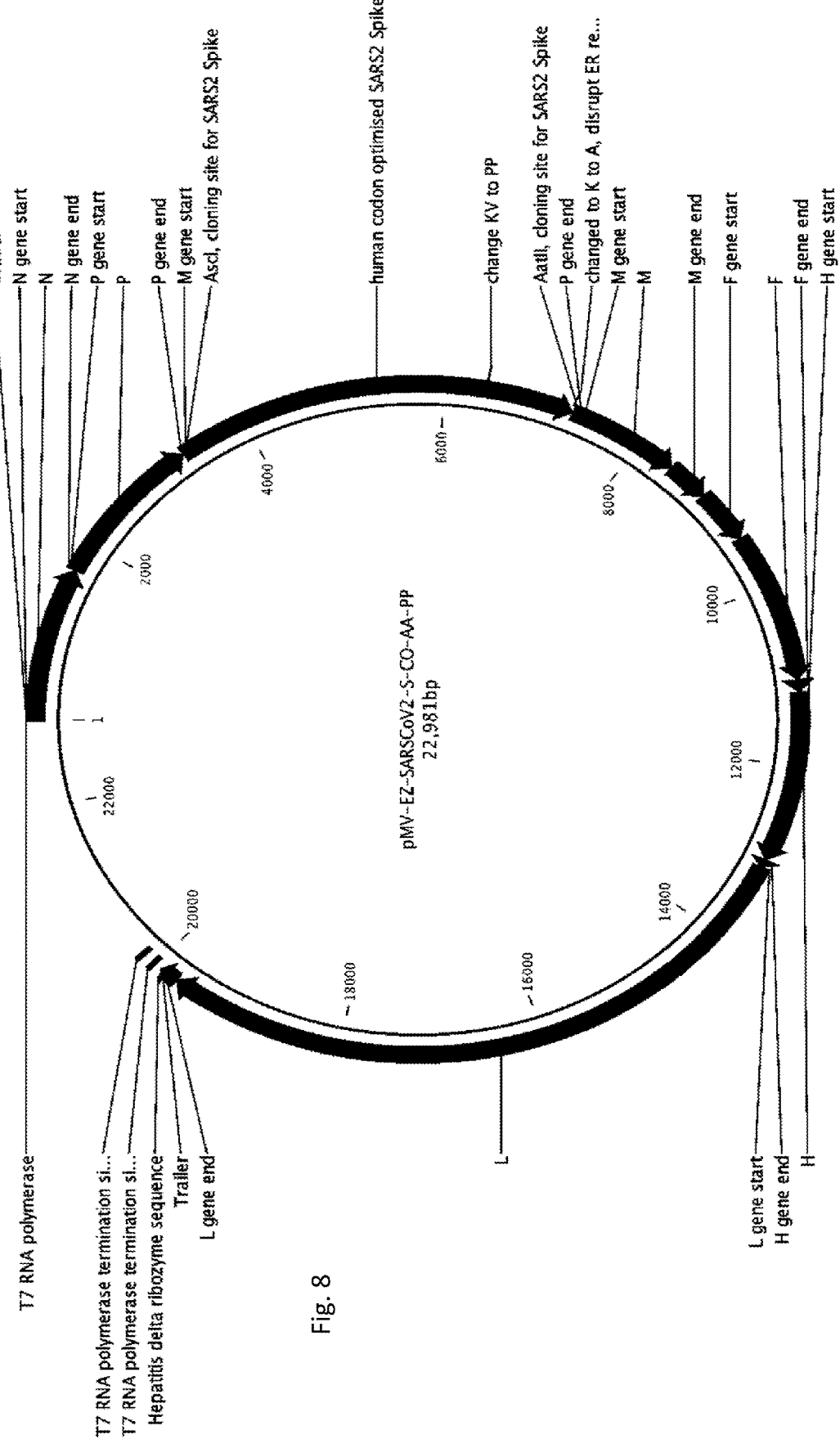
FIG. 8 is a vector map of $rMV^{EZ}SARS-CoV-2-S-COAA-PP$.
Figure 9:
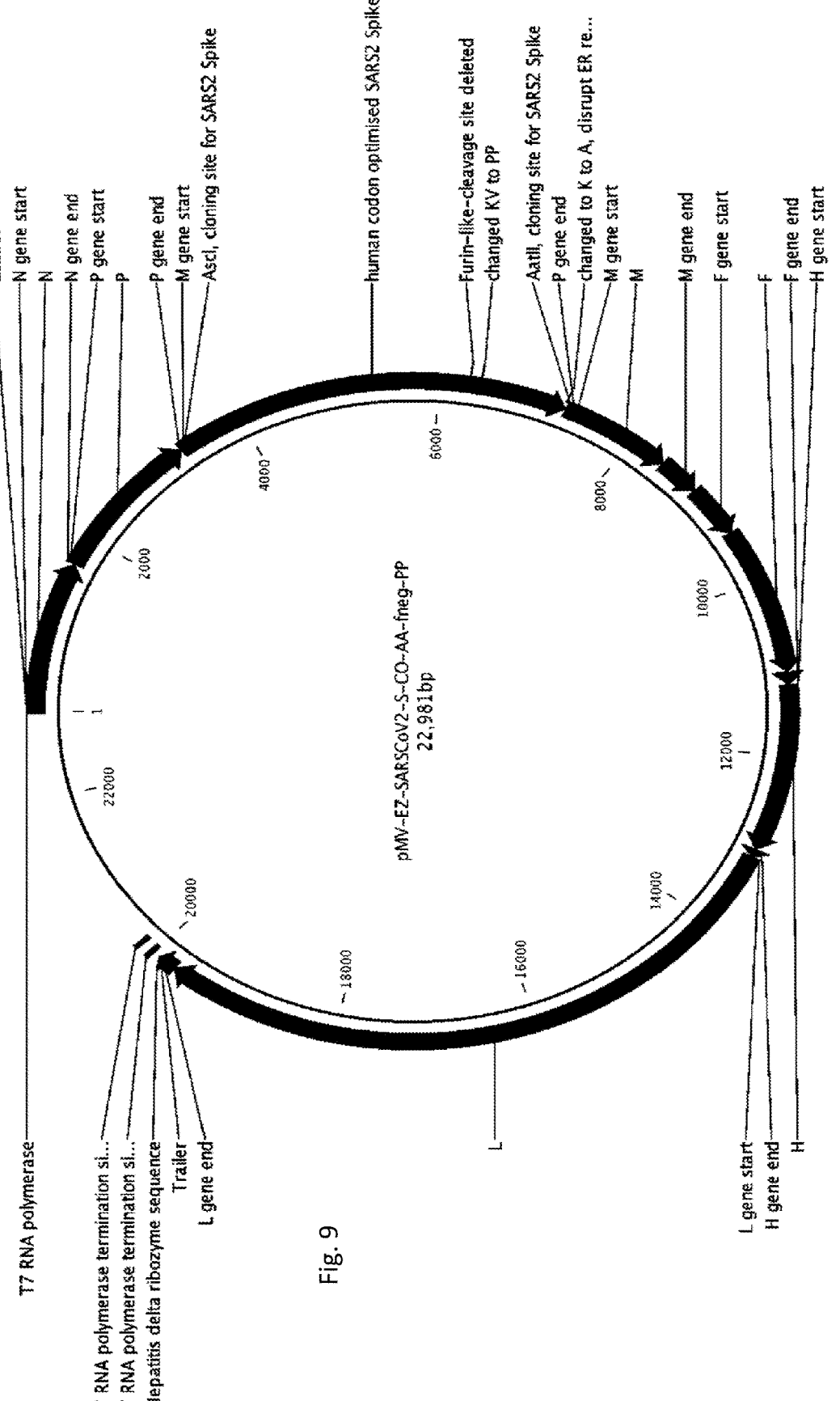
FIG. 9 is a vector map of $rMV^{EZ}SARS-CoV-2-S-COAA-fneg-PP$.
Figure 10:
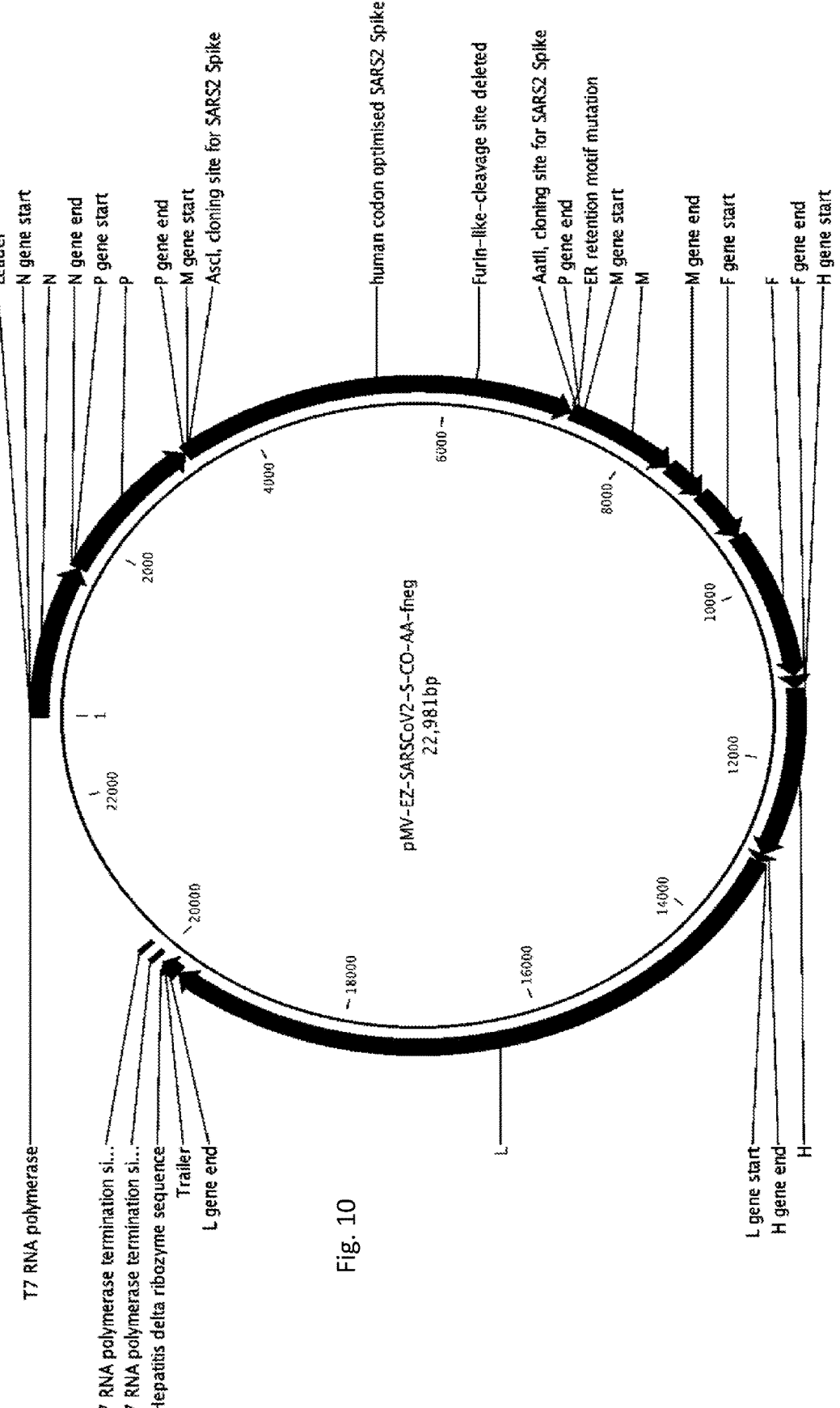
FIG. 10 is a vector map of and $rMV^{EZ}SARS-CoV-2-S-COAA-fneg$.

In one embodiment, the measles viral vector is an Edmonston-Zagreb (EZ) measles viral vector. Particular recombinant measles viral vectors of the Edmonston-Zagreb (EZ) strain include the following: rMV$^{EZ}$SARS-CoV-2-S6 (FIG. 4), rMV$^{EZ}$SARS-CoV-2-S-CO (FIG. 5), rMV$^{EZ}$SARS-CoV-2-S-COAA (FIG. 6), rMV$^{EZ}$SARS-CoV-2-S(FIG. 7), rMV$^{EZ}$SARS-CoV-2-S-COAA-PP (FIG. 8), rMV$^{EZ}$SARS-CoV-2-S-COAA-fneg-PP (FIG. 9), and rMV$^{EZ}$SARS-CoV-2-S-COAA-fneg (FIG. 10).

The recombinant measles vector comprises a nucleic acid encoding the SARS-CoV-2 spike glycoprotein, wherein the nucleic acid sequence encoding the SARS-CoV-2 spike glycoprotein can be any suitable nucleic acid sequence.

In one embodiment, the nucleic acid sequence encoding the SARS-CoV-2 spike glycoprotein is codon optimized. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by ribosomes using tRNAs that are more readily available within a cell, thus increasing translation efficiency and overall protein production. Optimization of the nucleotide sequence may also reduce secondary mRNA structures that would interfere with translation, thus increasing translation efficiency. rMV$^{EZ}$SARS-CoV-2-S-CO, rMV$^{EZ}$SARS-CoV-2-S-COAA, rMV$^{EZ}$SARS-CoV-2-S-COAA-PP, rMV$^{EZ}$SARS-CoV-2-S-COAA-fneg-PP, and rMV$^{EZ}$SARS-CoV-2-S-COAA-fneg each contain codon optimized SARS-CoV-2 spike glycoprotein sequences. Techniques for codon optimization are known in the art.

The nucleic acid sequence encoding the SARS-CoV-2 spike glycoprotein can contain at least one modification that disrupts the endoplasmic reticulum (ER) retention sequence of the SARS-CoV-2 spike glycoprotein. For example, the modification can result in an ER retention sequence of the SARS-CoV-2 spike glycoprotein containing AxAxx rather than KxHxx in the cytoplasmic tail (as described in Case et al., *bioRxiv* (2020). doi:10.1101/2020.05.18.102038 and Example 2). rMV$^{EZ}$SARS-CoV2-S6, rMV$^{EZ}$SARS-CoV-2-S, rMV$^{EZ}$SARS-CoV-2-S-COAA, rMV$^{EZ}$SARS-CoV-2-S-COAA-PP, rMV$^{EZ}$SARS-CoV-2-S-COAA-fneg-PP, and rMV$^{EZ}$SARS-CoV-2-S-COAA-fneg each contain modifications to ablate the ER retention signal. In particular, the amino acid sequences of the SARS-CoV-2 spike glycoproteins encoded by rMV$^{EZ}$SARS-CoV2-S6, rMV$^{EZ}$SARS-CoV-2-S, rMV$^{EZ}$SARS-CoV-2-S-COAA, rMV$^{EZ}$SARS-CoV2-S, rMV$^{EZ}$SARS-CoV-2-S-COAA-PP, rMV$^{EZ}$SARS-CoV-2-S-COAA-fneg-PP, and rMV$^{EZ}$SARS-CoV-2-S-COAA-fneg each contain two alanine substitutions at residues 1269 and 1271 of SEQ ID NOs: 8 and 10-14, respectively.

The nucleic acid encoding the SARS-CoV-2 spike glycoprotein can contain at least one modification that locks in the prefusion conformation. The spike (S) glycoprotein is a trimeric class I fusion protein that exists in a metastable prefusion conformation that undergoes a substantial structural rearrangement to fuse the viral membrane with the host cell membrane (Wrapp et al., *Science*, 13: 1260-1263 (2020)). This process is triggered when the 51 subunit binds to a host cell receptor. Receptor binding destabilizes the prefusion trimer, resulting in shedding of the 51 subunit and transition of the S2 subunit to a stable postfusion conformation. To engage a host cell receptor, the receptor-binding domain (RBD) of S1 undergoes hinge-like conformational movements that transiently hide or expose the determinants of receptor binding. The amino acid sequences of the SARS-CoV-2 spike glycoproteins encoded by rMV$^{EZ}$SARS-CoV-2-S-COAA-PP and rMV$^{EZ}$SARS-CoV-2-S-COAA-fneg-PP each contain two proline modifications (PP) at residues 986 and 987 of SEQ ID NOs: 9 and 10, respectively, which lock in the prefusion conformation.

The nucleic acid encoding the SARS-CoV-2 spike glycoprotein can contain at least one modification that ablates the furin cleavage signal, such as by modifying the furin cleavage site so that furin no longer cleaves the sequence. The furin cleavage site can be any polypeptide site cleavable by furin. The minimal cleavage site typically is, in the single letter code for amino acid residues, R-X-X-R, with cleavage occurring after the second "R" (Duckert et al., *Protein Engineering, Design & Selection*, 17(1):107-112 (2004); and WO 2009/032954). Whether or not any particular sequence is cleavable by furin can be determined by methods known in the art. For example, whether or not a sequence is cleavable by furin can be tested by incubating the sequence with furin.

rMV$^{EZ}$SARS-CoV-2-S-COAA-fneg-PP and rMV$^{EZ}$SARS-CoV-2-S-COAA-fneg each contain modifications to ablate the furin cleavage signal. In particular, the amino acid sequences of the SARS-CoV-2 spike glycoproteins encoded by rMV$^{EZ}$SARS-CoV2-S-COAA-fneg-PP and rMV$^{EZ}$SARS-CoV-2-S-COAA-fneg each contain four amino acid changes (ASVG; SEQ ID NO: 23) at residues 682-685 of SEQ ID NOs: 13 and 14, respectively, that ablate the furin cleavage signal.

In one embodiment, the nucleic acid encoding the SARS-CoV-2 spike glycoprotein encodes an amino acid sequence selected from the group consisting of SEQ ID NO: 8 (S6 spike glycoprotein), SEQ ID NO: 9 (S-CO spike glycoprotein), SEQ ID NO: 10 (S-CO-AA spike glycoprotein), SEQ ID NO: 11 (S spike glycoprotein), SEQ ID NO: 12 (S-CO-AA-PP spike glycoprotein), SEQ ID NO: 13 (S-CO-AA-fneg-PP spike glycoprotein), and SEQ ID NO: 14 (S-CO-AA-fneg spike glycoprotein).

In another embodiment, the nucleic acid encoding the SARS-CoV-2 spike glycoprotein is selected from the group consisting of SEQ ID NO: 1 (S6), SEQ ID NO: 2 (S-CO), SEQ ID NO: 3 (S-CO-AA), SEQ ID NO: 4 (S), SEQ ID NO: 5 (S-CO-AA-PP), SEQ ID NO: 6 (S-CO-AA-fneg-PP), and SEQ ID NO: 7 (S-CO-AA-fneg).

The recombinant measles viral vector comprising a nucleic acid sequence encoding a SARS-CoV-2 spike glycoprotein can have any suitable nucleic acid sequence. For example, the recombinant measles viral vector can comprise, consist essentially of, or consist of a nucleic acid sequence selected from the group consisting of SEQ ID NO: 15 (rMV$^{EZ}$SARS-CoV-2-S6), SEQ ID NO: 16 (rMV$^{EZ}$SARS-CoV-2-S-CO), SEQ ID NO: 17 (rMV$^{EZ}$SARS-CoV-2-S-COAA), SEQ ID NO: 18 (rMV$^{EZ}$SARS-CoV-2-S), SEQ ID NO: 19 (rMV$^{EZ}$SARS-CoV-2-S-COAA-PP), SEQ ID NO: 20 (rMV$^{EZ}$SARS-CoV-2-S-COAA-fneg-PP), and SEQ ID NO: 21 (rMV$^{EZ}$SARS-CoV-2-S-COAA-fneg). The vector sequences can comprise one or more nucleic acid sequences encoding the N, P, S, M, F, H, and L genes as described in GenBank Accession Nos. AY486083.1 and AY486084.1.

An embodiment of the invention also provides a polypeptide comprising, consisting essentially of, or consisting of an amino acid sequence selected from the group consisting of SEQ ID NO: 8 (S6), SEQ ID NO: 9 (S-CO), SEQ ID NO: 10 (S-CO-AA), SEQ ID NO: 11 (S), SEQ ID NO: 12

(S-CO-AA-PP), SEQ ID NO: 13 (S-CO-AA-fneg-PP), and SEQ ID NO: 14 (S-CO-AA-fneg), corresponding a SARS-CoV-2 spike glycoprotein.

The polypeptide can be prepared by any of a number of conventional techniques. In this respect, the polypeptide sequence can be synthetic, recombinant, isolated, and/or purified.

The polypeptide can be isolated or purified from a recombinant source. For instance, a DNA fragment encoding a desired polypeptide can be subcloned into an appropriate vector using well-known molecular genetic techniques. The fragment can be transcribed and the polypeptide subsequently translated in vitro. Commercially available kits also can be employed. The polymerase chain reaction optionally can be employed in the manipulation of nucleic acids.

The polypeptide also can be synthesized using an automated peptide synthesizer in accordance with methods known in the art. Alternately, the polypeptide can be synthesized using standard peptide synthesizing techniques well-known to those of skill in the art. In particular, the polypeptide can be synthesized using the procedure of solid-phase synthesis. If desired, this can be done using an automated peptide synthesizer. Removal of the t-butyloxy-carbonyl (t-BOC) or 9-fluorenylmethyloxycarbonyl (Fmoc) amino acid blocking groups and separation of the polypeptide from the resin can be accomplished by, for example, acid treatment at reduced temperature. The protein-containing mixture then can be extracted, for instance, with diethyl ether, to remove non-peptidic organic compounds, and the synthesized polypeptide can be extracted from the resin powder (e.g., with about 25% w/v acetic acid). Following the synthesis of the polypeptide, further purification (e.g., using HPLC) optionally can be performed in order to eliminate any incomplete proteins, polypeptides, peptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation or through genetic means, such as are known to those skilled in the art. In this regard, an embodiment of the invention also provides a fusion protein comprising the polypeptide and one or more other protein(s) having any desired properties or functions, such as to facilitate isolation, purification, analysis, or stability of the fusion protein.

An embodiment of the invention also provides a nucleic acid encoding the polypeptide. In one embodiment, the nucleic acid comprises, consists essentially of, or consists of a nucleic acid sequence selected from the group consisting of SEQ ID NO: 1 (S6), SEQ ID NO: 2 (S-CO), SEQ ID NO: 3 (S-CO-AA), SEQ ID NO: 4 (SARS-CoV2-S), SEQ ID NO: 5 (S-CO-AA-PP), SEQ ID NO: 6 (S-CO-AA-fneg-PP), and SEQ ID NO: 7 (S-CO-AA-fneg).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In an embodiment, the nucleic acid is recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acid (e.g., DNA, RNA, cDNA, and the like) can be produced in any suitable matter including, but not limited to recombinant production and commercial synthesis. In this respect, the nucleic acid sequence can be synthetic, recombinant, isolated, and/or purified.

The nucleic acid can be constructed based on chemical synthesis and/or enzymatic ligation reactions using procedures known in the art. See, for example, Green et al. (eds.), *Molecular Cloning, A Laboratory Manual, 4th* Edition, Cold Spring Harbor Laboratory Press, New York (2012). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, CO) and Synthegen (Houston, TX).

The nucleic acid encoding the polypeptide can be provided as part of a construct comprising the nucleic acid and elements that enable delivery of the nucleic acid to a cell, and/or expression of the nucleic acid in a cell. For example, the polynucleotide sequence encoding the polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG/AUG) in front of a protein-encoding gene, splicing signal for introns, maintenance of the correct reading frame of that gene to permit proper translation of mRNA, and stop codons.

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system, the Ecdysone inducible system, the T-REX™ system (Invitrogen, Carlsbad, CA), LACSWITCH™ System (Stratagene, San Diego, CA), and the Cre-ERT tamoxifen inducible recombinase system.

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. For example, the nucleic acid encoding the polypeptide can be operably linked to a CMV enhancer/chicken β-actin promoter (also referred to as a "CAG promoter").

A nucleic acid encoding the polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the polypeptide can be isolated by polymerase chain reaction of cDNA using primers based on the DNA sequence of the molecule. A wide variety of cloning and in vitro amplification methodologies are well known to persons skilled in the art.

An embodiment of the invention also provides a recombinant vector comprising the nucleic acid. Examples of suitable vectors include plasmids (e.g., DNA plasmids), bacterial vectors, and viral vectors, such as poxvirus, retrovirus, adenovirus, adeno-associated virus, herpes virus, poliovirus, alphavirus, baculovirus, measles virus, and Sindbis virus. When the vector is a plasmid (e.g., DNA plasmid), the plasmid can be complexed with chitosan.

The polypeptide, nucleic acid, or vector (e.g., recombinant measles virus vector) can be formulated as a composition (e.g., pharmaceutical composition) comprising the polypeptide, nucleic acid, or vector (e.g., recombinant measles virus vector) and a carrier (e.g., a pharmaceutically or physiologically acceptable carrier). Furthermore, the polypeptide, nucleic acid, vector (e.g., recombinant measles virus vector), or composition can be used in the methods described herein alone or as part of a pharmaceutical formulation.

The composition (e.g., pharmaceutical composition) can comprise more than one polypeptide, nucleic acid, vector (e.g., recombinant measles virus vector), or composition of the invention. Alternatively, or in addition, the composition can comprise one or more (e.g., one, two, three, or more) additional pharmaceutically active agents or drugs, such as corticosteroids, antibiotics, and antivirals.

The carrier can be any of those conventionally used and is limited only by physio-chemical considerations, such as solubility and lack of reactivity with the active compound(s) and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular polypeptide, nucleic acid, vector, or composition thereof of the invention and other active agents or drugs used, as well as by the particular method used to administer the polypeptide, nucleic acid, vector (e.g., recombinant measles virus vector), or composition thereof.

The composition also can be formulated to enhance transduction efficiency. In addition, a person of ordinary skill in the art will appreciate that the one or more of the polypeptides, nucleic acids, or vectors (e.g., recombinant measles virus vectors) can be present in a composition with other therapeutic or biologically-active agents. For example, factors that control inflammation, such as ibuprofen or steroids, can be part of the composition to reduce swelling and inflammation associated with in vivo administration of one or more of the polypeptides, nucleic acids, or vectors (e.g., recombinant measles virus vector). Antibiotics, i.e., microbicides and fungicides, can be present to treat existing infection and/or reduce the risk of future infection.

The invention provides a method for preventing, inhibiting, reducing, eliminating, protecting, or delaying the onset of an infection or an infectious clinical condition caused by coronavirus in a subject comprising administering the polypeptide, nucleic acid, vector (e.g., recombinant measles virus vector), or composition thereof to a subject. The invention also provides a method for inducing an immune response against a coronavirus in a subject comprising administering the polypeptide, nucleic acid, vector (e.g., recombinant measles virus vector), or composition thereof to the subject.

Administration of the polypeptide, nucleic acid, vector (e.g., recombinant measles virus vector), or composition thereof to the subject can be used to protect against one or more strains of coronavirus (e.g., SARS-CoV-2), thereby treating, preventing, and/or protecting against coronavirus-based pathologies.

Administration of the polypeptide, nucleic acid, vector (e.g., recombinant measles virus vector), or composition thereof can significantly induce an immune response of a subject administered the polypeptide, nucleic acid, vector (e.g., recombinant measles virus vector), or composition thereof, thereby protecting against and treating coronavirus (e.g., SARS-CoV-2) infection.

Administration of the polypeptide, nucleic acid, vector (e.g., recombinant measles virus vector), or composition thereof can induce a humoral immune response in a subject. The induced humoral immune response can be specific for the SARS-CoV-2 spike glycoprotein. The humoral immune response can be induced in the subject administered the vaccine by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 16.5-fold, at least about 17-fold, at least about 17.5-fold, at least about 18-fold, at least about 18.5-fold, at least about 19-fold, at least about 19.5-fold, at least about 20-fold, or ranges of any combination of these values as compared to a subject not administered the polypeptide, nucleic acid, vector (e.g., recombinant measles virus vector), or composition thereof.

The induced humoral immune response can include an increased level of neutralizing antibodies as compared to a subject not administered the polypeptide, nucleic acid, vector (e.g., recombinant measles virus vector), or composition thereof. The neutralizing antibodies can be specific for the SARS-CoV-2 spike glycoprotein. The neutralizing antibodies can provide protection against and/or treatment of SARS-CoV-2 infection and its associated pathologies in the subject administered the polypeptide, nucleic acid, vector (e.g., recombinant measles virus vector), or composition thereof.

The induced humoral immune response can include an increased level of IgG antibodies as compared to a subject not administered the polypeptide, nucleic acid, vector (e.g., recombinant measles virus vector), or composition thereof. These IgG antibodies can be specific for the SARS-CoV-2 antigens. The level of IgG antibody can be increased by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 16.5-fold, at least about 17-fold, at least about 17.5-fold, at least about 18-fold, at least about 18.5-fold, at least about 19-fold, at least about 19.5-fold, at least about 20-fold, or ranges of any combination of these values as compared to a subject not administered the polypeptide, nucleic acid, vector (e.g., recombinant measles virus vector), or composition thereof.

The induced humoral immune response can include an increased level of IgM and/or IgA antibodies as compared to a subject not administered the polypeptide, nucleic acid, vector (e.g., recombinant measles virus vector), or composition thereof. These IgM and or IgA antibodies can be specific for the SARS-CoV-2 antigen. The level of IgM/IgA antibody can be increased by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 16.5-fold, at least about 17-fold, at least about 17.5-fold, at least about 18-fold, at least about 18.5-fold, at least about 19-fold, at least about 19.5-fold, at least about 20-fold, or ranges of any combination of these values as compared to a subject not administered the polypeptide, nucleic acid, vector (e.g., recombinant measles virus vector), or composition thereof.

Administration of the polypeptide, nucleic acid, vector (e.g., recombinant measles virus vector), or composition thereof can induce a cellular immune response in the subject. The induced cellular immune response can be specific for the SARS-CoV-2 antigen.

The induced cellular immune response can include eliciting a CD8+ T cell response, which can include eliciting a CD8+ T cell response in which the CD8+ T cells produce interferon-gamma (IFN-$\gamma$), tumor necrosis factor alpha (TNF-$\alpha$), interleukin-2 (IL-2), or a combination thereof (e.g., a combination of IFN-$\gamma$ and TNF-$\alpha$).

The CD8+ T cell response can be increased by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, at least about 30-fold, or ranges of any combination of these values as compared to the subject not administered the polypeptide, nucleic acid, vector (e.g., recombinant measles virus vector), or composition thereof.

Administration of the polypeptide, nucleic acid, vector (e.g., recombinant measles virus vector), or composition thereof can also include eliciting a CD4+ T cell response, which can include eliciting a CD4+ T cell response in which the CD4+ T cells produce IFN-$\gamma$, TNF-$\alpha$, IL-2, or a combination thereof (e.g., a combination of IFN-$\gamma$ and TNF-$\alpha$).

The polypeptide, nucleic acid, vector (e.g., recombinant measles virus vector), or composition thereof can be administered to the subject by various routes including, but not limited to, oral, sublingual, buccal, intradermal, topical, parenteral (using single or arrays of dissolvable and hybrid microneedles, in lyophilized or solution), subcutaneous, intravenous, intramuscular, intraarterial, intrathecal, interperitoneal, intranasal, large and/or small particle aerosol, dry-powder aerosols or intratracheal administration, or subretinal injection or intravitreal injection.

The invention includes a prime and boost protocol. In particular, the protocol includes an initial "prime" with the polypeptide, nucleic acid, vector (e.g., recombinant measles virus vector), or composition thereof, followed by one or preferably multiple "boosts" with the polypeptide, nucleic acid, vector (e.g., recombinant measles virus vector), or composition thereof. The boosts can be administered 1-3 times (e.g., 1, 2, or 3 times) at any suitable time period (e.g., every 3-4 weeks, every six months, or once a year) for any suitable length of time.

The polypeptide, nucleic acid, vector (e.g., recombinant measles virus vector), or composition thereof can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The polypeptide, nucleic acid, vector (e.g., recombinant measles virus vector), or composition thereof can be administered prophylactically or therapeutically. In prophylactic administration, the polypeptide, nucleic acid, vector (e.g., recombinant measles virus vector), or composition thereof are administered in an amount sufficient to induce an immune response. In therapeutic applications, the polypeptide, nucleic acid, vector (e.g., recombinant measles virus vector), or composition thereof are administered to a subject in need thereof in an amount sufficient to elicit a therapeutic effect. An amount adequate to accomplish this is defined as "therapeutically effective dose." Amounts effective for this use will depend on, e.g., the particular composition of the polypeptide, nucleic acid, vector (e.g., recombinant measles virus vector), or composition thereof administered to a subject, the manner of administration, the stage and severity of the infection, the general state of health of the patient, and the judgment of the prescribing physician.

The following examples further illustrate the invention but, of course, should not be construed as in any way limiting its scope.

Example 1

This example provides materials and methods for the studies described in Example 2.

Cell Lines, Viruses and Plasmids

Vero cells (African green monkey kidney cells; ATCC CCL-81) purchased from ATCC (Manassas, VA, USA) were grown in advanced Dulbecco's modified Eagle medium (DMEM; Gibco) supplemented with 10% (V/V) fetal bovine serum (HI FBS heat inactivated, Gibco) and GlutaMAX-I (Gibco). Cells were grown and maintained at 37° C. and 5% (V/V) $CO_2$, and tested negative for *mycoplasma* contamination prior to use in virus rescue experiments. MV plasmids expressing N, P and L, $pMV_{EZ}EGFP(3)$, as well as $rMV_{EZ}EGFP(3)$ virus have been described previously (Rennick et al., J. Virol. (2015). doi:10.1128/jvi.02924-14).

Construction of $MV^{EZ}$ cDNA Plasmids Expressing SARS-CoV-2 Spike Glycoprotein As described in Rennick et al., *J. Virol.* (2015). doi: 10.1128/jvi.02924-14), three recombinant viruses were generated that contained the open reading frame encoding enhanced green fluorescent protein (EGFP) within an additional transcriptional unit (ATU) at various positions within the genome. $rMV_{EZ}EGFP(1)$, $rMV^{EZ}EGFP(3)$, and $rMV_{EZ}EGFP(6)$ contained the ATU upstream of the N gene, following the P gene, and following the H gene, respectively. The viruses were compared in vitro by growth curves, which indicated that $rMV^{EZ}EGFP(1)$ was over-attenuated. Intratracheal infection of cynomolgus macaques with these recombinant viruses revealed differences in immunogenicity. $rMV^{EZ}EGFP(1)$ and $rMV^{EZ}EGFP(6)$ did not induce satisfactory serum antibody responses, whereas both in vitro and in vivo $rMV^{EZ}EGFP(3)$ was functionally equivalent to the commercial $MV^{EZ}$-containing vaccine. Intramuscular vaccination of macaques with $rMV^{EZ}EGFP(3)$ resulted in the identification of EGFP+ cells in the muscle at days 3, 5, and 7 post-vaccination. Therefore, rMV$^{EZ}$EGFP(3) was selected for further experiments.

pMV$^{EZ}$ versions expressing SARS-CoV-2 spike glycoprotein (Accession number MN908947) were generated by replacing the open reading frame of EGFP in pMV$^{EZ}$EGFP (3) (Rennick et al., *J. Virol.* (2015). doi:10.1128/jvi.02924-14).

Plasmid pMV$^{EZ}$EGFP(3) was linearized using restriction sites Asc I at genome position 3439 and Aat II at genome position 4176. These restriction sites were originally designed into pMV$^{EZ}$EGFP(3) to allow easy replacement of foreign genes in place of EGFP. SARS-CoV-2 spike with mutations in the endoplasmic reticulum (ER) retention signal sequence as previously described (Case et al., *bioRxiv* (2020). doi:10.1101/2020.05.18.102038) were obtained in two gene fragments. These fragments were ligated into the linearized pMV$^{EZ}$EGFP(3) using Gibson Assembly (NEBuilder® HiFi DNA assembly, NEB). This generated two versions pMV$_{EZ}$SARS-CoV-2-S and pMV$^{EZ}$SARS-CoV-2-S6.

A human codon optimized SARS-CoV-2 spike glycoprotein expressing plasmid was obtained from GenScript (Piscataway, NJ, USA). Spike was amplified from the plasmid using oligonucleotides that contained a 35 nucleotide homology (lower case sequence) to the linearized pMV$^{EZ}$EGFP(3) (Forward primer: 5'caaagtgattgcctcc-caagttccacaggcgcgccATGTTCGTCTTCCTGGTC3' (SEQ ID NO: 24) and reverse primer: 5'gttggcaggtaagtt-gagctgtaggacgtcgcgcgTTAGGTGTAATGCAGCTTCAC3' (SEQ ID NO: 25)). The amplified product was then ligated into linearized pMV$^{EZ}$EGFP(3) using Gibson Assembly (NEBuilder® HiFi DNA assembly, NEB). This generated pMV$_{EZ}$SARSCoV2-S-CO. pMV$_{EZ}$SARS-CoV-2-S-COAA was generated the same way, but using a reverse primer (5'ggttggcaggtaagttgagctgtaggacgtcgcgcgT-TAGGTGTAAGCCAGCGCCACGCC3' (SEQ ID NO: 26) with nucleotide changes (in bold) to disrupt the ER retention signal.

The spike sequence in all plasmids were sequence confirmed via Sanger sequencing (Genewiz, NJ, USA).

Generation of Recombinant rMV$_{EZ}$-SARS-CoV-2-Spike Glycoprotein Viruses

Vero cell monolayers in 6-well trays were infected with a recombinant vaccinia virus expressing T7 polymerase (MVA-T7) in Opti-MEM (Gibco) for 30 mins at 37° C. and then spinoculated at room temperature for another 30 mins. Virus inoculum was removed and 1 ml fresh Opti-MEM was added onto cells. Cells were then transfected with 5 μg of pMV$^{EZ}$SARS-CoV-2-S, pMV$^{EZ}$SARS-CoV-2-S6, pMV$^{EZ}$SARS-CoV-2-S-CO, or pMV$^{EZ}$SARS-CoV-2-S-COAA. MV plasmids expressing nucleoprotein (N), phosphoprotein (P) and polymerase (L) at 1 μg, 0.6 μg and 0.4 μg respectively, were also transfected into the cells. 24 hours post-transfection (h.p.t.), medium was removed from the cells and DMEM/2% (V/V) fetal bovine serum (FBS) was added. Cells were monitored daily for approximately 14 days post-transfection (d.p.t.) for syncytium formation. Plaque picked viruses were then grown in Vero cells and harvested by free-thaw when complete cytopathic effect was visible. Virus titers were determined by endpoint titration and expressed as 50% tissue culture infectious (TCID$_{50}$) units.

Reverse Transcription Polymerase Chain Reaction (RT/PCR) and Sequencing

Total RNA from working virus stocks was extracted using TRIzol LS reagent (ThermoFisher) according to manufacturer's recommendations and RNA pellet resuspended in 40 μl nuclease-free water (Invitrogen). cDNA was generated with 5 μl of resuspended RNA using SuperScript™ III First-strand synthesis system (Thermo Fisher Scientific) and random primers. 3 μl of the resultant cDNA was then used to amplify MV-spike fragments with primers using Phusion high-fidelity DNA polymerase (NEB) in a total volume of 50 μl (using a touch-down PCR amplification protocol). Amplified PCR products were analyzed on a 1% agarose gel and bands gel purified using QIAquick gel extraction kit (Qiagen). Products were sequenced confirmed via Sanger sequencing (Genewiz, NJ, USA).

Immunofluorescence

Confluent Vero cells in 24-well trays were infected with rMV$^{EZ}$SARS-CoV2-S6 or rMV$^{EZ}$SARS-CoV-2-S-CO at a multiplicity of infection (MOI) of 0.01. At 2 days post infection, cells were fixed with 4% paraformaldehyde for 10 minutes at room temperature. Cells were washed twice in PBS and permeabilized (0.1% Triton-X in PBS) at 37° C. for 30 minutes before incubating with primary antibody (Rabbit anti-SARS2-S, Sino biologicals 40150-R007; 1:500) made in PBS with 0.1% (V/V) Triton-X at 37° C. for 1 hour. Cells were then washed three times in PBS before incubating with secondary antibody (Chicken anti-rabbit Alexa Fluor 488, Invitrogen; 1:400) at 37° C. for 1 hour. Cells were washed three times in PBS and stained with DAPI nuclei stain (Invitrogen; 300 nM DAPI stain solution) for 10 minutes at room temperature in the dark. Images were obtained using a fluorescent microscope (Leica).

Virus Growth Kinetics

Vero cell monolayers at $2\times10^5$ cells in 24-well trays were infected with rMV$^{EZ}$EGFP(3), rMV$^{EZ}$SARS-CoV-2-S3, rMV$^{EZ}$SARS-CoV-2-S6, rMV$^{EZ}$SARS-CoV-2-S-CO, or rMV$^{EZ}$SARS-CoV-2-S-COAA at a 0.05 MOI. Cell monolayers were infected for 1 hour at 37° C. after which virus inoculum was removed and cell monolayers washed twice using phosphate-buffered saline (PBS; Gibco). DMEM/2% (V/V) FBS was added onto the cells and at the desired time points cells were scraped into culture medium and placed at −80° C. After freeze-thawing the cells and medium, cell debris were clarified and total virus measured by TCID$_{50}$.

Immunoplaque Assay

Confluent Vero cell monolayers in 6-well trays were infected with a 10-fold serial dilution of virus prepared in Opti-MEM. Cells were incubated for 1 h at 37° C. and then overlaid with 0.6% Avicel (FMC Biopolymer) supplemented with 2×MEM (10×MEM, no glutamine, Gibco) and 2% FBS. Cells were incubated for 5 days and then fixed using 4% paraformaldehyde for 30 minutes at room temperature. Cells were permeabilized (0.5% Triton X-100, 20 mM sucrose in PBS; 1 ml) for 30 minutes at room temperature and then washed (0.1% Tween-20 in PBS; 1 ml) once before incubating with primary antibody (Rabbit anti-SARS2-S, Sino biologicals 40150-R007; 1:1000) in blocking buffer (4% dried milk/0.1% Tween-20 in PBS) for 1 hour at room temperature. Cells were washed three times and incubated with secondary antibody (Goat anti-rabbit HRP, Abcam, ab6721; 1:1000) for 1 hour at room temperature. Plaques were visualized using KPL TrueBlue Peroxidase Substrate solution (Sera Care, 5510-0050). Plates were digitalized using a scanner.

Animal Study Design

All animal experiments were conducted in compliance with all applicable U.S. Federal policies and regulations and AAALAC International standards for the humane care and use of animals. All protocols were approved by the University of Pittsburgh Institutional Animal Care and Use Committee (IACUC).

Twenty-five IFNar1 knockout mice in groups of five were infected with $10^4$ $TCID_{50}$ of $rMV^{EZ}EGFP(3)$, $rMV^{EZ}SARS$-CoV-2-S3, $rMV^{EZ}SARS$-CoV-2-S6, $rMV^{EZ}SARS$-CoV-2-S-CO, or $rMV^{EZ}SARS$-CoV-2-S-COAA viruses via the intraperitoneal (IP) route. 21 days post-infection, mice were bled for serum, and then boosted with $10^5$ $TCID_{50}$ of the respective virus.

African green monkeys were immunized with either measles vaccine or $rMV^{EZ}SARS$-CoV-2-S-CO (in groups of 2 or 3) with $10^5$ $TCID_{50}$ of candidate vaccine. In our proof of principle study we focused on a prime/boost (day 0 and 21 days). Animals were challenged 42 days after immunization with $10^6$ plaque forming units of SARS-CoV-2.

All animals seroconverted generating antibodies to both measles and SARS-CoV-2. These antibodies neutralized both viruses, some at levels higher than what is seen in human convalescent serum.

Statistical Analysis

Statistical analyses were performed using GraphPad Prism software (La Jolla, CA).

Vector Maps

Vector maps are provided in FIGS. 4-10 for each of $rMV^{EZ}SARS$-CoV-2-S6, $rMV^{EZ}SARS$-CoV-2-S-CO, $rMV^{EZ}SARS$-CoV-2-S-COAA, $rMV^{EZ}SARS$-CoV-2-S, $rMV^{EZ}SARS$-CoV-2-S-COAA-PP, $rMV^{EZ}SARS$-CoV-2-S-COAA-fneg-PP, and $rMV^{EZ}SARS$-CoV-2-S-COAA-fneg, wherein the spike glycoprotein is inserted after the measles virus N and P genes (in the third (3) position).

Example 2

This example demonstrates the generation and characterization of recombinant MV vaccine strain viruses expressing SARS-CoV-2 spike glycoprotein.

Based on previously generated reverse genetics system for live-attenuated measles virus (MV) vaccine strain Edmonston-Zagreb (EZ) that expresses an enhanced green fluorescent protein (EGFP; $rMV^{EZ}$ EGFP(3)), recombinant MV vaccine viruses encoding SARS-CoV-2 spike glycoprotein were generated and rescued. The open reading frame for the spike glycoprotein lies within an additional transcriptional unit at position 3 in the MV genome in place of EGFP. These viruses were compared in vitro for replication and expression of the spike glycoprotein. The growth kinetics of all tested viruses were equivalent to $rMV_{EZ}EGFP(3)$.

$pMV^{EZ}EGFP(3)$ (Rennick et al., *J. Virol.* (2015). doi: 10.1128/jvi.02924-14) was modified to express SARS-CoV-2 spike glycoprotein in place of EGFP. In a manner similar to that described in Case et al, *bioRxiv* (2020). doi:10.1101/2020.05.18.102038, an endoplasmic reticulum (ER) retention signal sequence present in the cytoplasmic tail (CT) of the spike was altered from KxHxx to AxAxx-COOH, and anti-genomic plasmids expressing a non-codon and human codon optimized version ($pMV^{EZ}SARS$-CoV2-S and $pMV^{EZ}SARS$-CoV-2-COAA, respectively) were generated. An additional human codon optimized version with the authentic KxHxx-COOH sequence was also generated ($pMV^{EZ}SARS$-CoV-2-CO).

Recovery of a plasmid with the correct spike sequence proved challenging for the non-codon optimized version, and as a result two plasmids were generated: one with the authentic sequence ($pMV^{EZ}SARS$-CoV-2-S) and one with three nucleotide changes, one of which does not cause an amino acid change ($pMV^{EZ}SARS$-CoV-2-S6).

To recover recombinant viruses, Vero cells were transfected with either $pMV^{EZ}SARS$-CoV-2-S, $pMV^{EZ}SARS$-CoV-2-S6, $pMV^{EZ}SARS$-CoV-2-CO or $pMV^{EZ}SARS$-CoV-2-COAA along with expression plasmids for nucleoprotein (N), phosphoprotein (P) and polymerase (L) proteins. Sequence confirmation of the virus generated from clone $pMV^{EZ}SARS$-CoV-2-S revealed an amino acid change in the CT tail. This virus was subsequently named $rMV^{EZ}SARS$-CoV-2-S3 (FIG. 1A).

Figure 1A:
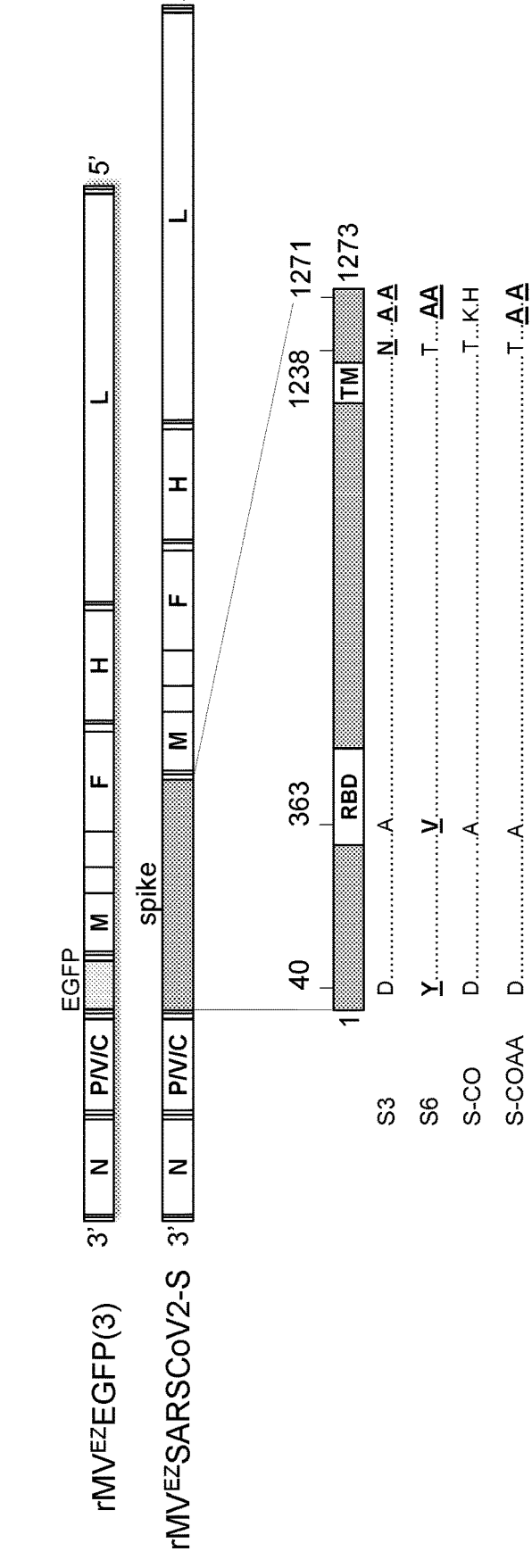
FIGS. 1A-1C demonstrate the generation of $rMV^{EZ}$ viruses expressing SARS-CoV-2 spike glycoprotein.
Figure 1C:
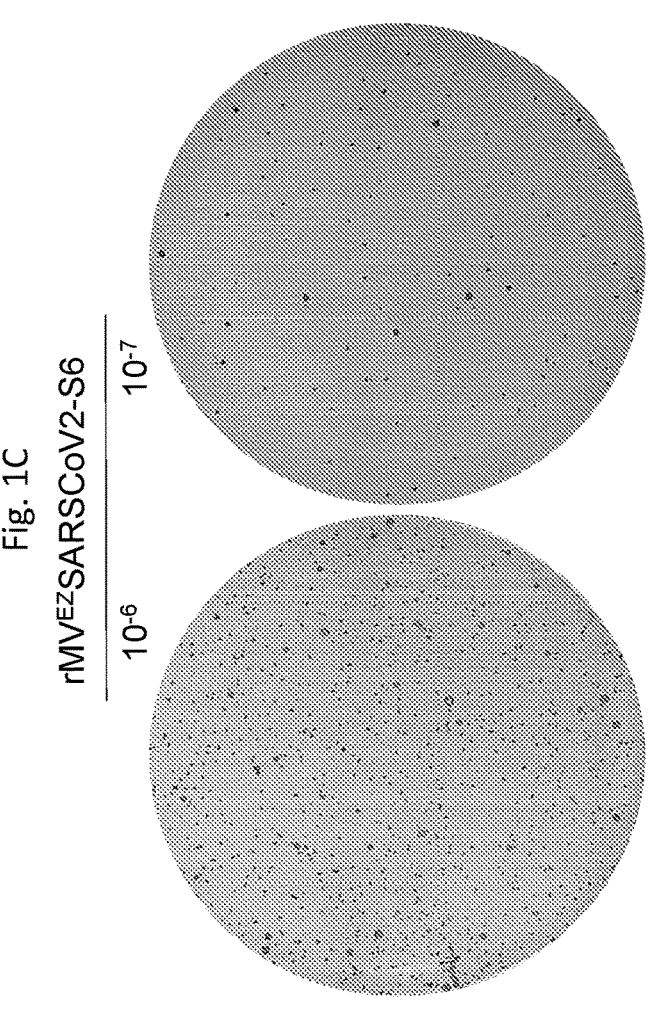
Figure 1B:
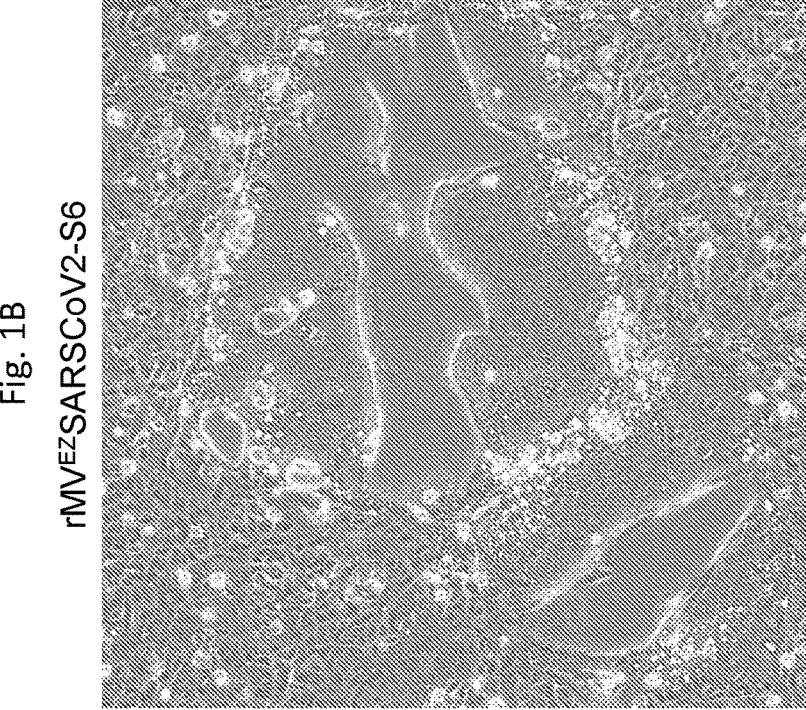

The spike glycoprotein sequences in $rMV^{EZ}SARS$-CoV-2-S6, $rMV^{EZ}SARS$-CoV-2-CO, and $rMV^{EZ}SARS$-CoV-2-COAA correspond to their cDNA clones (FIG. 1A). Rescue experiments were reproducible with syncytium formation about 14 days post transfection (FIG. 1B).

To test if the spike glycoprotein was expressed, Vero cells were infected and fixed and stained at 48 hours post-infection using an anti-SARS2-S antibody. Substantial amounts of spike expression were detectable in the infected cells, especially for $rMV^{EZ}SARS$-CoV-2-CO (FIG. 1C). Expression was further confirmed by staining viral plaques with anti-SARS2-S antibody (FIG. 1D).

Figure 2:
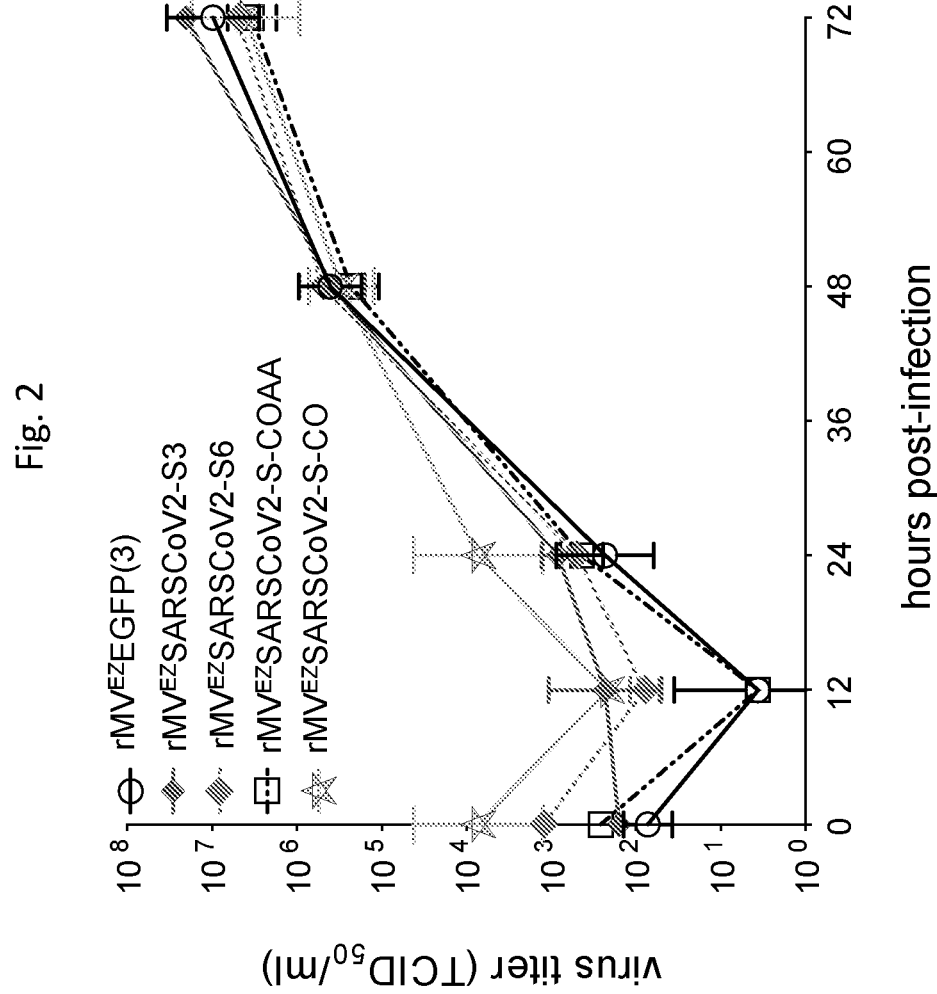
FIG. 2 demonstrates that growth kinetics of $rMV^{EZ}SARS-CoV-2-S3$, $rMV^{EZ}SARS-CoV-2-S6$, $rMV^{EZ}SARS-CoV-2-S-CO$, and $rMV^{EZ}SARS-CoV-2-S-COAA$ compared to $rMV^{EZ}EGFP(3)$. Vero cells were infected at a multiplicity of infections (MOI) of 0.05. Samples were harvested at the indicated time points and titrated on Vero cells. Error bars indicate standard deviation (n=3).

Growth analysis of $rMV^{EZ}SARS$-CoV-2-S3, $rMV^{EZ}SARS$-CoV-2-S6, $rMV^{EZ}SARS$-CoV-2-CO, and $rMV^{EZ}SARS$-CoV-2-COAA were compared to $rMV^{EZ}EGFP(3)$ in Vero cells over a 3 day period. Viruses replicated similar to $rMV^{EZ}EGFP(3)$ by reaching a titers close to $10^7$ $TCID_{50}$/ml (FIG. 2).

Additional vectors were generated with modifications to ablate the furin cleavage signal ($rMV^{EZ}SARS$-CoV-2-S-COAA-fneg and $rMV^{EZ}SARS$-CoV-2-S-COAA-fneg-PP), and to lock in the prefusion conformation by substitution of two proline residues ($rMV^{EZ}SARS$-CoV-2-S-COAA-PP and S-CO-AA-fneg-PP).

$rMV^{EZ}SARS$-CoV-2-S3 and $rMV^{EZ}SARS$-CoV-2-S6 encode a spike glycoprotein with nucleotide changes that arose during virus rescue and plasmid generation, respectively.

$rMV^{EZ}SARS$-CoV-2-S-CO, $rMV^{EZ}SARS$-CoV-2-S-COAA, $rMV^{EZ}SARS$-CoV-2-S-COAA-PP, $rMV^{EZ}SARS$-CoV-2-S-COAA-fneg, and $rMV^{EZ}SARS$-CoV-2-S-COAA-fneg-PP encode a human codon optimized spike glycoprotein.

$rMV^{EZ}SARS$-CoV-2-S3, $rMV^{EZ}SARS$-CoV-2-S6, $rMV^{EZ}SARS$-CoV-2-S, $rMV^{EZ}SARS$-CoV-2-S-COAA, $rMV^{EZ}SARS$-CoV-2-S-COAA-PP, $rMV^{EZ}SARS$-CoV-2-S-COAA-fneg-PP, and $rMV^{EZ}SARS$-CoV-2-S-COAA-fneg contain mutations in the spike glycoprotein to disrupt the endoplasmic reticulum (ER) retention sequence that has been described as essential for SARS-CoV-2 virion assembly via the ER-Golgi compartment.

The nucleic acid sequence encoding the spike glycoprotein of $rMV^{EZ}SARS$-CoV-2-S3 corresponds to SEQ ID NO: 22.

The following table summarizes the sequence information for each of the vectors and the corresponding nucleic acid and amino acid sequences of the spike glycoprotein.

| Vector Designation | Nucleic Acid Sequence of Spike Glycoprotein | Amino Acid Sequence of Spike Glycoprotein | Nucleic Acid Sequence of Vector | Modifications |
|---|---|---|---|---|
| rMV$^{EZ}$SARS-CoV-2-S6 | 1 | 8 | 15 | modifications to ablate ER retention signal |
| rMV$^{EZ}$SARS-CoV-2-S-CO | 2 | 9 | 16 | codon optimized |
| rMV$^{EZ}$SARS-CoV-2-S-COAA | 3 | 10 | 17 | codon optimized; modifications to ablate ER retention signal |
| rMV$^{EZ}$SARS-CoV-2-S | 4 | 11 | 18 | modifications to ablate ER retention signal |
| rMV$^{EZ}$SARS-CoV-2-S-COAA-PP | 5 | 12 | 19 | codon optimized; modifications to ablate ER retention signal; modifications to lock in prefusion conformation |
| rMV$^{EZ}$SARS-CoV-2-S-COAA-fneg-PP | 6 | 13 | 20 | codon optimized; modifications to ablate ER retention signal; modifications to lock in prefusion conformation; modifications to ablate furin cleavage signal |
| rMV$^{EZ}$SARS-CoV-2-S-COAA-fneg | 7 | 14 | 21 | codon optimized; modifications to ablate ER retention signal; modifications to ablate furin cleavage signal |
| rMV$^{EZ}$SARS-CoV-2-S3 | 22 | | | modifications to ablate ER retention signal |

Example 3

This example describes vaccination/challenge studies with recombinant MV vaccine strain viruses expressing SARS-CoV-2 spike glycoprotein.

Mice

Figures 3A, 3B:
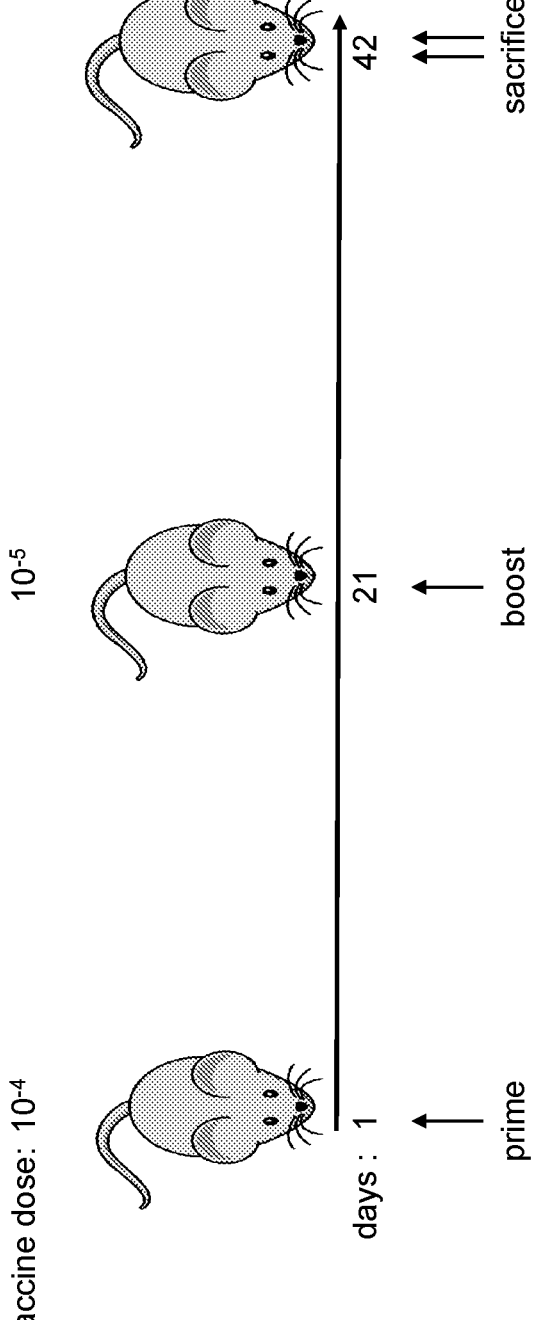
FIGS. 3A-3B demonstrate an experimental set-up for mice immunized with recombinant viruses.

The experimental set-up for mice immunized with recombinant viruses is described in FIG. 3A. Groups of 5 mice were infected with either rMV$^{EZ}$SARS-CoV-2-S3, rMV$^{EZ}$SARS-CoV-2-S6, rMV$^{EZ}$SARS-CoV-2-S-CO, rMV$^{EZ}$SARS-CoV-2-S-COAA, or rMV$^{EZ}$EGFP(3). Serum was collected on days 21 and 42, and splenocytes were collected on day 42. Neutralization of SARS-CoV-2 using the harvested mice serum indicates that SARS-CoV-2 neutralizing antibodies were produced in mice vaccinated with rMV$^{EZ}$SARS-CoV-2-S-CO and rMV$^{EZ}$SARS-CoV-2-S-COAA viruses (FIG. 3B).

Figure 12:
FIG. 12 is a graph demonstrating the secretion of IFN-γ in spleens from mice immunized with recombinant measles virus expressing SARS-CoV-2 codon-optimized spike protein. Splenocytes prepared from rMV$^{EZ}$, rMV$^{EZ}$SARS-CoV-2-CO, rMV$^{EZ}$SARS-CoV-2-S6, and rMV$^{EZ}$SARS-CoV-2-COAA immunized mice were used in an ELISPOT assay to detect the secretion of proinflammatory cytokine IFN-γ. Mice splenocytes were re-stimulated for 24 hours with four pools of synthetic peptides (51, S2, S3 and S4) designed to span the entire SARS-CoV-2 spike protein. Unstimulated splenocytes (medium) served as negative controls and splenocytes treated with PMA/ionomycin confirmed splenocyte re-stimulation. Dots represent individual animals (n=5) for each vaccinated group. The number of cells expressing IFN-γ after re-stimulation are represented as $1\times10^5$ cells.
Figure 12:
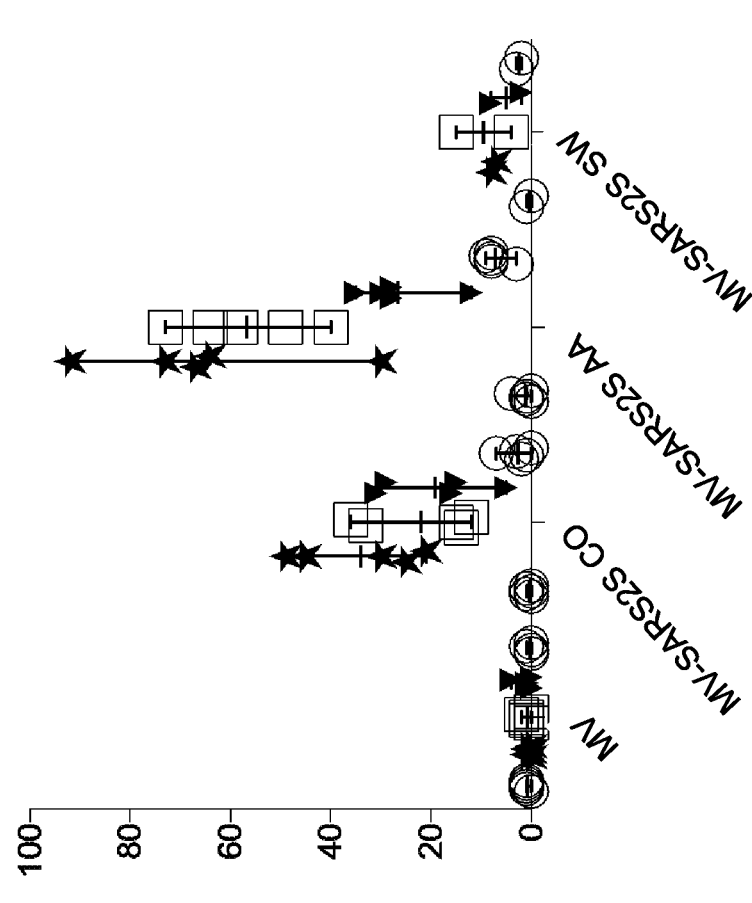

Splenocytes prepared from rMV$^{EZ}$, rMV$^{EZ}$SARS-CoV-2-CO, rMV$^{EZ}$SARS-CoV-2-S6, and rMV$^{EZ}$SARS-CoV-2-COAA immunized mice were used in an ELISPOT assay to detect the secretion of proinflammatory cytokine IFN-γ. Mice splenocytes were re-stimulated for 24 hours with four pools of synthetic peptides (51, S2, S3 and S4) designed to span the entire SARS-CoV-2 spike protein. Unstimulated splenocytes (medium) served as negative controls and splenocytes treated with PMA/ionomycin confirmed splenocyte re-stimulation. The number of cells expressing IFN-γ after re-stimulation are represented as $1 \times 10^5$ cells in FIG. 12. The results demonstrate that IFN-γ is secreted in spleens from mice immunized with recombinant measles virus expressing SARS-CoV-2 codon-optimized spike protein.

Figure 13A:
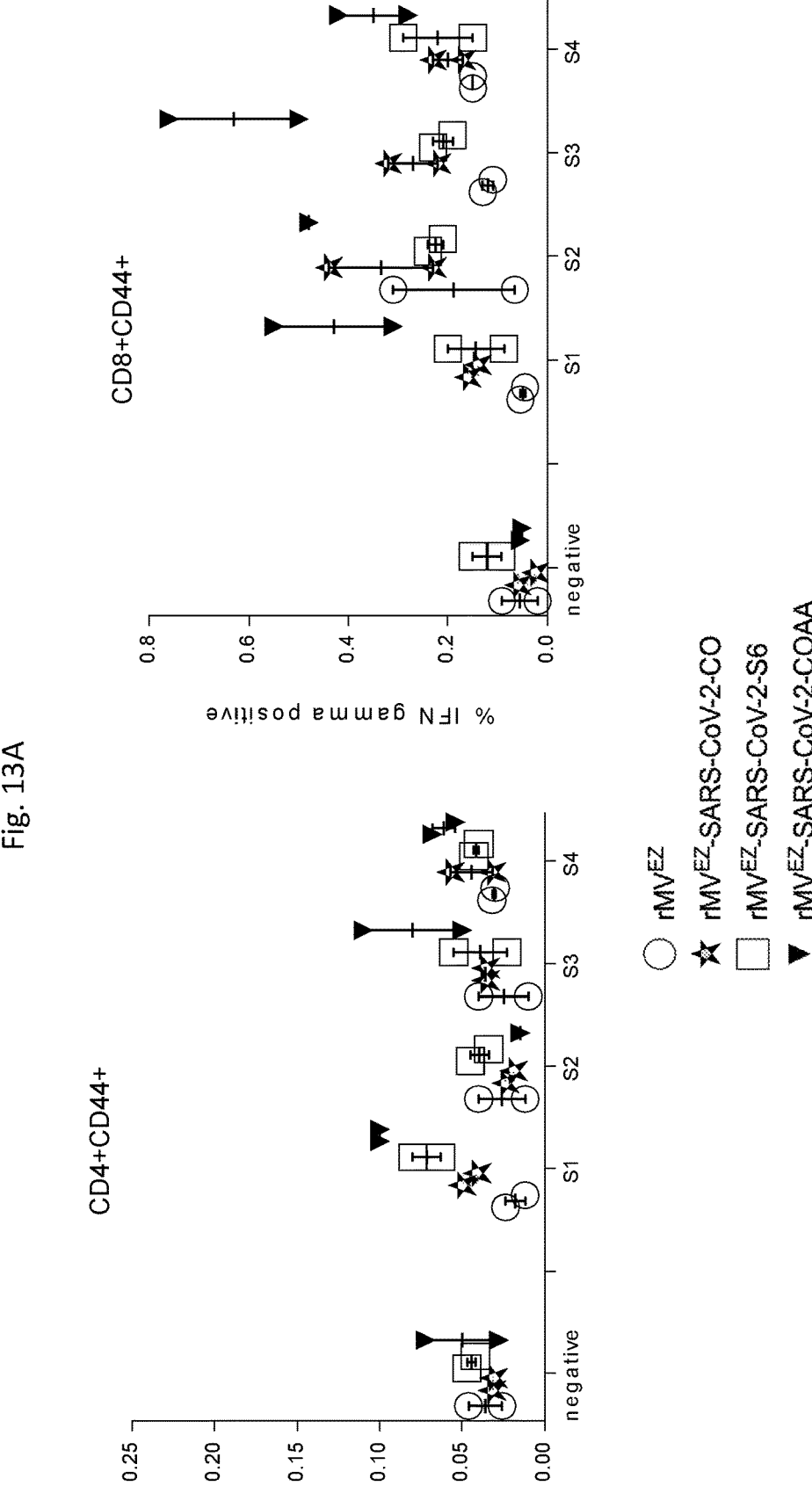
FIGS. 13A and 13B demonstrate the T cell responses in immunized mice. Flow cytometry was used to determine the proportion of CD4$^+$/CD44$^+$ and CD8$^+$/CD44$^+$ T cells in the spleens of mice immunized with rMV$_{EZ}$, rMV$^{EZ}$SARS-CoV-2-CO, rMV$^{EZ}$SARS-CoV-2-S6, and rMV$^{EZ}$SARS-CoV-2-COAA. To determine the optimal re-stimulation period splenocytes from two mice from each immunized group were first re-stimulated for 6 hours (FIG. 13A) while the remaining three mice spleens were re-stimulated for 12-hours (FIG. 13B). Cells were re-stimulated with spike specific peptide pools S1, S2, S3 and S4, or left unstimulated (negative control; medium). Re-stimulation was confirmed with a cell activation cocktail containing PMA/ionomycin and brefaldin-A. Intracellular cytokine staining for IFN-γ and IL-13 were then carried out to determine Th1 and Th2 responses, respectively. Dots represent individual animals.
Figure 13B:
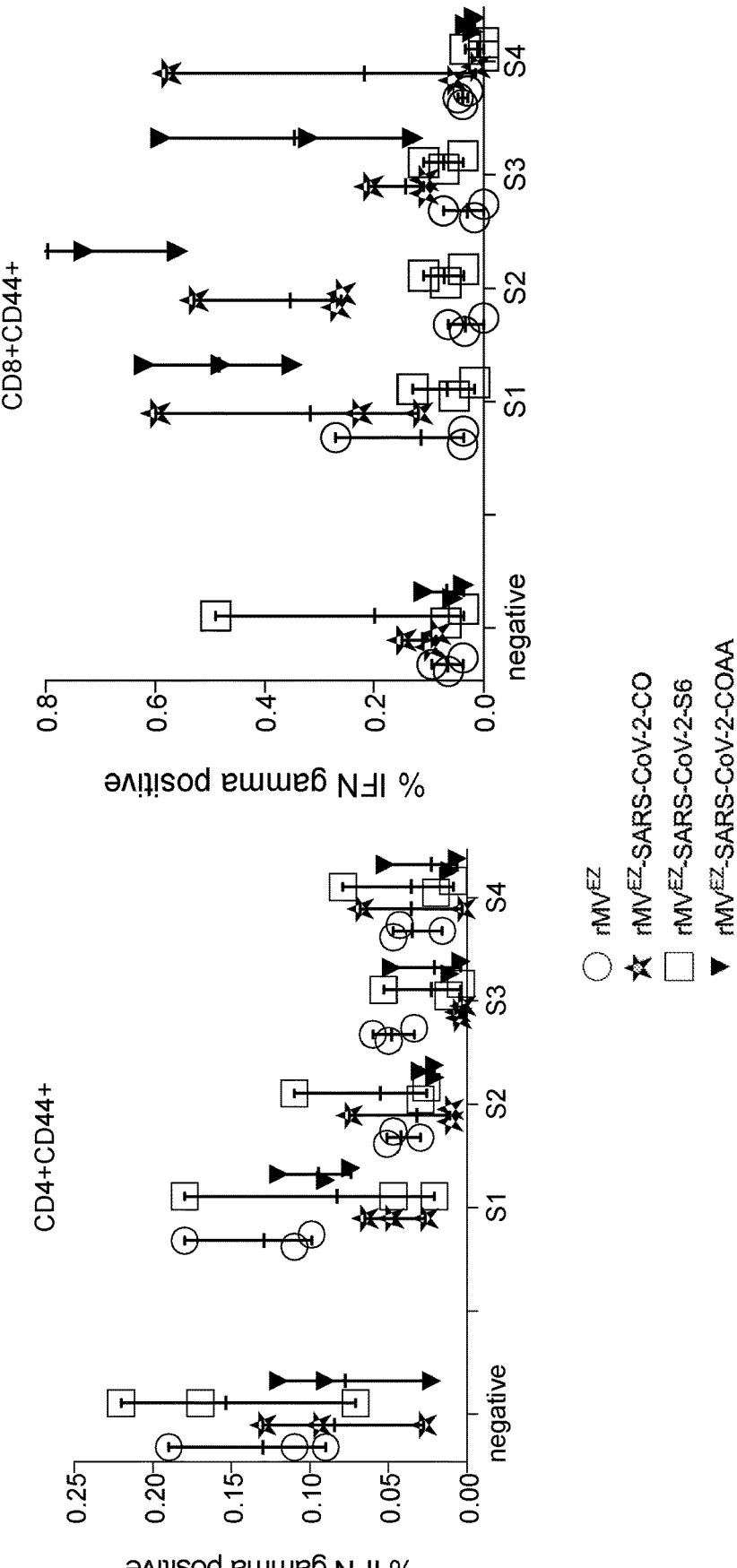
Figure 13B:
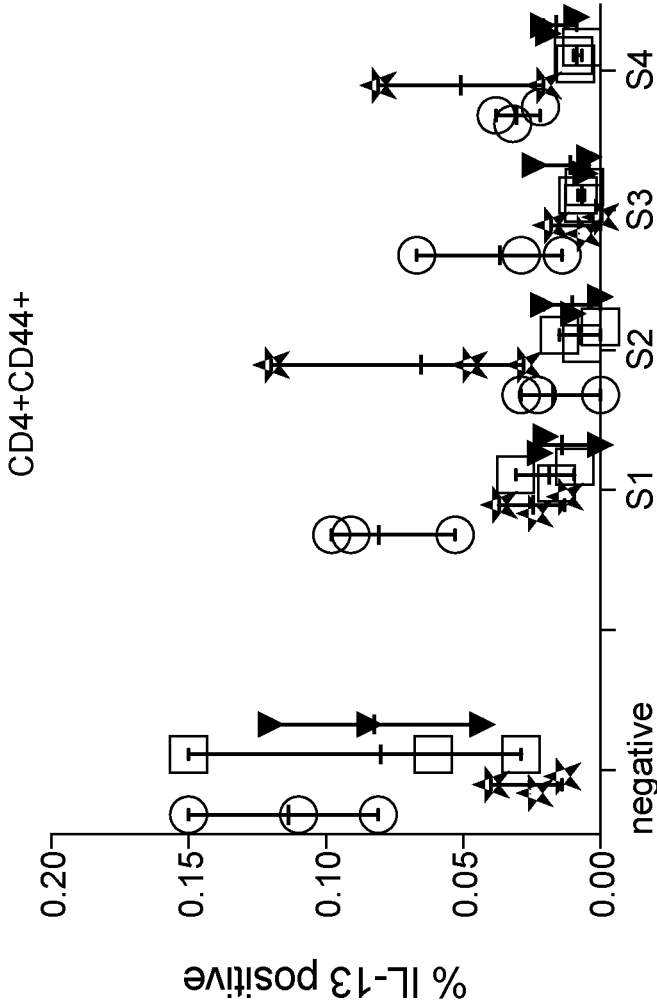

Flow cytometry was used to determine the proportion of CD4$^+$/CD44$^+$ and CD8$^+$/CD44$^+$ T cells in the spleens of mice immunized with rMV$^{EZ}$, rMV$^{EZ}$SARS-CoV-2-CO, rMV$^{EZ}$SARS-CoV-2-S6, and rMV$^{EZ}$SARS-CoV-2-COAA. To determine the optimal re-stimulation period splenocytes from two mice from each immunized group were first re-stimulated for 6 hours (FIG. 13A) while the remaining three mice spleens were re-stimulated for 12-hours (FIG. 13B). Cells were re-stimulated with spike specific peptide pools S1, S2, S3 and S4, or left unstimulated (negative control; medium). Re-stimulation was confirmed with a cell activation cocktail containing PMA/ionomycin and Brefaldin-A. Intracellular cytokine staining for IFN-γ and IL-13 were then carried out to determine Th1 and Th2 responses, respectively. The results in FIGS. 13A and 13B demonstrate the T cell responses in immunized mice.

Non-Human Primates

Multi-route delivery and challenge testing for natural measles is described in de Swart et al., *NPJ vaccines*, 2(1), pp. 1-11 (2017). Specifically, infection of rhesus macaques with rMV$^{EZ}$EGFP(3) vaccine via the intramuscular, intranasal, and aerosol routes, along with the intratracheal route as a control matching the usual experimental inoculation route, has been described. Serum antibody responses were detected by enzyme linked immunosorbent assay (ELISA), virus neutralization, or indirect immunofluorescence for MV fusion (MV-F) or hemagglutinin (MV-H) glycoprotein-specific antibodies. Animals vaccinated by the intramuscular (IM) route produced similar antibody responses to those inoculated via the aerosol route. In all assays, lowest serum antibody levels were consistently observed in animals immunized by intranasal instillation. All animals were protected from challenge after intratracheal instillation of a wild-type strain of MV.

For this study, African green monkeys (AGMs) were used since a SARS-CoV-2 challenge model has been established (Hartman et al., doi: doi.org/10.1101/2020.06.20.137687 (2020)—in press *PLoS Pathogens*). In this challenge model, AGMs were inoculated via a multi-route mucosal (oral, nasal, and ocular) exposure with a low passage, clinical isolate of SARS-CoV-2. The experimental design is detailed in FIGS. 11A and 11B.

All AGMs develop mild disease with pulmonary lesions detectable by PET/CT in the acute phase which subsequently resolve. All AGMs exhibit prolonged shedding of infectious virus from oral, nasal, conjunctival, and rectal mucosal surfaces with viral RNA (vRNA) detectable throughout the respiratory and gastrointestinal tissues at later timepoints in the absence of replication-competent virus.

Animals (maximum group size n=6) were vaccinated (IM) with the recombinant measles viral vector of the invention. Two animals were vaccinated with the standard measles virus Edmonston Zagreb vaccine strain. Some animals received a boost at 3 or 4 weeks post-vaccination. Animals were sampled before vaccination and then weekly over 6 or 8 weeks for the development of SARS-CoV-2 and MV serum antibody responses (IgG, IgM, IgA and neutralizing antibodies and T cell responses).

Development of MV-specific immune response will be compared to historical controls using banked samples from the studies analyzing intramuscular, aerosol, intranasal, and intratracheal administration of MV vaccine (de Swart et al., *NPJ vaccines*, 2(1), pp. 1-11 (2017)). EDTA blood samples will be collected in Vacuette tubes containing $K_3$EDTA as an anticoagulant. A sample of whole blood will be used directly for hematology analysis. Plasma will be separated from blood cells by low speed centrifugation and used in a commercial ELISA classic Measles Virus IgG assay (Serion) to assess anti-MV IgG alongside an in house MV-N-specific IgG ELISA.

Development of anti SARS-CoV-2 specific IgG and IgM will be determined using an in house ELISA that detects antibodies against the SARS-CoV-2 spike protein receptor binding domain (RBD). ELISA plates will be coated with 50 ng/well of SARS-CoV-2 RBD and subsequently blocked in 5% (V/V) FBS, 5% (W/V) skim milk in PBS with 0.1% (V/V) Tween-20 (PBS T) for 1 hour at 37° C. Serial dilutions of plasma will be made in block solution and incubated on the blocked plates for 2 h at 37° C. After washing with PBS T, bound antibodies will be detected by incubation with goat-anti-monkey IgM(p)-HRP (Seracare/KPL #5220-0334) or goat-anti-rhesus IgG (H+L)-HRP (Southern Biotech #6200-05), both used at a 1:5,000 dilution in blocking solution for 1 hour at 37° C. After washing with PBS T the assay will be developed by incubation with TMB (Seracare) for 7 min prior to the addition of TMB stop solution (Seracare). Absorbance values will be determined at 450 nm.

PBMC are isolated from the residual blood cell pellet by layering diluted whole blood onto Lymphoprep and subsequent density gradient centrifugation. A sample of PBMC will be used for MV virus isolation by plating dilutions of PBMC with Vero cells expressing human CD150 (Vero hCD150 cells). Assays are incubated at 37° C. for 3-5 days and then scored for cytopathic effect. A portion of PBMC will also be used for RNA extraction and subsequent RT/PCR analysis for detection of viral genome.

Figures 11A, 11B:
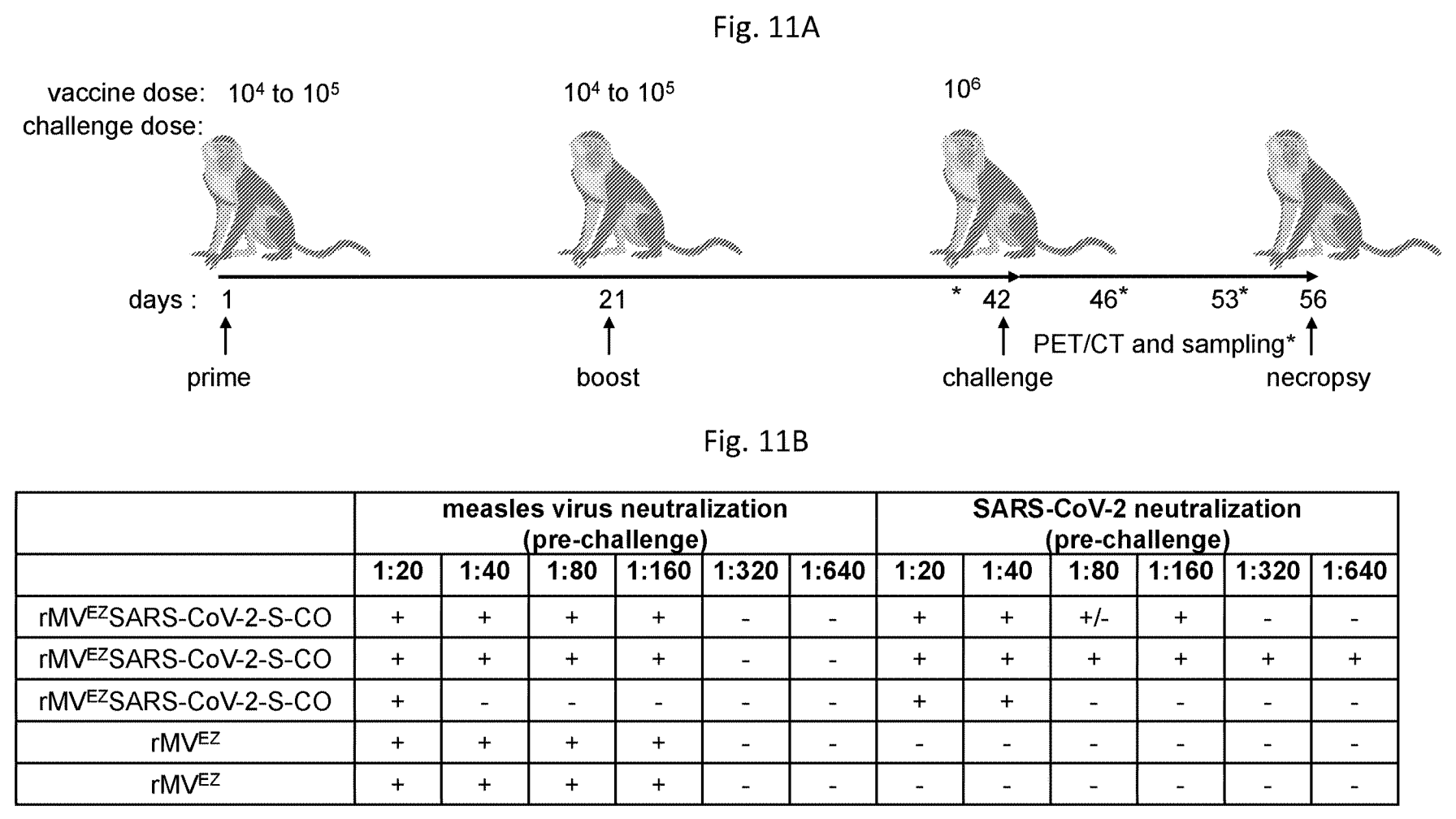

Blood samples for serum will be collected in Vacuette tubes (FIG. 11B). After coagulation, low speed centrifugation will be used to remove the clot from the serum supernatant. A sample will be used for serum biochemistry and the rest will be available for neutralizing antibody analysis. Virus neutralizing antibodies will be detected using a fluorescent focus reduction neutralization test (FRNT) for MV and a plaque reduction neutralization test (PRNT) for SARS-CoV-2. The FRNT uses a MV that expresses EGFP during replication; this facilitates rapid screening of assays. Detection of fluorescence indicates virus replication and seronegativity while lack of fluorescence indicates the presence of neutralizing antibodies which prevent virus infection. Serum dilutions will be mixed with 100 plaque forming units (p.f.u.) of MV and incubated at 37° C. for 1 hour. After addition of Vero cells expressing the MV receptor human CD150, assays will be incubated at 37° C. for 3-5 days before screening for fluorescence as a measure of virus replication. For the PRNT, serum dilutions will be mixed with 100 plu. of SARS-CoV-2 and incubated at 37° C. for 1 hour after which they will be added to confluent Vero E6 cell monolayers. After incubation at 37° C. for 1 hour, medium will be replaced by immunodiffusion agarose. After incubation at 37° C. for 72 hours, the agarose overlay will be removed and the cell monolayer fixed and stained with crystal violet. Plaques will be enumerated and the PRNT$_{80}$ calculated. The SARS-CoV-2 molecular, virological and immunological assays are described in Klimstra et al., *J. Gen. Virol.*, doi: 10.1099/jgv.0.001481 (2020).

The vaccinated and sham vaccinated animals will be challenged via multi route mucosal exposure with $10^6$ plu. of SARS-CoV-2. Protection will be assessed by sampling oral, ocular, rectal and nasal swabs for decreases in infectious virus and viral RNA copies following challenge, decreased PET/CT signals in lungs and lymph nodes and secondary immune responses. Brushes will be used to collect throat and rectal samples and swabs will be used to collect nasal and ocular samples into virus transport medium. After vortexing the brush/swab is removed and the remaining liquid is used directly for SARS-CoV-2 virus isolation by adding to VeroE6 cell monolayers, and for RNA isolation for RTqPCR analysis. For virus isolations, after incubation at 37° C. for 1 hour, medium will be replaced by immunodiffusion agarose. After incubation at 37° C. for 72 hours, the agarose overlay will be removed and the cell monolayer fixed and stained with crystal violet to allow visualization of plaques. After RNA isolation, one-step RT-qPCR will be performed using a One-Step Multiplex RT-qPCR Supermix (BioRad), and primers and probe targeting the SARS-CoV-2 N gene sequence. Quantitation of virus genome copies will be determined by comparing the cycle threshold values from the unknown samples to cycle threshold values from a positive-sense SARS-CoV-2 vRNA standard curve generated from 10-fold serial dilutions of in house synthesized template.

Serial PET/CT images will be acquired pre-infection and at 3 or 4 and 10 or 11 dpi. The scans will be performed on a MultiScan LFER 150 (Mediso Medical Imaging Systems). CT acquisition will be performed using the following parameters: Semi-circular single field-of-view, 360 projections, 80 kVp, 670 µA, exposure time 90 ms, binning 1:4, voxel size of final image: 500×500 µm. PET acquisition will be performed 55 min after intravenous injection of 18F-fluoro-2-deoxy-D-glucose (FDG) with the following parameters: 10 min acquisition, single field-of-view, 1-9 coincidence mode, 5 ns coincidence time window. PET images will be reconstructed with the following parameters: Tera-Tomo 3D reconstruction, 400-600 keV energy window, 1-9 coincidence mode, median filter on, spike filter on, voxel size 0.7 mm, 8 iterations, 9 subsets, scatter correction on, attenuation correction based on CT material map segmentation. Images will be analyzed using OsiriX MD or 64-bit (v.11, Pixmeo, Geneva, Switzerland). Before analysis, PET images will be Gaussian smoothed in OsiriX and smoothing will be applied to raw data with a 3×3 matrix size and a matrix normalization value of 24. Whole lung FDG uptake will be measured by first creating a whole lung region-of-interest (ROI) on the lung in the CT scan by creating a 3D growing region highlighting every voxel in the lungs between −1024 and −500 Hounsfield units. This whole lung ROI will be copied and pasted to the PET scan and gaps within the ROI will be filled in using a closing ROI brush tool with a structuring element radius of 3. All voxels within the lung ROI with a standard uptake value (SUV) below 1.5 will be set to zero and the SUVs of the remaining voxels will be summed for a total lung FDG uptake (total inflammation) value. Thoracic lymph nodes will be analyzed by measuring the maximum SUV within each lymph node using an oval drawing tool. Both total FDG uptake and lymph node uptake values will be normalized to back muscle FDG uptake measured by drawing cylinder ROIs on the back muscles adjacent to the spine at the same axial level as the carina (SUVCMR; cylinder-muscle-ratio). PET quantification values will be organized in Microsoft Excel and graphed using GraphPad Prism.

Blood samples will be collected and processed as for the vaccination phase of the study and the secondary immune response to SARS-CoV-2 will be measured as before using the SARS-CoV-2 spike protein receptor binding domain ELISA for detection of IgG and IgM, and the PRNT for detection of neutralizing antibodies and the T cells assays already established in the IFNAR mice (FIGS. 13A and 13B) to assess cellular immune responses.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

The invention claimed is:

1. A recombinant measles viral vector comprising a nucleic acid sequence encoding a Severe Acute Respiratory Syndrome Coronavirus 2 (SARS-CoV-2) spike glycoprotein, wherein the vector is a recombinant Edmonston-Zagreb (EZ) measles viral vector.

2. The recombinant measles viral vector of claim 1, wherein the nucleic acid sequence has been codon optimized.

3. The recombinant measles viral vector of claim 1, wherein the nucleic acid sequence contains at least one modification that disrupts the endoplasmic reticulum (ER) retention sequence of the SARS-COV-2 spike glycoprotein.

4. The recombinant measles viral vector of claim 3, wherein the ER retention sequence of the SARS-COV-2 spike glycoprotein contains AxAxx rather than KxHxx in the cytoplasmic tail.

5. The recombinant measles viral vector of claim 2, wherein the nucleic acid sequence contains at least one modification that disrupts the endoplasmic reticulum (ER) retention sequence of the SARS-COV-2 spike glycoprotein.

6. The recombinant measles viral vector of claim 5, wherein the ER retention sequence of the SARS-COV-2 spike glycoprotein contains AxAxx rather than KxHxx in the cytoplasmic tail.

7. The recombinant measles viral vector of claim 1, wherein the nucleic acid sequence encoding the SARS-COV-2 spike glycoprotein is selected from the group consisting of SEQ ID NO: 1 (S6), SEQ ID NO: 2 (S-CO), SEQ ID NO: 3 (S-CO-AA), SEQ ID NO: 4 (S), SEQ ID NO: 5 (S-CO-AA-PP), SEQ ID NO: 6 (S-CO-AA-fneg-PP), and SEQ ID NO: 7 (S-CO-AA-fneg).

8. The recombinant measles viral vector of claim 1, wherein the amino acid sequence of the SARS-CoV-2 spike glycoprotein is selected from the group consisting of SEQ ID NO: 8 (S6), SEQ ID NO: 9 (S-CO), SEQ ID NO: 10 (S-CO-AA), SEQ ID NO: 11 (CoV2-S), SEQ ID NO: 12 (S-CO-AA-PP), SEQ ID NO: 13 (CO-AA-fneg-PP), and SEQ ID NO: 14 (S-CO-AA-fneg).

9. The recombinant measles viral vector of claim 1 comprising a nucleic acid sequence selected from the group consisting of SEQ ID NO: 15 (pSARS-CoV2-S6), SEQ ID NO: 16 (SARS-CoV-2-S-CO), SEQ ID NO: 17 (SARS-CoV-2-S-CO-AA), SEQ ID NO: 18 (SARS-CoV-2-S), SEQ ID NO: 19 (SARS-CoV-2-S-CO-AA-PP), SEQ ID NO: 20 (SARS-CoV-2-S-CO-AA-fneg-PP), and SEQ ID NO: 21 (SARS-CoV-2-S-CO-AA-fneg).

10. A pharmaceutical composition comprising the recombinant measles viral vector of claim 1 and a pharmaceutically acceptable carrier.

11. A method for preventing, inhibiting, reducing, eliminating, protecting, or delaying the onset of an infection or an infectious clinical condition caused by coronavirus in a subject comprising administering to the subject (i) the recombinant measles viral vector of claim 1 or (ii) a pharmaceutical composition comprising the vector and a pharmaceutically acceptable carrier.

12. A method for inducing an immune response against a coronavirus in a subject comprising administering to the subject (i) the recombinant measles viral vector of claim 1 or (ii) pharmaceutical composition comprising the vector and a pharmaceutically acceptable carrier.

13. A polypeptide comprising an amino acid sequence selected from the group consisting of SEQ ID NO: 8 (S6), SEQ ID NO: 9 (S-CO), SEQ ID NO: 10 (S-CO-AA), SEQ ID NO: 11 (S), SEQ ID NO: 12 (S-CO-AA-PP), SEQ ID NO: 13 (S-CO-AA-fneg-PP), and SEQ ID NO: 14 (S-CO-AA-fneg).

14. A nucleic acid encoding the polypeptide of claim 13.

15. A nucleic acid comprising a nucleic acid sequence selected from the group consisting of SEQ ID NO: 1 (S6), SEQ ID NO: 2 (S-CO), SEQ ID NO: 3 (S-CO-AA), SEQ ID NO: 4 (SARS-CoV-2-S), SEQ ID NO: 5 (S-CO-AA-PP), SEQ ID NO: 6 (S-CO-AA-fneg-PP), and SEQ ID NO: 7 (S-CO-AA-fneg).

16. A pharmaceutical composition comprising (i) the polypeptide of claim 13, a nucleic acid encoding the polypeptide, or a recombinant vector comprising the nucleic acid and (ii) a pharmaceutically acceptable carrier.

17. The recombinant measles viral vector of claim 1, wherein the nucleic acid sequence encoding the SARS-COV-2 spike glycoprotein is SEQ ID NO: 3 (S-CO-AA).

18. The recombinant measles viral vector of claim 1, wherein the amino acid sequence of the SARS-COV-2 spike glycoprotein is SEQ ID NO: 10 (S-CO-AA).

19. The recombinant measles viral vector of claim 1, wherein the vector comprises a nucleic acid sequence of SEQ ID NO: 17 (SARS-COV-2-S-CO-AA).

20. The recombinant measles viral vector of claim 1, wherein the vector consists of a nucleic acid sequence of SEQ ID NO: 17 (SARS-COV-2-S-CO-AA).

* * * * *

SEQUENCE LISTING

```
<160> NUMBER OF SEQ ID NOS: 26

<210> SEQ ID NO 1
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Non-codon optimized SARS-CoV-2 Spike from
      rMV-EZ-SARS-CoV-2-S clone 6
<220> FEATURE:
<221> NAME/KEY: misc_feature
<222> LOCATION: (118)..(118)
<223> OTHER INFORMATION: mutation that arose during cloning
<220> FEATURE:
<221> NAME/KEY: misc_feature
<222> LOCATION: (1088)..(1088)
<223> OTHER INFORMATION: mutation that arose during cloning
<220> FEATURE:
<221> NAME/KEY: misc_feature
<222> LOCATION: (1239)..(1239)
<223> OTHER INFORMATION: mutation that arose during cloning
<220> FEATURE:
<221> NAME/KEY: misc_feature
<222> LOCATION: (3805)..(3807)
<223> OTHER INFORMATION: mutation that disrupts ER retention signal
<220> FEATURE:
<221> NAME/KEY: misc_feature
<222> LOCATION: (3811)..(3813)
<223> OTHER INFORMATION: mutation that disrupts ER retention signal

<400> SEQUENCE: 1
atgtttgttt ttcttgtttt attgccacta gtctctagtc agtgtgttaa tcttacaacc      60
agaactcaat taccccctgc atacactaat tctttcacac gtggtgttta ttacccttac     120
aaagtttTca gatcctcagt tttacattca actcaggact tgttcttacc tttctttTcc     180
aatgttactt ggttccatgc tatacatgtc tctgggacca atggtactaa gaggtttgat     240
```

-continued

```
aaccctgtcc taccatttaa tgatggtgtt tattttgctt ccactgagaa gtctaacata   300
ataagaggct ggatttttgg tactacttta gattcgaaga cccagtccct acttattgtt   360
aataacgcta ctaatgttgt tattaaagtc tgtgaatttc aattttgtaa tgatccattt   420
ttgggtgttt attaccacaa aaacaacaaa agttggatgg aaagtgagtt cagagtttat   480
tctagtgcga ataattgcac ttttgaatat gtctctcagc cttttcttat ggaccttgaa   540
ggaaaacagg gtaatttcaa aaatcttagg gaatttgtgt ttaagaatat tgatggttat   600
tttaaaatat attctaagca cacgcctatt aatttagtgc gtgatctccc tcagggtttt   660
tcggctttag aaccattggt agatttgcca ataggtatta acatcactag gtttcaaact   720
ttacttgctt tacatagaag ttatttgact cctggtgatt cttcttcagg ttggacagct   780
ggtgctgcag cttattatgt gggttatctt caacctagga ctttttctatt aaaatataat   840 gaaaatggaa ccattacaga tgctgtagac tgtgcacttg accctctctc agaaacaaag   900
tgtacgttga aatccttcac tgtagaaaaa ggaatctatc aaacttctaa ctttagagtc   960
caaccaacag aatctattgt tagatttcct aatattacaa acttgtgccc ttttggtgaa   1020 gttttttaacg ccaccagatt tgcatctgtt tatgcttgga acaggaagag aatcagcaac   1080
tgtgttgttg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccaggtc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920 aatgttttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagttttttgt   2280 acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460 ctactttttca acaaagtgac acttgcagat gctggcttca tcaaacaata tggtgattgc   2520
cttggtgata ttgctgctag agacctcatt tgtgcacaaa agtttaacgg ccttactgtt   2580
```

```
ttgccacctt tgctcacaga tgaaatgatt gctcaataca cttctgcact gttagcgggt    2640
acaatcactt ctggttggac ctttggtgca ggtgctgcat tacaaatacc atttgctatg    2700
caaatggctt ataggtttaa tggtattgga gttacacaga atgttctcta tgagaaccaa    2760
aaattgattg ccaaccaatt taatagtgct attggcaaaa ttcaagactc actttcttcc    2820
acagcaagtg cacttggaaa acttcaagat gtggtcaacc aaaatgcaca agctttaaac    2880
acgcttgtta aacaacttag ctccaatttt ggtgcaattt caagtgtttt aaatgatatc    2940
ctttcacgtc ttgacaaagt tgaggctgaa gtgcaaattg ataggttgat cacaggcaga    3000
cttcaaagtt tgcagacata tgtgactcaa caattaatta gagctgcaga aatcagagct    3060
tctgctaatc ttgctgctac taaaatgtca gagtgtgtac ttggacaatc aaaaagagtt    3120
gatttttgtg gaaagggcta tcatcttatg tccttccctc agtcagcacc tcatggtgta    3180
gtcttcttgc atgtgactta tgtccctgca caagaaaaga acttcacaac tgctcctgcc    3240
atttgtcatg atggaaaagc acactttcct cgtgaaggtg tctttgtttc aaatggcaca    3300
cactggtttg taacacaaag gaattttat gaaccacaaa tcattactac agacaacaca    3360
tttgtgtctg gtaactgtga tgttgtaata ggaattgtca caacacagt ttatgatcct    3420 ttgcaacctg aattagactc attcaaggag gagttagata atatttttaa gaatcataca    3480
tcaccagatg ttgatttagg tgacatctct ggcattaatg cttcagttgt aaacattcaa    3540
aaagaaattg accgcctcaa tgaggttgcc aagaatttaa atgaatctct catcgatctc    3600
caagaacttg aaagtatga gcagtatata aaatggccat ggtacatttg gctaggtttt    3660
atagctggct tgattgccat agtaatggtg acaattatgc tttgctgtat gaccagttgc    3720
tgtagttgtc tcaagggctg ttgttcttgt ggatcctgct gcaaatttga tgaagacgac    3780
tctgagccag tgctcaaagg agtcgcatta gcttacacat aa                       3822
```

<210> SEQ ID NO 2
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: Human codon optimized SARS-CoV-2 Spike from
      rMV-EZ-SARS-CoV-2-S-CO

<400> SEQUENCE: 2

```
atgttcgtct cctggtcct gctgcctctg gtctcctcac agtgcgtcaa tctgacaact     60
cggactcagc tgccacctgc ttatactaat agcttcacca gaggcgtgta ctatcctgac    120
aaggtgttta gaagctccgt gctgcactct acacaggatc tgtttctgcc attctttagc    180
aacgtgacct ggttccacgc catccacgtg agcggcacca tggcacaaa gcggttcgac    240 aatcccgtgc tgcctttaa cgatggcgtg tacttcgcct ctaccgagaa gagcaacatc    300
atcagaggct ggatctttgg caccacactg gactccaaga cacagtctct gctgatcgtg    360
aacaatgcca ccaacgtggt catcaaggtg tgcgagttcc agttttgtaa tgatcccttc    420
ctgggcgtgt actatcacaa gaacaataag agctggatgg agtccgagtt tagagtgtat    480
tctagcgcca caactgcac atttgagtac gtgagccagc ctttcctgat ggacctggag    540
ggcaagcagg gcaatttcaa gaacctgagg gagttcgtgt ttaagaatat cgacggctac    600
ttcaaaatct actctaagca cacccccatc aacctggtgc gcgacctgcc tcagggcttc    660
```

-continued

```
agcgccctgg agcccctggt ggatctgcct atcggcatca acatcacccg gtttcagaca    720
ctgctggccc tgcacagaag ctacctgaca cccggcgact cctctagcgg atggaccgcc    780
ggcgctgccg cctactatgt gggctacctc cagccccgga ccttcctgct gaagtacaac    840
gagaatggca ccatcacaga cgcagtggat tgcgccctgg acccctgag cgagacaaag     900 tgtacactga agtcctttac cgtggagaag ggcatctatc agacatccaa tttcagggtg    960
cagccaaccg agtctatcgt gcgctttcct aatatcacaa acctgtgccc atttggcgag   1020
gtgttcaacg caacccgctt cgccagcgtg tacgcctgga ataggaagcg gatcagcaac   1080
tgcgtggccg actatagcgt gctgtacaac tccgcctctt tcagcacctt taagtgctat   1140
ggcgtgtccc ccacaaagct gaatgacctg tgctttacca acgtctacgc cgattctttc   1200
gtgatcaggg gcgacgaggt gcgccagatc gccccccggcc agacaggcaa gatcgcagac   1260
tacaattata agctgccaga cgatttcacc ggctgcgtga tcgcctggaa cagcaacaat   1320
ctggattcca aagtgggcgg caactacaat tatctgtacc ggctgtttag aaagagcaat   1380
ctgaagccct tcgagaggga catctctaca gaaatctacc aggccggcag cacccccttgc  1440 aatggcgtgg agggctttaa ctgttatttc ccactccagt cctacggctt ccagcccaca   1500
aacggcgtgg gctatcagcc ttaccgcgtg gtggtgctga gctttgagct gctgcacgcc   1560
ccagcaacag tgtgcggccc caagaagtcc accaatctgg tgaagaacaa gtgcgtgaac   1620
ttcaacttca acggcctgac cggcacaggc gtgctgaccg agtccaacaa gaagttcctg   1680
ccatttcagc agttcggcag ggacatcgca gataccacag acgccgtgcg cgacccacag   1740
accctggaga tcctggacat cacaccctgc tctttcggcg gcgtgagcgt gatcacaccc   1800
ggcaccaata caagcaacca ggtggccgtg ctgtatcagg acgtgaattg taccgaggtg   1860
cccgtggcta tccacgccga tcagctgacc ccaacatggc gggtgtacag caccggctcc   1920
aacgtcttcc agacaagagc cggatgcctg atcggagcag agcacgtgaa caattcctat   1980
gagtgcgaca tcccaatcgg cgccggcatc tgtgcctctt accagaccca gacaaactct   2040
cccagaagag cccggagcgt ggcctcccag tctatcatcg cctataccat gtccctgggc   2100
gccgagaaca gcgtggccta ctctaacaat agcatcgcca tcccaaccaa cttcacaatc   2160
tctgtgacca cagagatcct gcccgtgtcc atgaccaaga catctgtgga ctgcacaatg   2220
tatatctgtg gcgattctac cgagtgcagc aacctgctgc tccagtacgg cagcttttgt   2280
acccagctga atagagccct gacaggcatc gccgtggagc aggataagaa cacacaggag   2340
gtgttcgccc aggtgaagca aatctacaag acccccccta tcaaggactt tggcggcttc   2400
aatttttccc agatcctgcc tgatccatcc aagccttcta gcggagcttt atcgaggac    2460 ctgctgttca caaggtgac cctggccgat gccggcttca tcaagcagta tggcgattgc   2520
ctgggcgaca tcgcagccag ggacctgatc tgcgcccaga gtttaatgg cctgaccgtg    2580 ctgccacccc tgctgacaga tgagatgatc gcacagtaca aagcgccct gctggccggc    2640 accatcacat ccggatggac cttcggcgca ggagccgccc tccagatccc ctttgccatg    2700
cagatggcct ataggttcaa cggcatcggc gtgacccaga atgtgctgta cgagaaccag   2760
aagctgatcg ccaatcagtt taactccgcc atcggcaaga tccaggacag cctgtcctct   2820
acagccagcg ccctgggcaa gctccaggat gtggtgaatc agaacgccca ggccctgaat   2880
accctggtga agcagctgag cagcaacttc ggcgccatct ctagcgtgct gaatgacatc   2940
ctgagccggc tggacaaggt ggaggcagag gtgcagatcg accggctgat caccggccgg   3000
ctccagagcc tccagaccta tgtgacacag cagctgatca gggccgccga gatcagggcc   3060
```

-continued

```
agcgccaatc tggcagcaac caagatgtcc gagtgcgtgc tgggccagtc taagagagtg    3120
gacttttgtg gcaagggcta tcacctgatg tccttccctc agtctgcccc acacggcgtg    3180
gtgtttctgc acgtgaccta cgtgcccgcc caggagaaga acttcaccac agccctgcc     3240 atctgccacg atggcaaggc ccactttcca agggagggcg tgttcgtgtc caacggcacc    3300
cactggtttg tgacacagcg caatttctac gagccccaga tcatcaccac agacaacacc    3360
ttcgtgagcg gcaactgtga cgtggtcatc ggcatcgtga acaataccgt gtatgatcca    3420
ctccagcccg agctggacag ctttaaggag gagctggata agtatttcaa gaatcacacc    3480
tcccctgacg tggatctggg cgacatcagc ggcatcaatg cctccgtggt gaacatccag    3540
aaggagatcg accgcctgaa cgaggtggct aagaatctga cgagagcct gatcgacctc     3600 caggagctgg gcaagtatga gcagtacatc aagtggccct ggtacatctg gctgggcttc    3660
atcgccggcc tgatcgccat cgtgatggtg accatcatgc tgtgctgtat gacatcctgc    3720
tgttcttgcc tgaagggctg ctgtagctgt ggctcctgct gtaagtttga cgaggatgac    3780
tctgaacctg tgctgaaggg cgtgaagctg cattacacct aa                       3822
```

<210> SEQ ID NO 3
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Human codon optimized SARS-CoV-2 Spike from
      rMV-EZ-SARS-CoV-2-S-CO-AA
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 3

```
atgttcgtct tcctggtcct gctgcctctg gtctcctcac agtgcgtcaa tctgacaact    60
cggactcagc tgccacctgc ttatactaat agcttcacca gaggcgtgta ctatcctgac    120
aaggtgttta aagctccgt gctgcactct acacaggatc tgtttctgcc attctttagc     180
aacgtgacct ggttccacgc catccacgtg agcggcacca atggcacaaa gcggttcgac    240
aatcccgtgt gccttttaa cgatggcgtg tacttcgcct ctaccgagaa gagcaacatc     300
atcagaggct ggatctttgg caccacactg gactccaaga cacagtctct gctgatcgtg    360
aacaatgcca ccaacgtggt catcaaggtg tgcgagttcc agttttgtaa tgatcccttc    420
ctgggcgtgt actatcacaa gaacaataag agctggatgg agtccgagtt tagagtgtat    480
tctagcgcca caactgcac atttgagtac gtgagccagc ctttcctgat ggacctggag     540
ggcaagcagg gcaatttcaa gaacctgagg gagttcgtgt ttaagaatat cgacggctac    600
ttcaaaatct actctaagca cacccccatc aacctggtgc gcgacctgcc tcagggcttc    660
agcgccctgg agcccctggt ggatctgcct atcggcatca acatcacccg gtttcagaca    720
ctgctggccc tgcacagaag ctacctgaca cccggcgact cctctagcgg atggaccgcc    780
ggcgctgccg cctactatgt gggctacctc cagcccga ccttcctgct gaagtacaac      840
gagaatggca ccatcacaga cgcagtggat tgcgccctgg accccctgag cgagacaaag    900
```

| | | | | |
|---|---|---|---|---|
| tgtacactga | agtcctttac | cgtggagaag | ggcatctatc | agacatccaa tttcagggtg | 960 |
| cagccaaccg | agtctatcgt | gcgctttcct | aatatcacaa | acctgtgccc atttggcgag | 1020 |
| gtgttcaacg | caacccgctt | cgccagcgtg | tacgcctgga | ataggaagcg gatcagcaac | 1080 |
| tgcgtggccg | actatagcgt | gctgtacaac | tccgcctctt | tcagcacctt taagtgctat | 1140 |
| ggcgtgtccc | ccacaaagct | gaatgacctg | tgctttacca | acgtctacgc cgattctttc | 1200 |
| gtgatcaggg | gcgacgaggt | gcgccagatc | gcccccggcc | agacaggcaa gatcgcagac | 1260 |
| tacaattata | agctgccaga | cgatttcacc | ggctgcgtga | tcgcctggaa cagcaacaat | 1320 |
| ctggattcca | aagtgggcgg | caactacaat | tatctgtacc | ggctgtttag aaagagcaat | 1380 |
| ctgaagccct | tcgagaggga | catctctaca | gaaatctacc | aggccggcag caccccttgc | 1440 |
| aatggcgtgg | agggctttaa | ctgttatttc | ccactccagt | cctacggctt ccagcccaca | 1500 |
| aacggcgtgg | gctatcagcc | ttaccgcgtg | gtggtgctga | gctttgagct gctgcacgcc | 1560 |
| ccagcaacag | tgtgcggccc | caagaagtcc | accaatctgg | tgaagaacaa gtgcgtgaac | 1620 |
| ttcaacttca | acggcctgac | cggcacaggc | gtgctgaccg | agtccaacaa gaagttcctg | 1680 |
| ccatttcagc | agttcggcag | ggacatcgca | gataccacag | acgccgtgcg cgacccacag | 1740 |
| accctggaga | tcctggacat | cacaccctgc | tctttcggcg | gcgtgagcgt gatcacaccc | 1800 |
| ggcaccaata | caagcaacca | ggtggccgtg | ctgtatcagg | acgtgaattg taccgaggtg | 1860 |
| cccgtggcta | tccacgccga | tcagctgacc | ccaacatggc | gggtgtacag caccggctcc | 1920 |
| aacgtcttcc | agacaagagc | cggatgcctg | atcggagcag | agcacgtgaa caattcctat | 1980 |
| gagtgcgaca | tcccaatcgg | cgccggcatc | tgtgcctctt | accagaccca gacaaactct | 2040 |
| cccagaagag | cccggagcgt | ggcctcccag | tctatcatcg | cctataccat gtccctgggc | 2100 |
| gccgagaaca | gcgtggccta | ctctaacaat | agcatcgcca | tcccaaccaa cttcacaatc | 2160 |
| tctgtgacca | cagagatcct | gcccgtgtcc | atgaccaaga | catctgtgga ctgcacaatg | 2220 |
| tatatctgtg | gcgattctac | cgagtgcagc | aacctgctgc | tccagtacgg cagctttttgt | 2280 |
| acccagctga | atagagccct | gacaggcatc | gccgtggagc | aggataagaa cacacaggag | 2340 |
| gtgttcgccc | aggtgaagca | aatctacaag | acccccccta | tcaaggactt tggcggcttc | 2400 |
| aattttttccc | agatcctgcc | tgatccatcc | aagccttcta | gcggagctt tatcgaggac | 2460 |
| ctgctgttca | acaaggtgac | cctggccgat | gccggcttca | tcaagcagta tggcgattgc | 2520 |
| ctgggcgaca | tcgcagccag | ggacctgatc | tgcgcccaga | agtttaatgg cctgaccgtg | 2580 |
| ctgccacccc | tgctgacaga | tgagatgatc | gcacagtaca | caagcgccct gctggccggc | 2640 |
| accatcacat | ccggatggac | cttcggcgca | ggagccgccc | tccagatccc ctttgccatg | 2700 |
| cagatggcct | ataggttcaa | cggcatcggc | gtgacccaga | atgtgctgta cgagaaccag | 2760 |
| aagctgatcg | ccaatcagtt | taactccgcc | atcggcaaga | tccaggacag cctgtcctct | 2820 |
| acagccagcg | ccctgggcaa | gctccaggat | gtggtgaatc | agaacgccca ggccctgaat | 2880 |
| accctggtga | agcagctgag | cagcaacttc | ggcgccatct | ctagcgtgct gaatgacatc | 2940 |
| ctgagccggc | tggacaaggt | ggaggcagag | gtgcagatcg | accggctgat caccggccgg | 3000 |
| ctccagagcc | tccagaccta | tgtgacacag | cagctgatca | gggccgccga gatcagggcc | 3060 |
| agcgccaatc | tggcagcaac | caagatgtcc | gagtgcgtgc | tgggccagtc taagagagtg | 3120 |
| gactttgtgt | gcaagggcta | tcacctgatg | tccttccctc | agtctgcccc acacggcgtg | 3180 |
| gtgtttctgc | acgtgaccta | cgtgcccgcc | caggagaaga | acttcaccac agcccctgcc | 3240 |
| atctgccacg | atggcaaggc | ccactttcca | agggagggcg | tgttcgtgtc caacggcacc | 3300 |

-continued

```
cactggtttg tgacacagcg caatttctac gagccccaga tcatcaccac agacaacacc    3360
ttcgtgagcg gcaactgtga cgtggtcatc ggcatcgtga acaataccgt gtatgatcca    3420
ctccagcccg agctggacag ctttaaggag gagctggata agtatttcaa gaatcacacc    3480
tcccctgacg tggatctggg cgacatcagc ggcatcaatg cctccgtggt gaacatccag    3540
aaggagatcg accgcctgaa cgaggtggct aagaatctga cgagagcct gatcgacctc    3600 caggagctgg gcaagtatga gcagtacatc aagtggccct ggtacatctg gctgggcttc    3660
atcgccggcc tgatcgccat cgtgatggtg accatcatgc tgtgctgtat gacatcctgc    3720
tgttcttgcc tgaagggctg ctgtagctgt ggctcctgct gtaagtttga cgaggatgac    3780
tctgaacctg tgctgaaggg cgtggcgctg gcttacacct aa                        3822
```

```
<210> SEQ ID NO 4
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Non-codon optimized SARS-CoV-2 Spike from
      rMV-EZ-SARS-CoV-2-S
<220> FEATURE:
<221> NAME/KEY: misc_feature
<222> LOCATION: (3805)..(3807)
<223> OTHER INFORMATION: mutation that disrupts ER retention signal
<220> FEATURE:
<221> NAME/KEY: misc_feature
<222> LOCATION: (3811)..(3813)
<223> OTHER INFORMATION: mutation that disrupts ER retention signal
```

```
<400> SEQUENCE: 4
```

```
atgtttgttt ttcttgtttt attgccacta gtctctagtc agtgtgttaa tcttacaacc      60
agaactcaat tacccctgc atacactaat tctttcacac gtggtgttta ttaccctgac      120
aaagttttca gatcctcagt tttacattca actcaggact tgttcttacc tttcttttcc      180
aatgttactt ggttccatgc tatacatgtc tctgggacca atggtactaa gaggtttgat      240
aaccctgtcc taccatttaa tgatggtgtt attttgctt ccactgagaa gtctaacata      300
ataagaggct ggatttttgg tactacttta gattcgaaga cccagtccct acttattgtt      360
aataacgcta ctaatgttgt tattaaagtc tgtgaatttc aattttgtaa tgatccattt      420
ttgggtgttt attaccacaa aaacaacaaa agttggatgg aaagtgagtt cagagtttat      480
tctagtgcga ataattgcac ttttgaatat gtctctcagc ctttctatt ggaccttgaa       540 ggaaaacagg gtaatttcaa aaatcttagg gaatttgtgt ttaagaatat tgatggttat      600
tttaaaatat attctaagca cacgcctatt aatttagtgc gtgatctccc tcagggtttt      660
tcggctttag aaccattggt agatttgcca ataggtatta acatcactag gtttcaaact      720
ttacttgctt tacatagaag ttatttgact cctggtgatt cttcttcagg ttggacagct      780
ggtgctgcag cttattatgt gggttatctt caacctagga ctttctatt aaaatataat      840 gaaaatggaa ccattacaga tgctgtagac tgtgcacttg accctctctc agaaacaaag      900
tgtacgttga atccttcac tgtagaaaaa ggaatctatc aaacttctaa ctttagagtc       960
caaccaacag aatctattgt tagatttcct aatattacaa acttgtgccc ttttggtgaa      1020
gtttttaacg ccaccagatt tgcatctgtt tatgcttgga acaggaagag aatcagcaac      1080
tgtgttgctg attattctgt cctatataat tccgcatcat tttccactt taagtgttat      1140
```

```
ggagtgtctc ctactaaatt aaatgatctc tgctttacta atgtctatgc agattcattt      1200
gtaattagag gtgatgaagt cagacaaatc gctccagggc aaactggaaa gattgctgat      1260
tataattata aattaccaga tgattttaca ggctgcgtta tagcttggaa ttctaacaat      1320
cttgattcta aggttggtgg taattataat tacctgtata gattgtttag gaagtctaat      1380
ctcaaacctt ttgagagaga tatttcaact gaaatctatc aggccggtag cacaccttgt      1440
aatggtgttg aaggttttaa ttgttacttt cctttacaat catatggttt ccaacccact      1500
aatggtgttg gttaccaacc atacagagta gtagtacttt cttttgaact tctacatgca      1560
ccagcaactg tttgtggacc taaaaagtct actaatttgg ttaaaaacaa atgtgtcaat      1620
ttcaacttca atggtttaac aggcacaggt gttcttactg agtctaacaa aaagtttctg      1680
cctttccaac aatttggcag agacattgct gacactactg atgctgtccg tgatccacag      1740
acacttgaga ttcttgacat tacaccatgt tcttttggtg gtgtcagtgt tataacacca      1800
ggaacaaata cttctaacca ggttgctgtt ctttatcagg atgttaactg cacagaagtc      1860
cctgttgcta ttcatgcaga tcaacttact cctacttggc gtgtttattc tacaggttct      1920
aatgtttttc aaacacgtgc aggctgttta ataggggctg aacatgtcaa caactcatat      1980
gagtgtgaca tacccattgg tgcaggtata tgcgctagtt atcagactca gactaattct      2040
cctcggcggg cacgtagtgt agctagtcaa tccatcattg cctacactat gtcacttggt      2100
gcagaaaatt cagttgctta ctctaataac tctattgcca tacccacaaa ttttactatt      2160
agtgttacca cagaaattct accagtgtct atgaccaaga catcagtaga ttgtacaatg      2220
tacatttgtg gtgattcaac tgaatgcagc aatcttttgt tgcaatatgg cagtttttgt      2280
acacaattaa accgtgcttt aactggaata gctgttgaac aagacaaaaa cacccaagaa      2340 gttttttgcac aagtcaaaca aatttacaaa acaccaccaa ttaaagattt tggtggtttt      2400 aattttttcac aaatattacc agatccatca aaaccaagca agaggtcatt tattgaagat      2460
ctacttttca caaagtgac acttgcagat gctggcttca tcaaacaata tggtgattgc      2520
cttggtgata ttgctgctag agacctcatt tgtgcacaaa agtttaacgg ccttactgtt      2580
ttgccacctt tgctcacaga tgaaatgatt gctcaataca cttctgcact gttagcgggt      2640
acaatcactt ctggttggac ctttggtgca ggtgctgcat tacaaatacc atttgctatg      2700
caaatggctt ataggtttaa tggtattgga gttacacaga tgttctcta tgagaaccaa      2760 aaattgattg ccaaccaatt taatagtgct attggcaaaa ttcaagactc actttcttcc      2820
acagcaagtg cacttggaaa acttcaagat gtggtcaacc aaaatgcaca agcttttaaac      2880 acgcttgtta acaacttag ctccaatttt ggtgcaattt caagtgtttt aaatgatatc      2940
ctttcacgtc ttgacaaagt tgaggctgaa gtgcaaattg ataggttgat cacaggcaga      3000
cttcaaagtt tgcagacata tgtgactcaa caattaatta gagctgcaga aatcagagct      3060
tctgctaatc ttgctgctac taaaatgtca gagtgtgtac ttggacaatc aaaaagagtt      3120 gattttgtg gaaagggcta tcatcttatg tccttccctc agtcagcacc tcatggtgta      3180
gtcttcttgc atgtgactta tgtccctgca caagaaaaga acttcacaac tgctcctgcc      3240
atttgtcatg atggaaaagc acactttcct cgtgaaggtg tctttgtttc aaatggcaca      3300
cactggtttg taacacaaag gaattttat gaaccacaaa tcattactac agacaacaca      3360
tttgtgtctg gtaactgtga tgttgtaata ggaattgtca acaacacagt ttatgatcct      3420
ttgcaacctg aattagactc attcaaggag gagttagata aatatttaa gaatcataca      3480 tcaccagatg ttgatttagg tgacatctct ggcattaatg cttcagttgt aaacattcaa      3540
```

-continued

```
aaagaaattg accgcctcaa tgaggttgcc aagaatttaa atgaatctct catcgatctc    3600
caagaacttg gaaagtatga gcagtatata aaatggccat ggtacatttg ctaggtttt    3660 atagctggct tgattgccat agtaatggtg acaattatgc tttgctgtat gaccagttgc    3720
tgtagttgtc tcaagggctg ttgttcttgt ggatcctgct gcaaatttga tgaagacgac    3780
tctgagccag tgctcaaagg agtcgcatta gcttacacat aa                      3822
```

```
<210> SEQ ID NO 5
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: codon optimized SARS-CoV-2 S sequence from
      rMV-EZ-SARS-CoV-2-S-CO-AA-PPP
<220> FEATURE:
<221> NAME/KEY: misc_feature
<222> LOCATION: (2956)..(2961)
<223> OTHER INFORMATION: mutation to lock in the prefusion conformation
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 5
```

```
atgttcgtct tcctggtcct gctgcctctg gtctcctcac agtgcgtcaa tctgacaact     60
cggactcagc tgccacctgc ttatactaat agcttcacca gaggcgtgta ctatcctgac    120
aaggtgttta gaagctccgt gctgcactct acacaggatc tgtttctgcc attctttagc    180
aacgtgacct ggttccacgc catccacgtg agcggcacca atggcacaaa gcggttcgac    240
aatcccgtgc tgccttttaa cgatggcgtg tacttcgcct ctaccgagaa gagcaacatc    300
atcagaggct ggatctttgg caccacactg gactccaaga cacagtctct gctgatcgtg    360
aacaatgcca ccaacgtggt catcaaggtg tgcgagttcc agttttgtaa tgatcccttc    420
ctgggcgtgt actatcacaa gaacaataag agctggatgg agtccgagtt tagagtgtat    480
tctagcgcca caactgcac atttgagtac gtgagccagc ctttcctgat ggacctggag    540
ggcaagcagg gcaatttcaa gaacctgagg gagttcgtgt ttaagaatat cgacggctac    600
ttcaaaatct actctaagca cacccccatc aacctggtgc gcgacctgcc tcagggcttc    660
agcgccctgg agcccctggt ggatctgcct atcggcatca acatcacccg gtttcagaca    720
ctgctggccc tgcacagaag ctacctgaca cccggcgact cctctagcgg atggaccgcc    780
ggcgctgccg cctactatgt gggctacctc agccccgga ccttcctgct gaagtacaac    840
gagaatggca ccatcacaga cgcagtggat tgcgccctgg accccctgag cgagacaaag    900
tgtacactga gtcctttac cgtggagaag ggcatctatc agacatccaa tttcagggtg    960
cagccaaccg agtctatcgt cgcgctttcct aatatacaa acctgtgccc atttggcgag   1020
gtgttcaacg caacccgctt cgccagcgtg tacgcctgga ataggaagcg gatcagcaac   1080
tgcgtggccg actatagcgt gctgtacaac tccgcctctt tcagcacctt taagtgctat   1140
ggcgtgtccc ccacaaagct gaatgacctg tgctttacca cgtctacgc cgattctttc   1200 gtgatcaggg gcgacgaggt cgcgcagatc gcccccggcc agacaggcaa gatcgcagac   1260
```

-continued

```
tacaattata agctgccaga cgatttcacc ggctgcgtga tcgcctggaa cagcaacaat    1320
ctggattcca aagtgggcgg caactacaat tatctgtacc ggctgtttag aaagagcaat    1380
ctgaagccct tcgagaggga catctctaca gaaatctacc aggccggcag caccccttgc    1440
aatggcgtgg agggctttaa ctgttatttc ccactccagt cctacggctt ccagcccaca    1500
aacggcgtgg gctatcagcc ttaccgcgtg gtggtgctga gctttgagct gctgcacgcc    1560
ccagcaacag tgtgcggccc caagaagtcc accaatctgg tgaagaacaa gtgcgtgaac    1620
ttcaacttca acggcctgac cggcacaggc gtgctgaccg agtccaacaa gaagttcctg    1680
ccatttcagc agttcggcag ggacatcgca gataccacag acgccgtgcg cgacccacag    1740
accctggaga tcctggacat cacaccctgc tctttcggcg gcgtgagcgt gatcacaccc    1800
ggcaccaata caagcaacca ggtggccgtg ctgtatcagg acgtgaattg taccgaggtg    1860
cccgtggcta tccacgccga tcagctgacc ccaacatggc gggtgtacag caccggctcc    1920
aacgtcttcc agacaagagc cggatgcctg atcggagcag agcacgtgaa caattcctat    1980
gagtgcgaca tcccaatcgg cgccggcatc tgtgcctctt accagaccca gacaaactct    2040
cccagaagag cccggagcgt ggcctcccag tctatcatcg cctataccat gtccctgggc    2100
gccgagaaca gcgtggccta ctctaacaat agcatcgcca tcccaaccaa cttcacaatc    2160
tctgtgacca cagagatcct gcccgtgtcc atgaccaaga catctgtgga ctgcacaatg    2220
tatatctgtg gcgattctac cgagtgcagc aacctgctgc tccagtacgg cagcttttgt    2280
acccagctga atagagccct gacaggcatc gccgtggagc aggataagaa cacacaggag    2340
gtgttcgccc aggtgaagca aatctacaag acccccccta tcaaggactt tggcggcttc    2400 aattttttccc agatcctgcc tgatccatcc aagccttcta agcggagctt tatcgaggac    2460
ctgctgttca acaaggtgac cctggccgat gccggcttca tcaagcagta tggcgattgc    2520
ctgggcgaca tcgcagccag ggacctgatc tgcgcccaga gtttaatgg cctgaccgtg    2580 ctgccacccc tgctgacaga tgagatgatc gcacagtaca caagcgccct gctggccggc    2640
accatcacat ccggatggac cttcggcgca ggagccgccc tccagatccc ctttgccatg    2700
cagatggcct ataggttcaa cggcatcggc gtgacccaga atgtgctgta cgagaaccag    2760
aagctgatcg ccaatcagtt taactccgcc atcggcaaga tccaggacag cctgtcctct    2820
acagccagcg ccctgggcaa gctccaggat gtggtgaatc agaacgccca ggccctgaat    2880
accctggtga gcagctgag cagcaacttc ggcgccatct ctagcgtgct gaatgacatc    2940
ctgagccggc tggaccctcc tgaggcagag gtgcagatcg accggctgat caccggccgg    3000
ctccagagcc tccagaccta tgtgacacag cagctgatca gggccgccga tcagggcc    3060 agcgccaatc tggcagcaac caagatgtcc gagtgcgtgc tgggccagtc taagagagtg    3120 gactttttgtg caagggcta tcacctgatg tccttccctc agtctgcccc acacggcgtg    3180
gtgtttctgc acgtgaccta cgtgcccgcc caggagaaga acttcaccac agcccctgcc    3240
atctgccacg atggcaaggc ccactttcca agggagggcg tgttcgtgtc caacggcacc    3300
cactggtttg tgacacagcg caatttctac gagccccaga tcatcaccac agacaacacc    3360
ttcgtgagcg gcaactgtga cgtggtcatc ggcatcgtga caataccgt gtatgatcca    3420 ctccagcccg agctggacag ctttaaggag gagctggata agtatttcaa gaatcacacc    3480
tcccctgacg tggatctggg cgacatcagc ggcatcaatg cctccgtggt gaacatccag    3540
aaggagatcg accgcctgaa cgaggtggct aagaatctga cgagagcct gatcgacctc    3600
```

-continued

```
caggagctgg gcaagtatga gcagtacatc aagtggccct ggtacatctg gctgggcttc      3660
atcgccggcc tgatcgccat cgtgatggtg accatcatgc tgtgctgtat gacatcctgc      3720
tgttcttgcc tgaagggctg ctgtagctgt ggctcctgct gtaagtttga cgaggatgac      3780
tctgaacctg tgctgaaggg cgtggcgctg gcttacacct aa                        3822
```

```
<210> SEQ ID NO 6
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: codon optimized SARS-CoV-2 S sequence from
     rMV-EZ-SARS-CoV-2-S-CO-AA-fneg-PP
<220> FEATURE:
<221> NAME/KEY: misc_feature
<222> LOCATION: (2044)..(2045)
<223> OTHER INFORMATION: mutation to ablate the furin cleavage signal
<220> FEATURE:
<221> NAME/KEY: misc_feature
<222> LOCATION: (2047)..(2049)
<223> OTHER INFORMATION: mutation to ablate the furin cleavage signal
<220> FEATURE:
<221> NAME/KEY: misc_feature
<222> LOCATION: (2051)..(2053)
<223> OTHER INFORMATION: mutation to ablate the furin cleavage signal
<220> FEATURE:
<221> NAME/KEY: misc_feature
<222> LOCATION: (2055)..(2055)
<223> OTHER INFORMATION: mutation to ablate the furin cleavage signal
<220> FEATURE:
<221> NAME/KEY: misc_feature
<222> LOCATION: (2956)..(2961)
<223> OTHER INFORMATION: mutation to lock in the prefusion conformation
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 6
```

```
atgttcgtct tcctggtcct gctgcctctg gtctcctcac agtgcgtcaa tctgacaact      60
cggactcagc tgccacctgc ttatactaat agcttcacca gaggcgtgta ctatcctgac      120
aaggtgttta gaagctccgt gctgcactct acacaggatc tgtttctgcc attctttagc      180
aacgtgacct ggttccacgc catccacgtg agcggcacca atggcacaaa gcggttcgac      240
aatcccgtgc tgccttttaa cgatggcgtg tacttcgcct ctaccgagaa gagcaacatc      300
atcagaggct ggatctttgg caccacactg gactccaaga cacagtctct gctgatcgtg      360
aacaatgcca ccaacgtggt catcaaggtg tgcgagttcc agttttgtaa tgatcccttc      420
ctgggcgtgt actatcacaa gaacaataag agctggatgg agtccgagtt tagagtgtat      480
tctagcgcca caactgcac atttgagtac gtgagccagc ctttcctgat ggacctggag      540
ggcaagcagg gcaatttcaa gaacctgagg gagttcgtgt ttaagaatat cgacggctac      600
ttcaaaatct actctaagca cacccccatc aacctggtgc gcgacctgcc tcagggcttc      660
agcgccctgg agcccctggt ggatctgcct atcggcatca acatcacccg gtttcagaca      720
ctgctggccc tgcacagaag ctacctgaca cccggcgact cctctagcgg atggaccgcc      780
ggcgctgccg cctactatgt gggctacctc cagccccgga ccttcctgct gaagtacaac      840
```

-continued

```
gagaatggca ccatcacaga cgcagtggat tgcgccctgg accccctgag cgagacaaag      900
tgtacactga agtcctttac cgtggagaag ggcatctatc agacatccaa tttcagggtg      960
cagccaaccg agtctatcgt gcgctttcct aatatcacaa acctgtgccc atttggcgag     1020
gtgttcaacg caacccgctt cgccagcgtg tacgcctgga ataggaagcg gatcagcaac     1080
tgcgtggccg actatagcgt gctgtacaac tccgcctctt tcagcacctt taagtgctat     1140
ggcgtgtccc ccacaaagct gaatgacctg tgctttacca acgtctacgc cgattctttc     1200
gtgatcaggg gcgacgaggt gcgccagatc gcccccggcc agacaggcaa gatcgcagac     1260
tacaattata agctgccaga cgatttcacc ggctgcgtga tcgcctggaa cagcaacaat     1320
ctggattcca aagtgggcgg caactacaat tatctgtacc ggctgtttag aaagagcaat     1380
ctgaagccct tcgagaggga catctctaca gaaatctacc aggccggcag caccccttgc     1440
aatggcgtgg agggctttaa ctgttatttc ccactccagt cctacggctt ccagcccaca     1500
aacggcgtgg gctatcagcc ttaccgcgtg gtggtgctga gctttgagct gctgcacgcc     1560
ccagcaacag tgtgcggccc caagaagtcc accaatctgg tgaagaacaa gtgcgtgaac     1620
ttcaacttca cggcctgac cggcacaggc gtgctgaccg agtccaacaa gaagttcctg     1680
ccatttcagc agtccggcag ggacatcgca gataccacac acgccgtgcg cgacccacag     1740
accctggaga tcctggacat cacaccctgc tctttcggcg gcgtgagcgt gatcacaccc     1800
ggcaccaata caagcaacca ggtggccgtg ctgtatcagg acgtgaattg taccgaggtg     1860
cccgtggcta tccacgccga tcagctgacc ccaacatggc gggtgtacag caccggctcc     1920
aacgtcttcc agacaagagc cggatgcctg atcggagcag agcacgtgaa caattcctat     1980
gagtgcgaca tcccaatcgg cgccggcatc tgtgcctctt accagaccca gacaaactct     2040
cccgcatctg tgggcagcgt ggcctcccag tctatcatcg cctataccat gtccctgggc     2100
gccgagaaca gcgtggccta ctctaacaat agcatcgcca tcccaaccaa cttcacaatc     2160
tctgtgacca cagagatcct gcccgtgtcc atgaccaaga catctgtgga ctgcacaatg     2220
tatatctgtg gcgattctac cgagtgcagc aacctgctgc tccagtacgg cagctttttgt     2280 acccagctga atagagccct gacaggcatc gccgtggagc aggataagaa cacacaggag     2340
gtgttcgccc aggtgaagca aatctacaag accccccta tcaaggactt tggcggcttc     2400 aattttttccc agatcctgcc tgatccatcc aagccttcta agcggagctt tatcgaggac     2460
ctgctgttca caaaggtgac cctggccgat gccggcttca tcaagcagta tggcgattgc     2520
ctgggcgaca tcgcagccag ggacctgatc tgcgcccaga gtttaatgg cctgaccgtg     2580 ctgccacccc tgctgacaga tgagatgatc gcacagtaca agcgccct gctggccggc     2640 accatcacat ccggatggac cttcggcgca ggagccgccc tccagatccc ctttgccatg     2700
cagatggcct ataggttcaa cggcatcggc gtgacccaga atgtgctgta cgagaaccag     2760
aagctgatcg ccaatcagtt taactccgcc atcggcaaga tccaggacag cctgtcctct     2820
acagccagcg ccctgggcaa gctccaggat gtggtgaatc agaacgccca ggccctgaat     2880
accctggtga agcagctgag cagcaacttc ggcgccatct ctagcgtgct gaatgacatc     2940
ctgagccggc tggaccctcc tgaggcagag gtgcagatcg accggctgat caccggccgg     3000
ctccagagcc tccagaccta tgtgacacag cagctgatca gggccgccga gatcagggcc     3060
agcgccaatc tggcagcaac caagatgtcc gagtgcgtgc tgggccagtc taagagagtg     3120 gactttgtg gcaagggcta tcacctgatg tccttccctc agtctgcccc acacggcgtg     3180
gtgtttctgc acgtgaccta cgtgcccgcc caggagaaga acttcaccac agcccctgcc     3240
```

-continued

```
atctgccacg atggcaaggc ccactttcca agggagggcg tgttcgtgtc caacggcacc    3300
cactggtttg tgacacagcg caatttctac gagccccaga tcatcaccac agacaacacc    3360
ttcgtgagcg gcaactgtga cgtggtcatc ggcatcgtga acaataccgt gtatgatcca    3420
ctccagcccg agctggacag ctttaaggag gagctggata agtatttcaa gaatcacacc    3480
tcccctgacg tggatctggg cgacatcagc ggcatcaatg cctccgtggt gaacatccag    3540
aaggagatcg accgcctgaa cgaggtggct aagaatctga cgagagcct gatcgacctc    3600 caggagctgg gcaagtatga gcagtacatc aagtggccct ggtacatctg gctgggcttc    3660
atcgccggcc tgatcgccat cgtgatggtg accatcatgc tgtgctgtat gacatcctgc    3720
tgttcttgcc tgaagggctg ctgtagctgt ggctcctgct gtaagtttga cgaggatgac    3780
tctgaacctg tgctgaaggg cgtggcgctg gcttacacct aa                       3822
```

```
<210> SEQ ID NO 7
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: codon optimized SARS-CoV-2 S from rMV-EZ-SARS-
      CoV-2-S-CO-AA-fneg
<220> FEATURE:
<221> NAME/KEY: misc_feature
<222> LOCATION: (2044)..(2045)
<223> OTHER INFORMATION: mutation to ablate the furin cleavage signal
<220> FEATURE:
<221> NAME/KEY: misc_feature
<222> LOCATION: (2047)..(2049)
<223> OTHER INFORMATION: mutation to ablate the furin cleavage signal
<220> FEATURE:
<221> NAME/KEY: misc_feature
<222> LOCATION: (2051)..(2053)
<223> OTHER INFORMATION: mutation to ablate the furin cleavage signal
<220> FEATURE:
<221> NAME/KEY: misc_feature
<222> LOCATION: (2055)..(2055)
<223> OTHER INFORMATION: mutation to ablate the furin cleavage signal
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 7
atgttcgtct cctggtcct gctgcctctg gtctcctcac agtgcgtcaa tctgacaact     60
cggactcagc tgccacctgc ttatactaat agcttcacca gaggcgtgta ctatcctgac    120
aaggtgttta gaagctccgt gctgcactct acacaggatc tgtttctgcc attctttagc    180
aacgtgacct ggttccacgc catccacgtg agcggcacca atggcacaaa gcggttcgac    240
aatcccgtgc tgccttttaa cgatggcgtg tacttcgcct ctaccgagaa gagcaacatc    300
atcagaggct ggatctttgg caccacactg gactccaaga cacagtctct gctgatcgtg    360
aacaatgcca ccaacgtggt catcaaggtg tgcgagttcc agtttgtaa tgatcccttc    420 ctgggcgtgt actatcacaa gaacaataag agctggatgg agtccgagtt tagagtgtat    480
tctagcgcca caactgcac atttgagtac gtgagccagc cttttcctgat ggacctggag    540 ggcaagcagg gcaatttcaa gaacctgagg gagttcgtgt ttaagaatat cgacggctac    600
```

-continued

```
ttcaaaatct actctaagca caccccatc aacctggtgc gcgacctgcc tcagggcttc      660
agcgccctgg agccctggt ggatctgcct atcggcatca acatcacccg gtttcagaca      720
ctgctggccc tgcacagaag ctacctgaca cccggcgact cctctagcgg atggaccgcc      780
ggcgctgccg cctactatgt gggctacctc cagccccgga ccttcctgct gaagtacaac      840
gagaatggca ccatcacaga cgcagtggat tgcgccctgg acccctgag cgagacaaag      900 tgtacactga agtcctttac cgtggagaag ggcatctatc agacatccaa tttcagggtg      960
cagccaaccg agtctatcgt gcgctttcct aatatcacaa acctgtgccc atttggcgag      1020
gtgttcaacg caacccgctt cgccagcgtg tacgcctgga ataggaagcg gatcagcaac      1080
tgcgtggccg actatagcgt gctgtacaac tccgcctctt tcagcacctt taagtgctat      1140
ggcgtgtccc ccacaaagct gaatgacctg tgctttacca acgtctacgc cgattctttc      1200
gtgatcaggg gcgacgaggt gcgccagatc gcccccggcc agacaggcaa gatcgcagac      1260
tacaattata agctgccaga cgatttcacc ggctgcgtga tcgcctggaa cagcaacaat      1320
ctggattcca aagtgggcgg caactacaat tatctgtacc ggctgtttag aaagagcaat      1380
ctgaagcccc tcgagaggga catctctaca gaaatctacc aggccggcag cacccccttgc      1440 aatggcgtgg agggcttta ctgttatttc ccactccagt cctacggctt ccagcccaca      1500
aacggcgtgg gctatcagcc ttaccgcgtg gtggtgctga gctttgagct gctgcacgcc      1560
ccagcaacag tgtgcggccc caagaagtcc accaatctgg tgaagaacaa gtgcgtgaac      1620
ttcaacttca acggcctgac cggcacaggc gtgctgaccg agtccaacaa gaagttcctg      1680
ccatttcagc agttcggcag ggacatcgca gataccacag acgccgtgcg cgacccacag      1740
accctggaga tcctggacat cacacccctgc tctttcggcg gcgtgagcgt gatcacaccc      1800
ggcaccaata caagcaacca ggtggccgtg ctgtatcagg acgtgaattg taccgaggtg      1860
cccgtggcta tccacgccga tcagctgacc ccaacatggc gggtgtacag caccggctcc      1920
aacgtcttcc agacaagagc cggatgcctg atcggagcag agcacgtgaa caattcctat      1980
gagtgcgaca tcccaatcgg cgccggcatc tgtgcctctt accagaccca gacaaaactct      2040 cccgcatctg tgggcagcgt ggcctcccag tctatcatcg cctataccat gtccctgggc      2100
gccgagaaca gcgtggccta ctctaacaat agcatcgcca tcccaaccaa cttcacaatc      2160
tctgtgacca cagagatcct gcccgtgtcc atgaccaaga catctgtgga ctgcacaatg      2220
tatatctgtg gcgattctac cgagtgcagc aacctgctgc tccagtacgg cagctttttgt      2280 acccagctga atagagccct gacaggcatc gccgtggagc aggataagaa cacacaggag      2340
gtgttcgccc aggtgaagca aatctacaag acccccccta tcaaggactt tggcggcttc      2400 aattttttccc agatcctgcc tgatccatcc aagccttcta agcggagctt tatcgaggac      2460
ctgctgttca caaaggtgac cctggccgat gccggcttca tcaagcagta tggcgattgc      2520
ctgggcgaca tcgcagccag ggacctgatc tgcgcccaga gtttaatgg cctgaccgtg      2580 ctgccacccc tgctgacaga tgagatgatc gcacagtaca aagcgccct gctggccggc      2640 accatcacat ccggatggac cttcggcgca ggagccgccc tccagatccc ctttgccatg      2700
cagatggcct ataggttcaa cggcatcggc gtgacccaga atgtgctgta cgagaaccag      2760
aagctgatcg ccaatcagtt taactccgcc atcggcaaga tccaggacag cctgtcctct      2820
acagccagcg ccctgggcaa gctccaggat gtggtgaatc agaacgccca ggccctgaat      2880
accctggtga agcagctgag cagcaacttc ggcgccatct ctagcgtgct gaatgacatc      2940
```

```
ctgagccggc tggacaaggt ggaggcagag gtgcagatcg accggctgat caccggccgg    3000
ctccagagcc tccagaccta tgtgacacag cagctgatca gggccgccga gatcagggcc    3060
agcgccaatc tggcagcaac caagatgtcc gagtgcgtgc tgggccagtc taagagagtg    3120 gactttgtg gcaagggcta tcacctgatg tccttccctc agtctgcccc acacggcgtg     3180
gtgtttctgc acgtgaccta cgtgcccgcc caggagaaga acttcaccac agcccctgcc    3240
atctgccacg atggcaaggc ccactttcca agggagggcg tgttcgtgtc caacggcacc    3300
cactggtttg tgacacagcg caatttctac gagccccaga tcatcaccac agacaacacc    3360
ttcgtgagcg gcaactgtga cgtggtcatc ggcatcgtga acaataccgt gtatgatcca    3420
ctccagcccg agctggacag ctttaaggag gagctggata agtatttcaa gaatcacacc    3480
tcccctgacg tggatctggg cgacatcagc ggcatcaatg cctccgtggt gaacatccag    3540
aaggagatcg accgcctgaa cgaggtggct aagaatctga cgagagcct gatcgacctc     3600 caggagctgg gcaagtatga gcagtacatc aagtggccct ggtacatctg gctgggcttc    3660
atcgccggcc tgatcgccat cgtgatggtg accatcatgc tgtgctgtat gacatcctgc    3720
tgttcttgcc tgaagggctg ctgtagctgt ggctcctgct gtaagtttga cgaggatgac    3780
tctgaacctg tgctgaaggg cgtggcgctg gcttacacct aa    3822
```

```
<210> SEQ ID NO 8
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3822)
<223> OTHER INFORMATION: Non-codon optimized SARS-CoV-2 Spike from
      rMV-EZ-SARS-CoV-2-S clone 6
<220> FEATURE:
<221> NAME/KEY: MISC_FEATURE
<222> LOCATION: (40)..(40)
<223> OTHER INFORMATION: residue differs from designed sequence
<220> FEATURE:
<221> NAME/KEY: MISC_FEATURE
<222> LOCATION: (363)..(363)
<223> OTHER INFORMATION: residue differs from designed sequence
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 8

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Tyr Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95
```

-continued

```
Lys Ser Asn Ile Ile Arg Gly Trp Ile Phe Gly Thr Thr Leu Asp Ser
            100             105             110

Lys Thr Gln Ser Leu Leu Ile Val Asn Asn Ala Thr Asn Val Val Ile
            115             120             125

Lys Val Cys Glu Phe Gln Phe Cys Asn Asp Pro Phe Leu Gly Val Tyr
        130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
                165             170             175

Met Asp Leu Glu Gly Lys Gln Gly Asn Phe Lys Asn Leu Arg Glu Phe
            180             185             190

Val Phe Lys Asn Ile Asp Gly Tyr Phe Lys Ile Tyr Ser Lys His Thr
            195             200             205

Pro Ile Asn Leu Val Arg Asp Leu Pro Gln Gly Phe Ser Ala Leu Glu
        210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
            275             280             285

Val Asp Cys Ala Leu Asp Pro Leu Ser Glu Thr Lys Cys Thr Leu Lys
        290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
            325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Val Asp Tyr Ser Val Leu
            355             360             365

Tyr Asn Ser Ala Ser Phe Ser Thr Phe Lys Cys Tyr Gly Val Ser Pro
        370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
            435             440             445

Tyr Asn Tyr Leu Tyr Arg Leu Phe Arg Lys Ser Asn Leu Lys Pro Phe
        450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
                485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
```

-continued

```
                515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
    675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
    755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
    835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
    915                 920                 925

Ser Ala Ile Gly Lys Ile Gln Asp Ser Leu Ser Ser Thr Ala Ser Ala
    930                 935                 940
```

-continued

```
Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Ala Leu  Ala Tyr Thr
    1265                 1270
```

```
<210> SEQ ID NO 9
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: Human codon optimized SARS-CoV-2 Spike from
      rMV-EZ-SARS-CoV-2-S-CO
```

-continued

<400> SEQUENCE: 9

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
```

-continued

```
                  405                 410                 415

Lys Ile Ala Asp Tyr Asn Tyr Lys Leu Pro Asp Asp Phe Thr Gly Cys
              420                 425                 430

Val Ile Ala Trp Asn Ser Asn Asn Leu Asp Ser Lys Val Gly Gly Asn
              435                 440                 445

Tyr Asn Tyr Leu Tyr Arg Leu Phe Arg Lys Ser Asn Leu Lys Pro Phe
          450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
              485                 490                 495

Phe Gln Pro Thr Asn Gly Val Gly Tyr Gln Pro Tyr Arg Val Val Val
              500                 505                 510

Leu Ser Phe Glu Leu Leu His Ala Pro Ala Thr Val Cys Gly Pro Lys
          515                 520                 525

Lys Ser Thr Asn Leu Val Lys Asn Lys Cys Val Asn Phe Asn Phe Asn
          530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
              565                 570                 575

Arg Asp Pro Gln Thr Leu Glu Ile Leu Asp Ile Thr Pro Cys Ser Phe
              580                 585                 590

Gly Gly Val Ser Val Ile Thr Pro Gly Thr Asn Thr Ser Asn Gln Val
              595                 600                 605

Ala Val Leu Tyr Gln Asp Val Asn Cys Thr Glu Val Pro Val Ala Ile
          610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
              645                 650                 655

Asn Asn Ser Tyr Glu Cys Asp Ile Pro Ile Gly Ala Gly Ile Cys Ala
              660                 665                 670

Ser Tyr Gln Thr Gln Thr Asn Ser Pro Arg Arg Ala Arg Ser Val Ala
          675                 680                 685

Ser Gln Ser Ile Ile Ala Tyr Thr Met Ser Leu Gly Ala Glu Asn Ser
          690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
              725                 730                 735

Asp Cys Thr Met Tyr Ile Cys Gly Asp Ser Thr Glu Cys Ser Asn Leu
              740                 745                 750

Leu Leu Gln Tyr Gly Ser Phe Cys Thr Gln Leu Asn Arg Ala Leu Thr
          755                 760                 765

Gly Ile Ala Val Glu Gln Asp Lys Asn Thr Gln Glu Val Phe Ala Gln
          770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
              805                 810                 815

Phe Ile Glu Asp Leu Leu Phe Asn Lys Val Thr Leu Ala Asp Ala Gly
              820                 825                 830
```

```
Phe Ile Lys Gln Tyr Gly Asp Cys Leu Gly Asp Ile Ala Ala Arg Asp
    835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
    915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230
```

US 12,653,881 B2

63

64

-continued

```
Leu Cys  Cys Met Thr Ser Cys  Cys Ser Cys Leu Lys  Gly Cys Cys
    1235             1240             1245

Ser Cys  Gly Ser Cys Cys Lys  Phe Asp Glu Asp Asp  Ser Glu Pro
    1250             1255             1260

Val Leu  Lys Gly Val Lys Leu  His Tyr Thr
    1265             1270

<210> SEQ ID NO 10
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: Human codon optimized SARS-CoV-2 Spike from
      rMV-EZ-SARS-CoV-2-S-CO-AA
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 10

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255
```

-continued

```
Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
    305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670
```

-continued

```
Ser Tyr Gln Thr Gln Thr Asn Ser Pro Arg Arg Ala Arg Ser Val Ala
        675             680             685

Ser Gln Ser Ile Ile Ala Tyr Thr Met Ser Leu Gly Ala Glu Asn Ser
        690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
                725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
        755             760             765

Gly Ile Ala Val Glu Gln Asp Lys Asn Thr Gln Glu Val Phe Ala Gln
        770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
        850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
        915             920             925

Ser Ala Ile Gly Lys Ile Gln Asp Ser Leu Ser Ser Thr Ala Ser Ala
        930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Lys Val Glu Ala Glu Val Gln
        980             985             990

Ile Asp Arg Leu Ile Thr Gly Arg  Leu Gln Ser Leu Gln  Thr Tyr Val
        995             1000            1005

Thr Gln  Gln Leu Ile Arg Ala  Ala Glu Ile Arg Ala  Ser Ala Asn
    1010            1015            1020

Leu Ala  Ala Thr Lys Met Ser  Glu Cys Val Leu Gly  Gln Ser Lys
    1025            1030            1035

Arg Val  Asp Phe Cys Gly Lys  Gly Tyr His Leu Met  Ser Phe Pro
    1040            1045            1050

Gln Ser  Ala Pro His Gly Val  Val Phe Leu His Val  Thr Tyr Val
    1055            1060            1065

Pro Ala  Gln Glu Lys Asn Phe  Thr Thr Ala Pro Ala  Ile Cys His
    1070            1075            1080

Asp Gly  Lys Ala His Phe Pro  Arg Glu Gly Val Phe  Val Ser Asn
```

-continued

```
      1085              1090              1095

Gly Thr  His Trp Phe Val Thr  Gln Arg Asn Phe Tyr  Glu Pro Gln
      1100              1105              1110

Ile Ile  Thr Thr Asp Asn Thr  Phe Val Ser Gly Asn  Cys Asp Val
      1115              1120              1125

Val Ile  Gly Ile Val Asn Asn  Thr Val Tyr Asp Pro  Leu Gln Pro
      1130              1135              1140

Glu Leu  Asp Ser Phe Lys Glu  Glu Leu Asp Lys Tyr  Phe Lys Asn
      1145              1150              1155

His Thr  Ser Pro Asp Val Asp  Leu Gly Asp Ile Ser  Gly Ile Asn
      1160              1165              1170

Ala Ser  Val Val Asn Ile Gln  Lys Glu Ile Asp Arg  Leu Asn Glu
      1175              1180              1185

Val Ala  Lys Asn Leu Asn Glu  Ser Leu Ile Asp Leu  Gln Glu Leu
      1190              1195              1200

Gly Lys  Tyr Glu Gln Tyr Ile  Lys Trp Pro Trp Tyr  Ile Trp Leu
      1205              1210              1215

Gly Phe  Ile Ala Gly Leu Ile  Ala Ile Val Met Val  Thr Ile Met
      1220              1225              1230

Leu Cys  Cys Met Thr Ser Cys  Cys Ser Cys Leu Lys  Gly Cys Cys
      1235              1240              1245

Ser Cys  Gly Ser Cys Cys Lys  Phe Asp Glu Asp Asp  Ser Glu Pro
      1250              1255              1260

Val Leu  Lys Gly Val Ala Leu  Ala Tyr Thr
      1265              1270
```

```
<210> SEQ ID NO 11
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: SARS-CoV-2 Spike from rMV-EZ-SARS-CoV-2-S-CO-S
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 11

Met Phe Val Phe Leu Val Leu Leu Pro Leu Val Ser Ser Gln Cys Val
1               5               10              15

Asn Leu Thr Thr Arg Thr Gln Leu Pro Pro Ala Tyr Thr Asn Ser Phe
            20              25              30

Thr Arg Gly Val Tyr Tyr Pro Asp Lys Val Phe Arg Ser Ser Val Leu
        35              40              45

His Ser Thr Gln Asp Leu Phe Leu Pro Phe Phe Ser Asn Val Thr Trp
    50              55              60

Phe His Ala Ile His Val Ser Gly Thr Asn Gly Thr Lys Arg Phe Asp
65              70              75              80

Asn Pro Val Leu Pro Phe Asn Asp Gly Val Tyr Phe Ala Ser Thr Glu
                85              90              95

Lys Ser Asn Ile Ile Arg Gly Trp Ile Phe Gly Thr Thr Leu Asp Ser
```

```
                  100              105              110

Lys Thr Gln Ser Leu Leu Ile Val Asn Asn Ala Thr Asn Val Val Ile
             115              120              125

Lys Val Cys Glu Phe Gln Phe Cys Asn Asp Pro Phe Leu Gly Val Tyr
        130              135              140

Tyr His Lys Asn Asn Lys Ser Trp Met Glu Ser Glu Phe Arg Val Tyr
145              150              155              160

Ser Ser Ala Asn Asn Cys Thr Phe Glu Tyr Val Ser Gln Pro Phe Leu
                  165              170              175

Met Asp Leu Glu Gly Lys Gln Gly Asn Phe Lys Asn Leu Arg Glu Phe
             180              185              190

Val Phe Lys Asn Ile Asp Gly Tyr Phe Lys Ile Tyr Ser Lys His Thr
        195              200              205

Pro Ile Asn Leu Val Arg Asp Leu Pro Gln Gly Phe Ser Ala Leu Glu
        210              215              220

Pro Leu Val Asp Leu Pro Ile Gly Ile Asn Ile Thr Arg Phe Gln Thr
225              230              235              240

Leu Leu Ala Leu His Arg Ser Tyr Leu Thr Pro Gly Asp Ser Ser Ser
                  245              250              255

Gly Trp Thr Ala Gly Ala Ala Ala Tyr Tyr Val Gly Tyr Leu Gln Pro
             260              265              270

Arg Thr Phe Leu Leu Lys Tyr Asn Glu Asn Gly Thr Ile Thr Asp Ala
        275              280              285

Val Asp Cys Ala Leu Asp Pro Leu Ser Glu Thr Lys Cys Thr Leu Lys
        290              295              300

Ser Phe Thr Val Glu Lys Gly Ile Tyr Gln Thr Ser Asn Phe Arg Val
305              310              315              320

Gln Pro Thr Glu Ser Ile Val Arg Phe Pro Asn Ile Thr Asn Leu Cys
                  325              330              335

Pro Phe Gly Glu Val Phe Asn Ala Thr Arg Phe Ala Ser Val Tyr Ala
             340              345              350

Trp Asn Arg Lys Arg Ile Ser Asn Cys Val Ala Asp Tyr Ser Val Leu
        355              360              365

Tyr Asn Ser Ala Ser Phe Ser Thr Phe Lys Cys Tyr Gly Val Ser Pro
        370              375              380

Thr Lys Leu Asn Asp Leu Cys Phe Thr Asn Val Tyr Ala Asp Ser Phe
385              390              395              400

Val Ile Arg Gly Asp Glu Val Arg Gln Ile Ala Pro Gly Gln Thr Gly
                  405              410              415

Lys Ile Ala Asp Tyr Asn Tyr Lys Leu Pro Asp Asp Phe Thr Gly Cys
             420              425              430

Val Ile Ala Trp Asn Ser Asn Asn Leu Asp Ser Lys Val Gly Gly Asn
             435              440              445

Tyr Asn Tyr Leu Tyr Arg Leu Phe Arg Lys Ser Asn Leu Lys Pro Phe
        450              455              460

Glu Arg Asp Ile Ser Thr Glu Ile Tyr Gln Ala Gly Ser Thr Pro Cys
465              470              475              480

Asn Gly Val Glu Gly Phe Asn Cys Tyr Phe Pro Leu Gln Ser Tyr Gly
                  485              490              495

Phe Gln Pro Thr Asn Gly Val Gly Tyr Gln Pro Tyr Arg Val Val Val
             500              505              510

Leu Ser Phe Glu Leu Leu His Ala Pro Ala Thr Val Cys Gly Pro Lys
             515              520              525
```

-continued

```
Lys Ser Thr Asn Leu Val Lys Asn Lys Cys Val Asn Phe Asn Phe Asn
    530                 535             540

Gly Leu Thr Gly Thr Gly Val Leu Thr Glu Ser Asn Lys Lys Phe Leu
545                 550             555             560

Pro Phe Gln Gln Phe Gly Arg Asp Ile Ala Asp Thr Thr Asp Ala Val
                565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
    610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Arg Arg Ala Arg Ser Val Ala
            675             680             685

Ser Gln Ser Ile Ile Ala Tyr Thr Met Ser Leu Gly Ala Glu Asn Ser
    690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
            755             760             765

Gly Ile Ala Val Glu Gln Asp Lys Asn Thr Gln Glu Val Phe Ala Gln
    770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
    850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
            915             920             925

Ser Ala Ile Gly Lys Ile Gln Asp Ser Leu Ser Ser Thr Ala Ser Ala
    930             935             940
```

-continued

```
Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
            995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Ala Leu  Ala Tyr Thr
    1265                 1270
```

```
<210> SEQ ID NO 12
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: codon optimized SARS-CoV-2 S sequence from
      rMV-EZ-SARS-CoV-2-S-CO-AA-PP
<220> FEATURE:
```

-continued

<221> NAME/KEY: MISC_FEATURE
<222> LOCATION: (986)..(987)
<223> OTHER INFORMATION: mutation to lock in the prefusion conformation
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 12

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
            85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
            130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350
```

-continued

```
Trp Asn Arg Lys Arg Ile Ser Asn Cys Val Ala Asp Tyr Ser Val Leu
    355             360             365

Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
            435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
            485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
            515             520             525

Lys Ser Thr Asn Leu Val Lys Asn Lys Cys Val Asn Phe Asn Phe Asn
    530             535             540

Gly Leu Thr Gly Thr Gly Val Leu Thr Glu Ser Asn Lys Lys Phe Leu
545             550             555             560

Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
    610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Arg Arg Ala Arg Ser Val Ala
            675             680             685

Ser Gln Ser Ile Ile Ala Tyr Thr Met Ser Leu Gly Ala Glu Asn Ser
    690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
    755             760             765
```

-continued

```
Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
    915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
                980                 985                 990

Ile Asp Arg Leu Ile Thr Gly Arg  Leu Gln Ser Leu Gln  Thr Tyr Val
                995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
```

-continued

```
          1175               1180               1185

Val Ala  Lys Asn Leu Asn Glu  Ser Leu Ile Asp Leu  Gln Glu Leu
    1190               1195               1200

Gly Lys  Tyr Glu Gln Tyr Ile  Lys Trp Pro Trp Tyr  Ile Trp Leu
    1205               1210               1215

Gly Phe  Ile Ala Gly Leu Ile  Ala Ile Val Met Val  Thr Ile Met
    1220               1225               1230

Leu Cys  Cys Met Thr Ser Cys  Cys Ser Cys Leu Lys  Gly Cys Cys
    1235               1240               1245

Ser Cys  Gly Ser Cys Cys Lys  Phe Asp Glu Asp Asp  Ser Glu Pro
    1250               1255               1260

Val Leu  Lys Gly Val Ala Leu  Ala Tyr Thr
    1265               1270
```

```
<210> SEQ ID NO 13
<211> LENGTH: 1281
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: codon optimized SARS-CoV-2 S sequence from
      rMV-EZ-SARS-CoV-2-S-CO-AA-fneg-PP
<220> FEATURE:
<221> NAME/KEY: MISC_FEATURE
<222> LOCATION: (682)..(685)
<223> OTHER INFORMATION: mutation to ablate the furin cleavage signal
<220> FEATURE:
<221> NAME/KEY: MISC_FEATURE
<222> LOCATION: (986)..(987)
<223> OTHER INFORMATION: mutation to lock in the prefusion conformation
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 13

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
```

-continued

```
145               150               155               160

Ser Ser Ala Asn Asn Cys Thr Phe Glu Tyr Val Ser Gln Pro Phe Leu
                165               170               175

Met Asp Leu Glu Gly Lys Gln Gly Asn Phe Lys Asn Leu Arg Glu Phe
            180               185               190

Val Phe Lys Asn Ile Asp Gly Tyr Phe Lys Ile Tyr Ser Lys His Thr
        195               200               205

Pro Ile Asn Leu Val Arg Asp Leu Pro Gln Gly Phe Ser Ala Leu Glu
    210               215               220

Pro Leu Val Asp Leu Pro Ile Gly Ile Asn Ile Thr Arg Phe Gln Thr
225               230               235               240

Leu Leu Ala Leu His Arg Ser Tyr Leu Thr Pro Gly Asp Ser Ser Ser
                245               250               255

Gly Trp Thr Ala Gly Ala Ala Ala Tyr Tyr Val Gly Tyr Leu Gln Pro
            260               265               270

Arg Thr Phe Leu Leu Lys Tyr Asn Glu Asn Gly Thr Ile Thr Asp Ala
        275               280               285

Val Asp Cys Ala Leu Asp Pro Leu Ser Glu Thr Lys Cys Thr Leu Lys
    290               295               300

Ser Phe Thr Val Glu Lys Gly Ile Tyr Gln Thr Ser Asn Phe Arg Val
305               310               315               320

Gln Pro Thr Glu Ser Ile Val Arg Phe Pro Asn Ile Thr Asn Leu Cys
                325               330               335

Pro Phe Gly Glu Val Phe Asn Ala Thr Arg Phe Ala Ser Val Tyr Ala
            340               345               350

Trp Asn Arg Lys Arg Ile Ser Asn Cys Val Ala Asp Tyr Ser Val Leu
        355               360               365

Tyr Asn Ser Ala Ser Phe Ser Thr Phe Lys Cys Tyr Gly Val Ser Pro
    370               375               380

Thr Lys Leu Asn Asp Leu Cys Phe Thr Asn Val Tyr Ala Asp Ser Phe
385               390               395               400

Val Ile Arg Gly Asp Glu Val Arg Gln Ile Ala Pro Gly Gln Thr Gly
                405               410               415

Lys Ile Ala Asp Tyr Asn Tyr Lys Leu Pro Asp Asp Phe Thr Gly Cys
            420               425               430

Val Ile Ala Trp Asn Ser Asn Asn Leu Asp Ser Lys Val Gly Gly Asn
        435               440               445

Tyr Asn Tyr Leu Tyr Arg Leu Phe Arg Lys Ser Asn Leu Lys Pro Phe
    450               455               460

Glu Arg Asp Ile Ser Thr Glu Ile Tyr Gln Ala Gly Ser Thr Pro Cys
465               470               475               480

Asn Gly Val Glu Gly Phe Asn Cys Tyr Phe Pro Leu Gln Ser Tyr Gly
                485               490               495

Phe Gln Pro Thr Asn Gly Val Gly Tyr Gln Pro Tyr Arg Val Val Val
            500               505               510

Leu Ser Phe Glu Leu Leu His Ala Pro Ala Thr Val Cys Gly Pro Lys
        515               520               525

Lys Ser Thr Asn Leu Val Lys Asn Lys Cys Val Asn Phe Asn Phe Asn
    530               535               540

Gly Leu Thr Gly Thr Gly Val Leu Thr Glu Ser Asn Lys Lys Phe Leu
545               550               555               560

Pro Phe Gln Gln Phe Gly Arg Asp Ile Ala Asp Thr Thr Asp Ala Val
                565               570               575
```

-continued

```
Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Ala Ser Val Gly Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
            850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Pro Pro Glu Ala Glu Val Gln
            980                 985                 990
```

```
Ile Asp Arg Leu Ile Thr Gly Arg  Leu Gln Ser Leu Gln  Thr Tyr Val
        995             1000             1005

Thr Gln  Gln Leu Ile Arg Ala  Ala Glu Ile Arg Ala  Ser Ala Asn
    1010             1015             1020

Leu Ala  Ala Thr Lys Met Ser  Glu Cys Val Leu Gly  Gln Ser Lys
    1025             1030             1035

Arg Val  Asp Phe Cys Gly Lys  Gly Tyr His Leu Met  Ser Phe Pro
    1040             1045             1050

Gln Ser  Ala Pro His Gly Val  Val Phe Leu His Val  Thr Tyr Val
    1055             1060             1065

Pro Ala  Gln Glu Lys Asn Phe  Thr Thr Ala Pro Ala  Ile Cys His
    1070             1075             1080

Asp Gly  Lys Ala His Phe Pro  Arg Glu Gly Val Phe  Val Ser Asn
    1085             1090             1095

Gly Thr  His Trp Phe Val Thr  Gln Arg Asn Phe Tyr  Glu Pro Gln
    1100             1105             1110

Ile Ile  Thr Thr Asp Asn Thr  Phe Val Ser Gly Asn  Cys Asp Val
    1115             1120             1125

Val Ile  Gly Ile Val Asn Asn  Thr Val Tyr Asp Pro  Leu Gln Pro
    1130             1135             1140

Glu Leu  Asp Ser Phe Lys Glu  Glu Leu Asp Lys Tyr  Phe Lys Asn
    1145             1150             1155

His Thr  Ser Pro Asp Val Asp  Leu Gly Asp Ile Ser  Gly Ile Asn
    1160             1165             1170

Ala Ser  Val Val Asn Ile Gln  Lys Glu Ile Asp Arg  Leu Asn Glu
    1175             1180             1185

Val Ala  Lys Asn Leu Asn Glu  Ser Leu Ile Asp Leu  Gln Glu Leu
    1190             1195             1200

Gly Lys  Tyr Glu Gln Tyr Ile  Lys Trp Pro Trp Tyr  Ile Trp Leu
    1205             1210             1215

Gly Phe  Ile Ala Gly Leu Ile  Ala Ile Val Met Val  Thr Ile Met
    1220             1225             1230

Leu Cys  Cys Met Thr Ser Cys  Cys Ser Cys Leu Lys  Gly Cys Cys
    1235             1240             1245

Ser Cys  Gly Ser Cys Cys Lys  Phe Asp Glu Asp Asp  Ser Glu Pro
    1250             1255             1260

Val Leu  Lys Gly Val Ala Leu  Ala Tyr Thr Arg Arg  Ala Arg Ser
    1265             1270             1275

Val Ala  Ser
    1280
```

<210> SEQ ID NO 14
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: codon optimized SARS-CoV-2 S from rMV-EZ-SARS-
     CoV-2-S-CO-AA-fneg
<220> FEATURE:
<221> NAME/KEY: MISC_FEATURE
<222> LOCATION: (682)..(685)
<223> OTHER INFORMATION: mutation to ablate the furin cleavage signal
<220> FEATURE:
<221> NAME/KEY: MISC_FEATURE
<222> LOCATION: (1269)..(1269)

-continued

<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 14

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
        180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
        260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
        340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380
```

-continued

```
Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
        450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Ala Ser Val Gly Ser Val Ala
        675                 680                 685

Ser Gln Ser Ile Ile Ala Tyr Thr Met Ser Leu Gly Ala Glu Asn Ser
        690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
        770                 775                 780

Val Lys Gln Ile Tyr Lys Thr Pro Pro Ile Lys Asp Phe Gly Gly Phe
785                 790                 795                 800
```

-continued

```
Asn Phe Ser Gln Ile Leu Pro Asp Pro Ser Lys Pro Ser Lys Arg Ser
                805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
            915             920             925

Ser Ala Ile Gly Lys Ile Gln Asp Ser Leu Ser Ser Thr Ala Ser Ala
930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Lys Val Glu Ala Glu Val Gln
            980             985             990

Ile Asp Arg Leu Ile Thr Gly Arg  Leu Gln Ser Leu Gln  Thr Tyr Val
            995             1000                1005

Thr Gln  Gln Leu Ile Arg Ala  Ala Glu Ile Arg Ala  Ser Ala Asn
    1010            1015                1020

Leu Ala  Ala Thr Lys Met Ser  Glu Cys Val Leu Gly  Gln Ser Lys
    1025            1030                1035

Arg Val  Asp Phe Cys Gly Lys  Gly Tyr His Leu Met  Ser Phe Pro
    1040            1045                1050

Gln Ser  Ala Pro His Gly Val  Val Phe Leu His Val  Thr Tyr Val
    1055            1060                1065

Pro Ala  Gln Glu Lys Asn Phe  Thr Thr Ala Pro Ala  Ile Cys His
    1070            1075                1080

Asp Gly  Lys Ala His Phe Pro  Arg Glu Gly Val Phe  Val Ser Asn
    1085            1090                1095

Gly Thr  His Trp Phe Val Thr  Gln Arg Asn Phe Tyr  Glu Pro Gln
    1100            1105                1110

Ile Ile  Thr Thr Asp Asn Thr  Phe Val Ser Gly Asn  Cys Asp Val
    1115            1120                1125

Val Ile  Gly Ile Val Asn Asn  Thr Val Tyr Asp Pro  Leu Gln Pro
    1130            1135                1140

Glu Leu  Asp Ser Phe Lys Glu  Glu Leu Asp Lys Tyr  Phe Lys Asn
    1145            1150                1155

His Thr  Ser Pro Asp Val Asp  Leu Gly Asp Ile Ser  Gly Ile Asn
    1160            1165                1170

Ala Ser  Val Val Asn Ile Gln  Lys Glu Ile Asp Arg  Leu Asn Glu
    1175            1180                1185

Val Ala  Lys Asn Leu Asn Glu  Ser Leu Ile Asp Leu  Gln Glu Leu
    1190            1195                1200

Gly Lys  Tyr Glu Gln Tyr Ile  Lys Trp Pro Trp Tyr  Ile Trp Leu
```

-continued

```
      1205              1210              1215

Gly Phe  Ile Ala Gly Leu Ile  Ala Ile Val Met Val  Thr Ile Met
    1220              1225              1230

Leu Cys  Cys Met Thr Ser Cys  Cys Ser Cys Leu Lys  Gly Cys Cys
    1235              1240              1245

Ser Cys  Gly Ser Cys Cys Lys  Phe Asp Glu Asp Asp  Ser Glu Pro
    1250              1255              1260

Val Leu  Lys Gly Val Ala Leu  Ala Tyr Thr
    1265              1270
```

```
<210> SEQ ID NO 15
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-clone 6

<400> SEQUENCE: 15
accaaacaaa gttgggtaag gatagttcaa tcaatgatca ttttctagtg cacttaggat        60
tcaagatcct attatcaggg acaagagcag gattaaggat atccgagatg gccacacttt       120
taaggagctt agcattgttc aaaagaaaca aggacaaacc acccattaca tcaggatccg       180
gtggagccat cagaggaatc aaacacatta ttatagtacc aatccctgga gattcctcaa       240
ttaccactcg atccagactt ctggaccggt tggtcaggtt aattggaaac ccggatgtga       300
gcgggcccaa actaacaggg cactaatag gtatattatc cttatttgtg gagtctccag         360
gtcaattgat tcagaggatc accgatgacc ctgacgttag cataaggctg ttagaggttg       420
tccagagtga ccagtcacaa tctggcctta ccttcgcatc aagaggtacc aacatggagg       480
atgaggcgga ccaatacttt tcacatgatg atccaattag tagtgatcaa tccaggttcg       540
gatggttcga gaacaaggaa atctcagata ttgaagtgca agaccctgag ggattcaaca       600
tgattctggg taccatccta gctcaaattt gggtcttgct cgcaaaggcg gttacggccc       660
cagacacggc agctgattcg gagctaagaa ggtggataaa gtacacccaa caaagaaggg       720
tagttggtga atttagattg gagagaaaat ggttggatgt ggtgaggaac aggattgccg       780
aggacctctc cttacgccga ttcatggtcg ctctaatcct ggatatcaag agaacacccg       840
gaaacaaacc caggattgct gaaatgatat gtgacattga tacatatatc gtagaggcag       900
gattagccag ttttatcctg actattaagt ttgggataga aactatgtat cctgctcttg       960
gactgcatga atttgctggt gagttatcca cacttgagtc cttgatgaac ctttaccagc      1020
aaatggggga aactgcaccc tacatggtaa tcctggagaa ctcaattcag aacaagttca      1080
gtgcaggatc ataccctctg ctctggagct atgccatggg agtaggagtg aacttgaaa       1140 actccatggg aggtttgaac tttggccgat cttactttga tccagcatat tttagattag      1200
ggcaagagat ggtaaggagg tcagctggaa aggtcagttc cacattggca tctgaactcg      1260
gtatcactgc cgaggatgca aggcttgttt cagagattgc aatgcatact actgaggaca      1320
agatcagtag agcggttgga cccagacaag cccaagtatc atttctacac ggtgatcaaa      1380
gtgagaatga gctaccgaga ttggggggca aggaagatag gagggtcaaa cagagtcgag      1440
gagaagccag ggagagctac agagaaaccg ggcccagcag agcaagtgat gcgagagctg      1500
cccatcttcc aaccggcaca cccctagaca ttgacactgc atcggagtcc agccaagatc      1560
```

-continued

```
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag gaccagaaca acatccgcct accctccatc attgttataa   1740
aaaacttagg aaccaggtcc acacagccgc cagcccatca accatccact cccacgattg   1800
gagccgatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc tccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aaggggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt tgttcctga caccggcct   3180 gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtac aacctaaatc cattataaaa aacttaggag caaagtgatt   3420
gcctcccaag ttccacaggc gcgccatgtt tgttttttctt gttttattgc cactagtctc   3480
tagtcagtgt gttaatctta caaccagaac tcaattaccc cctgcataca ctaattcttt   3540
cacacgtggt gtttattacc cttacaaagt tttcagatcc tcagtttac attcaactca   3600 ggacttgttc ttacctttct tttccaatgt tacttggttc catgctatac atgtctctgg   3660
gaccaatggt actaagaggt ttgataaccc tgtcctacca tttaatgatg gtgtttattt   3720
tgcttccact gagaagtcta acataataag aggctggatt tttggtacta ctttagattc   3780
gaagacccag tccctactta ttgttaataa cgctactaat gttgttatta aagtctgtga   3840
atttcaattt tgtaatgatc cattttgggg tgtttattac cacaaaaaca acaaaagttg   3900
```

-continued

```
gatggaaagt gagttcagag tttattctag tgcgaataat tgcactttg aatatgtctc      3960 tcagccttt cttatggacc ttgaaggaaa acagggtaat ttcaaaaatc ttagggaatt       4020
tgtgtttaag aatattgatg gttattttaa aatatattct aagcacacgc ctattaattt      4080
agtgcgtgat ctccctcagg gtttttcggc tttagaacca ttggtagatt tgccaatagg      4140
tattaacatc actaggtttc aaactttact tgctttacat agaagttatt tgactcctgg      4200
tgattcttct tcaggttgga cagctggtgc tgcagcttat tatgtgggtt atcttcaacc      4260
taggactttt ctattaaaat ataatgaaaa tggaaccatt acagatgctg tagactgtgc      4320
acttgaccct ctctcagaaa caaagtgtac gttgaaatcc ttcactgtag aaaaaggaat      4380
ctatcaaact tctaacttta gagtccaacc aacagaatct attgttagat ttcctaatat      4440
tacaaacttg tgccctttg gtgaagtttt taacgccacc agatttgcat ctgtttatgc       4500
ttggaacagg aagagaatca gcaactgtgt tgttgattat tctgtcctat ataattccgc      4560
atcattttcc acttttaagt gttatggagt gtctcctact aaattaaatg atctctgctt      4620
tactaatgtc tatgcagatt catttgtaat tagaggtgat gaagtcagac aaatcgctcc      4680
aggtcaaact ggaaagattg ctgattataa ttataaatta ccagatgatt ttacaggctg      4740
cgttatagct tggaattcta acaatcttga ttctaaggtt ggtggtaatt ataattacct      4800
gtatagattg tttaggaagt ctaatctcaa accttttgag agagatattt caactgaaat      4860
ctatcaggcc ggtagcacac cttgtaatgg tgttgaaggt tttaattgtt actttccttt      4920
acaatcatat ggtttccaac ccactaatgg tgttggttac caaccataca gagtagtagt      4980
actttctttt gaacttctac atgcaccagc aactgtttgt ggacctaaaa agtctactaa      5040
tttggttaaa aacaaatgtg tcaatttcaa cttcaatggt ttaacaggca caggtgttct      5100
tactgagtct aacaaaaagt ttctgccttt ccaacaattt ggcagagaca ttgctgacac      5160
tactgatgct gtccgtgatc cacagacact tgagattctt gacattacac catgttcttt      5220
tggtggtgtc agtgttataa caccaggaac aaatacttct aaccaggttg ctgttcttta      5280
tcaggatgtt aactgcacag aagtccctgt tgctattcat gcagatcaac ttactcctac      5340
ttggcgtgtt tattctacag gttctaatgt ttttcaaaca cgtgcaggct gtttaatagg      5400
ggctgaacat gtcaacaact catatgagtg tgacataccc attggtgcag gtatatgcgc      5460
tagttatcag actcagacta attctcctcg gcgggcacgt agtgtagcta gtcaatccat      5520
cattgcctac actatgtcac ttggtgcaga aaattcagtt gcttactcta ataactctat      5580
tgccataccc acaaatttta ctattagtgt taccacagaa attctaccag tgtctatgac      5640
caagacatca gtagattgta caatgtacat ttgtggtgat tcaactgaat gcagcaatct      5700
tttgttgcaa tatggcagtt tttgtacaca attaaaccgt gctttaactg gaatagctgt      5760
tgaacaagac aaaaacaccc aagaagtttt tgcacaagtc aaacaaattt acaaaacacc      5820
accaattaaa gattttggtg gttttaattt ttcacaaata ttaccagatc catcaaaacc      5880
aagcaagagg tcatttattg aagatctact tttcaacaaa gtgacacttg cagatgctgg      5940
cttcatcaaa caatatggtg attgccttgg tgatattgct gctagagacc tcatttgtgc      6000
acaaaagttt aacggcctta ctgttttgcc acctttgctc acagatgaaa tgattgctca      6060
atacacttct gcactgttag cgggtacaat cacttctggt tggacctttg gtgcaggtgc      6120
tgcattacaa ataccatttg ctatgcaaat ggcttatagg tttaatggta ttggagttac      6180
acagaatgtt ctctatgaga accaaaaatt gattgccaac caatttaata gtgctattgg      6240
caaaattcaa gactcacttt cttccacagc aagtgcactt ggaaaacttc aagatgtggt      6300
```

-continued

```
caaccaaaat gcacaagctt taaacacgct tgttaaacaa cttagctcca attttggtgc   6360
aatttcaagt gttttaaatg atatcctttc acgtcttgac aaagttgagg ctgaagtgca   6420
aattgatagg ttgatcacag gcagacttca aagtttgcag acatatgtga ctcaacaatt   6480
aattagagct gcagaaatca gagcttctgc taatcttgct gctactaaaa tgtcagagtg   6540
tgtacttgga caatcaaaaa gagttgattt ttgtggaaag ggctatcatc ttatgtcctt   6600
ccctcagtca gcacctcatg gtgtagtctt cttgcatgtg acttatgtcc ctgcacaaga   6660
aaagaacttc acaactgctc ctgccatttg tcatgatgga aaagcacact ttcctcgtga   6720
aggtgtcttt gtttcaaatg gcacacactg gtttgtaaca caaaggaatt tttatgaacc   6780
acaaatcatt actacagaca acacatttgt gtctggtaac tgtgatgttg taataggaat   6840
tgtcaacaac acagtttatg atcctttgca acctgaatta gactcattca aggaggagtt   6900
agataaatat tttaagaatc atacatcacc agatgttgat ttaggtgaca tctctggcat   6960
taatgcttca gttgtaaaca ttcaaaaaga aattgaccgc ctcaatgagg ttgccaagaa   7020
tttaaatgaa tctctcatcg atctccaaga acttggaaag tatgagcagt atataaaatg   7080
gccatggtac atttggctag gttttatagc tggcttgatt gccatagtaa tggtgacaat   7140
tatgctttgc tgtatgacca gttgctgtag ttgtctcaag ggctgttgtt cttgtggatc   7200
ctgctgcaaa tttgatgaag acgactctga gccagtgctc aaaggagtcg cattagctta   7260
cacataacgc gcgacgtcct acagctcaac ttacctgcca accccatgcc agtcgaccca   7320
actagtacaa cctaaatcca ttataaaaaa cttaggagca aagtgattgc ctcccaagtt   7380
ccacaatgac agagatctac gacttcgaca agtcggcatg ggacatcaaa gggttgatcg   7440
ctccgataca acccaccacc tacagtgatg gcaggctggt gccccaggtc agagtcatag   7500
atcctggtct aggcgacagg aaggatgaat gctttatgta catgtttctg ctgggggttg   7560
ttgaggacag cgatccccta gggcctccaa tcgggcgagc atttgggtcc ctgcccttag   7620
gtgttggcag atccacagca aagcccgaaa aactcctcaa agaggccact gagcttgaca   7680
tagttgttag acgtacagca gggctcaatg aaaaactggt gttctacaac aacaccccac   7740
taactctcct cacaccttgg agaaaggtcc taacaacagg gagtgtcttc aacgcaaacc   7800
aagtgtgcaa tgcggttaat ctgataccgc tcgataccc gcagaggttc cgtgttgttt   7860
atatgagcat cacccgtctt tcggataacg ggtattacac cgttcctaga agaatgctgg   7920
aattcagatc ggtcaatgca gtggccttca acctgctggt gacccttagg attgacaagg   7980
cgataggccc tgggaagatc atcgacaata cagagcaact tcctgaggca acatttatgg   8040
tccacatcgg gaacttcagg agaaagaaga gtgaagtcta ctctgccgat tattgcaaaa   8100
tgaaaatcga aaagatgggc ctggtttttg cacttggtgg gataggggc accagtcttc   8160 acattagaag cacaggcaaa atgagcaaga ctctccatgc acaactcggg ttcaagaaga   8220
ccttatgtta cccgctgata gatatcaatg aagaccttaa tcgattactc tggaggagca   8280
gatgcaagat agtaagaatc caggcagttt tgcagccatc agttcctcaa gaattccgca   8340
tttacgacga cgtgatcata aatgatgacc aaggactatt caaagttctg tagaccgtag   8400
tgcccagcaa tgcccgaaaa cgaccccct cacaatgaca gccagaaggc ccggacaaaa   8460 aagcccctc cgaaagactc cacggaccaa gcgagaggcc agccagcagc cgacggcaag   8520
cgcgaacacc aggcggcccc agcacagaac agccctgata caaggccacc accagccacc   8580
ccaatctgca tcctcctcgt gggaccccg aggaccaacc cccaaggctg cccccgatcc   8640
```

-continued

```
aaaccaccaa ccgcatcccc accacccccg ggaaagaaac ccccagcaat tggaaggccc       8700
ctccccctct tcctcaacac aagaactcca caaccgaacc gcacaagcga ccgaggtgac       8760
ccaaccgcag gcatccgact ccctagacag atcctctctc cccggcaaac taaacaaaac       8820
ttagggccaa ggaacataca cacccaacag aacccagacc ccggcccacg gcgccgcgcc       8880
cccaaccccc gacaaccaga gggagccccc aaccaatccc gccggctccc ccggtgccca       8940
caggcaggga caccaacccc cgaacagacc cagcacccaa ccatcgacaa tccaagacgg       9000
gggggccccc ccaaaaaaag gcccccaggg gccgacagcc agcaccgcga ggaagcccac       9060
ccaccccaca cacgaccacg gcaaccaaac cagaacccag accaccctgg gccaccagct       9120
cccagactcg gccatcaccc cgcagaaagg aaaggccaca acccgcgcac cccagccccg       9180
atccggcggg gagccaccca acccgaacca gcacccaaga gcgatccccg aaggaccccc       9240
gaaccgcaaa ggacatcagt atcccacagc ctctccaagt cccccggtct cctccccttc       9300
tcgaagggac caaaagatca atccaccaca cccgacgaca ctcaactccc cacccctaaa       9360
ggagacaccg ggaatcccag aatcaagact catccaatgt ccatcatggg tctcaaggtg       9420
aacgtctctg ccatattcat ggcagtactg ttaactctcc aaacacccac cggtcaaatc       9480 cattgggca atctctctaa gataggggtg gtaggaatag gaagtgcaag ctacaaagtt        9540
atgactcgtt ccagccatca atcattagtc ataaaattaa tgcccaatat aactctcctc       9600
aataactgca cgagggtaga gattgcagaa tacaggagac tactgagaac agttttggaa       9660
ccaattagag atgcacttaa tgcaatgacc cagaatataa gaccggttca gagtgtagct       9720
tcaagtagga gacacaagag atttgcggga gtagtcctgg caggtgcggc cctaggcgtc       9780
gccacagctg ctcagataac agccggcatt gcacttcacc agtccatgct gaactctcaa       9840
gccatcgaca atctgagagc gagcctggaa actactaatc aggcaattga ggcaatcaga       9900
caagcagggc aggagatgat attggctgtt cagggtgtcc aagactacat caataatgag       9960
ctgataccgt ctatgaacca actatcttgt gatttaatcg gccagaagct cgggctcaaa      10020
ttgctcagat actatacaga aatcctgtca ttatttggcc ccagcttacg ggaccccata      10080
tctgcggaga tatctatcca ggctttgagc tatgcgcttg gaggagacat caataaggtg      10140
ttagaaaagc tcggatacag tggaggtgat ttactgggca tcttagagag cagaggaata      10200
aaggcccgga taactcacgt cgacacagag tcctacttca ttgtcctcag tatagcctat      10260
ccgacgctgt ccgagattaa gggggtgatt gtccaccggc tagaggggt ctcgtacaac      10320 ataggctctc aagagtggta taccactgtg cccaagtatg ttgcaaccca agggtacctt      10380
atctcgaatt ttgatgagtc atcgtgtact ttcatgccag aggggactgt gtgcagccaa      10440
aatgccttgt acccgatgag tcctctgctc caagaatgcc tccggggggtc caccaagtcc      10500 tgtgctcgta cactcgtatc cgggtctttt gggaaccggt tcattttatc acaagggaac      10560
ctaatagcca attgtgcatc aatcctttgc aagtgttaca caacaggaac gatcattaat      10620
caagaccctg acaagatcct aacatacatt gctgccgatc actgcccggt agtcgaggtg      10680
aacggcgtga ccatccaagt cgggagcagg aggtatccag atgctgtgta cttgcacaga      10740
attgacctcg gtcctcccat atcattggag aggttggacg tagggacaaa tctggggaat      10800
gcaattgcta agttggagga tgccaaggaa ttgttggagt catcggacca gatattgagg      10860
agtatgaaag gtttatcgag cactagcata gtctacatcc tgattgcagt gtgtcttgga      10920
gggttgatag gatcccccgc tttaatatgt tgctgcaggg ggcgttgtaa caaaaaggga      10980
gaacaagttg gtatgtcaag accaggccta aagcctgatc ttacgggaac atcaaaatcc      11040
```

-continued

```
tatgtaaggt cgctctgatc ctctacaact cttgaaacac aaatgtccca caagtctcct   11100
cttcgtcatc aagcaaccac cgcacccagc atcaagccca cctgaaatta tctccggctt   11160
ccctctggcc gaacaatatc ggtagttaat taaaacttag ggtgcaagat catccacaat   11220
gtcaccacaa cgagaccgga taaatgcctt ctacaaagat aacccccatc ccaagggaag   11280
taggatagtc attaacagag aacatcttat gattgataga ccttatgttt tgctggctgt   11340
tctgtttgtc atgtttctga gcttgatcgg gttgctagcc attgcaggca ttagacttca   11400
tcgggcagcc atctacaccg cagagatcca taaaagcctc agcaccaatc tagatgtaac   11460
taactcaatc gagcatcagg tcaaggacgt gctgacacca ctcttcaaaa tcatcggtga   11520
tgaagtgggc ctgaggacac ctcagagatt cactgaccta gtgaaattca tctctgacaa   11580
gattaaattc cttaatccgg ataggggagta cgacttcaga gatctcactt ggtgtatcaa   11640
cccgccagag agaatcaaat tggattatga tcaatactgt gcagatgtgg ctgctgaaga   11700
gctcatgaat gcattggtga actcaactct actggagacc agaacaacca atcagttcct   11760
agctgtctca aagggaaact gctcagggcc cactacaatc agaggtcaat tctcaaacat   11820
gtcgctgtcc ctgttagact tgtatttagg tcgaggttac aatgtgtcat ctatagtcac   11880
tatgacatcc cagggaatgt atgggggaac ttacctagtg gaaaagccta atctgagcag   11940
caaaaggtca gagttgtcac aactgagcat gtaccgagtg tttgaagtag gtgttatcag   12000
aaatccgggt ttgggggctc cggtgttcca tatgacaaac tatcttgagc aaccagccag   12060
taatgatctc agcaactgta tggtggcttt gggggagctc aaactcgcag ccctttgtca   12120
cggggaagat tctatcacaa ttccctatca gggatcaggg aaaggtgtca gcttccagct   12180
cgtcaagcta ggtgtctgga aatccccaac cgacatgcaa tcctgggtcc ccttatcaac   12240
ggatgatcca gtgatagaca ggctttacct ctcatctcac agaggtgtta tcgctgacaa   12300
tcaagcaaaa tgggctgtcc cgacaacacg aacagatgac aagttgcgaa tggagacatg   12360
cttccaacag gcgtgtaagg gtaaaatcca agcactctgc gagaatcccg agtgggcacc   12420
attgaaggat aacaggattc cttcatacgg ggtcttgtct gttgatctga gtctgacagt   12480
tgagcttaaa atcaaaattg cttcgggatt cgggccattg atcacacacg gttcaggggat   12540 ggacctatac aaatccaacc acaacaatgt gtattggctg actatcccgc caatgaagaa   12600
cctagcctta ggtgtaatca acacattgga gtggataccg agattcaagg ttagtcccta   12660
cctcttcaat gtcccaatta aggaagcagg cgaagactgc catgccccaa catacctacc   12720
tgcggaggtg gatggtgatg tcaaactcag ttccaatctg gtgattctac ctggtcaaga   12780
tctccaatat gttttggcaa cctacgatac ttccagggtt gaacatgctg tggtttatta   12840
cgtttacagc ccaggccgct cattttctta cttttatcct tttaggttgc ctataaaggg   12900
ggtccccatc gaattacaag tggaatgctt cacatgggac caaaaactct ggtgccgtca   12960
cttctgtgtg cttgcggact cagaatctgg tggacatatc actcactctg ggatggtggg   13020
catgggagtc agctgcacag tcacccggga agatggaacc aatcgcagat agggctgcta   13080
gtgaaccaat ctcatgatgt cacccagaca tcaggcatac ccactagtgt gaaatagaca   13140
tcagaattaa gaaaaacgta gggtccaagt ggttccccgt tatggactcg ctatctgtca   13200
accagatctt ataccctgaa gttcacctag atagcccgat agttaccaat aagatagtag   13260
ccatcctgga gtatgctcga gtccctcacg cttacagcct ggaggaccct acactgtgtc   13320
agaacatcaa gcaccgccta aaaaacggat tttccaacca aatgattata aacaatgtgg   13380
```

-continued

```
aagttgggaa tgtcatcaag tccaagctta ggagttatcc ggcccactct catattccat    13440
atccaaattg taatcaggat ttatttaaca tagaagacaa agagtcaacg aggaagatcc    13500
gtgaactcct caaaaagggg aattcgctgt actccaaagt cagtgataag gttttccaat    13560
gcttaaggga cactaactca cggcttggcc taggctccga attgagggag gacatcaagg    13620
agaaagttat taacttggga gtttacatgc acagctccca gtggtttgag ccctttctgt    13680
tttggtttac agtcaagact gagatgaggt cagtgattaa atcacaaacc catacttgcc    13740
ataggaggag acacacacct gtattcttca ctggtagttc agttgagttg ctaatctctc    13800
gtgaccttgt tgctataatc agtaaagagt ctcaacatgt atattacctg acatttgaac    13860
tggttttgat gtattgtgat gtcatagagg ggaggttaat gacagagacc gctatgacta    13920
ttgatgctag gtatacagag cttctaggaa gagtcagata catgtggaaa ctgatagatg    13980
gtttcttccc tgcactcggg aatccaactt atcaaattgt agccatgctg gagcctcttt    14040
cacttgctta cctgcagctg agggatataa cagtagaact cagaggtgct ttccttaacc    14100
actgctttac tgaaatacat gatgttcttg accaaaacgg gttttctgat gaaggtactt    14160
atcatgagtt aattgaagct ctagattaca ttttcataac tgatgacata catctgacag    14220
gggagatttt ctcatttttc agaagtttcg gccaccccag acttgaagca gtaacggctg    14280
ctgaaaatgt taggaaatac atgaatcagc ctaaagtcat tgtgtatgag actctgatga    14340
aaggtcatgc catattttgt ggaatcataa tcaacggcta tcgtgacagg cacggaggca    14400
gttggccacc gctgaccctc cccctgcatg ctgcagacac aatccggaat gctcaagctt    14460
caggtgaagg gttaacacat gagcagtgcg ttgataactg gagatctttt gctggagtga    14520
aatttggctg ctttatgcct cttagcctgg atagtgatct gacaatgtac ctaaaggaca    14580
aggcacttgc tgctctccaa agggaatggg attcagttta cccgaaagag ttcctgcgtt    14640
acgaccctcc caagggaacc gggtcacgga ggcttgtaga tgttttcctt aatgattcga    14700
gctttgaccc atatgatgtg ataatgtatg ttgtaagtgg agcttacctc catgaccctg    14760
agttcaacct gtcttacagc ctgaaagaaa aggagatcaa ggaaacaggt agacttttg    14820 ctaaaatgac ttacaaaatg agggcatgcc aagtgattgc tgaaaatcta atctcaaacg    14880
ggattggcaa atattttaag gacaatggga tggccaagga tgagcacgat ttgactaagg    14940
cactccacac tctagctgtc tcaggagtcc ccaaagatct caaagaaagt cacaggggg    15000 ggccagtctt aaaaacctac tcccgaagcc cagtccacac aagtaccagg aacgtgagag    15060
cagcaaaagg gtttataggg ttccctcaag taattcggca ggaccaagac actgatcatc    15120
cggagaatat ggaagcttac gagacagtca gtgcatttat cacgactgat ctcaagaagt    15180
actgccttaa ttggagatat gagaccatca gcttgtttgc acagaggcta aatgagattt    15240
acggattgcc ctcattttc cagtggctgc ataagaggct tgagacctct gtcctgtatg    15300
taagtgaccc tcattgccc cccgaccttg acgcccatat cccgttatat aaagtcccca    15360
atgatcaaat cttcattaag taccctatgg gaggtataga agggtattgt cagagctgt    15420 ggaccatcag caccattccc tatctatacc tggctgctta tgagagcgga gtaaggattg    15480
cttcgttagt gcaaggggac aatcagacca tagccgtaac aaaaaggta cccagcacat    15540 ggcccta caa ccttaagaaa cgggaagctg ctagagtaac tagagattac tttgtaattc    15600
ttaggcaaag gctacatgat attggccatc acctcaaggc aaatgagaca attgtttcat    15660 cacattttt tgtctattca aaaggaatat attatgatgg gctacttgtg tcccaatcac    15720
tcaagagcat cgcaagatgt gtattctggt cagagactat agttgatgaa acaagggcag    15780
```

-continued

```
catgcagtaa tattgctaca acaatggcta aaagcatcga gagaggttat gaccgttacc   15840
ttgcatattc cctgaacgtc ctaaaagtga tacagcaaat tctgatctct cttggcttca   15900
caatcaattc aaccatgacc cgggatgtag tcatacccct cctcacgaac aacgacctct   15960
taataaggat ggcactgttg cccgctccta ttggggggat gaattatctg aatatgagca   16020
ggctgtttgt cagaaacatc ggtgatccag taacatcatc aattgctgat ctcaagagaa   16080
tgattctcgc ctcactaatg cctgaagaga ccctccatca agtaatgaca caacaaccgg   16140
gggactcttc attcctagac tgggctagcg acccttactc agcaaatctt gtatgtgtcc   16200
agagcatcac tagactcctc aagaacataa ctgcaaggtt tgtcctgatc catagtccaa   16260
acccaatgtt aaaaggatta ttccatgatg acagtaaaga agaggacgag ggactggcgg   16320
cattcctcat ggacaggcat attatagtac ctagggcagc tcatgaaatc ctggatcata   16380
gtgtcacagg ggcaagagag tctattgcag gcatgctgga taccacaaaa ggcctgattc   16440
gagccagcat gaggaagggg gggttaacct ctcgagtgat aaccagattg tccaattatg   16500
actatgaaca attcagagca gggatggtgc tattgacagg aagaaagaga aatgtcctca   16560
ttgacaaaga gtcatgttca gtgcagctgg cgagagctct aagaagccat atgtgggcga   16620
ggctagctcg aggacggcct atttacggcc ttgaggtccc tgatgtacta gaatctatgc   16680
gaggccacct tattcggcgt catgagacat gtgtcatctg cgagtgtgga tcagtcaact   16740
acggatggtt ttttgtcccc tcgggttgcc aactggatga tattgacaag gaaacatcat   16800
ccttgagagt cccatatatt ggttctacca ctgatgagag aacagacatg aagcttgcct   16860
tcgtaagagc cccaagtcga tccttgcgat ctgctgttag aatagcaaca gtgtactcat   16920
gggcttacgg tgatgatgat agctcttgga acgaagcctg gttgttggct aggcaaaggg   16980
ccaatgtgag cctggaggag ctaagggtga tcactcccat ctcaacttcg actaatttag   17040
cgcataggtt gagggatcgt agcactcaag tgaaatactc aggtacatcc cttgtccgag   17100
tggcgaggta taccacaatc tccaacgaca atctctcatt tgtcatatca gataagaagg   17160
ttgatactaa ctttatatac caacaaggaa tgcttctagg gttgggtgtt ttagaaacat   17220
tgtttcgact cgagaaagat accggatcat ctaaacacggt attacatctt cacgtcgaaa   17280
cagattgttg cgtgatcccg atgatagatc atcccaggat acccagctcc cgcaagctag   17340
agctgagggc agagctatgt accaacccat tgatatatga taatgcacct ttaattgaca   17400
gagatacaac aaggctatac acccagagcc ataggaggca ccttgtggaa tttgttacat   17460
ggtccacacc ccaactatat cacattttag ctaagtccac agcactatct atgattgacc   17520
tggtaacaaa atttgagaag gaccatatga atgaaatttc agctctcata ggggatgacg   17580
atatcaatag tttcataact gagtttctgc tcatagagcc aagattattc actatctact   17640
tgggccagtg tgcggccatc aattgggcat ttgatgtaca ttatcataga ccatcaggga   17700
aatatcagat gggtgagctg ttgtcatcgt tcctttctag aatgagcaaa ggagtgttta   17760
aggtgcttgt caatgctcta agccacccaa agatctacaa gaaattctgg cattgtggta   17820
ttatagagcc tatccatggt ccttcacttg atgctcaaaa cttgcacaca actgtgtgca   17880
acatggttta cacatgctat atgacctacc tcgacctgtt gttgaatgaa gagttagaag   17940
agttcacatt tctcttgtgt gaaagcgacg aggatgtagt accggacaga ttcgacaaca   18000
tccaggcaaa acacttatgt gttctggcag atttgtactg tcaaccaggg acctgcccac   18060
caattcgagg tctaagaccg gtagagaaat gtgcagttct aaccgaccat atcaaggcag   18120
```

-continued

```
aggctaggtt atctccagca ggatcttcgt ggaacataaa tccaattatt gtagaccatt   18180
actcatgctc tctgacttat ctccggcgag gatcgatcaa acagataaga ttgagagttg   18240
atccaggatt cattttcgac gccctcgctg aggtaaatgt cagtcagcca aagatcggca   18300
gcaacaacat ctcaaatatg agcatcaagg ctttcagacc cccacacgat gatgttgcaa   18360
aattgctcaa agatatcaac acaagcaagc acaatcttcc catttcaggg ggcaatctcg   18420
ccaattatga aatccatgct ttccgcagaa tcgggttgaa ctcatctgct tgctacaaag   18480
ctgttgagat atcaacatta attaggagat gccttgagcc aggggaggac ggcttgttct   18540
tgggtgaggg atcgggttcc atgttgatca cttataagga gatacttaaa ctaaacaagt   18600
gcttctataa tagtggggtt tccgccaatt ctagatctgg tcaaagggaa ttagcaccct   18660
atccctccga agttggcctt gtcgaacaca gaatgggagt aggtaatatt gtcaaagtgc   18720
tctttaacgg gaggcccgaa gtcacgtggg taggcagtgt agattgcttc aatttcatag   18780
ttagtaatat ccctacctct agtgtggggt ttatccattc agatatagag accttgccta   18840
acaaagatac tatagagaag ctagaggaat tggcagccat cttatcgatg gctctgctcc   18900
tgggcaaaat aggatcaata ctggtgatta agcttatgcc tttcagcggg gattttgttc   18960
agggatttat aagttatgta gggtcccatt atagagaagt gaaccttgta taccctagat   19020
acagcaactt catatctact gaatcttatt tggttatgac agatctcaag gctaaccggc   19080
taatgaatcc tgaaaagatt aagcagcaga taattgaatc atctgtgagg acttcacctg   19140
gacttatagg tcacatccta tccattaagc aactaagctg catacaagca attgtgggag   19200
acgcagttag tagaggtgat atcaatccta ctctgaaaaa acttacacct atagagcagg   19260
tgctgatcaa ttgcgggttg gcaattaacg gacctaagct gtgcaaagaa ttgatccacc   19320
atgatgttgc ctcagggcaa gatggattgc ttaattctat actcatcctc tacagggagt   19380
tggcaagatt caaagacaac caaagaagtc aacaagggat gttccacgct taccccgtat   19440
tggtaagtag caggcaacga gaacttatat ctaggatcac ccgcaaattt tgggggcaca   19500
ttcttcttta ctccgggaac agaaagttga taaataagtt tatccagaat ctcaagtccg   19560
gctatctgat actagactta caccagaata tcttcgttaa gaatctatcc aagtcagaga   19620
aacagattat tatgacgggg ggtttgaaac gtgagtgggt ttttaaggta acagtcaagg   19680
agaccaaaga atggtataag ttagtcggat acagtgccct gattaaggac taattggttg   19740
aactccggaa ccctaatcct gccctaggtg gttaggcatt atttgcaata gattaaagaa   19800
aactttgaaa atacgaagtt tctattccca gctttgtctg gtggccggca tggtcccagc   19860
ctcctcgctg gcgccggctg ggcaacattc cgaggggacc gtccctcgg taatggcgaa   19920 tgggacgcgg ccgatccggc tgctaacaaa gcccgaaagg aagctgagtt ggctgctgcc   19980
accgctgagc aataactagc ataaccccctt ggggcctcta aacgggtctt gaggggtttt   20040
ttgctgaaag gaggaactat atccggatgc ggccgatccg gctgctaaca aagcccgaaa   20100
ggaagctgag ttggctgctg ccaccgctga gcaataacta gcataacccc ttggggcctc   20160
taaacgggtc ttgaggggtt ttttgctgaa aggaggaact atatccggat ggccgccacc   20220
ggccggtggg ccttgcagca catccccctt tcgccagctg gcgtaatagc gaagaggccc   20280
gcaccgatcg cccttcccaa cagttgcgca gcctgaatgg cgaatgggac gcgccctgta   20340
gcggcgcatt aagcgcggcg ggtgtggtgg ttacgcgcag cgtgaccgct acacttgcca   20400
gcgccctagc gcccgctcct ttcgctttct tcccttcctt tctcgccacg ttcgccggct   20460
ttccccgtca agctctaaat cggggggctcc ctttagggtt ccgatttagt gctttacggc   20520
```

-continued

```
acctcgaccc caaaaaactt gattagggtg atggttcacg tgggccatcg ccctgataga  20580 cggttttcg ccctttgacg ttggagtcca cgttctttaa tagtggactc ttgttccaaa   20640
ctggaacaac actcaaccct atctcggtct attcttttga tttataaggg attttgccga   20700
tttcggccta ttggttaaaa aatgagctga tttaacaaaa atttaacgcg aattttaaca   20760
aaatattaac gcttacaatt taggtggcac ttttcgggga aatgtgcgcg gaacccctat   20820
ttgtttattt ttctaaatac attcaaatat gtatccgctc atgagacaat aaccctgata   20880
aatgcttcaa taatattgaa aaaggaagag tatgagtatt caacatttcc gtgtcgccct   20940
tattcccttt tttgcggcat tttgccttcc tgtttttgct cacccagaaa cgctggtgaa   21000
agtaaaagat gctgaagatc agttgggtgc acgagtgggt tacatcgaac tggatctcaa   21060
cagcggtaag atccttgaga gttttcgccc cgaagaacgt tttccaatga tgagcacttt   21120
taaagttctg ctatgtggcg cggtattatc ccgtattgac gccgggcaag agcaactcgg   21180
tcgccgcata cactattctc agaatgactt ggttgagtac tcaccagtca cagaaaagca   21240
tcttacggat ggcatgacag taagagaatt atgcagtgct gccataacca tgagtgataa   21300
cactgcggcc aacttacttc tgacaacgat cggaggaccg aaggagctaa ccgcttttt    21360 gcacaacatg ggggatcatg taactcgcct tgatcgttgg gaaccggagc tgaatgaagc   21420
cataccaaac gacgagcgtg acaccacgat gcctgtagca atggcaacaa cgttgcgcaa   21480
actattaact ggcgaactac ttacactagc ttcccggcaa caattaatag actggatgga   21540
ggcggataaa gttgcaggac cacttctgcg ctcggccctt ccggctggct ggtttattgc   21600
tgataaatct ggagccggtg agcgtgggtc tcgcggtatc attgcagcac tggggccaga   21660
tggtaagccc tcccgtatcg tagttatcta cacgacgggg agtcaggcaa ctatggatga   21720
acgaaataga cagatcgctg agataggtgc ctcactgatt aagcattggt aactgtcaga   21780
ccaagtttac tcatatatac tttagattga tttaaaactt catttttaat ttaaaaggat   21840
ctaggtgaag atcctttttg ataatctcat gaccaaaatc ccttaacgtg agttttcgtt   21900
ccactgagcg tcagaccccg tagaaaagat caaaggatct tcttgagatc cttttttttct  21960 gcgcgtaatc tgctgcttgc aaacaaaaaa accaccgcta ccagcggtgg tttgtttgcc   22020
ggatcaagag ctaccaactc tttttccgaa ggtaactggc ttcagcagag cgcagatacc   22080
aaatactgtt cttctagtgt agccgtagtt aggccaccac ttcaagaact ctgtagcacc   22140
gcctacatac ctcgctctgc taatcctgtt accagtggct gctgccagtg gcgataagtc   22200
gtgtcttacc gggttggact caagacgata gttaccggat aaggcgcagc ggtcgggctg   22260
aacggggggt tcgtgcacac agcccagctt ggagcgaacg acctacaccg aactgagata   22320
cctacagcgt gagctatgag aaagcgccac gcttcccgaa gggagaaagg cggacaggta   22380
tccggtaagc ggcagggtcg aacaggaga gcgcacgagg gagcttccag ggggaaacgc     22440
ctggtatctt tatagtcctg tcgggtttcg ccacctctga cttgagcgtc gatttttgtg   22500
atgctcgtca gggggggcgga gcctatggaa aaacgccagc aacgcggcct ttttacggtt   22560
cctggccttt tgctggcctt ttgctcacat gttctttcct gcgttatccc ctgattctgt   22620
ggataaccgt attaccgcct ttgagtgagc tgataccgct cgccgcagcc gaacgaccga   22680
gcgcagcgag tcagtgagcg aggaagcgga agagcgccca atacgcaaac cgcctctccc   22740
cgcgcgttgg ccgattcatt aatgcagctg gcacgacagg tttcccgact ggaaagcggg   22800
cagtgagcgc aacgcaatta atgtgagtta gctcactcat taggcacccc aggctttaca   22860
```

-continued

```
ctttatgctt ccggctcgta tgttgtgtgg aattgtgagc ggacaacaat ttcacacagg   22920
aaacagctat gaccatgatt acgccaagct cgggcggccg cttgtaatac gactcactat   22980
a                                                                    22981
```

<210> SEQ ID NO 16
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO

<400> SEQUENCE: 16

```
accaaacaaa gttgggtaag gatagttcaa tcaatgatca ttttctagtg cacttaggat     60
tcaagatcct attatcaggg acaagagcag gattaaggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtcaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcga gaacaaggaa atctcagata ttgaagtgca agaccctgag ggattcaaca    600
tgattctggg taccatccta gctcaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg aacttgaaa    1140 actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttggggggca aggaagatat gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc tatagtgta caatgacaga aatcttctag    1680
actaggtgcg agaggccgag gaccagaaca acatccgcct accctccatc attgttataa   1740
aaaacttagg aaccaggtcc acacagccgc cagcccatca accatccact cccacgattg   1800
```

-continued

```
gagccgatgg cagaagagca ggcacgccat gtcaaaaacg gactggaatg catccgggct      1860
ctcaaggccg agcccatcgg ctcactggcc atcgaggaag ctatggcagc atggtcagaa      1920
atatcagaca acccaggaca ggagcgagcc acctgcaggg aagagaaggc aggcagttcg      1980
ggtctcagca aaccatgcct ctcagcaatt ggatcaactg aaggcggtgc acctcgcatc      2040
cgcggtcagg gacctggaga gagcgatgac gacgctgaaa ctttgggaat cccccaaga      2100 aatctccagc atcaagcac tgggttacag tgttattatg tttatgatca cagcggtgaa      2160
gcggttaagg gaatccaaga tgctgactct atcatggttc aatcaggcct tgatggtgat      2220
agcaccctct caggaggaga caatgaatct gaaaacagcg atgtggatat tggcgaacct      2280
gataccgagg gatatgctat cactgaccgg ggatctgctc ccatctctat ggggttcagg      2340
gcttctgatg ttgaaactgc agaaggaggg gagatccacg agctcctgag actccaatcc      2400
agaggcaaca actttccgaa gcttgggaaa actctcaatg ttcctccgcc tccggacccc      2460
ggtagggcca gcacttccgg gacacccatt aaaaagggca cagacgcgag attagcctca      2520
tttggaacgg agatcgcgtc tttattgaca ggtggtgcaa cccaatgtgc tcgaaagtca      2580
ccctcggaac catcagggcc aggtgcacct gcggggaatg tccccgagtg tgtgagcaat      2640
gccgcactga tacaggagtg gacacccgaa tctggtacca caatctcccc gagatcccag      2700
aataatgaag aaggggggaga ctattatgat gatgagctgt tctctgatgt ccaagatatt      2760
aaaacagcct tggccaaaat acacgaggat aatcagaaga taatctccaa gctagaatca      2820
ctgctgttat tgaagggaga agttgagtca attaagaagc agatcaacag gcaaaatatc      2880
agcatatcca ccctggaagg acacctctca agcatcatga tcgccattcc tggacttggg      2940
aaggatccca acgaccccac tgcagatgtc gaaatcaatc ccgacttgaa acccatcata      3000
ggcagagatt caggccgagc actggccgaa gttctcaaga aacccgttgc cagccgacaa      3060
ctccaaggaa tgacaaatgg acggaccagt tccagaggac agctgctgaa ggaatttcag      3120
ctaaagccga tcgggaaaaa gatgagctca gccgtcgggt ttgttcctga caccggccct      3180
gcatcacgca gtgtaatccg ctccattata aaatccagcc ggctagagga ggatcggaag      3240
cgttacctga tgactctcct tgatgatatc aaaggagcca atgatcttgc caagttccac      3300
cagatgctga tgaagataat aatgaagtag ctacagctca acttacctgc caaccccatg      3360
ccagtcgacc caactagtac aacctaaatc cattataaaa aacttaggag caaagtgatt      3420
gcctcccaag ttccacaggc gcgccatgtt cgtcttcctg gtcctgctgc ctctggtctc      3480
ctcacagtgc gtcaatctga caactcggac tcagctgcca cctgcttata ctaatagctt      3540
caccagaggc gtgtactatc ctgacaaggt gtttagaagc tccgtgctgc actctacaca      3600
ggatctgttt ctgccattct ttagcaacgt gacctggttc cacgccatcc acgtgagcgg      3660
caccaatggc acaaagcggt tcgacaatcc cgtgctgcct tttaacgatg gcgtgtactt      3720
cgcctctacc gagaagagca acatcatcag aggctggatc tttggcacca cactggactc      3780
caagacacag tctctgctga tcgtgaacaa tgccaccaac gtggtcatca aggtgtgcga      3840
gttccagttt tgtaatgatc ccttcctggg cgtgtactat cacaagaaca ataagagctg      3900
gatggagtcc gagtttagag tgtattctag cgccaacaac tgcacatttg agtacgtgag      3960
ccagcctttc ctgatggacc tggagggcaa gcagggcaat ttcaagaacc tgagggagtt      4020
cgtgtttaag aatatcgacg gctacttcaa aatctactct aagcacaccc ccatcaacct      4080
ggtgcgcgac ctgcctcagg gcttcagcgc cctggagccc ctggtggatc tgcctatcgg      4140
```

-continued

```
catcaacatc acccggtttc agacactgct ggccctgcac agaagctacc tgacacccgg   4200
cgactcctct agcggatgga ccgccggcgc tgccgcctac tatgtgggct acctccagcc   4260
ccggaccttc ctgctgaagt acaacgagaa tggcaccatc acagacgcag tggattgcgc   4320
cctggacccc ctgagcgaga caaagtgtac actgaagtcc tttaccgtgg agaagggcat   4380
ctatcagaca tccaatttca gggtgcagcc aaccgagtct atcgtgcgct ttcctaatat   4440
cacaaacctg tgcccatttg gcgaggtgtt caacgcaacc cgcttcgcca gcgtgtacgc   4500
ctggaatagg aagcggatca gcaactgcgt ggccgactat agcgtgctgt acaactccgc   4560
ctctttcagc acctttaagt gctatggcgt gtcccccaca aagctgaatg acctgtgctt   4620
taccaacgtc tacgccgatt ctttcgtgat caggggcgac gaggtgcgcc agatcgcccc   4680
cggccagaca ggcaagatcg cagactacaa ttataagctg ccagacgatt tcaccggctg   4740
cgtgatcgcc tggaacagca acaatctgga ttccaaagtg ggcggcaact acaattatct   4800
gtaccggctg tttagaaaga gcaatctgaa gcccttcgag agggacatct ctacagaaat   4860
ctaccaggcc ggcagcaccc cttgcaatgg cgtggagggc tttaactgtt atttcccact   4920
ccagtcctac ggcttccagc ccacaaacgg cgtgggctat cagccttacc gcgtggtggt   4980
gctgagcttt gagctgctgc acgccccagc aacagtgtgc ggccccaaga agtccaccaa   5040
tctggtgaag aacaagtgcg tgaacttcaa cttcaacggc ctgaccggca caggcgtgct   5100
gaccgagtcc aacaagaagt tcctgccatt tcagcagttc ggcagggaca tcgcagatac   5160
cacagacgcc gtgcgcgacc cacagaccct ggagatcctg gacatcacac cctgctcttt   5220
cggcggcgtg agcgtgatca cacccggcac caatacaagc aaccaggtgg ccgtgctgta   5280
tcaggacgtg aattgtaccg aggtgcccgt ggctatccac gccgatcagc tgaccccaac   5340
atggcgggtg tacagcaccg gctccaacgt cttccagaca agagccggat gcctgatcgg   5400
agcagagcac gtgaacaatt cctatgagtg cgacatccca atcggcgccg gcatctgtgc   5460
ctcttaccag acccagacaa actctcccag aagagcccgg agcgtggcct cccagtctat   5520
catcgcctat accatgtccc tgggcgccga aacagcgtg gcctactcta acaatagcat   5580
cgccatccca accaacttca caatctctgt gaccacagag atcctgcccg tgtccatgac   5640
caagacatct gtggactgca caatgtatat ctgtggcgat tctaccgagt gcagcaacct   5700
gctgctccag tacggcagct tttgtaccca gctgaataga gccctgacag catcgccgt   5760 ggagcaggat aagaacacac aggaggtgtt cgcccaggtg aagcaaatct acaagacccc   5820
ccctatcaag gactttggcg gcttcaattt ttcccagatc ctgcctgatc catccaagcc   5880
ttctaagcgg agctttatcg aggacctgct gttcaacaag gtgaccctgg ccgatgccgg   5940
cttcatcaag cagtatggcg attgcctggg cgacatcgca gccagggacc tgatctcgc   6000 ccagaagttt aatggcctga ccgtgctgcc accctgctg acagatgaga tgatcgcaca   6060
gtacacaagc gccctgctgg ccggcaccat cacatccgga tggaccttcg gcgcaggagc   6120
cgccctccag atccccctttg ccatgcagat ggcctatagg ttcaacggca tcggcgtgac   6180
ccagaatgtg ctgtacgaga accagaagct gatcgccaat cagtttaact ccgccatcgg   6240
caagatccag gacagcctgt cctctacagc cagcgccctg ggcaagctcc aggatgtggt   6300
gaatcagaac gcccaggccc tgaataccct ggtgaagcag ctgagcagca acttcggcgc   6360
catctctagc gtgctgaatg acatcctgag ccggctggac aaggtggagg cagaggtgca   6420
gatcgaccgc ctgatcaccg gccggctcca gagcctccag acctatgtga cacagcagct   6480
gatcagggcc gccgagatca gggccagcgc caatctggca gcaaccaaga gtgtccgagtg   6540
```

-continued

```
cgtgctgggc cagtctaaga gagtggactt ttgtggcaag ggctatcacc tgatgtcctt   6600
ccctcagtct gccccacacg gcgtggtgtt tctgcacgtg acctacgtgc ccgcccagga   6660
gaagaacttc accacagccc ctgccatctg ccacgatggc aaggcccact ttccaaggga   6720
gggcgtgttc gtgtccaacg gcacccactg gtttgtgaca cagcgcaatt tctacgagcc   6780
ccagatcatc accacagaca acaccttcgt gagcggcaac tgtgacgtgg tcatcggcat   6840
cgtgaacaat accgtgtatg atccactcca gcccgagctg gacagcttta aggaggagct   6900
ggataagtat ttcaagaatc acacctcccc tgacgtggat ctgggcgaca tcagcggcat   6960
caatgcctcc gtggtgaaca tccagaagga gatcgaccgc ctgaacgagg tggctaagaa   7020
tctgaacgag agcctgatcg acctccagga gctgggcaag tatgagcagt acatcaagtg   7080
gccctggtac atctggctgg gcttcatcgc cggcctgatc gccatcgtga tggtgaccat   7140
catgctgtgc tgtatgacat cctgctgttc ttgcctgaag ggctgctgta gctgtggctc   7200
ctgctgtaag tttgacgagg atgactctga acctgtgctg aagggcgtga agctgcatta   7260
cacctaacgc gcgacgtcct acagctcaac ttacctgcca accccatgcc agtcgaccca   7320
actagtacaa cctaaatcca ttataaaaaa cttaggagca aagtgattgc ctcccaagtt   7380
ccacaatgac agagatctac gacttcgaca agtcggcatg ggacatcaaa gggttgatcg   7440
ctccgataca acccaccacc tacagtgatg gcaggctggt gccccaggtc agagtcatag   7500
atcctggtct aggcgacagg aaggatgaat gctttatgta catgtttctg ctggggggttg   7560 ttgaggacag cgatccccta gggcctccaa tcgggcgagc atttgggtcc ctgcccttag   7620
gtgttggcag atccacagca aagcccgaaa aactcctcaa agaggccact gagcttgaca   7680
tagttgttag acgtacagca gggctcaatg aaaaactggt gttctacaac aacaccccac   7740
taactctcct cacaccttgg agaaaggtcc taacaacagg gagtgtcttc aacgcaaacc   7800
aagtgtgcaa tgcggttaat ctgataccgc tcgataccccc gcagaggttc cgtgttgttt   7860
atatgagcat caccgtctt tcggataacg ggtattacac cgttcctaga agaatgctgg   7920
aattcagatc ggtcaatgca gtggccttca acctgctggt gaccccttagg attgacaagg   7980 cgataggccc tgggaagatc atcgacaata cagagcaact tcctgaggca acatttatgg   8040
tccacatcgg gaacttcagg agaaagaaga gtgaagtcta ctctgccgat tattgcaaaa   8100
tgaaaatcga aaagatgggc ctggtttttg cacttggtgg gatagggggc accagtcttc   8160
acattagaag cacaggcaaa atgagcaaga ctctccatgc acaactcggg ttcaagaaga   8220
ccttatgtta cccgctgata gatatcaatg aagaccttaa tcgattactc tggaggagca   8280
gatgcaagat agtaagaatc caggcagttt tgcagccatc agttcctcaa gaattccgca   8340
tttacgacga cgtgatcata aatgatgacc aaggactatt caaagttctg tagaccgtag   8400
tgcccagcaa tgcccgaaaa cgaccccct cacaatgaca gccagaaggc ccggacaaaa   8460 aagcccctc cgaaagactc cacgaccaa gcgagaggcc agccagcagc cgacggcaag   8520
cgcgaacacc aggcggcccc agcacagaac agccctgata caaggccacc accagccacc   8580
ccaatctgca tcctcctcgt gggaccccccg aggaccaacc cccaaggctg ccccgatcc   8640 aaaccaccaa ccgcatcccc accaccccg ggaaagaaac ccccagcaat tggaaggccc   8700
ctccccctct tcctcaacac aagaactcca caaccgaacc gcacaagcga ccgaggtgac   8760
ccaaccgcag gcatccgact ccctagacag atcctctctc cccggcaaac taaacaaaac   8820
ttagggccaa ggaacataca cacccaacag aacccagacc ccggcccacg gcgccgcgcc   8880
```

-continued

```
cccaacccc gacaaccaga gggagccccc aaccaatccc gccggctccc ccggtgccca   8940
caggcaggga caccaacccc cgaacagacc cagcacccaa ccatcgacaa tccaagacgg   9000
gggggccccc ccaaaaaaag gcccccaggg gccgacagcc agcaccgcga ggaagcccac   9060
ccaccccaca cacgaccacg gcaaccaaac cagaacccag accaccctgg gccaccagct   9120
cccagactcg gccatcaccc cgcagaaagg aaaggccaca acccgcgcac cccagccccg   9180
atccggcggg gagccaccca acccgaacca gcacccaaga gcgatccccg aaggacccc   9240 gaaccgcaaa ggacatcagt atcccacagc ctctccaagt cccccggtct cctccccttc   9300
tcgaagggac caaaagatca atccaccaca cccgacgaca ctcaactccc cacccctaaa   9360
ggagacaccg ggaatcccag aatcaagact catccaatgt ccatcatggg tctcaaggtg   9420
aacgtctctg ccatattcat ggcagtactg ttaactctcc aaacacccac cggtcaaatc   9480 cattgggggca atctctctaa gatagggggtg gtaggaatag gaagtgcaag ctacaaagtt   9540
atgactcgtt ccagccatca atcattagtc ataaaattaa tgcccaatat aactctcctc   9600
aataactgca cgagggtaga gattgcagaa tacaggagac tactgagaac agttttggaa   9660
ccaattagag atgcacttaa tgcaatgacc cagaatataa gaccggttca gagtgtagct   9720
tcaagtagga gacacaagag atttgcggga gtagtcctgg caggtgcggc cctaggcgtc   9780
gccacagctg ctcagataac agccggcatt gcacttcacc agtccatgct gaactctcaa   9840
gccatcgaca atctgagagc gagcctggaa actactaatc aggcaattga ggcaatcaga   9900
caagcagggc aggagatgat attggctgtt cagggtgtcc aagactacat caataatgag   9960
ctgataccgt ctatgaacca actatcttgt gatttaatcg gccagaagct cgggctcaaa   10020
ttgctcagat actatacaga aatcctgtca ttatttggcc ccagcttacg ggaccccata   10080
tctgcggaga tatctatcca ggctttgagc tatgcgcttg gaggagacat caataaggtg   10140
ttagaaaagc tcggatacag tggaggtgat ttactgggca tcttagagag cagaggaata   10200
aaggcccgga taactcacgt cgacacagag tcctacttca ttgtcctcag tatagcctat   10260
ccgacgctgt ccgagattaa gggggtgatt gtccaccggc tagagggggt ctcgtacaac   10320
ataggctctc aagagtggta taccactgtg cccaagtatg ttgcaaccca agggtacctt   10380
atctcgaatt ttgatgagtc atcgtgtact ttcatgccag aggggactgt gtgcagccaa   10440
aatgccttgt acccgatgag tcctctgctc caagaatgcc tccgggggtc caccaagtcc   10500
tgtgctcgta cactcgtatc cgggtctttt gggaaccggt tcattttatc acaagggaac   10560
ctaatagcca attgtgcatc aatcctttgc aagtgttaca caacaggaac gatcattaat   10620
caagaccctg acaagatcct aacatacatt gctgccgatc actgcccggt agtcgaggtg   10680
aacggcgtga ccatccaagt cgggagcagg aggtatccag atgctgtgta cttgcacaga   10740
attgacctcg gtcctcccat atcattggag aggttggacg tagggacaaa tctggggaat   10800
gcaattgcta agttggagga tgccaaggaa ttgttggagt catcggacca gatattgagg   10860
agtatgaaag gtttatcgag cactagcata gtctacatcc tgattgcagt gtgtcttgga   10920
gggttgatag ggatccccgc tttaatatgt tgctgcaggg ggcgttgtaa caaaaaggga   10980
gaacaagttg gtatgtcaag accaggccta aagcctgatc ttacgggaac atcaaaatcc   11040
tatgtaaggt cgctctgatc ctctacaact cttgaaacac aaatgtccca caagtctcct   11100
cttcgtcatc aagcaaccac cgcacccagc atcaagccca cctgaaatta tctccggctt   11160
ccctctggcc gaacaatatc ggtagttaat taaaacttag ggtgcaagat catccacaat   11220
gtcaccacaa cgagaccgga taaatgcctt ctacaaagat aacccccatc ccaagggaag   11280
```

```
taggatagtc attaacagag aacatcttat gattgataga ccttatgttt tgctggctgt  11340
tctgtttgtc atgtttctga gcttgatcgg gttgctagcc attgcaggca ttagacttca  11400
tcgggcagcc atctacaccg cagagatcca taaaagcctc agcaccaatc tagatgtaac  11460
taactcaatc gagcatcagg tcaaggacgt gctgacacca ctcttcaaaa tcatcggtga  11520
tgaagtgggc ctgaggacac ctcagagatt cactgaccta gtgaaattca tctctgacaa  11580
gattaaattc cttaatccgg atagggagta cgacttcaga gatctcactt ggtgtatcaa  11640
cccgccagag agaatcaaat tggattatga tcaatactgt gcagatgtgg ctgctgaaga  11700
gctcatgaat gcattggtga actcaactct actggagacc agaacaacca atcagttcct  11760
agctgtctca aagggaaact gctcagggcc cactacaatc agaggtcaat tctcaaacat  11820
gtcgctgtcc ctgttagact tgtatttagg tcgaggttac aatgtgtcat ctatagtcac  11880
tatgacatcc cagggaatgt atgggggaac ttacctagtg gaaaagccta atctgagcag  11940
caaaaggtca gagttgtcac aactgagcat gtaccgagtg tttgaagtag gtgttatcag  12000
aaatccgggt ttgggggctc cggtgttcca tatgacaaac tatcttgagc aaccagccag  12060
taatgatctc agcaactgta tggtggcttt gggggagctc aaactcgcag ccctttgtca  12120
cggggaagat tctatcacaa ttccctatca gggatcaggg aaaggtgtca gcttccagct  12180
cgtcaagcta ggtgtctgga aatccccaac cgacatgcaa tcctgggtcc ccttatcaac  12240
ggatgatcca gtgatagaca ggctttacct ctcatctcac agaggtgtta tcgctgacaa  12300
tcaagcaaaa tgggctgtcc cgacaacacg aacagatgac aagttgcgaa tggagacatg  12360
cttccaacag gcgtgtaagg gtaaaatcca agcactctgc gagaatcccg agtgggcacc  12420
attgaaggat aacaggattc cttcatacgg ggtcttgtct gttgatctga gtctgacagt  12480
tgagcttaaa atcaaaattg cttcgggatt cgggccattg atcacacacg gttcagggat  12540
ggacctatac aaatccaacc acaacaatgt gtattggctg actatcccgc caatgaagaa  12600
cctagcctta ggtgtaatca acacattgga gtggataccg agattcaagg ttagtcccta  12660
cctcttcaat gtcccaatta aggaagcagg cgaagactgc catgccccaa catacctacc  12720
tgcggaggtg gatggtgatg tcaaactcag ttccaatctg gtgattctac ctggtcaaga  12780
tctccaatat gttttggcaa cctacgatac ttccagggtt gaacatgctg tggtttatta  12840
cgtttacagc ccaggccgct cattttctta ctttttatcct tttaggttgc ctataaaggg  12900
ggtccccatc gaattacaag tggaatgctt cacatgggac caaaaactct ggtgccgtca  12960
cttctgtgtg cttgcggact cagaatctgg tggacatatc actcactctg ggatggtggg  13020
catgggagtc agctgcacag tcacccggga agatggaacc aatcgcagat agggctgcta  13080
gtgaaccaat ctcatgatgt cacccagaca tcaggcatac ccactagtgt gaaatagaca  13140
tcagaattaa gaaaaacgta gggtccaagt ggttccccgt tatggactcg ctatctgtca  13200
accagatctt ataccctgaa gttcacctag atagcccgat agttaccaat aagatagtag  13260
ccatcctgga gtatgctcga gtccctcacg cttacagcct ggaggaccct acactgtgtc  13320
agaacatcaa gcaccgccta aaaaacggat tttccaacca aatgattata aacaatgtgg  13380
aagttgggaa tgtcatcaag tccaagctta ggagttatcc ggcccactct catattccat  13440
atccaaattg taatcaggat ttatttaaca tagaagacaa agagtcaacg aggaagatcc  13500
gtgaactcct caaaaagggg aattcgctgt actccaaagt cagtgataag gtttttccaat  13560 gcttaaggga cactaactca cggcttggcc taggctccga attgagggag gacatcaagg  13620
```

-continued

```
agaaagttat taacttggga gtttacatgc acagctccca gtggtttgag ccctttctgt   13680
tttggtttac agtcaagact gagatgaggt cagtgattaa atcacaaacc catacttgcc   13740
ataggaggag acacacacct gtattcttca ctggtagttc agttgagttg ctaatctctc   13800
gtgaccttgt tgctataatc agtaaagagt ctcaacatgt atattacctg acatttgaac   13860 tggtttttgat gtattgtgat gtcatagagg ggaggttaat gacagagacc gctatgacta   13920
ttgatgctag gtatacagag cttctaggaa gagtcagata catgtggaaa ctgatagatg   13980
gtttcttccc tgcactcggg aatccaactt atcaaattgt agccatgctg gagcctcttt   14040
cacttgctta cctgcagctg agggatataa cagtagaact cagaggtgct ttccttaacc   14100
actgctttac tgaaatacat gatgttcttg accaaaacgg gttttctgat gaaggtactt   14160
atcatgagtt aattgaagct ctagattaca ttttcataac tgatgacata catctgacag   14220
gggagatttt ctcattttc agaagtttcg gccaccccag acttgaagca gtaacggctg   14280
ctgaaaatgt taggaaatac atgaatcagc ctaaagtcat tgtgtatgag actctgatga   14340
aaggtcatgc catattttgt ggaatcataa tcaacggcta tcgtgacagg cacggaggca   14400
gttggccacc gctgaccctc cccctgcatg ctgcagacac aatccggaat gctcaagctt   14460
caggtgaagg gttaacacat gagcagtgcg ttgataactg gagatctttt gctggagtga   14520
aatttggctg ctttatgcct cttagcctgg atagtgatct gacaatgtac ctaaaggaca   14580
aggcacttgc tgctctccaa agggaatggg attcagttta cccgaaagag ttcctgcgtt   14640
acgaccctcc caagggaacc gggtcacgga ggcttgtaga tgttttcctt aatgattcga   14700
gctttgaccc atatgatgtg ataatgtatg ttgtaagtgg agcttacctc catgaccctg   14760
agttcaacct gtcttacagc ctgaaagaaa aggagatcaa ggaaacaggt agactttttg   14820
ctaaaatgac ttacaaaatg aggggcatgcc aagtgattgc tgaaaatcta atctcaaacg   14880
ggattggcaa atattttaag gacaatggga tggccaagga tgagcacgat ttgactaagg   14940
cactccacac tctagctgtc tcaggagtcc ccaaagatct caaagaaagt cacagggggg   15000
ggccagtctt aaaaacctac tcccgaagcc cagtccacac aagtaccagg aacgtgagag   15060
cagcaaaagg gtttataggg ttccctcaag taattcggca ggaccaagac actgatcatc   15120
cggagaatat ggaagcttac gagacagtca gtgcatttat cacgactgat ctcaagaagt   15180
actgccttaa ttggagatat gagaccatca gcttgtttgc acagaggcta aatgagattt   15240
acggattgcc ctcattttc cagtggctgc ataagaggct tgagacctct gtcctgtatg   15300
taagtgaccc tcattgcccc cccgaccttg acgcccatat cccgttatat aaagtcccca   15360
atgatcaaat cttcattaag taccctatgg gaggtataga agggtattgt cagaagctgt   15420
ggaccatcag caccattccc tatctatacc tggctgctta tgagagcgga gtaaggattg   15480
cttcgttagt gcaaggggac aatcagacca tagccgtaac aaaaagggta cccagcacat   15540
ggccctacaa ccttaagaaa cgggaagctg ctagagtaac tagagattac tttgtaattc   15600
ttaggcaaag gctacatgat attggccatc acctcaaggc aaatgagaca attgtttcat   15660
cacatttttt tgtctattca aaaggaatat attatgatgg gctacttgtg tcccaatcac   15720
tcaagagcat cgcaagatgt gtattctggt cagagactat agttgatgaa acaagggcag   15780
catgcagtaa tattgctaca acaatggcta aaagcatcga gagaggttat gaccgttacc   15840
ttgcatattc cctgaacgtc ctaaaagtga tacagcaaat tctgatctct cttggcttca   15900
caatcaattc aaccatgacc cgggatgtag tcataccccct cctcacgaac aacgacctct   15960
taataaggat ggcactgttg cccgctccta ttggggggat gaattatctg aatatgagca   16020
```

```
ggctgtttgt cagaaacatc ggtgatccag taacatcatc aattgctgat ctcaagagaa   16080
tgattctcgc ctcactaatg cctgaagaga ccctccatca agtaatgaca caacaaccgg   16140
gggactcttc attcctagac tgggctagcg acccttactc agcaaatctt gtatgtgtcc   16200
agagcatcac tagactcctc aagaacataa ctgcaaggtt tgtcctgatc catagtccaa   16260
acccaatgtt aaaaggatta ttccatgatg acagtaaaga agaggacgag ggactggcgg   16320
cattcctcat ggacaggcat attatagtac ctagggcagc tcatgaaatc ctggatcata   16380
gtgtcacagg ggcaagagag tctattgcag gcatgctgga taccacaaaa ggcctgattc   16440
gagccagcat gaggaagggg gggttaacct ctcgagtgat aaccagattg tccaattatg   16500
actatgaaca attcagagca gggatggtgc tattgacagg aagaaagaga aatgtcctca   16560
ttgacaaaga gtcatgttca gtgcagctgg cgagagctct aagaagccat atgtgggcga   16620
ggctagctcg aggacggcct atttacggcc ttgaggtccc tgatgtacta gaatctatgc   16680
gaggccacct tattcggcgt catgagacat gtgtcatctg cgagtgtgga tcagtcaact   16740
acggatggtt ttttgtcccc tcgggttgcc aactggatga tattgacaag gaaacatcat   16800
ccttgagagt cccatatatt ggttctacca ctgatgagag aacagacatg aagcttgcct   16860
tcgtaagagc cccaagtcga tccttgcgat ctgctgttag aatagcaaca gtgtactcat   16920
gggcttacgg tgatgatgat agctcttgga acgaagcctg gttgttggct aggcaaaggg   16980
ccaatgtgag cctggaggag ctaaggggtga tcactcccat ctcaacttcg actaatttag   17040
cgcataggtt gagggatcgt agcactcaag tgaaatactc aggtacatcc cttgtccgag   17100
tggcgaggta taccacaatc tccaacgaca atctctcatt tgtcatatca gataagaagg   17160
ttgatactaa cttttatatac caacaaggaa tgcttctagg gttgggtgtt ttagaaacat   17220
tgtttcgact cgagaaagat accggatcat ctaacacggt attacatctt cacgtcgaaa   17280
cagattgttg cgtgatcccg atgatagatc atcccaggat acccagctcc cgcaagctag   17340
agctgagggc agagctatgt accaacccat tgatatatga taatgcacct ttaattgaca   17400
gagatacaac aaggctatac acccagagcc ataggaggca ccttgtggaa tttgttacat   17460
ggtccacacc ccaactatat cacattttag ctaagtccac agcactatct atgattgacc   17520
tggtaacaaa atttgagaag gaccatatga atgaaatttc agctctcata ggggatgacg   17580
atatcaatag tttcataact gagtttctgc tcatagagcc aagattattc actatctact   17640
tgggccagtg tgcggccatc aattgggcat ttgatgtaca ttatcataga ccatcaggga   17700
aatatcagat gggtgagctg ttgtcatcgt tcctttctag aatgagcaaa ggagtgttta   17760
aggtgcttgt caatgctcta agccacccaa agatctacaa gaaattctgg cattgtggta   17820
ttatagagcc tatccatggt ccttcacttg atgctcaaaa cttgcacaca actgtgtgca   17880 acatggtttta cacatgctat atgacctacc tcgacctgtt gttgaatgaa gagttagaag   17940
agttcacatt tctcttgtgt gaaagcgacg aggatgtagt accggacaga ttcgacaaca   18000
tccaggcaaa acacttatgt gttctggcag atttgtactg tcaaccaggg acctgcccac   18060
caattcgagg tctaagaccg gtagagaaat gtgcagttct aaccgaccat atcaaggcag   18120
aggctaggtt atctccagca ggatcttcgt ggaacataaa tccaattatt gtagaccatt   18180
actcatgctc tctgacttat ctccggcgag gatcgatcaa acagataaga ttgagagttg   18240
atccaggatt cattttcgac gccctcgctg aggtaaatgt cagtcagcca aagatcggca   18300
gcaacaacat ctcaaatatg agcatcaagg ctttcagacc cccacacgat gatgttgcaa   18360
```

-continued

```
aattgctcaa agatatcaac acaagcaagc acaatcttcc catttcaggg ggcaatctcg   18420
ccaattatga aatccatgct ttccgcagaa tcgggttgaa ctcatctgct tgctacaaag   18480
ctgttgagat atcaacatta attaggagat gccttgagcc aggggaggac ggcttgttct   18540
tgggtgaggg atcgggttcc atgttgatca cttataagga gatacttaaa ctaaacaagt   18600
gcttctataa tagtggggtt tccgccaatt ctagatctgg tcaaagggaa ttagcaccct   18660
atccctccga agttggcctt gtcgaacaca gaatgggagt aggtaatatt gtcaaagtgc   18720
tctttaacgg gaggcccgaa gtcacgtggg taggcagtgt agattgcttc aatttcatag   18780
ttagtaatat ccctacctct agtgtggggt ttatccattc agatatagag accttgccta   18840
acaaagatac tatagagaag ctagaggaat tggcagccat cttatcgatg gctctgctcc   18900
tgggcaaaat aggatcaata ctggtgatta agcttatgcc tttcagcggg gattttgttc   18960
agggatttat aagttatgta gggtcccatt atagagaagt gaaccttgta taccctagat   19020
acagcaactt catatctact gaatcttatt tggttatgac agatctcaag gctaaccggc   19080
taatgaatcc tgaaaagatt aagcagcaga taattgaatc atctgtgagg acttcacctg   19140
gacttatagg tcacatccta tccattaagc aactaagctg catacaagca attgtgggag   19200
acgcagttag tagaggtgat atcaatccta ctctgaaaaa acttacacct atagagcagg   19260
tgctgatcaa ttgcgggttg gcaattaacg gacctaagct gtgcaaagaa ttgatccacc   19320
atgatgttgc ctcagggcaa gatgggattgc ttaattctat actcatcctc tacagggagt   19380
tggcaagatt caaagacaac caaagaagtc aacaagggat gttccacgct taccccgtat   19440
tggtaagtag caggcaacga gaacttatat ctaggatcac ccgcaaattt tgggggcaca   19500 ttcttctta ctccgggaac agaaagttga taaataagtt tatccagaat ctcaagtccg   19560
gctatctgat actagactta caccagaata tcttcgttaa gaatctatcc aagtcagaga   19620
aacagattat tatgacgggg ggtttgaaac gtgagtgggt ttttaaggta acagtcaagg   19680
agaccaaaga atggtataag ttagtcggat acagtgccct gattaaggac taattggttg   19740
aactccggaa ccctaatcct gccctaggtg gttaggcatt atttgcaata gattaaagaa   19800
aactttgaaa atacgaagtt tctattccca gctttgtctg gtggccggca tggtcccagc   19860
ctcctcgctg gcgccggctg ggcaacattc cgaggggacc gtcccctcgg taatggcgaa   19920
tgggacgcgg ccgatccggc tgctaacaaa gcccgaaagg aagctgagtt ggctgctgcc   19980
accgctgagc aataactagc ataaccccct ggggcctcta aacgggtctt gaggggtttt   20040
ttgctgaaag gaggaactat atccggatgc ggccgatccg gctgctaaca aagcccgaaa   20100
ggaagctgag ttggctgctg ccaccgctga gcaataacta gcataacccc ttggggcctc   20160
taaacgggtc ttgagggggtt ttttgctgaa aggaggaact atatccggat ggccgccacc   20220
ggccggtggg ccttgcagca catcccccct tcgccagctg gcgtaatagc gaagaggccc   20280
gcaccgatcg cccttcccaa cagttgcgca gcctgaatgg cgaatgggac gcgccctgta   20340
gcggcgcatt aagcgcggcg ggtgtggtgg ttacgcgcag cgtgaccgct acacttgcca   20400
gcgccctagc gcccgctcct ttcgctttct tcccttcctt tctcgccacg ttcgccggct   20460
ttccccgtca agctctaaat cggggggctcc ctttagggtt ccgatttagt gctttacggc   20520
acctcgaccc caaaaaactt gattagggtg atggttcacg tgggccatcg ccctgataga   20580
cggtttttcg cccttt gacg ttggagtcca cgttctttaa tagtggactc ttgttccaaa   20640
ctggaacaac actcaaccct atctcggtct attcttttga tttataaggg attttgccga   20700
tttcggccta ttggttaaaa aatgagctga tttaacaaaa atttaacgcg aatttttaaca   20760
```

-continued

```
aaatattaac gcttacaatt taggtggcac ttttcgggga aatgtgcgcg gaacccctat    20820
ttgtttattt ttctaaatac attcaaatat gtatccgctc atgagacaat aaccctgata    20880
aatgcttcaa taatattgaa aaaggaagag tatgagtatt caacatttcc gtgtcgccct    20940
tattcccttt tttgcggcat tttgccttcc tgttttttgct cacccagaaa cgctggtgaa    21000
agtaaaagat gctgaagatc agttgggtgc acgagtgggt tacatcgaac tggatctcaa    21060
cagcggtaag atccttgaga gttttcgccc cgaagaacgt tttccaatga tgagcacttt    21120
taaagttctg ctatgtggcg cggtattatc ccgtattgac gccgggcaag agcaactcgg    21180
tcgccgcata cactattctc agaatgactt ggttgagtac tcaccagtca cagaaaagca    21240
tcttacggat ggcatgacag taagagaatt atgcagtgct gccataacca tgagtgataa    21300
cactgcggcc aacttacttc tgacaacgat cggaggaccg aaggagctaa ccgctttttt    21360
gcacaacatg ggggatcatg taactcgcct tgatcgttgg gaaccggagc tgaatgaagc    21420
cataccaaac gacgagcgtg acaccacgat gcctgtagca atggcaacaa cgttgcgcaa    21480
actattaact ggcgaactac ttacactagc ttcccggcaa caattaatag actggatgga    21540
ggcggataaa gttgcaggac cacttctgcg ctcggccctt ccggctggct ggtttattgc    21600
tgataaatct ggagccggtg agcgtgggtc tcgcggtatc attgcagcac tggggccaga    21660
tggtaagccc tcccgtatcg tagttatcta cacgacgggg agtcaggcaa ctatggatga    21720
acgaaataga cagatcgctg agataggtgc ctcactgatt aagcattggt aactgtcaga    21780
ccaagtttac tcatatatac tttagattga tttaaaactt catttttaat ttaaaaggat    21840
ctaggtgaag atcctttttg ataatctcat gaccaaaatc ccttaacgtg agttttcgtt    21900
ccactgagcg tcagaccccg tagaaaagat caaaggatct tcttgagatc cttttttttct    21960 gcgcgtaatc tgctgcttgc aaacaaaaaa accaccgcta ccagcggtgg tttgtttgcc    22020
ggatcaagag ctaccaactc tttttccgaa ggtaactggc ttcagcagag cgcagatacc    22080
aaatactgtt cttctagtgt agccgtagtt aggccaccac ttcaagaact ctgtagcacc    22140
gcctacatac ctcgctctgc taatcctgtt accagtggct gctgccagtg gcgataagtc    22200
gtgtcttacc gggttggact caagacgata gttaccggat aaggcgcagc ggtcgggctg    22260
aacggggggt tcgtgcacac agcccagctt ggagcgaacg acctacaccg aactgagata    22320
cctacagcgt gagctatgag aaagcgccac gcttcccgaa gggagaaagg cggacaggta    22380
tccggtaagc ggcagggtcg aacaggagag cgcacgagg gagcttccag ggggaaacgc    22440
ctggtatctt tatagtcctg tcgggtttcg ccacctctga cttgagcgtc gatttttgtg    22500
atgctcgtca gggggcgga gcctatggaa aaacgccagc aacgcggcct ttttacggtt    22560
cctggccttt tgctggcctt ttgctcacat gttctttcct gcgttatccc ctgattctgt    22620
ggataaccgt attaccgcct ttgagtgagc tgataccgct cgccgcagcc gaacgaccga    22680
gcgcagcgag tcagtgagcg aggaagcgga gagcgccca atacgcaaac cgcctctccc    22740
cgcgcgttgg ccgattcatt aatgcagctg gcacgacagg tttcccgact ggaaagcggg    22800
cagtgagcgc aacgcaatta atgtgagtta gctcactcat taggcacccc aggctttaca    22860
ctttatgctt ccggctcgta tgttgtgtgg aattgtgagc ggacaacaat ttcacacagg    22920
aaacagctat gaccatgatt acgccaagct cgggcggccg cttgtaatac gactcactat    22980
a                                                                     22981
```

<210> SEQ ID NO 17

-continued

```
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA

<400> SEQUENCE: 17
accaaacaaa gttgggtaag gatagttcaa tcaatgatca ttttctagtg cacttaggat        60
tcaagatcct attatcaggg acaagagcag gattaaggat atccgagatg gccacacttt       120
taaggagctt agcattgttc aaaagaaaca aggacaaacc acccattaca tcaggatccg       180
gtggagccat cagaggaatc aaacacatta ttatagtacc aatccctgga gattcctcaa       240
ttaccactcg atccagactt ctggaccggt tggtcaggtt aattggaaac ccggatgtga       300
gcgggcccaa actaacaggg gcactaatag gtatattatc cttatttgtg gagtctccag       360
gtcaattgat tcagaggatc accgatgacc ctgacgttag cataaggctg ttagaggttg       420
tccagagtga ccagtcacaa tctggcctta ccttcgcatc aagaggtacc aacatggagg       480
atgaggcgga ccaatacttt tcacatgatg atccaattag tagtgatcaa tccaggttcg       540
gatggttcga gaacaaggaa atctcagata ttgaagtgca agaccctgag ggattcaaca       600
tgattctggg taccatccta gctcaaattt gggtcttgct cgcaaaggcg gttacggccc       660
cagacacggc agctgattcg gagctaagaa ggtggataaa gtacacccaa caaagaaggg       720
tagttggtga atttagattg gagagaaaat ggttggatgt ggtgaggaac aggattgccg       780
aggacctctc cttacgccga ttcatggtcg ctctaatcct ggatatcaag agaacacccg       840
gaaacaaacc caggattgct gaaatgatat gtgacattga tacatatatc gtagaggcag       900
gattagccag ttttatcctg actattaagt ttgggataga aactatgtat cctgctcttg       960
gactgcatga atttgctggt gagttatcca cacttgagtc cttgatgaac ctttaccagc      1020 aaatgggggga aactgcaccc tacatggtaa tcctggagaa ctcaattcag aacaagttca      1080
gtgcaggatc ataccctctg ctctggagct atgccatggg agtaggagtg aacttgaaa       1140 actccatggg aggtttgaac tttggccgat cttactttga tccagcatat tttagattag      1200
ggcaagagat ggtaaggagg tcagctggaa aggtcagttc cacattggca tctgaactcg      1260
gtatcactgc cgaggatgca aggcttgttt cagagattgc aatgcatact actgaggaca      1320
agatcagtag agcggttgga cccagacaag cccaagtatc atttctacac ggtgatcaaa      1380
gtgagaatga gctaccgaga ttgggggggca aggaagatag gagggtcaaa cagagtcgag      1440
gagaagccag ggagagctac agagaaaccg ggcccagcag agcaagtgat gcgagagctg      1500
cccatcttcc aaccggcaca cccctagaca ttgacactgc atcggagtcc agccaagatc      1560
cgcaggacag tcgaaggtca gctgacgccc tgcttaggct gcaagccatg gcaggaatct      1620
cggaagaaca aggctcagac acggacaccc ctatagtgta caatgacaga aatcttctag      1680
actaggtgcg agaggccgag gaccagaaca catccgcct accctccatc attgttataa       1740
aaaacttagg aaccaggtcc acacagccgc cagcccatca accatccact cccacgattg      1800
gagccgatgg cagaagagca ggcacgccat gtcaaaaacg gactggaatg catccgggct      1860
ctcaaggccg agcccatcgg ctcactggcc atcgaggaag ctatggcagc atggtcagaa      1920
atatcagaca acccaggaca ggagcgagcc acctgcaggg aagagaaggc aggcagttcg      1980
ggtctcagca aaccatgcct ctcagcaatt ggatcaactg aaggcggtgc acctcgcatc      2040
```

-continued

```
cgcggtcagg gacctggaga gagcgatgac gacgctgaaa ctttgggaat cccccccaaga    2100 aatctccagg catcaagcac tgggttacag tgttattatg tttatgatca cagcggtgaa    2160
gcggttaagg gaatccaaga tgctgactct atcatggttc aatcaggcct tgatggtgat    2220
agcaccctct caggaggaga caatgaatct gaaaacagcg atgtggatat tggcgaacct    2280
gataccgagg gatatgctat cactgaccgg ggatctgctc ccatctctat ggggttcagg    2340
gcttctgatg ttgaaactgc agaaggaggg gagatccacg agctcctgag actccaatcc    2400
agaggcaaca actttccgaa gcttgggaaa actctcaatg ttcctccgcc tccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aagggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg acacctctca agcatcatga tcgccattcc tggacttggg    2940
aaggatccca acgacccaca tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt ttgttcctga caccggccct    3180
gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagtac aacctaaatc cattataaaa aacttaggag caaagtgatt    3420
gcctcccaag ttccacaggc gcgccatgtt cgtcttcctg gtcctgctgc ctctggtctc    3480
ctcacagtgc gtcaatctga caactcggac tcagctgcca cctgcttata ctaatagctt    3540
caccagaggc gtgtactatc ctgacaaggt gtttagaagc tccgtgctgc actctacaca    3600
ggatctgttt ctgccattct ttagcaacgt gacctggttc cacgccatcc acgtgagcgg    3660
caccaatggc acaaagcggt tcgacaatcc cgtgctgcct tttaacgatg gcgtgtactt    3720
cgcctctacc gagaagagca acatcatcag aggctggatc tttggcacca cactggactc    3780
caagacacag tctctgctga tcgtgaacaa tgccaccaac gtggtcatca aggtgtgcga    3840
gttccagttt tgtaatgatc ccttcctggg cgtgtactat cacaagaaca ataagagctg    3900
gatggagtcc gagtttagag tgtattctag cgccaacaac tgcacatttg agtacgtgag    3960
ccagcctttc ctgatggacc tggagggcaa gcagggcaat ttcaagaacc tgagggagtt    4020
cgtgtttaag aatatcgacg gctacttcaa aatctactct aagcacaccc ccatcaacct    4080
ggtgcgcgac ctgcctcagg gcttcagcgc cctggagccc ctggtggatc tgcctatcgg    4140
catcaacatc acccggtttc agacactgct ggccctgcac agaagctacc tgacaccgg    4200 cgactcctct agcggatgga ccgccggcgc tgccgcctac tatgtgggct acctccagcc    4260
ccggaccttc ctgctgaagt acaacgagaa tggcaccatc acagacgcag tggattgcgc    4320
cctggacccc ctgagcgaga caaagtgtac actgaagtcc tttaccgtgg agaagggcat    4380
```

-continued

```
ctatcagaca tccaatttca gggtgcagcc aaccgagtct atcgtgcgct ttcctaatat      4440
cacaaacctg tgcccatttg gcgaggtgtt caacgcaacc cgcttcgcca gcgtgtacgc      4500
ctggaatagg aagcggatca gcaactgcgt ggccgactat agcgtgctgt acaactccgc      4560
ctctttcagc acctttaagt gctatggcgt gtcccccaca aagctgaatg acctgtgctt      4620
taccaacgtc tacgccgatt ctttcgtgat caggggcgac gaggtgcgcc agatcgcccc      4680
cggccagaca ggcaagatcg cagactacaa ttataagctg ccagacgatt tcaccggctg      4740
cgtgatcgcc tggaacagca acaatctgga ttccaaagtg ggcggcaact acaattatct      4800
gtaccggctg tttagaaaga gcaatctgaa gcccttcgag agggacatct ctacagaaat      4860
ctaccaggcc ggcagcaccc cttgcaatgg cgtggagggc tttaactgtt atttcccact      4920
ccagtcctac ggcttccagc ccacaaacgc gtgggctat cagccttacc gcgtggtggt      4980
gctgagcttt gagctgctgc acgccccagc aacagtgtgc ggccccaaga agtccaccaa      5040
tctggtgaag aacaagtgcg tgaacttcaa cttcaacggc ctgaccggca caggcgtgct      5100
gaccgagtcc aacaagaagt tcctgccatt tcagcagttc ggcagggaca tcgcagatac      5160
cacagacgcc gtgcgcgacc cacagaccct ggagatcctg gacatcacac cctgctcttt      5220
cggcggcgtg agcgtgatca cacccggcac caatacaagc aaccaggtgg ccgtgctgta      5280
tcaggacgtg aattgtaccg aggtgcccgt ggctatccac gccgatcagc tgacccaac      5340 atggcgggtg tacagcaccg gctccaacgt cttccagaca agagccggat gcctgatcgg      5400
agcagagcac gtgaacaatt cctatgagtg cgacatccca atcggcgccg gcatctgtgc      5460
ctcttaccag acccagacaa actctcccag aagagcccgg agcgtggcct cccagtctat      5520
catcgcctat accatgtccc tgggcgccga aacagcgtg gcctactcta acaatagcat      5580
cgccatccca accaacttca caatctctgt gaccacagag atcctgcccg tgtccatgac      5640
caagacatct gtggactgca caatgtatat ctgtggcgat tctaccgagt gcagcaacct      5700
gctgctccag tacggcagct tttgtaccca gctgaataga gccctgacag catcgccgt      5760 ggagcaggat aagaacacac aggaggtgtt cgcccaggtg aagcaaatct acaagacccc      5820
ccctatcaag gactttggcg gcttcaattt ttcccagatc ctgcctgatc catccaagcc      5880
ttctaagcgg agctttatcg aggacctgct gttcaacaag gtgaccctgg ccgatgccgg      5940
cttcatcaag cagtatggcg attgcctggg cgacatcgca gccagggacc tgatctgcgc      6000
ccagaagttt aatggcctga ccgtgctgcc accctgctg acagatgaga tgatcgcaca      6060
gtacacaagc gccctgctgg ccggcaccat cacatccgga tggaccttcg gcgcaggagc      6120
cgccctccag atcccctttg ccatgcagat ggcctatagg ttcaacggca tcggcgtgac      6180
ccagaatgtg ctgtacgaga accagaagct gatcgccaat cagtttaact ccgccatcgg      6240
caagatccag gacagcctgt cctctacagc cagcgccctg ggcaagctcc aggatgtggt      6300
gaatcagaac gcccaggccc tgaataccct ggtgaagcag ctgagcagca acttcggcgc      6360
catctctagc gtgctgaatg acatcctgag ccggctggac aaggtggagg cagaggtgca      6420
gatcgaccgg ctgatcaccg gccggctcca gagcctccag acctatgtga cacagcagct      6480
gatcagggcc gccgagatca gggccagcgc caatctggca gcaaccaaga gtccgagtg      6540 cgtgctgggc cagtctaaga gagtggactt ttgtggcaag ggctatcacc tgatgtcctt      6600
ccctcagtct gccccacacg gcgtggtgtt tctgcacgtg acctacgtgc ccgcccagga      6660
gaagaacttc accacagccc ctgccatctg ccacgatggc aaggcccact tccaaggga      6720 gggcgtgttc gtgtccaacg gcacccactg gtttgtgaca cagcgcaatt tctacgagcc      6780
```

-continued

```
ccagatcatc accacagaca acaccttcgt gagcggcaac tgtgacgtgg tcatcggcat    6840
cgtgaacaat accgtgtatg atccactcca gcccgagctg gacagcttta aggaggagct    6900
ggataagtat ttcaagaatc acacctcccc tgacgtggat ctgggcgaca tcagcggcat    6960
caatgcctcc gtggtgaaca tccagaagga gatcgaccgc ctgaacgagg tggctaagaa    7020
tctgaacgag agcctgatcg acctccagga gctgggcaag tatgagcagt acatcaagtg    7080
gccctggtac atctggctgg gcttcatcgc cggcctgatc gccatcgtga tggtgaccat    7140
catgctgtgc tgtatgacat cctgctgttc ttgcctgaag ggctgctgta gctgtggctc    7200
ctgctgtaag tttgacgagg atgactctga acctgtgctg aagggcgtgg cgctggctta    7260
cacctaacgc gcgacgtcct acagctcaac ttacctgcca accccatgcc agtcgaccca    7320
actagtacaa cctaaatcca ttataaaaaa cttaggagca aagtgattgc ctcccaagtt    7380
ccacaatgac agagatctac gacttcgaca agtcggcatg ggacatcaaa gggttgatcg    7440
ctccgataca acccaccacc tacagtgatg gcaggctggt gccccaggtc agagtcatag    7500
atcctggtct aggcgacagg aaggatgaat gctttatgta catgtttctg ctgggggttg    7560
ttgaggacag cgatcccta gggcctccaa tcgggcgagc atttgggtcc ctgcccttag    7620
gtgttggcag atccacagca aagcccgaaa aactcctcaa agaggccact gagcttgaca    7680
tagttgttag acgtacagca gggctcaatg aaaaactggt gttctacaac aacaccccac    7740
taactctcct cacaccttgg agaaaggtcc taacaacagg gagtgtcttc aacgcaaacc    7800
aagtgtgcaa tgcggttaat ctgataccgc tcgataccccc gcagaggttc cgtgttgttt    7860
atatgagcat cacccgtctt tcggataacg ggtattacac cgttcctaga agaatgctgg    7920
aattcagatc ggtcaatgca gtggccttca acctgctggt gacccttagg attgacaagg    7980
cgataggccc tgggaagatc atcgacaata cagagcaact tcctgaggca acatttatgg    8040
tccacatcgg gaacttcagg agaaagaaga gtgaagtcta ctctgccgat tattgcaaaa    8100
tgaaaatcga aaagatgggc ctggtttttg cacttggtgg gatagggggc accagtcttc    8160
acattagaag cacaggcaaa atgagcaaga ctctccatgc acaactcggg ttcaagaaga    8220
ccttatgtta cccgctgata gatatcaatg aagaccttaa tcgattactc tggaggagca    8280
gatgcaagat agtaagaatc caggcagttt tgcagccatc agttcctcaa gaattccgca    8340
tttacgacga cgtgatcata aatgatgacc aaggactatt caaagttctg tagaccgtag    8400
tgcccagcaa tgcccgaaaa cgaccccct cacaatgaca gccagaaggc ccggacaaaa    8460 aagcccctc cgaaagactc cacggaccaa gcgagaggcc agccagcagc cgacggcaag    8520
cgcgaacacc aggcggcccc agcacagaac agccctgata caaggccacc accagccacc    8580
ccaatctgca tcctcctcgt gggaccccg aggaccaacc cccaaggctg ccccgatcc    8640 aaaccaccaa ccgcatcccc accacccccg ggaaagaaac ccccagcaat tggaaggccc    8700
ctccccctct tcctcaacac aagaactcca caaccgaacc gcacaagcga ccgaggtgac    8760
ccaaccgcag gcatccgact ccctagacag atcctctctc cccggcaaac taaacaaaac    8820
ttagggccaa ggaacataca cacccaacag aacccagacc ccggcccacg gcgccgcgcc    8880
cccaaccccc gacaaccaga gggagccccc aaccaatccc gccggctccc ccggtgccca    8940
caggcaggga caccaacccc cgaacagacc cagcacccaa ccatcgacaa tccaagacgg    9000
gggggccccc ccaaaaaaag gcccccaggg gccgacagcc agcaccgcga ggaagcccac    9060 ccacccaca cacgaccacg gcaaccaaac cagaacccag accaccctgg gccaccagct    9120
```

US 12,653,881 B2

145                                                              146

-continued

```
cccagactcg gccatcaccc cgcagaaagg aaaggccaca acccgcgcac cccagccccg  9180
atccggcggg gagccaccca acccgaacca gcacccaaga gcgatccccg aaggacccc  9240 gaaccgcaaa ggacatcagt atcccacagc ctctccaagt cccccggtct cctcccttc  9300 tcgaagggac caaaagatca atccaccaca cccgacgaca ctcaactccc caccctaaa  9360 ggagacaccg ggaatcccag aatcaagact catccaatgt ccatcatggg tctcaaggtg  9420
aacgtctctg ccatattcat ggcagtactg ttaactctcc aaacacccac cggtcaaatc  9480
cattggggca atctctctaa gatagggtg gtaggaatag gaagtgcaag ctacaaagtt  9540
atgactcgtt ccagccatca atcattagtc ataaaattaa tgcccaatat aactctcctc  9600
aataactgca cgagggtaga gattgcagaa tacaggagac tactgagaac agttttggaa  9660
ccaattagag atgcacttaa tgcaatgacc cagaatataa gaccggttca gagtgtagct  9720
tcaagtagga gacacaagag atttgcggga gtagtcctgg caggtgcggc cctaggcgtc  9780
gccacagctg ctcagataac agccggcatt gcacttcacc agtccatgct gaactctcaa  9840
gccatcgaca atctgagagc gagcctggaa actactaatc aggcaattga ggcaatcaga  9900
caagcagggc aggagatgat attggctgtt cagggtgtcc aagactacat caataatgag  9960
ctgataccgt ctatgaacca actatcttgt gatttaatcg gccagaagct cgggctcaaa  10020
ttgctcagat actatacaga aatcctgtca ttatttggcc ccagcttacg ggaccccata  10080
tctgcggaga tatctatcca ggctttgagc tatgcgcttg gaggagacat caataaggtg  10140
ttagaaaagc tcggatacag tggaggtgat ttactgggca tcttagagag cagaggaata  10200
aaggcccgga taactcacgt cgacacagag tcctacttca ttgtcctcag tatagcctat  10260
ccgacgctgt ccgagattaa gggggtgatt gtccaccggc tagagggggt ctcgtacaac  10320
ataggctctc aagagtggta taccactgtg cccaagtatg ttgcaaccca agggtacctt  10380
atctcgaatt ttgatgagtc atcgtgtact ttcatgccag aggggactgt gtgcagccaa  10440
aatgccttgt acccgatgag tcctctgctc caagaatgcc tccggggggtc caccaagtcc  10500 tgtgctcgta cactcgtatc cgggtctttt gggaaccggt tcattttatc acaagggaac  10560
ctaatagcca attgtgcatc aatcctttgc aagtgttaca caacaggaac gatcattaat  10620
caagaccctg acaagatcct aacatacatt gctgccgatc actgcccggt agtcgaggtg  10680
aacggcgtga ccatccaagt cgggagcagg aggtatccag atgctgtgta cttgcacaga  10740
attgacctcg gtcctcccat atcattggag aggttggacg tagggacaaa tctggggaat  10800
gcaattgcta agttggagga tgccaaggaa ttgttggagt catcggacca gatattgagg  10860
agtatgaaag gtttatcgag cactagcata gtctacatcc tgattgcagt gtgtcttgga  10920
gggttgatag ggatccccgc tttaatatgt tgctgcaggg ggcgttgtaa caaaaaggga  10980
gaacaagttg gtatgtcaag accaggccta aagcctgatc ttacgggaac atcaaaatcc  11040
tatgtaaggt cgctctgatc ctctacaact cttgaaacac aaatgtccca caagtctcct  11100
cttcgtcatc aagcaaccac cgcacccagc atcaagccca cctgaaatta tctccggctt  11160
ccctctggcc gaacaatatc ggtagttaat taaaacttag ggtgcaagat catccacaat  11220
gtcaccacaa cgagaccgga taaatgcctt ctacaaagat aacccccatc ccaagggaag  11280
taggatagtc attaacagag aacatcttat gattgataga ccttatgttt tgctggctgt  11340
tctgtttgtc atgtttctga gcttgatcgg gttgctagcc attgcaggca ttagacttca  11400
tcgggcagcc atctacaccg cagagatcca taaaagcctc agcaccaatc tagatgtaac  11460
taactcaatc gagcatcagg tcaaggacgt gctgacacca ctcttcaaaa tcatcggtga  11520
```

-continued

```
tgaagtgggc ctgaggacac ctcagagatt cactgaccta gtgaaattca tctctgacaa   11580
gattaaattc cttaatccgg ataggggagta cgacttcaga gatctcactt ggtgtatcaa   11640
cccgccagag agaatcaaat tggattatga tcaatactgt gcagatgtgg ctgctgaaga   11700
gctcatgaat gcattggtga actcaactct actggagacc agaacaacca atcagttcct   11760
agctgtctca aagggaaact gctcagggcc cactacaatc agaggtcaat tctcaaacat   11820
gtcgctgtcc ctgttagact tgtatttagg tcgaggttac aatgtgtcat ctatagtcac   11880
tatgacatcc cagggaatgt atgggggaac ttacctagtg gaaaagccta atctgagcag   11940
caaaaggtca gagttgtcac aactgagcat gtaccgagtg tttgaagtag gtgttatcag   12000
aaatccgggt ttgggggctc cggtgttcca tatgacaaac tatcttgagc aaccagccag   12060
taatgatctc agcaactgta tggtggcttt gggggagctc aaactcgcag cccttttgtca   12120 cggggaagat tctatcacaa ttccctatca gggatcaggg aaaggtgtca gcttccagct   12180
cgtcaagcta ggtgtctgga aatccccaac cgacatgcaa tcctgggtcc ccttatcaac   12240
ggatgatcca gtgatagaca ggctttacct ctcatctcac agaggtgtta tcgctgacaa   12300
tcaagcaaaa tgggctgtcc cgacaacacg aacagatgac aagttgcgaa tggagacatg   12360
cttccaacag gcgtgtaagg gtaaaatcca agcactctgc gagaatcccg agtgggcacc   12420
attgaaggat aacaggattc cttcatacgg ggtcttgtct gttgatctga gtctgacagt   12480
tgagcttaaa atcaaaattg cttcgggatt cgggccattg atcacacacg gttcagggat   12540
ggacctatac aaatccaacc acaacaatgt gtattggctg actatcccgc caatgaagaa   12600
cctagcctta ggtgtaatca acacattgga gtggataccg agattcaagg ttagtcccta   12660
cctcttcaat gtcccaatta aggaagcagg cgaagactgc catgccccaa catacctacc   12720
tgcggaggtg gatggtgatg tcaaactcag ttccaatctg gtgattctac ctggtcaaga   12780
tctccaatat gttttggcaa cctacgatac ttccagggtt gaacatgctg tggtttatta   12840
cgtttacagc ccaggccgct cattttctta cttttatcct tttaggttgc ctataaaggg   12900
ggtccccatc gaattacaag tggaatgctt cacatgggac caaaaactct ggtgccgtca   12960
cttctgtgtg cttgcggact cagaatctgg tggacatatc actcactctg ggatggtggg   13020
catgggagtc agctgcacag tcacccggga agatggaacc aatcgcagat agggctgcta   13080
gtgaaccaat ctcatgatgt cacccagaca tcaggcatac ccactagtgt gaaatagaca   13140
tcagaattaa gaaaaacgta gggtccaagt ggttccccgt tatggactcg ctatctgtca   13200
accagatctt atacctgaa gttcacctag atagcccgat agttaccaat aagatagtag   13260
ccatcctgga gtatgctcga gtccctcacg cttacagcct ggaggaccct acactgtgtc   13320
agaacatcaa gcaccgccta aaaaacggat tttccaacca aatgattata aacaatgtgg   13380
aagttgggaa tgtcatcaag tccaagctta ggagttatcc ggcccactct catattccat   13440
atccaaattg taatcaggat ttatttaaca tagaagacaa agagtcaacg aggaagatcc   13500
gtgaactcct caaaaagggg aattcgctgt actccaaagt cagtgataag gttttccaat   13560
gcttaaggga cactaactca cggcttggcc taggctccga attgagggag gacatcaagg   13620
agaaagttat taacttggga gtttacatgc acagctccca gtggtttgag cccttttctgt   13680 tttggtttac agtcaagact gagatgaggt cagtgattaa atcacaaacc catacttgcc   13740
ataggaggag acacacacct gtattcttca ctggtagttc agttgagttg ctaatctctc   13800
gtgaccttgt tgctataatc agtaaagagt ctcaacatgt atattacctg acatttgaac   13860
```

-continued

```
tggtttttgat gtattgtgat gtcatagagg ggaggttaat gacagagacc gctatgacta   13920
ttgatgctag gtatacagag cttctaggaa gagtcagata catgtggaaa ctgatagatg   13980
gtttcttccc tgcactcggg aatccaactt atcaaattgt agccatgctg gagcctcttt   14040
cacttgctta cctgcagctg agggatataa cagtagaact cagaggtgct ttccttaacc   14100
actgctttac tgaaatacat gatgttcttg accaaaacgg gttttctgat gaaggtactt   14160
atcatgagtt aattgaagct ctagattaca ttttcataac tgatgacata catctgacag   14220
gggagatttt ctcattttc agaagtttcg gccaccccag acttgaagca gtaacggctg   14280
ctgaaaatgt taggaaatac atgaatcagc ctaaagtcat tgtgtatgag actctgatga   14340
aaggtcatgc catattttgt ggaatcataa tcaacggcta tcgtgacagg cacggaggca   14400
gttggccacc gctgaccctc cccctgcatg ctgcagacac aatccggaat gctcaagctt   14460
caggtgaagg gttaacacat gagcagtgcg ttgataactg gagatctttt gctggagtga   14520
aatttggctg ctttatgcct cttagcctgg atagtgatct gacaatgtac ctaaaggaca   14580
aggcacttgc tgctctccaa agggaatggg attcagttta cccgaaagag ttcctgcgtt   14640
acgaccctcc caagggaacc gggtcacgga ggcttgtaga tgttttcctt aatgattcga   14700
gctttgaccc atatgatgtg ataatgtatg ttgtaagtgg agcttacctc catgaccctg   14760
agttcaacct gtcttacagc ctgaaagaaa aggagatcaa ggaaacaggt agactttttg   14820
ctaaaatgac ttacaaaatg agggcatgcc aagtgattgc tgaaaatcta atctcaaacg   14880
ggattggcaa atattttaag gacaatggga tggccaagga tgagcacgat ttgactaagg   14940
cactccacac tctagctgtc tcaggagtcc ccaaagatct caaagaaagt cacagggggg   15000
ggccagtctt aaaaacctac tcccgaagcc cagtccacac aagtaccagg aacgtgagag   15060
cagcaaaagg gtttataggg ttccctcaag taattcggca ggaccaagac actgatcatc   15120
cggagaatat ggaagcttac gagacagtca gtgcatttat cacgactgat ctcaagaagt   15180
actgccttaa ttggagatat gagaccatca gcttgtttgc acagaggcta aatgagattt   15240
acggattgcc ctcattttc cagtggctgc ataagaggct tgagacctct gtcctgtatg   15300
taagtgaccc tcattgcccc cccgaccttg acgcccatat cccgttatat aaagtcccca   15360
atgatcaaat cttcattaag taccctatgg gaggtataga agggtattgt cagaagctgt   15420
ggaccatcag caccattccc tatctatacc tggctgctta tgagagcgga gtaaggattg   15480
cttcgttagt gcaaggggac aatcagacca tagccgtaac aaaaagggta cccagcacat   15540
ggccctacaa ccttaagaaa cgggaagctg ctagagtaac tagagattac tttgtaattc   15600
ttaggcaaag gctacatgat attggccatc acctcaaggc aaatgagaca attgtttcat   15660 cacattttt tgtctattca aaaggaatat attatgatgg gctacttgtg tcccaatcac   15720
tcaagagcat cgcaagatgt gtattctggt cagagactat agttgatgaa acaagggcag   15780
catgcagtaa tattgctaca acaatggcta aaagcatcga gagaggttat gaccgttacc   15840
ttgcatattc cctgaacgtc ctaaaagtga tacagcaaat tctgatctct cttggcttca   15900
caatcaattc aaccatgacc cgggatgtag tcataccct cctcacgaac aacgacctct   15960
taataaggat ggcactgttg cccgctccta ttggggggat gaattatctg aatatgagca   16020
ggctgtttgt cagaaacatc ggtgatccag taacatcatc aattgctgat ctcaagagaa   16080
tgattctcgc ctcactaatg cctgaagaga ccctccatca gtaatgacaa caacaaccgg   16140
gggactcttc attcctagac tgggctagcg acccttactc agcaaatctt gtatgtgtcc   16200
agagcatcac tagactcctc aagaacataa ctgcaaggtt tgtcctgatc catagtccaa   16260
```

-continued

```
acccaatgtt aaaaggatta ttccatgatg acagtaaaga agaggacgag ggactggcgg   16320
cattcctcat ggacaggcat attatagtac ctagggcagc tcatgaaatc ctggatcata   16380
gtgtcacagg ggcaagagag tctattgcag gcatgctgga taccacaaaa ggcctgattc   16440
gagccagcat gaggaagggg gggttaacct ctcgagtgat aaccagattg tccaattatg   16500
actatgaaca attcagagca gggatggtgc tattgacagg aagaaagaga aatgtcctca   16560
ttgacaaaga gtcatgttca gtgcagctgg cgagagctct aagaagccat atgtgggcga   16620
ggctagctcg aggacggcct atttacggcc ttgaggtccc tgatgtacta gaatctatgc   16680
gaggccacct tattcggcgt catgagacat gtgtcatctg cgagtgtgga tcagtcaact   16740
acggatggtt ttttgtcccc tcgggttgcc aactggatga tattgacaag gaaacatcat   16800
ccttgagagt cccatatatt ggttctacca ctgatgagag aacagacatg aagcttgcct   16860
tcgtaagagc cccaagtcga tccttgcgat ctgctgttag aatagcaaca gtgtactcat   16920
gggcttacgg tgatgatgat agctcttgga acgaagcctg gttgttggct aggcaaaggg   16980
ccaatgtgag cctggaggag ctaagggtga tcactcccat ctcaacttcg actaatttag   17040
cgcataggtt gagggatcgt agcactcaag tgaaatactc aggtacatcc cttgtccgag   17100
tggcgaggta taccacaatc tccaacgaca atctctcatt tgtcatatca gataagaagg   17160
ttgatactaa ctttatatac caacaaggaa tgcttctagg gttgggtgtt ttagaaacat   17220
tgtttcgact cgagaaagat accggatcat ctaacacggt attacatctt cacgtcgaaa   17280
cagattgttg cgtgatcccg atgatagatc atcccaggat acccagctcc cgcaagctag   17340
agctgagggc agagctatgt accaacccat tgatatatga taatgcacct ttaattgaca   17400
gagatacaac aaggctatac acccagagcc ataggaggca ccttgtggaa tttgttacat   17460
ggtccacacc ccaactatat cacattttag ctaagtccac agcactatct atgattgacc   17520
tggtaacaaa atttgagaag gaccatatga atgaaatttc agctctcata ggggatgacg   17580
atatcaatag tttcataact gagtttctgc tcatagagcc aagattattc actatctact   17640
tgggccagtg tgcggccatc aattgggcat ttgatgtaca ttatcataga ccatcaggga   17700
aatatcagat gggtgagctg ttgtcatcgt tcctttctag aatgagcaaa ggagtgttta   17760
aggtgcttgt caatgctcta agccacccaa agatctacaa gaaattctgg cattgtggta   17820
ttatagagcc tatccatggt ccttcacttg atgctcaaaa cttgcacaca actgtgtgca   17880
acatggttta cacatgctat atgacctacc tcgacctgtt gttgaatgaa gagttagaag   17940
agttcacatt tctcttgtgt gaaagcgacg aggatgtagt accggacaga ttcgacaaca   18000
tccaggcaaa acacttatgt gttctggcag atttgtactg tcaaccaggg acctgcccac   18060
caattcgagg tctaagaccg gtagagaaat gtgcagttct aaccgaccat atcaaggcag   18120
aggctaggtt atctccagca ggatcttcgt ggaacataaa tccaattatt gtagaccatt   18180
actcatgctc tctgacttat ctccggcgag gatcgatcaa acagataaga ttgagagttg   18240
atccaggatt cattttcgac gccctcgctg aggtaaatgt cagtcagcca aagatcggca   18300
gcaacaacat ctcaaatatg agcatcaagg ctttcagacc cccacacgat gatgttgcaa   18360
aattgctcaa agatatcaac acaagcaagc acaatcttcc catttcaggg ggcaatctcg   18420
ccaattatga aatccatgct ttccgcagaa tcgggttgaa ctcatctgct tgctacaaag   18480
ctgttgagat atcaacatta attaggagat gccttgagcc aggggaggac ggcttgttct   18540
tgggtgaggg atcgggttcc atgttgatca cttataagga gatacttaaa ctaaacaagt   18600
```

-continued

```
gcttctataa tagtgggggtt tccgccaatt ctagatctgg tcaaagggaa ttagcaccct   18660
atccctccga agttggcctt gtcgaacaca gaatgggagt aggtaatatt gtcaaagtgc   18720
tctttaacgg gaggcccgaa gtcacgtggg taggcagtgt agattgcttc aatttcatag   18780
ttagtaatat ccctacctct agtgtggggt ttatccattc agatatagag accttgccta   18840
acaaagatac tatagagaag ctagaggaat tggcagccat cttatcgatg gctctgctcc   18900
tgggcaaaat aggatcaata ctggtgatta agcttatgcc tttcagcggg gattttgttc   18960
agggatttat aagttatgta gggtcccatt atagagaagt gaaccttgta taccctagat   19020
acagcaactt catatctact gaatcttatt tggttatgac agatctcaag gctaaccggc   19080
taatgaatcc tgaaaagatt aagcagcaga taattgaatc atctgtgagg acttcacctg   19140
gacttatagg tcacatccta tccattaagc aactaagctg catacaagca attgtgggag   19200
acgcagttag tagaggtgat atcaatccta ctctgaaaaa acttacacct atagagcagg   19260
tgctgatcaa ttgcgggttg gcaattaacg gacctaagct gtgcaaagaa ttgatccacc   19320
atgatgttgc ctcagggcaa gatggattgc ttaattctat actcatcctc tacagggagt   19380
tggcaagatt caaagacaac caaagaagtc aacaagggat gttccacgct tacccccgtat  19440 tggtaagtag caggcaacga gaacttatat ctaggatcac ccgcaaattt tgggggcaca   19500 ttcttctta ctccgggaac agaaagttga taaataagtt tatccagaat ctcaagtccg     19560
gctatctgat actagactta caccagaata tcttcgttaa gaatctatcc aagtcagaga   19620
aacagattat tatgacgggg ggtttgaaac gtgagtgggt tttttaaggta acagtcaagg   19680 agaccaaaga atggtataag ttagtcggat acagtgccct gattaaggac taattggttg   19740
aactccggaa ccctaatcct gccctaggtg gttaggcatt atttgcaata gattaaagaa   19800
aactttgaaa atacgaagtt tctattccca gctttgtctg gtggccggca tggtcccagc   19860
ctcctcgctg gcgccggctg ggcaacattc cgaggggacc gtccctcgg taatggcgaa     19920 tgggacgcgg ccgatccggc tgctaacaaa gcccgaaagg aagctgagtt ggctgctgcc   19980
accgctgagc aataactagc ataacccctt ggggcctcta aacgggtctt gaggggtttt   20040
ttgctgaaag gaggaactat atccggatgc ggccgatccg gctgctaaca aagcccgaaa   20100
ggaagctgag ttggctgctg ccaccgctga gcaataacta gcataacccc ttggggcctc   20160
taaacgggtc ttgaggggtt ttttgctgaa aggaggaact atatccggat ggccgccacc   20220
ggccggtggg ccttgcagca catccccctt tcgccagctg gcgtaatagc gaagaggccc   20280
gcaccgatcg cccttcccaa cagttgcgca gcctgaatgg cgaatgggac gcgccctgta   20340
gcggcgcatt aagcgcggcg ggtgtggtgg ttacgcgcag cgtgaccgct acacttgcca   20400
gcgccctagc gcccgctcct ttcgctttct tcccttcctt tctcgccacg ttcgccggct   20460
ttccccgtca gctctaaat cggggggctcc ctttagggtt ccgatttagt gctttacggc    20520
acctcgaccc caaaaaactt gattagggtg atggttcacg tgggccatcg ccctgataga   20580 cggttttcg ccctttgacg ttggagtcca cgttctttaa tagtggactc ttgttccaaa     20640
ctggaacaac actcaaccct atctcggtct attctttga tttataaggg attttgccga    20700
tttcggccta ttggttaaaa aatgagctga tttaacaaaa atttaacgcg aattttaaca   20760
aaatattaac gcttacaatt taggtggcac ttttcgggga aatgtgcgcg gaacccctat   20820
ttgtttattt ttctaaatac attcaaatat gtatccgctc atgagacaat aaccctgata   20880
aatgcttcaa taatattgaa aaaggaagag tatgagtatt caacatttcc gtgtcgccct   20940
tattcccttt tttgcggcat tttgccttcc tgttttttgct cacccagaaa cgctggtgaa   21000
```

-continued

```
agtaaaagat gctgaagatc agttgggtgc acgagtgggt tacatcgaac tggatctcaa    21060
cagcggtaag atccttgaga gttttcgccc cgaagaacgt tttccaatga tgagcacttt    21120
taaagttctg ctatgtggcg cggtattatc ccgtattgac gccgggcaag agcaactcgg    21180
tcgccgcata cactattctc agaatgactt ggttgagtac tcaccagtca cagaaaagca    21240
tcttacggat ggcatgacag taagagaatt atgcagtgct gccataacca tgagtgataa    21300
cactgcggcc aacttacttc tgacaacgat cggaggaccg aaggagctaa ccgctttttt    21360
gcacaacatg ggggatcatg taactcgcct tgatcgttgg gaaccggagc tgaatgaagc    21420
cataccaaac gacgagcgtg acaccacgat gcctgtagca atggcaacaa cgttgcgcaa    21480
actattaact ggcgaactac ttacactagc ttcccggcaa caattaatag actggatgga    21540
ggcggataaa gttgcaggac cacttctgcg ctcggccctt ccggctggct ggtttattgc    21600
tgataaatct ggagccggtg agcgtgggtc tcgcggtatc attgcagcac tggggccaga    21660
tggtaagccc tcccgtatcg tagttatcta cacgacgggg agtcaggcaa ctatggatga    21720
acgaaataga cagatcgctg agataggtgc ctcactgatt aagcattggt aactgtcaga    21780
ccaagtttac tcatatatac tttagattga tttaaaactt catttttaat ttaaaaggat    21840
ctaggtgaag atcctttttg ataatctcat gaccaaaatc ccttaacgtg agttttcgtt    21900
ccactgagcg tcagaccccg tagaaaagat caaaggatct tcttgagatc cttttttttct    21960 gcgcgtaatc tgctgcttgc aaacaaaaaa accaccgcta ccagcggtgg tttgtttgcc    22020
ggatcaagag ctaccaactc tttttccgaa ggtaactggc ttcagcagag cgcagatacc    22080
aaatactgtt cttctagtgt agccgtagtt aggccaccac ttcaagaact ctgtagcacc    22140
gcctacatac ctcgctctgc taatcctgtt accagtggct gctgccagtg gcgataagtc    22200
gtgtcttacc gggttggact caagacgata gttaccggat aaggcgcagc ggtcgggctg    22260
aacggggggt tcgtgcacac agcccagctt ggagcgaacg acctacaccg aactgagata    22320
cctacagcgt gagctatgag aaagcgccac gcttcccgaa gggagaaagg cggacaggta    22380
tccggtaagc ggcagggtcg aacaggaga gcgcacgagg gagcttccag ggggaaacgc    22440
ctggtatctt tatagtcctg tcgggtttcg ccacctctga cttgagcgtc gatttttgtg    22500
atgctcgtca ggggggcgga gcctatggaa aaacgccagc aacgcggcct ttttacggtt    22560
cctggccttt tgctggcctt ttgctcacat gttctttcct gcgttatccc ctgattctgt    22620
ggataaccgt attaccgcct ttgagtgagc tgataccgct cgccgcagcc gaacgaccga    22680
gcgcagcgag tcagtgagcg aggaagcgga agagcgccca atacgcaaac cgcctctccc    22740
cgcgcgttgg ccgattcatt aatgcagctg gcacgacagg tttcccgact ggaaagcggg    22800
cagtgagcgc aacgcaatta atgtgagtta gctcactcat taggcacccc aggctttaca    22860
ctttatgctt ccggctcgta tgttgtgtgg aattgtgagc ggacaacaat ttcacacagg    22920
aaacagctat gaccatgatt acgccaagct cgggcggccg cttgtaatac gactcactat    22980
a                                                                   22981
```

<210> SEQ ID NO 18
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)

<223> OTHER INFORMATION: rMV-EZ-SARS-CoV-2-S

<400> SEQUENCE: 18

```
accaaacaaa gttgggtaag gatagttcaa tcaatgatca ttttctagtg cacttaggat        60
tcaagatcct attatcaggg acaagagcag gattaaggat atccgagatg gccacacttt       120
taaggagctt agcattgttc aaaagaaaca aggacaaacc acccattaca tcaggatccg       180
gtggagccat cagaggaatc aaacacatta ttatagtacc aatccctgga gattcctcaa       240
ttaccactcg atccagactt ctggaccggt tggtcaggtt aattggaaac ccggatgtga       300
gcgggcccaa actaacaggg gcactaatag gtatattatc cttatttgtg gagtctccag       360
gtcaattgat tcagaggatc accgatgacc ctgacgttag cataaggctg ttagaggttg       420
tccagagtga ccagtcacaa tctggcctta ccttcgcatc aagaggtacc aacatggagg       480
atgaggcgga ccaatacttt tcacatgatg atccaattag tagtgatcaa tccaggttcg       540
gatggttcga gaacaaggaa atctcagata ttgaagtgca agaccctgag ggattcaaca       600
tgattctggg taccatccta gctcaaattt gggtcttgct cgcaaaggcg gttacggccc       660
cagacacggc agctgattcg gagctaagaa ggtggataaa gtacacccaa caaagaaggg       720
tagttggtga atttagattg gagagaaaat ggttggatgt ggtgaggaac aggattgccg       780
aggacctctc cttacgccga ttcatggtcg ctctaatcct ggatatcaag agaacacccg       840
gaaacaaacc caggattgct gaaatgatat gtgacattga tacatatatc gtagaggcag       900
gattagccag ttttatcctg actattaagt ttgggataga aactatgtat cctgctcttg       960
gactgcatga atttgctggt gagttatcca cacttgagtc cttgatgaac ctttaccagc      1020
aaatggggga aactgcaccc tacatggtaa tcctggagaa ctcaattcag aacaagttca      1080
gtgcaggatc ataccctctg tctctggagct atgccatggg agtaggagtg aacttgaaa      1140 actccatggg aggtttgaac tttggccgat cttactttga tccagcatat tttagattag      1200
ggcaagagat ggtaaggagg tcagctggaa aggtcagttc cacattggca tctgaactcg      1260
gtatcactgc cgaggatgca aggcttgttt cagagattgc aatgcatact actgaggaca      1320
agatcagtag agcggttgga cccagacaag cccaagtatc atttctacac ggtgatcaaa      1380
gtgagaatga gctaccgaga ttggggggca aggaagatag gagggtcaaa cagagtcgag      1440
gagaagccag ggagagctac agagaaaccg ggcccagcag agcaagtgat gcgagagctg      1500
cccatcttcc aaccggcaca cccctagaca ttgacactgc atcggagtcc agccaagatc      1560
cgcaggacag tcgaaggtca gctgacgccc tgcttaggct gcaagccatg gcaggaatct      1620
cggaagaaca aggctcagac acggacaccc ctatagtgta caatgacaga aatcttctag      1680
actaggtgcg agaggccgag gaccagaaca acatccgcct accctccatc attgttataa      1740
aaaacttagg aaccaggtcc acacagccgc cagcccatca accatccact cccacgattg      1800
gagccgatgg cagaagagca ggcacgccat gtcaaaaacg gactggaatg catccgggct      1860
ctcaaggccg agcccatcgg ctcactggcc atcgaggaag ctatggcagc atggtcagaa      1920
atatcagaca acccaggaca ggagcgagcc acctgcaggg aagagaaggc aggcagttcg      1980
ggtctcagca aaccatgcct ctcagcaatt ggatcaactg aaggcggtgc acctcgcatc      2040
cgcggtcagg gacctggaga gagcgatgac gacgctgaaa ctttgggaat cccccccaaga      2100 aatctccagg catcaagcac tgggttacag tgttattatg tttatgatca cagcggtgaa      2160
gcggttaagg gaatccaaga tgctgactct atcatggttc aatcaggcct tgatggtgat      2220
agcaccctct caggaggaga caatgaatct gaaaacagcg atgtggatat ggcgaacct      2280
```

-continued

```
gataccgagg gatatgctat cactgaccgg ggatctgctc ccatctctat ggggttcagg       2340
gcttctgatg ttgaaactgc agaaggaggg gagatccacg agctcctgag actccaatcc       2400
agaggcaaca actttccgaa gcttgggaaa actctcaatg ttcctccgcc tccggacccc       2460
ggtagggcca gcacttccgg gacacccatt aaaaagggca cagacgcgag attagcctca       2520
tttggaacgg agatcgcgtc tttattgaca ggtggtgcaa cccaatgtgc tcgaaagtca       2580
ccctcggaac catcagggcc aggtgcacct gcggggaatg tccccgagtg tgtgagcaat       2640
gccgcactga tacaggagtg gacacccgaa tctggtacca caatctcccc gagatcccag       2700
aataatgaag aagggggaga ctattatgat gatgagctgt tctctgatgt ccaagatatt       2760
aaaacagcct tggccaaaat acacgaggat aatcagaaga taatctccaa gctagaatca       2820
ctgctgttat tgaagggaga agttgagtca attaagaagc agatcaacag gcaaaatatc       2880
agcatatcca ccctggaagg acacctctca agcatcatga tcgccattcc tggacttggg       2940
aaggatccca acgaccccac tgcagatgtc gaaatcaatc ccgacttgaa acccatcata       3000
ggcagagatt caggccgagc actggccgaa gttctcaaga aacccgttgc cagccgacaa       3060
ctccaaggaa tgacaaatgg acggaccagt tccagaggac agctgctgaa ggaatttcag       3120
ctaaagccga tcgggaaaaa gatgagctca gccgtcgggt ttgttcctga caccggccct       3180
gcatcacgca gtgtaatccg ctccattata aaatccagcc ggctagagga ggatcggaag       3240
cgttacctga tgactctcct tgatgatatc aaaggagcca atgatcttgc caagttccac       3300
cagatgctga tgaagataat aatgaagtag ctacagctca acttacctgc caaccccatg       3360
ccagtcgacc caactagtac aacctaaatc cattataaaa aacttaggag caaagtgatt       3420
gcctcccaag ttccacaggc gcgccatgtt tgttttctt gttttattgc cactagtctc        3480
tagtcagtgt gttaatctta caaccagaac tcaattaccc cctgcataca ctaattcttt       3540
cacacgtggt gtttattacc ctgacaaagt tttcagatcc tcagttttac attcaactca       3600
ggacttgttc ttacctttct tttccaatgt tacttggttc catgctatac atgtctctgg       3660
gaccaatggt actaagaggt ttgataaccc tgtcctacca tttaatgatg gtgtttattt       3720
tgcttccact gagaagtcta acataataag aggctggatt tttggtacta ctttagattc        3780
gaagacccag tccctactta ttgttaataa cgctactaat gttgttatta aagtctgtga       3840
atttcaattt tgtaatgatc catttttggg tgtttattac cacaaaaaca acaaaagttg       3900
gatggaaagt gagttcagag tttattctag tgcgaataat tgcacttttg aatatgtctc       3960
tcagcctttt cttatggacc ttgaaggaaa acagggtaat ttcaaaaatc ttagggaatt       4020
tgtgtttaag aatattgatg gttattttaa aatatattct aagcacacgc ctattaattt       4080
agtgcgtgat ctccctcagg gttttctcggc tttagaacca ttggtagatt gccaatagg        4140 tattaacatc actaggtttc aaactttact tgctttacat agaagttatt tgactcctgg       4200
tgattcttct tcaggttgga cagctggtgc tgcagcttat tatgtgggtt atcttcaacc       4260
taggactttt ctattaaaat ataatgaaaa tggaaccatt acagatgctg tagactgtgc       4320
acttgaccct ctctcagaaa caaagtgtac gttgaaatcc ttcactgtag aaaaaggaat       4380
ctatcaaact tctaacttta gagtccaacc aacagaatct attgttagat ttcctaatat       4440
tacaaacttg tgccctttttg gtgaagtttt taacgccacc agatttgcat ctgtttatgc       4500
ttggaacagg aagagaatca gcaactgtgt tgctgattat tctgtcctat ataattccgc       4560
atcattttcc acttttaagt gttatggagt gtctcctact aaattaaatg atctctgctt       4620
```

-continued

```
tactaatgtc tatgcagatt catttgtaat tagaggtgat gaagtcagac aaatcgctcc    4680
agggcaaact ggaaagattg ctgattataa ttataaatta ccagatgatt ttacaggctg    4740
cgttatagct tggaattcta acaatcttga ttctaaggtt ggtggtaatt ataattacct    4800
gtatagattg tttaggaagt ctaatctcaa accttttgag agagatattt caactgaaat    4860
ctatcaggcc ggtagcacac cttgtaatgg tgttgaaggt tttaattgtt actttccttt    4920
acaatcatat ggtttccaac ccactaatgg tgttggttac caaccataca gagtagtagt    4980
actttctttt gaacttctac atgcaccagc aactgtttgt ggacctaaaa agtctactaa    5040
tttggttaaa aacaaatgtg tcaatttcaa cttcaatggt ttaacaggca caggtgttct    5100
tactgagtct aacaaaaagt ttctgccttt ccaacaattt ggcagagaca ttgctgacac    5160
tactgatgct gtccgtgatc cacagacact tgagattctt gacattacac catgttcttt    5220
tggtggtgtc agtgttataa caccaggaac aaatacttct aaccaggttg ctgttcttta    5280
tcaggatgtt aactgcacag aagtccctgt tgctattcat gcagatcaac ttactcctac    5340
ttggcgtgtt tattctacag gttctaatgt ttttcaaaca cgtgcaggct gtttaatagg    5400
ggctgaacat gtcaacaact catatgagtg tgacataccc attggtgcag gtatatgcgc    5460
tagttatcag actcagacta attctcctcg gcgggcacgt agtgtagcta gtcaatccat    5520
cattgcctac actatgtcac ttggtgcaga aaattcagtt gcttactcta ataactctat    5580
tgccataccc acaaatttta ctattagtgt taccacagaa attctaccag tgtctatgac    5640
caagacatca gtagattgta caatgtacat ttgtggtgat tcaactgaat gcagcaatct    5700
tttgttgcaa tatggcagtt tttgtacaca attaaaccgt gctttaactg gaatagctgt    5760
tgaacaagac aaaaacaccc aagaagtttt tgcacaagtc aaacaaattt acaaaacacc    5820
accaattaaa gattttggtg gttttaattt ttcacaaata ttaccagatc catcaaaacc    5880
aagcaagagg tcatttattg aagatctact tttcaacaaa gtgacacttg cagatgctgg    5940
cttcatcaaa caatatggtg attgccttgg tgatattgct gctagagacc tcatttgtgc    6000
acaaaagttt aacggcctta ctgttttgcc acctttgctc acagatgaaa tgattgctca    6060
atacacttct gcactgttag cgggtacaat cacttctggt tggacctttg gtgcaggtgc    6120
tgcattacaa ataccatttg ctatgcaaat ggcttatagg tttaatggta ttggagttac    6180
acagaatgtt ctctatgaga accaaaaatt gattgccaac caatttaata gtgctattgg    6240
caaaattcaa gactcacttt cttccacagc aagtgcactt ggaaaacttc aagatgtggt    6300
caaccaaaat gcacaagctt taaacacgct tgttaaacaa cttagctcca attttggtgc    6360
aatttcaagt gtttttaaatg atatcctttc acgtcttgac aaagttgagg ctgaagtgca    6420
aattgatagg ttgatcacag gcagacttca aagtttgcag acatatgtga ctcaacaatt    6480
aattagagct gcagaaatca gagcttctgc taatcttgct gctactaaaa tgtcagagtg    6540
tgtacttgga caatcaaaaa gagttgattt ttgtggaaag ggctatcatc ttatgtcctt    6600
ccctcagtca gcacctcatg gtgtagtctt cttgcatgtg acttatgtcc ctgcacaaga    6660
aaagaacttc acaactgctc ctgccatttg tcatgatgga aaagcacact tcctcgtga    6720 aggtgtcttt gtttcaaatg gcacacactg gtttgtaaca caaaggaatt tttatgaacc    6780
acaaatcatt actacagaca acacatttgt gtctggtaac tgtgatgttg taataggaat    6840
tgtcaacaac acagtttatg atcctttgca acctgaatta gactcattca aggaggagtt    6900
agataaatat tttaagaatc atacatcacc agatgttgat ttaggtgaca tctctggcat    6960
taatgcttca gttgtaaaca ttcaaaaaga aattgaccgc ctcaatgagg ttgccaagaa    7020
```

```
tttaaatgaa tctctcatcg atctccaaga acttggaaag tatgagcagt atataaaatg    7080
gccatggtac atttggctag gttttatagc tggcttgatt gccatagtaa tggtgacaat    7140
tatgctttgc tgtatgacca gttgctgtag ttgtctcaag ggctgttgtt cttgtggatc    7200
ctgctgcaaa tttgatgaag acgactctga gccagtgctc aaaggagtcg cattagctta    7260
cacataacgc gcgacgtcct acagctcaac ttacctgcca accccatgcc agtcgaccca    7320
actagtacaa cctaaatcca ttataaaaaa cttaggagca aagtgattgc ctcccaagtt    7380
ccacaatgac agagatctac gacttcgaca agtcggcatg ggacatcaaa gggttgatcg    7440
ctccgataca acccaccacc tacagtgatg gcaggctggt gccccaggtc agagtcatag    7500
atcctggtct aggcgacagg aaggatgaat gctttatgta catgtttctg ctgggggttg    7560
ttgaggacag cgatccccta gggcctccaa tcgggcgagc atttgggtcc ctgcccttag    7620
gtgttggcag atccacagca aagcccgaaa aactcctcaa agaggccact gagcttgaca    7680
tagttgttag acgtacagca gggctcaatg aaaaactggt gttctacaac aacaccccac    7740
taactctcct cacaccttgg agaaaggtcc taacaacagg gagtgtcttc aacgcaaacc    7800
aagtgtgcaa tgcggttaat ctgataccgc tcgatacccc gcagaggttc cgtgttgttt    7860
atatgagcat cacccgtctt tcggataacg ggtattacac cgttcctaga agaatgctgg    7920
aattcagatc ggtcaatgca gtggccttca acctgctggt gacccttagg attgacaagg    7980
cgataggccc tgggaagatc atcgacaata cagagcaact tcctgaggca acatttatgg    8040
tccacatcgg gaacttcagg agaaagaaga gtgaagtcta ctctgccgat tattgcaaaa    8100
tgaaaatcga aaagatgggc ctggtttttg cacttggtgg gatagggggc accagtcttc    8160
acattagaag cacaggcaaa atgagcaaga ctctccatgc acaactcggg ttcaagaaga    8220
ccttatgtta cccgctgata gatatcaatg aagaccttaa tcgattactc tggaggagca    8280
gatgcaagat agtaagaatc caggcagttt tgcagccatc agttcctcaa gaattccgca    8340
tttacgacga cgtgatcata aatgatgacc aaggactatt caaagttctg tagaccgtag    8400
tgcccagcaa tgcccgaaaa cgaccccct cacaatgaca gccagaaggc ccggacaaaa    8460 aagcccctc cgaaagactc cacggaccaa gcgagaggcc agccagcagc cgacggcaag    8520
cgcgaacacc aggcggcccc agcacagaac agccctgata caaggccacc accagccacc    8580
ccaatctgca tcctcctcgt gggacccccg aggaccaacc cccaaggctg cccccgatcc    8640
aaaccaccaa ccgcatcccc accacccccg ggaaagaaac ccccagcaat tggaaggccc    8700
ctccccctct tcctcaacac aagaactcca caaccgaacc gcacaagcga ccgaggtgac    8760
ccaaccgcag gcatccgact ccctagacag atcctctctc cccggcaaac taaacaaaac    8820
ttagggccaa ggaacataca cacccaacag aacccagacc ccggcccacg gcgccgcgcc    8880 cccaacccccc gacaaccaga gggagccccc aaccaatccc gccggctccc ccggtgccca    8940
caggcaggga caccaacccc cgaacagacc cagcacccaa ccatcgacaa tccaagacgg    9000 ggggccccc ccaaaaaaag gccccaggg gccgacagcc agcaccgcga ggaagcccac    9060
ccaccccaca cacgaccacg gcaaccaaac cagaacccag accaccctgg gccaccagct    9120
cccagactcg gccatcaccc cgcagaaagg aaaggccaca acccgcgcac cccagccccg    9180
atccggcggg gagccacccca acccgaacca gcacccaaga gcgatccccg aaggacccccc    9240 gaaccgcaaa ggacatcagt atcccacagc ctctccaagt cccccggtct cctcccttc    9300 tcgaagggac caaaagatca atccaccaca cccgacgaca ctcaactccc cacccctaaa    9360
```

-continued

```
ggagacaccg ggaatcccag aatcaagact catccaatgt ccatcatggg tctcaaggtg    9420
aacgtctctg ccatattcat ggcagtactg ttaactctcc aaacacccac cggtcaaatc    9480
cattggggca atctctctaa gatagggtg gtaggaatag gaagtgcaag ctacaaagtt     9540
atgactcgtt ccagccatca atcattagtc ataaaattaa tgcccaatat aactctcctc    9600
aataactgca cgagggtaga gattgcagaa tacaggagac tactgagaac agttttggaa    9660
ccaattagag atgcacttaa tgcaatgacc cagaatataa gaccggttca gagtgtagct    9720
tcaagtagga gacacaagag atttgcggga gtagtcctgg caggtgcggc cctaggcgtc    9780
gccacagctg ctcagataac agccggcatt gcacttcacc agtccatgct gaactctcaa    9840
gccatcgaca atctgagagc gagcctggaa actactaatc aggcaattga ggcaatcaga    9900
caagcagggc aggagatgat attggctgtt cagggtgtcc aagactacat caataatgag    9960
ctgataccgt ctatgaacca actatcttgt gatttaatcg gccagaagct cgggctcaaa    10020
ttgctcagat actatacaga aatcctgtca ttatttggcc ccagcttacg ggaccccata    10080
tctgcggaga tatctatcca ggctttgagc tatgcgcttg gaggagacat caataaggtg    10140
ttagaaaagc tcggatacag tggaggtgat ttactgggca tcttagagag cagaggaata    10200
aaggcccgga taactcacgt cgacacagag tcctacttca ttgtcctcag tatagcctat    10260
ccgacgctgt ccgagattaa gggggtgatt gtccaccggc tagagggggt ctcgtacaac    10320
ataggctctc aagagtggta taccactgtg cccaagtatg ttgcaaccca agggtacctt    10380
atctcgaatt ttgatgagtc atcgtgtact ttcatgccag aggggactgt gtgcagccaa    10440
aatgccttgt acccgatgag tcctctgctc caagaatgcc tccgggggtc caccaagtcc    10500
tgtgctcgta cactcgtatc cgggtctttt gggaaccggt tcattttatc acaagggaac    10560
ctaatagcca attgtgcatc aatcctttgc aagtgttaca caacaggaac gatcattaat    10620
caagaccctg acaagatcct aacatacatt gctgccgatc actgcccggt agtcgaggtg    10680 aacgcgtga ccatccaagt cgggagcagg aggtatccag atgctgtgta cttgcacaga    10740
attgacctcg gtcctcccat atcattggag aggttggacg tagggacaaa tctggggaat    10800
gcaattgcta agttggagga tgccaaggaa ttgttggagt catcggacca gatattgagg    10860
agtatgaaag gtttatcgag cactagcata gtctacatcc tgattgcagt gtgtcttgga    10920
gggttgatag gatccccgc tttaatatgt tgctgcaggg ggcgttgtaa caaaaaggga    10980
gaacaagttg gtatgtcaag accaggccta aagcctgatc ttacgggaac atcaaaatcc    11040
tatgtaaggt cgctctgatc ctctacaact cttgaaacac aaatgtccca caagtctcct    11100
cttcgtcatc aagcaaccac cgcacccagc atcaagccca cctgaaatta tctccggctt    11160
ccctctggcc gaacaatatc ggtagttaat taaaacttag ggtgcaagat catccacaat    11220
gtcaccacaa cgagaccgga taaatgcctt ctacaaagat aaccccatc ccaagggaag    11280 taggatagtc attaacagag aacatcttat gattgataga ccttatgttt tgctggctgt    11340
tctgtttgtc atgtttctga gcttgatcgg gttgctagcc attgcaggca ttagacttca    11400
tcgggcagcc atctacaccg cagagatcca taaaagcctc agcaccaatc tagatgtaac    11460
taactcaatc gagcatcagg tcaaggacgt gctgacacca ctcttcaaaa tcatcggtga    11520
tgaagtgggc ctgaggacac ctcagagatt cactgaccta gtgaaattca tctctgacaa    11580
gattaaattc cttaatccgg atagggagta cgacttcaga gatctcactt ggtgtatcaa    11640
cccgccagag agaatcaaat tggattatga tcaatactgt gcagatgtgg ctgctgaaga    11700
gctcatgaat gcattggtga actcaactct actggagacc agaacaacca atcagttcct    11760
```

```
agctgtctca aagggaaact gctcagggcc cactacaatc agaggtcaat tctcaaacat   11820
gtcgctgtcc ctgttagact tgtatttagg tcgaggttac aatgtgtcat ctatagtcac   11880
tatgacatcc cagggaatgt atgggggaac ttacctagtg gaaaagccta atctgagcag   11940
caaaaggtca gagttgtcac aactgagcat gtaccgagtg tttgaagtag gtgttatcag   12000
aaatccgggt ttgggggctc cggtgttcca tatgacaaac tatcttgagc aaccagccag   12060
taatgatctc agcaactgta tggtggcttt gggggagctc aaactcgcag cccttttgtca  12120 cggggaagat tctatcacaa ttccctatca gggatcaggg aaaggtgtca gcttccagct   12180
cgtcaagcta ggtgtctgga aatccccaac cgacatgcaa tcctgggtcc ccttatcaac   12240
ggatgatcca gtgatagaca ggctttacct ctcatctcac agaggtgtta tcgctgacaa   12300
tcaagcaaaa tgggctgtcc cgacaacacg aacagatgac aagttgcgaa tggagacatg   12360
cttccaacag gcgtgtaagg gtaaaatcca agcactctgc gagaatcccg agtgggcacc   12420
attgaaggat aacaggattc cttcatacgg ggtcttgtct gttgatctga gtctgacagt   12480
tgagcttaaa atcaaaattg cttcgggatt cgggccattg atcacacacg gttcagggat   12540
ggacctatac aaatccaacc acaacaatgt gtattggctg actatcccgc caatgaagaa   12600
cctagcctta ggtgtaatca acacattgga gtggataccg agattcaagg ttagtcccta   12660
cctcttcaat gtcccaatta aggaagcagg cgaagactgc catgccccaa catacctacc   12720
tgcggaggtg gatggtgatg tcaaactcag ttccaatctg gtgattctac ctggtcaaga   12780
tctccaatat gttttggcaa cctacgatac ttccagggtt gaacatgctg tggtttatta   12840
cgtttacagc ccaggccgct cattttctta cttttatcct tttaggttgc ctataaaggg   12900
ggtccccatc gaattacaag tggaatgctt cacatgggac caaaaactct ggtgccgtca   12960
cttctgtgtg cttgcggact cagaatctgg tggacatatc actcactctg ggatggtggg   13020
catgggagtc agctgcacag tcacccggga agatggaacc aatcgcagat agggctgcta   13080
gtgaaccaat ctcatgatgt cacccagaca tcaggcatac ccactagtgt gaaatagaca   13140
tcagaattaa gaaaaacgta gggtccaagt ggttccccgt tatggactcg ctatctgtca   13200
accagatctt ataccctgaa gttcacctag atagcccgat agttaccaat aagatagtag   13260
ccatcctgga gtatgctcga gtccctcacg cttacagcct ggaggaccct acactgtgtc   13320
agaacatcaa gcaccgccta aaaaacggat tttccaacca aatgattata aacaatgtgg   13380
aagttgggaa tgtcatcaag tccaagctta ggagttatcc ggcccactct catattccat   13440
atccaaattg taatcaggat ttatttaaca tagaagacaa agagtcaacg aggaagatcc   13500
gtgaactcct caaaaagggg aattcgctgt actccaaagt cagtgataag gttttccaat   13560
gcttaaggga cactaactca cggcttggcc taggctccga attgagggag gacatcaagg   13620
agaaagttat taacttggga gtttacatgc acagctccca gtggtttgag ccctttctgt   13680
tttggtttac agtcaagact gagatgaggt cagtgattaa atcacaaacc catacttgcc   13740
ataggaggag acacacacct gtattcttca ctggtagttc agttgagttg ctaatctctc   13800
gtgaccttgt tgctataatc agtaaagagt ctcaacatgt atattacctg acatttgaac   13860
tggtttttga tgtattgtgat gtcatagagg ggaggttaat gacagagacc gctatgacta   13920
ttgatgctag gtatacagag cttctaggaa gagtcagata catgtggaaa ctgatagatg   13980
gtttcttccc tgcactcggg aatccaactt atcaaattgt agccatgctg gagcctcttt   14040
cacttgctta cctgcagctg agggatataa cagtagaact cagaggtgct ttccttaacc   14100
```

-continued

```
actgctttac tgaaatacat gatgttcttg accaaaacgg gttttctgat gaaggtactt  14160
atcatgagtt aattgaagct ctagattaca ttttcataac tgatgacata catctgacag  14220
gggagatttt ctcatttttc agaagtttcg gccaccccag acttgaagca gtaacggctg  14280
ctgaaaatgt taggaaatac atgaatcagc ctaaagtcat tgtgtatgag actctgatga  14340
aaggtcatgc catattttgt ggaatcataa tcaacggcta tcgtgacagg cacggaggca  14400
gttggccacc gctgaccctc cccctgcatg ctgcagacac aatccggaat gctcaagctt  14460
caggtgaagg gttaacacat gagcagtgcg ttgataactg gagatctttt gctggagtga  14520
aatttggctg ctttatgcct cttagcctgg atagtgatct gacaatgtac ctaaaggaca  14580
aggcacttgc tgctctccaa agggaatggg attcagttta cccgaaagag ttcctgcgtt  14640
acgaccctcc caagggaacc gggtcacgga ggcttgtaga tgttttcctt aatgattcga  14700
gctttgaccc atatgatgtg ataatgtatg ttgtaagtgg agcttacctc catgaccctg  14760
agttcaacct gtcttacagc ctgaaagaaa aggagatcaa ggaaacaggt agactttttg  14820
ctaaaatgac ttacaaaatg agggcatgcc aagtgattgc tgaaaatcta atctcaaacg  14880
ggattggcaa atattttaag gacaatggga tggccaagga tgagcacgat ttgactaagg  14940
cactccacac tctagctgtc tcaggagtcc ccaaagatct caaagaaagt cacaggggggg  15000 ggccagtctt aaaaacctac tcccgaagcc cagtccacac aagtaccagg aacgtgagag  15060
cagcaaaagg gtttataggg ttccctcaag taattcggca ggaccaagac actgatcatc  15120
cggagaatat ggaagcttac gagacagtca gtgcatttat cacgactgat ctcaagaagt  15180
actgccttaa ttggagatat gagaccatca gcttgtttgc acagaggcta aatgagattt  15240
acggattgcc ctcatttttc cagtggctgc ataagaggct tgagacctct gtcctgtatg  15300
taagtgaccc tcattgcccc cccgaccttg acgcccatat cccgttatat aaagtcccca  15360
atgatcaaat cttcattaag taccctatgg gaggtataga agggtattgt cagaagctgt  15420
ggaccatcag caccattccc tatctatacc tggctgctta tgagagcgga gtaaggattg  15480
cttcgttagt gcaaggggac aatcagacca tagccgtaac aaaaagggta cccagcacat  15540
ggccctacaa ccttaagaaa cgggaagctg ctagagtaac tagagattac tttgtaattc  15600
ttaggcaaag gctacatgat attggccatc acctcaaggc aaatgagaca attgtttcat  15660
cacatttttt tgtctattca aaaggaatat attatgatgg gctacttgtg tcccaatcac  15720
tcaagagcat cgcaagatgt gtattctggt cagagactat agttgatgaa acaagggcag  15780
catgcagtaa tattgctaca acaatggcta aaagcatcga gagaggttat gaccgttacc  15840
ttgcatattc cctgaacgtc ctaaaagtga tacagcaaat tctgatctct cttggcttca  15900
caatcaattc aaccatgacc cgggatgtag tcatacccct cctcacgaac aacgacctct  15960
taataaggat ggcactgttg cccgctccta ttggggggat gaattatctg aatatgagca  16020
ggctgtttgt cagaaacatc ggtgatccag taacatcatc aattgctgat ctcaagagaa  16080
tgattctcgc ctcactaatg cctgaagaga ccctccatca gtaatgaca caacaaccgg  16140 gggactcttc attcctagac tgggctagcg acccttactc agcaaatctt gtatgtgtcc  16200
agagcatcac tagactcctc aagaacataa ctgcaaggtt tgtcctgatc catagtccaa  16260
acccaatgtt aaaaggatta ttccatgatg acagtaaaga gaggacgag ggactggcgg  16320 cattcctcat ggacaggcat attatagtac ctaggggcagc tcatgaaatc ctggatcata  16380
gtgtcacagg ggcaagagag tctattgcag gcatgctgga taccacaaaa ggcctgattc  16440
gagccagcat gaggaagggg gggttaacct ctcgagtgat aaccagattg tccaattatg  16500
```

-continued

```
actatgaaca attcagagca gggatggtgc tattgacagg aagaaagaga aatgtcctca   16560
ttgacaaaga gtcatgttca gtgcagctgg cgagagctct aagaagccat atgtgggcga   16620
ggctagctcg aggacggcct atttacggcc ttgaggtccc tgatgtacta gaatctatgc   16680
gaggccacct tattcggcgt catgagacat gtgtcatctg cgagtgtgga tcagtcaact   16740
acggatggtt ttttgtcccc tcgggttgcc aactggatga tattgacaag gaaacatcat   16800
ccttgagagt cccatatatt ggttctacca ctgatgagag aacagacatg aagcttgcct   16860
tcgtaagagc cccaagtcga tccttgcgat ctgctgttag aatagcaaca gtgtactcat   16920
gggcttacgg tgatgatgat agctcttgga acgaagcctg gttgttggct aggcaaaggg   16980
ccaatgtgag cctggaggag ctaagggtga tcactcccat ctcaacttcg actaatttag   17040
cgcataggtt gagggatcgt agcactcaag tgaaatactc aggtacatcc cttgtccgag   17100
tggcgaggta taccacaatc tccaacgaca atctctcatt tgtcatatca gataagaagg   17160
ttgatactaa ctttatatac caacaaggaa tgcttctagg gttgggtgtt ttagaaacat   17220
tgtttcgact cgagaaagat accggatcat ctaacacggt attacatctt cacgtcgaaa   17280
cagattgttg cgtgatcccg atgatagatc atcccaggat acccagctcc cgcaagctag   17340
agctgagggc agagctatgt accaacccat tgatatatga taatgcacct ttaattgaca   17400
gagatacaac aaggctatac acccagagcc ataggaggca ccttgtggaa tttgttacat   17460
ggtccacacc ccaactatat cacattttag ctaagtccac agcactatct atgattgacc   17520
tggtaacaaa atttgagaag gaccatatga atgaaatttc agctctcata ggggatgacg   17580
atatcaatag tttcataact gagtttctgc tcatagagcc aagattattc actatctact   17640
tgggccagtg tgcggccatc aattgggcat ttgatgtaca ttatcataga ccatcaggga   17700
aatatcagat gggtgagctg ttgtcatcgt tcctttctag aatgagcaaa ggagtgttta   17760
aggtgcttgt caatgctcta agccacccaa agatctacaa gaaattctgg cattgtggta   17820
ttatagagcc tatccatggt ccttcacttg atgctcaaaa cttgcacaca actgtgtgca   17880
acatggttta cacatgctat atgacctacc tcgacctgtt gttgaatgaa gagttagaag   17940
agttcacatt tctcttgtgt gaaagcgacg aggatgtagt accggacaga ttcgacaaca   18000
tccaggcaaa acacttatgt gttctggcag atttgtactg tcaaccaggg acctgcccac   18060
caattcgagg tctaagaccg gtagagaaat gtgcagttct aaccgaccat atcaaggcag   18120
aggctaggtt atctccagca ggatcttcgt ggaacataaa tccaattatt gtagaccatt   18180
actcatgctc tctgacttat ctccggcgag gatcgatcaa acagataaga ttgagagttg   18240
atccaggatt cattttcgac gccctcgctg aggtaaatgt cagtcagcca aagatcggca   18300
gcaacaacat ctcaaatatg agcatcaagg ctttcagacc cccacacgat gatgttgcaa   18360
aattgctcaa agatatcaac acaagcaagc acaatcttcc catttcaggg ggcaatctcg   18420
ccaattatga aatccatgct ttccgcagaa tcgggttgaa ctcatctgct tgctacaaag   18480
ctgttgagat atcaacatta attaggagat gccttgagcc aggggaggac ggcttgttct   18540
tgggtgaggg atcgggttcc atgttgatca cttataagga gatacttaaa ctaaacaagt   18600
gcttctataa tagtgggggt tccgccaatt ctagatctgg tcaaagggaa ttagcaccct   18660
atccctccga agttggcctt gtcgaacaca gaatgggagt aggtaatatt gtcaaagtgc   18720
tctttaacgg gaggcccgaa gtcacgtggg taggcagtgt agattgcttc aatttcatag   18780
ttagtaatat ccctacctct agtgtggggt ttatccattc agatatagag accttgccta   18840
```

-continued

```
acaaagatac tatagagaag ctagaggaat tggcagccat cttatcgatg gctctgctcc   18900
tgggcaaaat aggatcaata ctggtgatta agcttatgcc tttcagcggg gattttgttc   18960
agggatttat aagttatgta gggtcccatt atagagaagt gaaccttgta taccctagat   19020
acagcaactt catatctact gaatcttatt tggttatgac agatctcaag gctaaccggc   19080
taatgaatcc tgaaaagatt aagcagcaga taattgaatc atctgtgagg acttcacctg   19140
gacttatagg tcacatccta tccattaagc aactaagctg catacaagca attgtgggag   19200
acgcagttag tagaggtgat atcaatccta ctctgaaaaa acttacacct atagagcagg   19260
tgctgatcaa ttgcgggttg gcaattaacg gacctaagct gtgcaaagaa ttgatccacc   19320
atgatgttgc ctcagggcaa gatggattgc ttaattctat actcatcctc tacagggagt   19380
tggcaagatt caaagacaac caaagaagtc aacaagggat gttccacgct taccccgtat   19440
tggtaagtag caggcaacga gaacttatat ctaggatcac ccgcaaattt tggggggcaca   19500 ttcttcttta ctccgggaac agaaagttga taaataagtt tatccagaat ctcaagtccg   19560
gctatctgat actagactta caccagaata tcttcgttaa gaatctatcc aagtcagaga   19620
aacagattat tatgacgggg ggtttgaaac gtgagtgggt ttttaaggta acagtcaagg   19680
agaccaaaga atggtataag ttagtcggat acagtgccct gattaaggac taattggttg   19740
aactccggaa ccctaatcct gccctaggtg gttaggcatt atttgcaata gattaaagaa   19800
aactttgaaa atacgaagtt tctattccca gctttgtctg gtggccggca tggtcccagc   19860
ctcctcgctg gcgccggctg ggcaacattc cgaggggacc gtcccctcgg taatggcgaa   19920
tgggacgcgg ccgatccggc tgctaacaaa gcccgaaagg aagctgagtt ggctgctgcc   19980
accgctgagc aataactagc ataacccctt ggggcctcta aacgggtctt gaggggtttt   20040
ttgctgaaag gaggaactat atccggatgc ggccgatccg gctgctaaca aagcccgaaa   20100
ggaagctgag ttggctgctg ccaccgctga gcaataacta gcataacccc ttggggcctc   20160
taaacgggtc ttgagggggt ttttgctgaa aggaggaact atatccggat ggccgccacc   20220
ggccggtggg ccttgcagca catccccctt cgccagctg gcgtaatagc gaagaggccc   20280
gcaccgatcg cccttcccaa cagttgcgca gcctgaatgg cgaatgggac gcgccctgta   20340
gcggcgcatt aagcgcggcg ggtgtggtgg ttacgcgcag cgtgaccgct acacttgcca   20400
gcgccctagc gcccgctcct ttcgctttct tcccttcctt tctcgccacg ttcgccggct   20460
ttccccgtca gctctaaat cggggggctcc ctttagggtt ccgatttagt gctttacggc   20520
acctcgaccc caaaaaactt gattagggtg atggttcacg tgggccatcg ccctgataga   20580
cggtttttcg ccctttgacg ttggagtcca cgttctttaa tagtggactc ttgttccaaa   20640
ctggaacaac actcaaccct atctcggtct attcttttga tttataaggg attttgccga   20700
tttcggccta ttggttaaaa aatgagctga tttaacaaaa atttaacgcg aatttttaaca   20760 aaatattaac gcttacaatt taggtggcac ttttcgggga aatgtgcgcg gaacccctat   20820
ttgtttattt ttctaaatac attcaaatat gtatccgctc atgagacaat aaccctgata   20880
aatgcttcaa taatattgaa aaaggaagag tatgagtatt caacatttcc gtgtcgccct   20940
tattcccttt tttgcggcat tttgccttcc tgttttttgct cacccagaaa cgctggtgaa   21000
agtaaaagat gctgaagatc agttgggtgc acgagtgggt tacatcgaac tggatctcaa   21060
cagcggtaag atccttgaga gttttcgccc cgaagaacgt tttccaatga tgagcacttt   21120
taaagttctg ctatgtggcg cggtattatc ccgtattgac gccgggcaag agcaactcgg   21180
tcgccgcata cactattctc agaatgactt ggttgagtac tcaccagtca cagaaaagca   21240
```

```
tcttacggat ggcatgacag taagagaatt atgcagtgct gccataacca tgagtgataa    21300
cactgcggcc aacttacttc tgacaacgat cggaggaccg aaggagctaa ccgctttttt    21360
gcacaacatg ggggatcatg taactcgcct tgatcgttgg gaaccggagc tgaatgaagc    21420
cataccaaac gacgagcgtg acaccacgat gcctgtagca atggcaacaa cgttgcgcaa    21480
actattaact ggcgaactac ttacactagc ttcccggcaa caattaatag actggatgga    21540
ggcggataaa gttgcaggac cacttctgcg ctcggccctt ccggctggct ggtttattgc    21600
tgataaatct ggagccggtg agcgtgggtc tcgcggtatc attgcagcac tggggccaga    21660
tggtaagccc tcccgtatcg tagttatcta cacgacgggg agtcaggcaa ctatggatga    21720
acgaaataga cagatcgctg agataggtgc ctcactgatt aagcattggt aactgtcaga    21780
ccaagtttac tcatatatac tttagattga tttaaaactt catttttaat ttaaaaggat    21840
ctaggtgaag atcctttttg ataatctcat gaccaaaatc ccttaacgtg agttttcgtt    21900
ccactgagcg tcagaccccg tagaaaagat caaaggatct tcttgagatc ctttttttct    21960
gcgcgtaatc tgctgcttgc aaacaaaaaa accaccgcta ccagcggtgg tttgtttgcc    22020
ggatcaagag ctaccaactc tttttccgaa ggtaactggc ttcagcagag cgcagatacc    22080
aaatactgtt cttctagtgt agccgtagtt aggccaccac ttcaagaact ctgtagcacc    22140
gcctacatac ctcgctctgc taatcctgtt accagtggct gctgccagtg gcgataagtc    22200
gtgtcttacc gggttggact caagacgata gttaccggat aaggcgcagc ggtcgggctg    22260
aacggggggt tcgtgcacac agcccagctt ggagcgaacg acctacaccg aactgagata    22320
cctacagcgt gagctatgag aaagcgccac gcttcccgaa gggagaaagg cggacaggta    22380
tccggtaagc ggcagggtcg aacaggaga gcgcacgagg gagcttccag ggggaaacgc     22440
ctggtatctt tatagtcctg tcgggtttcg ccacctctga cttgagcgtc gatttttgtg    22500
atgctcgtca gggggggcgga gcctatggaa aaacgccagc aacgcggcct ttttacggtt    22560
cctggccttt tgctggcctt ttgctcacat gttctttcct gcgttatccc ctgattctgt    22620
ggataaccgt attaccgcct ttgagtgagc tgataccgct cgccgcagcc gaacgaccga    22680
gcgcagcgag tcagtgagcg aggaagcgga agagcgccca atacgcaaac cgcctctccc    22740
cgcgcgttgg ccgattcatt aatgcagctg gcacgacagg tttcccgact ggaaagcggg    22800
cagtgagcgc aacgcaatta atgtgagtta gctcactcat taggcacccc aggctttaca    22860
ctttatgctt ccggctcgta tgttgtgtgg aattgtgagc ggacaacaat ttcacacagg    22920
aaacagctat gaccatgatt acgccaagct cgggcggccg cttgtaatac gactcactat    22980
a                                                                    22981
```

```
<210> SEQ ID NO 19
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA-PP

<400> SEQUENCE: 19
accaaacaaa gttgggtaag gatagttcaa tcaatgatca ttttctagtg cacttaggat        60
tcaagatcct attatcaggg acaagagcag gattaaggat atccgagatg gccacacttt       120
```

```
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtcaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcga gaacaaggaa atctcagata ttgaagtgca agaccctgag ggattcaaca    600
tgattctggg taccatccta gctcaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020 aaatgggggga aactgcaccc tacatggtaa tcctggagaa ctcaattcag aacaagttca   1080
gtgcaggatc atacccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag gaccagaaca acatccgcct accctccatc attgttataa   1740
aaaacttagg aaccaggtcc acacagccgc cagcccatca accatccact cccacgattg   1800
gagccgatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa cttttgggaat ccccccaaga   2100 aatctccagg catcaagcac tgggttacag tgttattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc tccggacccc   2460
ggtagggcca gcacttccgg gacacccatt aaaaagggca cagacgcgag attagcctca   2520
```

-continued

```
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aaggggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtac aacctaaatc cattataaaa aacttaggag caaagtgatt   3420
gcctcccaag ttccacaggc gcgccatgtt cgtcttcctg gtcctgctgc ctctggtctc   3480
ctcacagtgc gtcaatctga caactcggac tcagctgcca cctgcttata ctaatagctt   3540
caccagaggc gtgtactatc ctgacaaggt gtttagaagc tccgtgctgc actctacaca   3600
ggatctgttt ctgccattct ttagcaacgt gacctggttc cacgccatcc acgtgagcgg   3660
caccaatggc acaaagcggt tcgacaatcc cgtgctgcct tttaacgatg gcgtgtactt   3720
cgcctctacc gagaagagca acatcatcag aggctggatc tttggcacca cactggactc   3780
caagacacag tctctgctga tcgtgaacaa tgccaccaac gtggtcatca aggtgtgcga   3840
gttccagttt tgtaatgatc ccttcctggg cgtgtactat cacaagaaca ataagagctg   3900
gatggagtcc gagtttagag tgtattctag cgccaacaac tgcacatttg agtacgtgag   3960
ccagcctttc ctgatggacc tggagggcaa gcagggcaat ttcaagaacc tgagggagtt   4020
cgtgtttaag aatatcgacg gctacttcaa aatctactct aagcacaccc ccatcaacct   4080
ggtgcgcgac ctgcctcagg gcttcagcgc cctggagccc ctggtggatc tgcctatcgg   4140
catcaacatc acccggtttc agacactgct ggccctgcac agaagctacc tgacacccgg   4200
cgactcctct agcggatgga ccgccggcgc tgccgcctac tatgtgggct acctccagcc   4260
ccggaccttc ctgctgaagt acaacgagaa tggcaccatc acagacgcag tggattgcgc   4320 cctgacccc ctgagcgaga caaagtgtac actgaagtcc tttaccgtgg agaagggcat   4380
ctatcagaca tccaatttca gggtgcagcc aaccgagtct atcgtgcgct ttcctaatat   4440
cacaaacctg tgcccatttg gcgaggtgtt caacgcaacc cgcttcgcca gcgtgtacgc   4500
ctggaatagg aagcggatca gcaactgcgt ggccgactat agcgtgctgt acaactccgc   4560
ctctttcagc acctttaagt gctatggcgt gtcccccaca aagctgaatg acctgtgctt   4620
taccaacgtc tacgccgatt ctttcgtgat caggggcgac gaggtgcgcc agatcgcccc   4680
cggccagaca ggcaagatcg cagactacaa ttataagctg ccagacgatt tcaccggctg   4740
cgtgatcgcc tggaacagca caatctgga ttccaaagtg ggcggcaact acaattatct   4800
gtaccggctg tttagaaaga gcaatctgaa gcccttcgag agggacatct ctacagaaat   4860
```

-continued

```
ctaccaggcc ggcagcaccc cttgcaatgg cgtggagggc tttaactgtt atttcccact    4920
ccagtcctac ggcttccagc ccacaaacgg cgtgggctat cagccttacc gcgtggtggt    4980
gctgagcttt gagctgctgc acgccccagc aacagtgtgc ggccccaaga agtccaccaa    5040
tctggtgaag aacaagtgcg tgaacttcaa cttcaacggc ctgaccggca caggcgtgct    5100
gaccgagtcc aacaagaagt tcctgccatt tcagcagttc ggcagggaca tcgcagatac    5160
cacagacgcc gtgcgcgacc cacagaccct ggagatcctg gacatcacac cctgctcttt    5220
cggcggcgtg agcgtgatca cacccggcac caatacaagc aaccaggtgg ccgtgctgta    5280
tcaggacgtg aattgtaccg aggtgcccgt ggctatccac gccgatcagc tgaccccaac    5340
atggcgggtg tacagcaccg gctccaacgt cttccagaca agagccggat gcctgatcgg    5400
agcagagcac gtgaacaatt cctatgagtg cgacatccca atcggcgccg gcatctgtgc    5460
ctcttaccag acccagacaa actctcccag aagagcccgg agcgtggcct cccagtctat    5520
catcgcctat accatgtccc tgggcgccga gaacagcgtg gcctactcta acaatagcat    5580
cgccatccca accaacttca caatctctgt gaccacagat atcctgcccg tgtccatgac    5640
caagacatct gtggactgca caatgtatat ctgtggcgat tctaccgagt gcagcaacct    5700
gctgctccag tacggcagct tttgtaccca gctgaataga gccctgacag gcatcgccgt    5760
ggagcaggat aagaacacac aggaggtgtt cgcccaggtg aagcaaatct acaagacccc    5820
ccctatcaag gactttggcg gcttcaattt ttcccagatc ctgcctgatc catccaagcc    5880
ttctaagcgg agctttatcg aggacctgct gttcaacaag gtgaccctgg ccgatgccgg    5940
cttcatcaag cagtatggcg attgcctggg cgacatcgca gccagggacc tgatctgcgc    6000
ccagaagttt aatggcctga ccgtgctgcc accectgctg acagatgaga tgatcgcaca    6060
gtacacaagc gccctgctgg ccggcaccat cacatccgga tggaccttcg gcgcaggagc    6120
cgccctccag atccccttg ccatgcagat ggcctatagg ttcaacggca tcggcgtgac    6180
ccagaatgtg ctgtacgaga accagaagct gatcgccaat cagtttaact ccgccatcgg    6240
caagatccag gacagcctgt cctctacagc cagcgccctg ggcaagctcc aggatgtggt    6300
gaatcagaac gcccaggccc tgaatacect ggtgaagcag ctgagcagca acttcggcgc    6360
catctctagc gtgctgaatg acatcctgag ccggctggac cctcctgagg cagaggtgca    6420
gatcgaccgg ctgatcaccg gccggctcca gagcctccag acctatgtga cacagcagct    6480
gatcagggcc gccgagatca gggccagcgc caatctggca gcaaccaaga gtgtccgagtg   6540 cgtgctgggc cagtctaaga gagtggactt ttgtggcaag ggctatcacc tgatgtcctt    6600
ccctcagtct gccccacacg gcgtggtgtt tctgcacgtg acctacgtgc ccgcccagga    6660
gaagaacttc accacagccc ctgccatctg ccacgatggc aaggcccact ttccaaggga    6720
gggcgtgttc gtgtccaacg gcacccactg gtttgtgaca cagcgcaatt tctacgagcc    6780
ccagatcatc accacagaca caccttcgt gagcggcaac tgtgacgtgg tcatcggcat    6840
cgtgaacaat accgtgtatg atccactcca gcccgagctg gacagcttta aggaggagct    6900
ggataagtat ttcaagaatc acacctcccc tgacgtggat ctgggcgaca tcagcggcat    6960
caatgcctcc gtggtgaaca tccagaagga gatcgaccgc ctgaacgagg tggctaagaa    7020
tctgaacgag agcctgatcg acctccagga gctgggcaag tatgagcagt acatcaagtg    7080
gccctggtac atctggctgg gcttcatcgc cggcctgatc gccatcgtga tggtgaccat    7140
catgctgtgc tgtatgacat cctgctgttc ttgcctgaag ggctgctgta gctgtggctc    7200
ctgctgtaag tttgacgagg atgactctga acctgtgctg aagggcgtgg cgctggctta    7260
```

-continued

```
cacctaacgc gcgacgtcct acagctcaac ttacctgcca accccatgcc agtcgaccca   7320
actagtacaa cctaaatcca ttataaaaaa cttaggagca aagtgattgc ctcccaagtt   7380
ccacaatgac agagatctac gacttcgaca agtcggcatg ggacatcaaa gggttgatcg   7440
ctccgataca acccaccacc tacagtgatg gcaggctggt gccccaggtc agagtcatag   7500
atcctggtct aggcgacagg aaggatgaat gctttatgta catgtttctg ctgggggttg   7560
ttgaggacag cgatccccta gggcctccaa tcgggcgagc atttgggtcc ctgcccttag   7620
gtgttggcag atccacagca aagcccgaaa aactcctcaa agaggccact gagcttgaca   7680
tagttgttag acgtacagca gggctcaatg aaaaactggt gttctacaac aacaccccac   7740
taactctcct cacaccttgg agaaaggtcc taacaacagg gagtgtcttc aacgcaaacc   7800
aagtgtgcaa tgcggttaat ctgataccgc tcgatacccc gcagaggttc cgtgttgttt   7860
atatgagcat cacccgtctt tcggataacg ggtattacac cgttcctaga agaatgctgg   7920
aattcagatc ggtcaatgca gtggccttca acctgctggt gacccttagg attgacaagg   7980
cgataggccc tgggaagatc atcgacaata cagagcaact tcctgaggca acatttatgg   8040
tccacatcgg gaacttcagg agaaagaaga gtgaagtcta ctctgccgat tattgcaaaa   8100
tgaaaatcga aaagatgggc ctggtttttg cacttggtgg gataggggc accagtcttc    8160 acattagaag cacaggcaaa atgagcaaga ctctccatgc acaactcggg ttcaagaaga   8220
ccttatgtta cccgctgata gatatcaatg aagaccttaa tcgattactc tggaggagca   8280
gatgcaagat agtaagaatc caggcagttt tgcagccatc agttcctcaa gaattccgca   8340
tttacgacga cgtgatcata aatgatgacc aaggactatt caaagttctg tagaccgtag   8400
tgcccagcaa tgcccgaaaa cgaccccct cacaatgaca gccagaaggc ccggacaaaa    8460 aagcccctc cgaaagactc cacggaccaa gcgagaggcc agccagcagc cgacggcaag    8520
cgcgaacacc aggcggcccc agcacagaac agccctgata caaggccacc accagccacc   8580
ccaatctgca tcctcctcgt gggacccccg aggaccaacc cccaaggctg cccccgatcc   8640
aaaccaccaa ccgcatcccc accaccccg ggaaagaaac ccccagcaat tggaaggccc    8700 ctcccctct tcctcaacac aagaactcca caaccgaacc gcacaagcga ccgaggtgac    8760
ccaaccgcag gcatccgact ccctagacag atcctctctc cccggcaaac taaacaaaac   8820
ttagggccaa ggaacataca cacccaacag aacccagacc ccggcccacg gcgccgcgcc   8880
cccaaccccc gacaaccaga gggagccccc aaccaatccc gccggctccc ccggtgccca   8940
caggcaggga caccaacccc cgaacagacc cagcacccaa ccatcgacaa tccaagacgg   9000 gggggcccc ccaaaaaaag gccccagggg gccgacagcc agcaccgcga ggaagcccac    9060
ccaccccaca cacgaccacg gcaaccaaac cagaacccag accaccctgg gccaccagct   9120
cccagactcg gccatcaccc cgcagaaagg aaaggccaca acccgcgcac cccagccccg   9180
atccggcggg gagccaccca acccgaacca gcacccaaga gcgatccccg aaggaccccc   9240
gaaccgcaaa ggacatcagt atcccacagc ctctccaagt cccccggtct cctccccttc   9300
tcgaagggac caaagatca atccaccaca cccgacgaca ctcaactccc caccctaaa    9360 ggagacaccg ggaatcccag aatcaagact catccaatgt ccatcatggg tctcaaggtg   9420
aacgtctctg ccatattcat ggcagtactg ttaactctcc aaacacccac cggtcaaatc   9480 cattgggca atctctctaa gatagggt gtaggaatag gaagtgcaag ctacaaagtt      9540
atgactcgtt ccagccatca atcattagtc ataaaattaa tgcccaatat aactctcctc   9600
```

-continued

```
aataactgca cgagggtaga gattgcagaa tacaggagac tactgagaac agttttggaa      9660
ccaattagag atgcacttaa tgcaatgacc cagaatataa gaccggttca gagtgtagct      9720
tcaagtagga gacacaagag atttgcggga gtagtcctgg caggtgcggc cctaggcgtc      9780
gccacagctg ctcagataac agccggcatt gcacttcacc agtccatgct gaactctcaa      9840
gccatcgaca atctgagagc gagcctggaa actactaatc aggcaattga ggcaatcaga      9900
caagcagggc aggagatgat attggctgtt cagggtgtcc aagactacat caataatgag      9960
ctgataccgt ctatgaacca actatcttgt gatttaatcg gccagaagct cgggctcaaa      10020
ttgctcagat actatacaga aatcctgtca ttatttggcc ccagcttacg ggaccccata      10080
tctgcggaga tatctatcca ggctttgagc tatgcgcttg gaggagacat caataaggtg      10140
ttagaaaagc tcggatacag tggaggtgat ttactgggca tcttagagag cagaggaata      10200
aaggcccgga taactcacgt cgacacagag tcctacttca ttgtcctcag tatagcctat      10260
ccgacgctgt ccgagattaa gggggtgatt gtccaccggc tagagggggt ctcgtacaac      10320
ataggctctc aagagtggta taccactgtg cccaagtatg ttgcaaccca agggtacctt      10380
atctcgaatt ttgatgagtc atcgtgtact ttcatgccag aggggactgt gtgcagccaa      10440
aatgccttgt acccgatgag tcctctgctc caagaatgcc tccgggggtc caccaagtcc      10500
tgtgctcgta cactcgtatc cgggtctttt gggaaccggt tcattttatc acaagggaac      10560
ctaatagcca attgtgcatc aatcctttgc aagtgttaca caacaggaac gatcattaat      10620
caagaccctg acaagatcct aacatacatt gctgccgatc actgcccggt agtcgaggtg      10680
aacggcgtga ccatccaagt cgggagcagg aggtatccag atgctgtgta cttgcacaga      10740
attgacctcg gtcctcccat atcattggag aggttggacg tagggacaaa tctggggaat      10800
gcaattgcta agttggagga tgccaaggaa ttgttggagt catcggacca gatattgagg      10860
agtatgaaag gtttatcgag cactagcata gtctacatcc tgattgcagt gtgtcttgga      10920
gggttgatag ggatccccgc tttaatatgt tgctgcaggg ggcgttgtaa caaaaaggga      10980
gaacaagttg gtatgtcaag accaggccta aagcctgatc ttacgggaac atcaaaatcc      11040
tatgtaaggt cgctctgatc ctctacaact cttgaaacac aaatgtccca caagtctcct      11100
cttcgtcatc aagcaaccac cgcacccagc atcaagccca cctgaaatta tctccggctt      11160
ccctctggcc gaacaatatc ggtagttaat taaaacttag ggtgcaagat catccacaat      11220
gtcaccacaa cgagaccgga taaatgcctt ctacaaagat aacccccatc ccaagggaag      11280
taggatagtc attaacagag aacatcttat gattgataga ccttatgttt tgctggctgt      11340
tctgtttgtc atgtttctga gcttgatcgg gttgctagcc attgcaggca ttagacttca      11400
tcgggcagcc atctacaccg cagagatcca taaaagcctc agcaccaatc tagatgtaac      11460
taactcaatc gagcatcagg tcaaggacgt gctgacacca ctcttcaaaa tcatcggtga      11520
tgaagtgggc ctgaggacac ctcagagatt cactgaccta gtgaaattca tctctgacaa      11580
gattaaattc cttaatccgg ataggagta cgacttcaga gatctcactt ggtgtatcaa      11640
cccgccagag agaatcaaat tggattatga tcaatactgt gcagatgtgg ctgctgaaga      11700
gctcatgaat gcattggtga actcaactct actggagacc agaacaacca atcagttcct      11760
agctgtctca aagggaaact gctcagggcc cactacaatc agaggtcaat tctcaaacat      11820
gtcgctgtcc ctgttagact tgtatttagg tcgaggttac aatgtgtcat ctatagtcac      11880
tatgacatcc cagggaatgt atgggggaac ttacctagtg gaaaagccta atctgagcag      11940
caaaaggtca gagttgtcac aactgagcat gtaccgagtg tttgaagtag gtgttatcag      12000
```

-continued

```
aaatccgggt ttgggggctc cggtgttcca tatgacaaac tatcttgagc aaccagccag  12060
taatgatctc agcaactgta tggtggcttt gggggagctc aaactcgcag ccctttgtca  12120
cggggaagat tctatcacaa ttccctatca gggatcaggg aaaggtgtca gcttccagct  12180
cgtcaagcta ggtgtctgga aatccccaac cgacatgcaa tcctgggtcc ccttatcaac  12240
ggatgatcca gtgatagaca ggctttacct ctcatctcac agaggtgtta tcgctgacaa  12300
tcaagcaaaa tgggctgtcc cgacaacacg aacagatgac aagttgcgaa tggagacatg  12360
cttccaacag gcgtgtaagg gtaaaatcca agcactctgc gagaatcccg agtgggcacc  12420
attgaaggat aacaggattc cttcatacgg ggtcttgtct gttgatctga gtctgacagt  12480
tgagcttaaa atcaaaattg cttcgggatt cgggccattg atcacacacg gttcagggat  12540
ggacctatac aaatccaacc acaacaatgt gtattggctg actatcccgc caatgaagaa  12600
cctagcctta ggtgtaatca acacattgga gtggataccg agattcaagg ttagtcccta  12660
cctcttcaat gtcccaatta aggaagcagg cgaagactgc catgccccaa catacctacc  12720
tgcggaggtg gatggtgatg tcaaactcag ttccaatctg gtgattctac ctggtcaaga  12780
tctccaatat gttttggcaa cctacgatac ttccagggtt gaacatgctg tggtttatta  12840
cgtttacagc ccaggccgct cattttctta cttttatcct tttaggttgc ctataaaggg  12900
ggtccccatc gaattacaag tggaatgctt cacatgggac caaaaactct ggtgccgtca  12960
cttctgtgtg cttgcggact cagaatctgg tggacatatc actcactctg ggatggtggg  13020
catgggagtc agctgcacag tcacccggga agatggaacc aatcgcagat agggctgcta  13080
gtgaaccaat ctcatgatgt cacccagaca tcaggcatac ccactagtgt gaaatagaca  13140
tcagaattaa gaaaaacgta gggtccaagt ggttccccgt tatggactcg ctatctgtca  13200
accagatctt ataccctgaa gttcacctag atagcccgat agttaccaat aagatagtag  13260
ccatcctgga gtatgctcga gtccctcacg cttacagcct ggaggaccct acactgtgtc  13320
agaacatcaa gcaccgccta aaaaacggat tttccaacca aatgattata aacaatgtgg  13380
aagttgggaa tgtcatcaag tccaagctta ggagttatcc ggcccactct catattccat  13440
atccaaattg taatcaggat ttatttaaca tagaagacaa agagtcaacg aggaagatcc  13500
gtgaactcct caaaaagggg aattcgctgt actccaaagt cagtgataag gttttccaat  13560
gcttaaggga cactaactca cggcttggcc taggctccga attgagggag gacatcaagg  13620
agaaagttat taacttggga gtttacatgc acagctccca gtggtttgag cccttttctgt  13680 tttggtttac agtcaagact gagatgaggt cagtgattaa atcacaaacc catacttgcc  13740
ataggaggag acacacacct gtattcttca ctggtagttc agttgagttg ctaatctctc  13800
gtgaccttgt tgctataatc agtaaagagt ctcaacatgt atattacctg acatttgaac  13860
tggttttgat gtattgtgat gtcatagagg ggaggttaat gacagagacc gctatgacta  13920
ttgatgctag gtatacagag cttctaggaa gagtcagata catgtggaaa ctgatagatg  13980
gtttcttccc tgcactcggg aatccaactt atcaaattgt agccatgctg gagcctcttt  14040
cacttgctta cctgcagctg agggatataa cagtagaact cagaggtgct ttccttaacc  14100
actgctttac tgaaatacat gatgttcttg accaaaacgg gttttctgat gaaggtactt  14160
atcatgagtt aattgaagct ctagattaca ttttcataac tgatgacata catctgacag  14220
gggagatttt ctcattttc agaagtttcg gccaccccag acttgaagca gtaacggctg  14280
ctgaaaatgt taggaaatac atgaatcagc ctaaagtcat tgtgtatgag actctgatga  14340
```

-continued

```
aaggtcatgc catattttgt ggaatcataa tcaacggcta tcgtgacagg cacggaggca   14400
gttggccacc gctgaccctc cccctgcatg ctgcagacac aatccggaat gctcaagctt   14460
caggtgaagg gttaacacat gagcagtgcg ttgataactg gagatctttt gctggagtga   14520
aatttggctg ctttatgcct cttagcctgg atagtgatct gacaatgtac ctaaaggaca   14580
aggcacttgc tgctctccaa agggaatggg attcagttta cccgaaagag ttcctgcgtt   14640
acgaccctcc caagggaacc gggtcacgga ggcttgtaga tgttttcctt aatgattcga   14700
gctttgaccc atatgatgtg ataatgtatg ttgtaagtgg agcttacctc catgaccctg   14760
agttcaacct gtcttacagc ctgaaagaaa aggagatcaa ggaaacaggt agacttttg    14820 ctaaaatgac ttacaaaatg agggcatgcc aagtgattgc tgaaaatcta atctcaaacg   14880
ggattggcaa atattttaag dacaatggga tggccaagga tgagcacgat ttgactaagg   14940
cactccacac tctagctgtc tcaggagtcc ccaaagatct caaagaaagt cacagggggg   15000
ggccagtctt aaaaacctac tcccgaagcc cagtccacac aagtaccagg aacgtgagag   15060
cagcaaaagg gtttataggg ttccctcaag taattcggca ggaccaagac actgatcatc   15120
cggagaatat ggaagcttac gagacagtca gtgcatttat cacgactgat ctcaagaagt   15180
actgccttaa ttggagatat gagaccatca gcttgtttgc acagaggcta aatgagattt   15240
acggattgcc ctcatttttc cagtggctgc ataagaggct tgagacctct gtcctgtatg   15300
taagtgaccc tcattgcccc cccgaccttg acgcccatat cccgttatat aaagtcccca   15360
atgatcaaat cttcattaag taccctatgg gaggtataga agggtattgt cagaagctgt   15420
ggaccatcag caccattccc tatctatacc tggctgctta tgagagcgga gtaaggattg   15480
cttcgttagt gcaaggggac aatcagacca tagccgtaac aaaaagggta cccagcacat   15540
ggccctacaa ccttaagaaa cgggaagctg ctagagtaac tagagattac tttgtaattc   15600
ttaggcaaag gctacatgat attggccatc acctcaaggc aaatgagaca attgtttcat   15660
cacatttttt tgtctattca aaaggaatat attatgatgg gctacttgtg tcccaatcac   15720
tcaagagcat cgcaagatgt gtattctggt cagagactat agttgatgaa acaagggcag   15780
catgcagtaa tattgctaca acaatggcta aaagcatcga gagaggttat gaccgttacc   15840
ttgcatattc cctgaacgtc ctaaaagtga tacagcaaat tctgatctct cttggcttca   15900
caatcaattc aaccatgacc cgggatgtag tcatacccct cctcacgaac aacgacctct   15960
taataaggat ggcactgttg cccgctccta ttgggggggat gaattatctg aatatgagca   16020
ggctgtttgt cagaaacatc ggtgatccag taacatcatc aattgctgat ctcaagagaa   16080
tgattctcgc ctcactaatg cctgaagaga ccctccatca agtaatgaca caacaaccgg   16140
gggactcttc attcctagac tgggctagcg acccttactc agcaaatctt gtatgtgtcc   16200
agagcatcac tagactcctc aagaacataa ctgcaaggtt tgtcctgatc catagtccaa   16260
acccaatgtt aaaaggatta ttccatgatg acagtaaaga gaggacgag ggactggcgg    16320 cattcctcat ggacaggcat attatagtac ctagggcagc tcatgaaatc ctggatcata   16380
gtgtcacagg ggcaagagag tctattgcag gcatgctgga taccacaaaa ggcctgattc   16440
gagccagcat gaggaagggg gggttaacct ctcgagtgat aaccagattg tccaattatg   16500
actatgaaca attcagagca gggatggtgc tattgacagg aagaagagag aatgtcctca   16560
ttgacaaaga gtcatgttca gtgcagctgg cgagagctct aagaagccat atgtgggcga   16620
ggctagctcg aggacggcct atttacggcc ttgaggtccc tgatgtacta gaatctatgc   16680
gaggccacct tattcggcgt catgagacat gtgtcatctg cgagtgtgga tcagtcaact   16740
```

-continued

```
acggatggtt ttttgtcccc tcgggttgcc aactggatga tattgacaag gaaacatcat   16800
ccttgagagt cccatatatt ggttctacca ctgatgagag aacagacatg aagcttgcct   16860
tcgtaagagc cccaagtcga tccttgcgat ctgctgttag aatagcaaca gtgtactcat   16920
gggcttacgg tgatgatgat agctcttgga acgaagcctg gttgttggct aggcaaaggg   16980
ccaatgtgag cctggaggag ctaagggtga tcactcccat ctcaacttcg actaatttag   17040
cgcataggtt gagggatcgt agcactcaag tgaaatactc aggtacatcc cttgtccgag   17100
tggcgaggta taccacaatc tccaacgaca atctctcatt tgtcatatca gataagaagg   17160
ttgatactaa ctttatatac caacaaggaa tgcttctagg gttgggtgtt ttagaaacat   17220
tgtttcgact cgagaaagat accggatcat ctaacacggt attacatctt cacgtcgaaa   17280
cagattgttg cgtgatcccg atgatagatc atcccaggat acccagctcc cgcaagctag   17340
agctgagggc agagctatgt accaacccat tgatatatga taatgcacct ttaattgaca   17400
gagatacaac aaggctatac acccagagcc ataggaggca ccttgtggaa tttgttacat   17460
ggtccacacc ccaactatat cacattttag ctaagtccac agcactatct atgattgacc   17520
tggtaacaaa atttgagaag gaccatatga atgaaatttc agctctcata ggggatgacg   17580
atatcaatag tttcataact gagtttctgc tcatagagcc aagattattc actatctact   17640
tgggccagtg tgcggccatc aattgggcat ttgatgtaca ttatcataga ccatcaggga   17700
aatatcagat gggtgagctg ttgtcatcgt tcctttctag aatgagcaaa ggagtgttta   17760
aggtgcttgt caatgctcta agccacccaa agatctacaa gaaattctgg cattgtggta   17820
ttatagagcc tatccatggt ccttcacttg atgctcaaaa cttgcacaca actgtgtgca   17880 acatggtttta cacatgctat atgacctacc tcgacctgtt gttgaatgaa gagttagaag   17940
agttcacatt tctcttgtgt gaaagcgacg aggatgtagt accggacaga ttcgacaaca   18000
tccaggcaaa acacttatgt gttctggcag atttgtactg tcaaccaggg acctgcccac   18060
caattcgagg tctaagaccg gtagagaaat gtgcagttct aaccgaccat atcaaggcag   18120
aggctaggtt atctccagca ggatcttcgt ggaacataaa tccaattatt gtagaccatt   18180
actcatgctc tctgacttat ctccggcgag gatcgatcaa acagataaga ttgagagttg   18240
atccaggatt cattttcgac gccctcgctg aggtaaatgt cagtcagcca aagatcggca   18300
gcaacaacat ctcaaatatg agcatcaagg ctttcagacc cccacacgat gatgttgcaa   18360
aattgctcaa agatatcaac acaagcaagc acaatcttcc catttcaggg ggcaatctcg   18420
ccaattatga aatccatgct ttccgcagaa tcgggttgaa ctcatctgct tgctacaaag   18480
ctgttgagat atcaacatta attaggagat gccttgagcc aggggaggac ggcttgttct   18540
tgggtgaggg atcgggttcc atgttgatca cttataagga gatacttaaa ctaaacaagt   18600
gcttctataa tagtgggggt tccgccaatt ctagatctgg tcaaagggaa ttagcaccct   18660
atccctccga agttggcctt gtcgaacaca gaatgggagt aggtaatatt gtcaaagtgc   18720
tctttaacgg gaggcccgaa gtcacgtggg taggcagtgt agattgcttc aatttcatag   18780
ttagtaatat ccctacctct agtgtggggt ttatccattc agatatagag accttgccta   18840
acaaagatac tatagagaag ctagaggaat tggcagccat cttatcgatg gctctgctcc   18900
tgggcaaaat aggatcaata ctggtgatta agcttatgcc tttcagcggg gattttgttc   18960
agggatttat aagttatgta gggtcccatt atagagaagt gaaccttgta taccctagat   19020
acagcaactt catatctact gaatcttatt tggttatgac agatctcaag gctaaccggc   19080
```

-continued

```
taatgaatcc tgaaaagatt aagcagcaga taattgaatc atctgtgagg acttcacctg    19140
gacttatagg tcacatccta tccattaagc aactaagctg catacaagca attgtgggag    19200
acgcagttag tagaggtgat atcaatccta ctctgaaaaa acttacacct atagagcagg    19260
tgctgatcaa ttgcgggttg gcaattaacg gacctaagct gtgcaaagaa ttgatccacc    19320
atgatgttgc ctcagggcaa gatggattgc ttaattctat actcatcctc tacagggagt    19380
tggcaagatt caaagacaac caaagaagtc aacaagggat gttccacgct taccccgtat    19440
tggtaagtag caggcaacga gaacttatat ctaggatcac ccgcaaattt tggggcaca    19500 ttcttcttta ctccgggaac agaaagttga taaataagtt tatccagaat ctcaagtccg    19560
gctatctgat actagactta caccagaata tcttcgttaa gaatctatcc aagtcagaga    19620
aacagattat tatgacgggg ggtttgaaac gtgagtgggt tttttaaggta acagtcaagg    19680 agaccaaaga atggtataag ttagtcggat acagtgccct gattaaggac taattggttg    19740
aactccggaa ccctaatcct gccctaggtg gttaggcatt atttgcaata gattaaagaa    19800
aactttgaaa atacgaagtt tctattccca gctttgtctg gtggccggca tggtcccagc    19860
ctcctcgctg gcgccggctg ggcaacattc cgaggggacc gtccctcgg taatggcgaa    19920 tgggacgcgg ccgatccggc tgctaacaaa gcccgaaagg aagctgagtt ggctgctgcc    19980
accgctgagc aataactagc ataacccctt ggggcctcta aacgggtctt gaggggtttt    20040
ttgctgaaag gaggaactat atccggatgc ggccgatccg gctgctaaca aagcccgaaa    20100
ggaagctgag ttggctgctg ccaccgctga gcaataacta gcataacccc ttggggcctc    20160
taaacgggtc ttgagggggt ttttgctgaa aggaggaact atatccggat ggccgccacc    20220
ggccggtggg ccttgcagca catccccctt cgccagctg gcgtaatagc gaagaggccc    20280
gcaccgatcg cccttcccaa cagttgcgca gcctgaatgg cgaatgggac gcgccctgta    20340
gcggcgcatt aagcgcggcg ggtgtggtgg ttacgcgcag cgtgaccgct cacttgcca    20400 gcgccctagc gcccgctcct ttcgctttct tcccttcctt tctcgccacg ttcgccggct    20460
ttccccgtca gctctaaat cggggggctcc ctttagggtt ccgatttagt gctttacggc    20520
acctcgaccc caaaaaactt gattagggtg atggttcacg tgggccatcg ccctgataga    20580 cggttttcg cccttgacg ttggagtcca cgttctttaa tagtggactc ttgttccaaa    20640
ctggaacaac actcaaccct atctcggtct attcttttga tttataaggg attttgccga    20700
tttcggccta ttggttaaaa aatgagctga tttaacaaaa atttaacgcg aattttaaca    20760
aaatattaac gcttacaatt taggtggcac ttttcgggga aatgtgcgcg gaaccccctat    20820 ttgtttattt ttctaaatac attcaaatat gtatccgctc atgagacaat aaccctgata    20880
aatgcttcaa taatattgaa aaaggaagag tatgagtatt caacatttcc gtgtcgccct    20940
tattcccttt tttgcggcat tttgccttcc tgttttttgct cacccagaaa cgctggtgaa    21000
agtaaaagat gctgaagatc agttgggtgc acgagtgggt tacatcgaac tggatctcaa    21060
cagcggtaag atccttgaga gttttcgccc cgaagaacgt tttccaatga tgagcacttt    21120
taaagttctg ctatgtggcg cggtattatc ccgtattgac gccgggcaag agcaactcgg    21180
tcgccgcata cactattctc agaatgactt ggttgagtac tcaccagtca cagaaaagca    21240
tcttacggat ggcatgacag taagagaatt atgcagtgct gccataacca tgagtgataa    21300
cactgcggcc aacttacttc tgacaacgat cggaggaccg aaggagctaa ccgcttttttt    21360 gcacaacatg gggatcatg taactcgcct tgatcgttgg gaaccggagc tgaatgaagc    21420
cataccaaac gacgagcgtg acaccacgat gcctgtagca atggcaacaa cgttgcgcaa    21480
```

-continued

```
actattaact ggcgaactac ttacactagc ttcccggcaa caattaatag actggatgga   21540
ggcggataaa gttgcaggac cacttctgcg ctcggccctt ccggctggct ggtttattgc   21600
tgataaatct ggagccggtg agcgtgggtc tcgcggtatc attgcagcac tggggccaga   21660
tggtaagccc tcccgtatcg tagttatcta cacgacgggg agtcaggcaa ctatggatga   21720
acgaaataga cagatcgctg agataggtgc ctcactgatt aagcattggt aactgtcaga   21780
ccaagtttac tcatatatac tttagattga tttaaaactt catttttaat ttaaaaggat   21840
ctaggtgaag atcctttttg ataatctcat gaccaaaatc ccttaacgtg agttttcgtt   21900
ccactgagcg tcagaccccg tagaaaagat caaaggatct tcttgagatc ctttttttct   21960
gcgcgtaatc tgctgcttgc aaacaaaaaa accaccgcta ccagcggtgg tttgtttgcc   22020
ggatcaagag ctaccaactc tttttccgaa ggtaactggc ttcagcagag cgcagatacc   22080
aaatactgtt cttctagtgt agccgtagtt aggccaccac ttcaagaact ctgtagcacc   22140
gcctacatac ctcgctctgc taatcctgtt accagtggct gctgccagtg gcgataagtc   22200
gtgtcttacc gggttggact caagacgata gttaccggat aaggcgcagc ggtcgggctg   22260
aacggggggt tcgtgcacac agcccagctt ggagcgaacg acctacaccg aactgagata   22320
cctacagcgt gagctatgag aaagcgccac gcttcccgaa gggagaaagg cggacaggta   22380
tccggtaagc ggcagggtcg aacaggaga gcgcacgagg gagcttccag ggggaaacgc   22440
ctggtatctt tatagtcctg tcgggtttcg ccacctctga cttgagcgtc gatttttgtg   22500
atgctcgtca gggggcgga gcctatggaa aaacgccagc aacgcggcct ttttacggtt   22560
cctggccttt tgctggcctt ttgctcacat gttctttcct gcgttatccc ctgattctgt   22620
ggataaccgt attaccgcct ttgagtgagc tgataccgct cgccgcagcc gaacgaccga   22680
gcgcagcgag tcagtgagcg aggaagcgga agagcgccca atacgcaaac cgcctctccc   22740
cgcgcgttgg ccgattcatt aatgcagctg gcacgacagg tttcccgact ggaaagcggg   22800
cagtgagcgc aacgcaatta atgtgagtta gctcactcat taggcacccc aggctttaca   22860
ctttatgctt ccggctcgta tgttgtgtgg aattgtgagc ggacaacaat ttcacacagg   22920
aaacagctat gaccatgatt acgccaagct cgggcggccg cttgtaatac gactcactat   22980
a                                                                    22981
```

```
<210> SEQ ID NO 20
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA-fneg-PP

<400> SEQUENCE: 20
```

```
accaaacaaa gttgggtaag atagttcaa tcaatgatca ttttctagtg cacttaggat      60
tcaagatcct attatcaggg acaagagcag gattaaggat atccgagatg cccacacttt     120
taaggagctt agcattgttc aaaagaaaca aggacaaacc acccattaca tcaggatccg     180
gtggagccat cagaggaatc aaacacatta ttatagtacc aatccctgga gattcctcaa     240
ttaccactcg atccagactt ctggaccggt tggtcaggtt aattggaaac ccggatgtga     300
gcgggcccaa actaacaggg gcactaatag gtatattatc cttatttgtg gagtctccag     360
```

-continued

```
gtcaattgat tcagaggatc accgatgacc ctgacgttag cataaggctg ttagaggttg        420
tccagagtga ccagtcacaa tctggcctta ccttcgcatc aagaggtacc aacatggagg        480
atgaggcgga ccaatacttt tcacatgatg atccaattag tagtgatcaa tccaggttcg        540
gatggttcga gaacaaggaa atctcagata ttgaagtgca agaccctgag ggattcaaca        600
tgattctggg taccatccta gctcaaattt gggtcttgct cgcaaaggcg gttacggccc        660
cagacacggc agctgattcg gagctaagaa ggtggataaa gtacacccaa caaagaaggg        720
tagttggtga atttagattg gagagaaaat ggttggatgt ggtgaggaac aggattgccg        780
aggacctctc cttacgccga ttcatggtcg ctctaatcct ggatatcaag agaacacccg        840
gaaacaaacc caggattgct gaaatgatat gtgacattga tacatatatc gtagaggcag        900
gattagccag ttttatcctg actattaagt ttgggataga aactatgtat cctgctcttg        960
gactgcatga atttgctggt gagttatcca cacttgagtc cttgatgaac ctttaccagc       1020
aaatggggga aactgcaccc tacatggtaa tcctggagaa ctcaattcag aacaagttca       1080
gtgcaggatc ataccctctg ctctggagct atgccatggg agtaggagtg gaacttgaaa       1140
actccatggg aggtttgaac tttggccgat cttactttga tccagcatat tttagattag       1200
ggcaagagat ggtaaggagg tcagctggaa aggtcagttc cacattggca tctgaactcg       1260
gtatcactgc cgaggatgca aggcttgttt cagagattgc aatgcatact actgaggaca       1320
agatcagtag agcggttgga cccagacaag cccaagtatc atttctacac ggtgatcaaa       1380
gtgagaatga gctaccgaga ttgggggggca aggaagatag gagggtcaaa cagagtcgag       1440
gagaagccag ggagagctac agagaaaccg ggcccagcag agcaagtgat gcgagagctg       1500
cccatcttcc aaccggcaca cccctagaca ttgacactgc atcggagtcc agccaagatc       1560
cgcaggacag tcgaaggtca gctgacgccc tgcttaggct gcaagccatg gcaggaatct       1620
cggaagaaca aggctcagac acggacaccc ctatagtgta caatgacaga aatcttctag       1680
actaggtgcg agaggccgag gaccagaaca acatccgcct accctccatc attgttataa       1740
aaaacttagg aaccaggtcc acacagccgc cagcccatca accatccact cccacgattg       1800
gagccgatgg cagaagagca ggcacgccat gtcaaaaacg gactggaatg catccgggct       1860
ctcaaggccg agcccatcgg ctcactggcc atcgaggaag ctatggcagc atggtcagaa       1920
atatcagaca acccaggaca ggagcgagcc acctgcaggg aagagaaggc aggcagttcg       1980
ggtctcagca aaccatgcct ctcagcaatt ggatcaactg aaggcggtgc acctcgcatc       2040
cgcggtcagg gacctggaga gagcgatgac gacgctgaaa cttttgggaat ccccccaaga      2100 aatctccagg catcaagcac tgggttacag tgttattatg tttatgatca cagcggtgaa       2160
gcggttaagg gaatccaaga tgctgactct atcatggttc aatcaggcct tgatggtgat       2220
agcaccctct caggaggaga caatgaatct gaaaacagcg atgtggatat tggcgaacct       2280
gataccgagg gatatgctat cactgaccgg ggatctgctc ccatctctat ggggttcagg       2340
gcttctgatg ttgaaactgc agaaggaggg gagatccacg agctcctgag actccaatcc       2400
agaggcaaca actttccgaa gcttgggaaa actctcaatg ttcctccgcc tccggacccc       2460
ggtagggcca gcacttccgg gacacccatt aaaaagggca cagacgcgag attagcctca       2520
tttggaacgg agatcgcgtc tttattgaca ggtggtgcaa cccaatgtgc tcgaaagtca       2580
ccctcggaac catcagggcc aggtgcacct gcggggaatg tccccgagtg tgtgagcaat       2640
gccgcactga tacaggagtg gacacccgaa tctggtacca caatctcccc gagatcccag       2700
aataatgaag aaggggggaga ctattatgat gatgagctgt tctctgatgt ccaagatatt      2760
```

-continued

```
aaaacagcct tggccaaaat acacgaggat aatcagaaga taatctccaa gctagaatca    2820
ctgctgttat tgaagggaga agttgagtca attaagaagc agatcaacag gcaaaatatc    2880
agcatatcca ccctggaagg acacctctca agcatcatga tcgccattcc tggacttggg    2940
aaggatccca acgaccccac tgcagatgtc gaaatcaatc ccgacttgaa acccatcata    3000
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt ttgttcctga caccggccct    3180
gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagtac aacctaaatc cattataaaa aacttaggag caaagtgatt    3420
gcctcccaag ttccacaggc gcgccatgtt cgtcttcctg gtcctgctgc ctctggtctc    3480
ctcacagtgc gtcaatctga caactcggac tcagctgcca cctgcttata ctaatagctt    3540
caccagaggc gtgtactatc ctgacaaggt gtttagaagc tccgtgctgc actctacaca    3600
ggatctgttt ctgccattct ttagcaacgt gacctggttc cacgccatcc acgtgagcgg    3660
caccaatggc acaaagcggt tcgacaatcc cgtgctgcct tttaacgatg gcgtgtactt    3720
cgcctctacc gagaagagca acatcatcag aggctggatc tttggcacca cactggactc    3780
caagacacag tctctgctga tcgtgaacaa tgccaccaac gtggtcatca aggtgtgcga    3840
gttccagttt tgtaatgatc ccttcctggg cgtgtactat cacaagaaca ataagagctg    3900
gatggagtcc gagtttagag tgtattctag cgccaacaac tgcacatttg agtacgtgag    3960
ccagcctttc ctgatggacc tggagggcaa gcagggcaat ttcaagaacc tgagggagtt    4020
cgtgtttaag aatatcgacg gctacttcaa aatctactct aagcacaccc ccatcaacct    4080
ggtgcgcgac ctgcctcagg gcttcagcgc cctggagccc ctggtggatc tgcctatcgg    4140
catcaacatc acccggtttc agacactgct ggccctgcac agaagctacc tgacacccgg    4200
cgactcctct agcggatgga ccgccggcgc tgccgcctac tatgtgggct acctccagcc    4260
ccggaccttc ctgctgaagt acaacgagaa tggcaccatc acagacgcag tggattgcgc    4320
cctggacccc ctgagcgaga caaagtgtac actgaagtcc tttaccgtgg agaagggcat    4380
ctatcagaca tccaatttca gggtgcagcc aaccgagtct atcgtgcgct ttcctaatat    4440
cacaaacctg tgcccatttg gcgaggtgtt caacgcaacc cgcttcgcca gcgtgtacgc    4500
ctggaatagg aagcggatca gcaactgcgt ggccgactat agcgtgctgt acaactccgc    4560
ctctttcagc acctttaagt gctatggcgt gtcccccaca aagctgaatg acctgtgctt    4620
taccaacgtc tacgccgatt ctttcgtgat cagggggcgac gaggtgcgcc agatcgcccc    4680
cggccagaca ggcaagatcg cagactacaa ttataagctg ccagacgatt tcaccggctg    4740
cgtgatcgcc tggaacagca caatctgga ttccaaagtg ggcggcaact acaattatct    4800
gtaccggctg tttagaaaga gcaatctgaa gcccttcgag agggacatct ctacagaaat    4860
ctaccaggcc ggcagcaccc cttgcaatgg cgtggagggc tttaactgtt atttcccact    4920
ccagtcctac ggcttccagc ccacaaacgg cgtgggctat cagccttacc gcgtggtggt    4980
gctgagcttt gagctgctgc acgccccagc aacagtgtgc ggccccaaga agtccaccaa    5040
tctggtgaag aacaagtgcg tgaacttcaa cttcaacggc ctgaccggca caggcgtgct    5100
```

-continued

```
gaccgagtcc aacaagaagt tcctgccatt tcagcagttc ggcagggaca tcgcagatac    5160
cacagacgcc gtgcgcgacc cacagaccct ggagatcctg gacatcacac cctgctcttt    5220
cggcggcgtg agcgtgatca cacccggcac caatacaagc aaccaggtgg ccgtgctgta    5280
tcaggacgtg aattgtaccg aggtgcccgt ggctatccac gccgatcagc tgaccccaac    5340
atggcgggtg tacagcaccg gctccaacgt cttccagaca agagccggat gcctgatcgg    5400
agcagagcac gtgaacaatt cctatgagtg cgacatccca atcggcgccg gcatctgtgc    5460
ctcttaccag acccagacaa actctcccgc atctgtgggc agcgtggcct cccagtctat    5520
catcgcctat accatgtccc tgggcgccga gaacagcgtg gcctactcta acaatagcat    5580
cgccatccca accaacttca caatctctgt gaccacagag atcctgcccg tgtccatgac    5640
caagacatct gtggactgca caatgtatat ctgtggcgat tctaccgagt gcagcaacct    5700
gctgctccag tacggcagct tttgtaccca gctgaataga gccctgacag gcatcgccgt    5760
ggagcaggat aagaacacac aggaggtgtt cgcccaggtg aagcaaatct acaagacccc    5820
ccctatcaag gactttggcg gcttcaattt ttcccagatc ctgcctgatc catccaagcc    5880
ttctaagcgg agctttatcg aggacctgct gttcaacaag gtgaccctgg ccgatgccgg    5940
cttcatcaag cagtatggcg attgcctggg cgacatcgca gccagggacc tgatctgcgc    6000
ccagaagttt aatggcctga ccgtgctgcc acccctgctg acagatgaga tgatcgcaca    6060
gtacacaagc gccctgctgg ccggcaccat cacatccgga tggaccttcg gcgcaggagc    6120
cgccctccag atcccctttg ccatgcagat ggcctatagg ttcaacggca tcggcgtgac    6180
ccagaatgtg ctgtacgaga accagaagct gatcgccaat cagtttaact ccgccatcgg    6240
caagatccag gacagcctgt cctctacagc cagcgccctg ggcaagctcc aggatgtggt    6300
gaatcagaac gcccaggccc tgaataccct ggtgaagcag ctgagcagca acttcggcgc    6360
catctctagc gtgctgaatg acatcctgag ccggctggac cctcctgagg cagaggtgca    6420
gatcgaccgg ctgatcaccg gccggctcca gagcctccag acctatgtga cacagcagct    6480
gatcagggcc gccgagatca gggccagcgc caatctggca gcaaccaaga gtccgagtg    6540 cgtgctgggc cagtctaaga gagtggactt ttgtggcaag ggctatcacc tgatgtcctt    6600
ccctcagtct gcccacacg gcgtggtgtt tctgcacgtg acctacgtgc ccgcccagga    6660
gaagaacttc accacagccc ctgccatctg ccacgatggc aaggcccact ttccaaggga    6720
gggcgtgttc gtgtccaacg gcacccactg gtttgtgaca cagcgcaatt tctacgagcc    6780
ccagatcatc accacagaca acaccttcgt gagcggcaac tgtgacgtgg tcatcggcat    6840
cgtgaacaat accgtgtatg atccactcca gcccgagctg gacagcttta aggaggagct    6900
ggataagtat ttcaagaatc acacctcccc tgacgtggat ctgggcgaca tcagcggcat    6960
caatgcctcc gtggtgaaca tccagaagga gatcgaccgc ctgaacgagg tggctaagaa    7020
tctgaacgag agcctgatcg acctccagga gctgggcaag tatgagcagt acatcaagtg    7080
gccctggtac atcggctggg gcttcatcgc cggcctgatc gccatcgtga tggtgaccat    7140
catgctgtgc tgtatgacat cctgctgttc ttgcctgaag ggctgctgta gctgtggctc    7200
ctgctgtaag tttgacgagg atgactctga acctgtgctg aagggcgtgg cgctggctta    7260
cacctaacgc gcgacgtcct acagctcaac ttacctgcca accccatgcc agtcgaccca    7320
actagtacaa cctaaatcca ttataaaaaa cttaggagca aagtgattgc ctcccaagtt    7380
ccacaatgac agagatctac gacttcgaca agtcggcatg ggcatcaaa gggttgatcg    7440 ctccgataca acccaccacc tacagtgatg gcaggctggt gccccaggtc agagtcatag    7500
```

```
atcctggtct aggcgacagg aaggatgaat gctttatgta catgtttctg ctggggttg      7560 ttgaggacag cgatccccta gggcctccaa tcgggcgagc atttgggtcc ctgcccttag      7620
gtgttggcag atccacagca aagcccgaaa aactcctcaa agaggccact gagcttgaca      7680
tagttgttag acgtacagca gggctcaatg aaaaactggt gttctacaac aacaccccac      7740
taactctcct cacaccttgg agaaaggtcc taacaacagg gagtgtcttc aacgcaaacc      7800
aagtgtgcaa tgcggttaat ctgataccgc tcgatacccc gcagaggttc cgtgttgttt      7860
atatgagcat cacccgtctt tcggataacg ggtattacac cgttcctaga agaatgctgg      7920
aattcagatc ggtcaatgca gtggccttca acctgctggt gacccttagg attgacaagg      7980
cgataggccc tgggaagatc atcgacaata cagagcaact tcctgaggca acatttatgg      8040
tccacatcgg gaacttcagg agaaagaaga gtgaagtcta ctctgccgat tattgcaaaa      8100
tgaaaatcga aaagatgggc ctggtttttg cacttggtgg gatagggggc accagtcttc      8160
acattagaag cacaggcaaa atgagcaaga ctctccatgc acaactcggg ttcaagaaga      8220
ccttatgtta cccgctgata gatatcaatg aagaccttaa tcgattactc tggaggagca      8280
gatgcaagat agtaagaatc caggcagttt tgcagccatc agttcctcaa gaattccgca      8340
tttacgacga cgtgatcata aatgatgacc aaggactatt caaagttctg tagaccgtag      8400
tgcccagcaa tgcccgaaaa cgaccccct cacaatgaca gccagaaggc ccggacaaaa      8460 aagcccctc cgaaagactc cacggaccaa gcgagaggcc agccagcagc cgacggcaag      8520
cgcgaacacc aggcggcccc agcacagaac agccctgata caaggccacc accagccacc      8580
ccaatctgca tcctcctcgt gggacccccg aggaccaacc cccaaggctg cccccgatcc      8640
aaaccaccaa ccgcatcccc accacccccg ggaaagaaac ccccagcaat tggaaggccc      8700 ctcccccctct tcctcaacac aagaactcca caaccgaacc gcacaagcga ccgaggtgac      8760
ccaaccgcag gcatccgact ccctagacag atcctctctc cccggcaaac taaacaaaac      8820
ttagggccaa ggaacataca cacccaacag aacccagacc ccggcccacg gcgccgcgcc      8880 cccaacccc gacaaccaga gggagccccc aaccaatccc gccggctccc ccggtgccca      8940
caggcaggga caccaacccc cgaacagacc cagcacccaa ccatcgacaa tccaagacgg      9000
gggggccccc ccaaaaaaag gcccccaggg gccgacagcc agcaccgcga ggaagcccac      9060 ccacccaca cacgaccacg gcaaccaaac cagaacccag accaccctgg gccaccagct      9120
cccagactcg gccatcaccc cgcagaaagg aaaggccaca acccgcgcac cccagcccg      9180 atccggcggg gagccaccca acccgaacca gcacccaaga gcgatccccg aaggaccccc      9240
gaaccgcaaa ggacatcagt atcccacagc ctctccaagt cccccggtct cctcccttc      9300 tcgaagggac caaaagatca atccaccaca cccgacgaca ctcaactccc caccctaaa      9360 ggagacaccg ggaatcccag aatcaagact catccaatgt ccatcatggg tctcaaggtg      9420
aacgtctctg ccatattcat ggcagtactg ttaactctcc aaacacccac cggtcaaatc      9480
cattggggca atctctctaa gatagggggtg gtaggaatag gaagtgcaag ctacaaagtt      9540
atgactcgtt ccagccatca atcattagtc ataaaattaa tgcccaatat aactctcctc      9600
aataactgca cgagggtaga gattgcagaa tacaggagac tactgagaac agttttggaa      9660
ccaattagag atgcacttaa tgcaatgacc cagaatataa gaccggttca gagtgtagct      9720
tcaagtagga gacacaagag atttgcggga gtagtcctgg caggtgcggc cctaggcgtc      9780
gccacagctg ctcagataac agccggcatt gcacttcacc agtccatgct gaactctcaa      9840
```

```
gccatcgaca atctgagagc gagcctggaa actactaatc aggcaattga ggcaatcaga    9900
caagcagggc aggagatgat attggctgtt cagggtgtcc aagactacat caataatgag    9960
ctgataccgt ctatgaacca actatcttgt gatttaatcg gccagaagct cgggctcaaa   10020
ttgctcagat actatacaga aatcctgtca ttatttggcc ccagcttacg ggaccccata   10080
tctgcggaga tatctatcca ggctttgagc tatgcgcttg gaggagacat caataaggtg   10140
ttagaaaagc tcggatacag tggaggtgat ttactgggca tcttagagag cagaggaata   10200
aaggcccgga taactcacgt cgacacagag tcctacttca ttgtcctcag tatagcctat   10260
ccgacgctgt ccgagattaa gggggtgatt gtccaccggc tagagggggt ctcgtacaac   10320
ataggctctc aagagtggta taccactgtg cccaagtatg ttgcaaccca agggtacctt   10380
atctcgaatt ttgatgagtc atcgtgtact ttcatgccag aggggactgt gtgcagccaa   10440
aatgccttgt acccgatgag tcctctgctc caagaatgcc tccgggggtc caccaagtcc   10500
tgtgctcgta cactcgtatc cgggtctttt gggaaccggt tcattttatc acaagggaac   10560
ctaatagcca attgtgcatc aatcctttgc aagtgttaca caacaggaac gatcattaat   10620
caagaccctg acaagatcct aacatacatt gctgccgatc actgcccggt agtcgaggtg   10680
aacgcgtgaa ccatccaagt cgggagcagg aggtatccag atgctgtgta cttgcacaga   10740
attgacctcg gtcctcccat atcattggag aggttggacg tagggacaaa tctggggaat   10800
gcaattgcta agttggagga tgccaaggaa ttgttggagt catcggacca gatattgagg   10860
agtatgaaag gtttatcgag cactagcata gtctacatcc tgattgcagt gtgtcttgga   10920
gggttgatag ggatccccgc tttaatatgt tgctgcaggg ggcgttgtaa caaaaaggga   10980
gaacaagttg gtatgtcaag accaggccta aagcctgatc ttacgggaac atcaaaatcc   11040
tatgtaaggt cgctctgatc ctctacaact cttgaaacac aaatgtccca caagtctcct   11100
cttcgtcatc aagcaaccac cgcacccagc atcaagccca cctgaaatta tctccggctt   11160
ccctctggcc gaacaatatc ggtagttaat taaaacttag ggtgcaagat catccacaat   11220
gtcaccacaa cgagaccgga taaatgcctt ctacaaagat aacccccatc ccaagggaag   11280
taggatagtc attaacagag aacatcttat gattgataga ccttatgttt tgctggctgt   11340
tctgtttgtc atgtttctga gcttgatcgg gttgctagcc attgcaggca ttagacttca   11400
tcgggcagcc atctacaccg cagagatcca taaaagcctc agcaccaatc tagatgtaac   11460
taactcaatc gagcatcagg tcaaggacgt gctgacacca ctcttcaaaa tcatcggtga   11520
tgaagtgggc ctgaggacac ctcagagatt cactgaccta gtgaaattca tctctgacaa   11580
gattaaattc cttaatccgg ataggagta cgacttcaga gatctcactt ggtgtatcaa   11640
cccgccagag agaatcaaat tggattatga tcaatactgt gcagatgtgg ctgctgaaga   11700
gctcatgaat gcattggtga actcaactct actggagacc agaacaacca atcagttcct   11760
agctgtctca aagggaaact gctcagggcc cactacaatc agaggtcaat tctcaaacat   11820
gtcgctgtcc ctgttagact tgtatttagg tcgaggttac aatgtgtcat ctatagtcac   11880
tatgacatcc cagggaatgt atgggggaac ttacctagtg gaaaagccta atctgagcag   11940
caaaaggtca gagttgtcac aactgagcat gtaccgagtg tttgaagtag gtgttatcag   12000
aaatccgggt ttgggggctc cggtgttcca tatgacaaac tatcttgagc aaccagccag   12060
taatgatctc agcaactgta tggtggcttt gggggagctc aaactcgcag cccttttgtca   12120 cgggaagat tctatcacaa ttccctatca gggatcaggg aaaggtgtca gcttccagct   12180
cgtcaagcta ggtgtctgga aatccccaac cgacatgcaa tcctgggtcc ccttatcaac   12240
```

-continued

```
ggatgatcca gtgatagaca ggctttacct ctcatctcac agaggtgtta tcgctgacaa  12300
tcaagcaaaa tgggctgtcc cgacaacacg aacagatgac aagttgcgaa tggagacatg  12360
cttccaacag gcgtgtaagg gtaaaatcca agcactctgc gagaatcccg agtgggcacc  12420
attgaaggat aacaggattc cttcatacgg ggtcttgtct gttgatctga gtctgacagt  12480
tgagcttaaa atcaaaattg cttcgggatt cgggccattg atcacacacg gttcagggat  12540
ggacctatac aaatccaacc acaacaatgt gtattggctg actatcccgc caatgaagaa  12600
cctagcctta ggtgtaatca acacattgga gtggataccg agattcaagg ttagtcccta  12660
cctcttcaat gtcccaatta aggaagcagg cgaagactgc catgccccaa catacctacc  12720
tgcggaggtg gatggtgatg tcaaactcag ttccaatctg gtgattctac ctggtcaaga  12780
tctccaatat gttttggcaa cctacgatac ttccagggtt gaacatgctg tggtttatta  12840
cgtttacagc ccaggccgct cattttctta cttttatcct tttaggttgc ctataaaggg  12900
ggtccccatc gaattacaag tggaatgctt cacatgggac caaaaactct ggtgccgtca  12960
cttctgtgtg cttgcggact cagaatctgg tggacatatc actcactctg ggatggtggg  13020
catgggagtc agctgcacag tcacccggga agatggaacc aatcgcagat agggctgcta  13080
gtgaaccaat ctcatgatgt cacccagaca tcaggcatac ccactagtgt gaaatagaca  13140
tcagaattaa gaaaaacgta gggtccaagt ggttccccgt tatggactcg ctatctgtca  13200
accagatctt ataccctgaa gttcacctag atagcccgat agttaccaat aagatagtag  13260
ccatcctgga gtatgctcga gtccctcacg cttacagcct ggaggaccct acactgtgtc  13320
agaacatcaa gcaccgccta aaaaacggat tttccaacca aatgattata aacaatgtgg  13380
aagttgggaa tgtcatcaag tccaagctta ggagttatcc ggcccactct catattccat  13440
atccaaattg taatcaggat ttatttaaca tagaagacaa agagtcaacg aggaagatcc  13500
gtgaactcct caaaaagggg aattcgctgt actccaaagt cagtgataag gttttccaat  13560
gcttaaggga cactaactca cggcttggcc taggctccga attgagggag gacatcaagg  13620
agaaagttat taacttggga gtttacatgc acagctccca gtggtttgag ccctttctgt  13680
tttggtttac agtcaagact gagatgaggt cagtgattaa atcacaaacc catacttgcc  13740
ataggaggag acacacacct gtattcttca ctggtagttc agttgagttg ctaatctctc  13800
gtgaccttgt tgctataatc agtaaagagt ctcaacatgt atattacctg acatttgaac  13860
tggttttgat gtattgtgat gtcatagagg ggaggttaat gacagagacc gctatgacta  13920
ttgatgctag gtatacagag cttctaggaa gagtcagata catgtggaaa ctgatagatg  13980
gtttcttccc tgcactcggg aatccaactt atcaaattgt agccatgctg gagcctcttt  14040
cacttgctta cctgcagctg agggatataa cagtagaact cagaggtgct ttccttaacc  14100
actgctttac tgaaatacat gatgttcttg accaaaacgg gttttctgat gaaggtactt  14160
atcatgagtt aattgaagct ctagattaca ttttcataac tgatgacata catctgacag  14220
gggagatttt ctcatttttc agaagtttcg gccaccccag acttgaagca gtaacggctg  14280
ctgaaaatgt taggaaatac atgaatcagc ctaaagtcat tgtgtatgag actctgatga  14340
aaggtcatgc catattttgt ggaatcataa tcaacggcta tcgtgacagg cacggaggca  14400
gttggccacc gctgacctc cccctgcatg ctgcagacac aatccggaat gctcaagctt  14460
caggtgaagg gttaacacat gagcagtgcg ttgataactg gagatctttt gctgagtga  14520 aatttggctg ctttatgcct cttagcctgg atagtgatct gacaatgtac ctaaaggaca  14580
```

-continued

```
aggcacttgc tgctctccaa agggaatggg attcagttta cccgaaagag ttcctgcgtt   14640
acgaccctcc caagggaacc gggtcacgga ggcttgtaga tgttttcctt aatgattcga   14700
gctttgaccc atatgatgtg ataatgtatg ttgtaagtgg agcttacctc catgaccctg   14760
agttcaacct gtcttacagc ctgaaagaaa aggagatcaa ggaaacaggt agactttttg   14820
ctaaaatgac ttacaaaatg agggcatgcc aagtgattgc tgaaaatcta atctcaaacg   14880
ggattggcaa atattttaag gacaatggga tggccaagga tgagcacgat ttgactaagg   14940
cactccacac tctagctgtc tcaggagtcc ccaaagatct caaagaaagt cacagggggg   15000
ggccagtctt aaaaacctac tcccgaagcc cagtccacac aagtaccagg aacgtgagag   15060
cagcaaaagg gtttataggg ttccctcaag taattcggca ggaccaagac actgatcatc   15120
cggagaatat ggaagcttac gagacagtca gtgcatttat cacgactgat ctcaagaagt   15180
actgccttaa ttggagatat gagaccatca gcttgtttgc acagaggcta aatgagattt   15240
acggattgcc ctcatttttc cagtggctgc ataagaggct tgagacctct gtcctgtatg   15300
taagtgaccc tcattgcccc cccgaccttg acgcccatat cccgttatat aaagtcccca   15360
atgatcaaat cttcattaag taccctatgg gaggtataga agggtattgt cagaagctgt   15420
ggaccatcag caccattccc tatctatacc tggctgctta tgagagcgga gtaaggattg   15480
cttcgttagt gcaaggggac aatcagacca tagccgtaac aaaaagggta cccagcacat   15540
ggccctacaa ccttaagaaa cgggaagctg ctagagtaac tagagattac tttgtaattc   15600
ttaggcaaag gctacatgat attggccatc acctcaaggc aaatgagaca attgtttcat   15660
cacatttttt tgtctattca aaaggaatat attatgatgg gctacttgtg tcccaatcac   15720
tcaagagcat cgcaagatgt gtattctggt cagagactat agttgatgaa acaagggcag   15780
catgcagtaa tattgctaca acaatggcta aaagcatcga gagaggttat gaccgttacc   15840
ttgcatattc cctgaacgtc ctaaaagtga tacagcaaat tctgatctct cttggcttca   15900
caatcaattc aaccatgacc cgggatgtag tcataccccct cctcacgaac aacgacctct   15960
taataaggat ggcactgttg cccgctccta ttgggggggat gaattatctg aatatgagca   16020
ggctgtttgt cagaaacatc ggtgatccag taacatcatc aattgctgat ctcaagagaa   16080
tgattctcgc ctcactaatg cctgaagaga ccctccatca agtaatgaca caacaaccgg   16140
gggactcttc attcctagac tgggctagcg acccttactc agcaaatctt gtatgtgtcc   16200
agagcatcac tagactcctc aagaacataa ctgcaaggtt tgtcctgatc catagtccaa   16260
acccaatgtt aaaaggatta ttccatgatg acagtaaaga agaggacgag ggactggcgg   16320
cattcctcat ggacaggcat attatagtac ctagggcagc tcatgaaatc ctggatcata   16380
gtgtcacagg ggcaagagag tctattgcag gcatgctgga taccacaaaa ggcctgattc   16440
gagccagcat gaggaagggg gggttaacct ctcgagtgat aaccagattg tccaattatg   16500
actatgaaca attcagagca gggatggtgc tattgacagg aagaaagaga aatgtcctca   16560
ttgacaaaga gtcatgttca gtgcagctgg cgagagctct aagaagccat atgtgggcga   16620
ggctagctcg aggacggcct atttacggcc ttgaggtccc tgatgtacta gaatctatgc   16680
gaggccacct tattcggcgt catgagacat gtgtcatctg cgagtgtgga tcagtcaact   16740
acggatggtt ttttgtcccc tcgggttgcc aactggatga tattgacaag gaaacatcat   16800
ccttgagagt cccatatatt ggttctacca ctgatgagag aacagacatg aagcttgcct   16860
tcgtaagagc cccaagtcga tccttgcgat ctgctgttag aatagcaaca gtgtactcat   16920
gggcttacgg tgatgatgat agctcttgga acgaagcctg gttgttggct aggcaaaggg   16980
```

```
ccaatgtgag cctggaggag ctaagggtga tcactcccat ctcaacttcg actaatttag   17040
cgcataggtt gagggatcgt agcactcaag tgaaatactc aggtacatcc cttgtccgag   17100
tggcgaggta taccacaatc tccaacgaca atctctcatt tgtcatatca gataagaagg   17160
ttgatactaa ctttatatac caacaaggaa tgcttctagg gttgggtgtt ttagaaacat   17220
tgtttcgact cgagaaagat accggatcat ctaacacggt attacatctt cacgtcgaaa   17280
cagattgttg cgtgatcccg atgatagatc atcccaggat acccagctcc cgcaagctag   17340
agctgagggc agagctatgt accaacccat tgatatatga taatgcacct ttaattgaca   17400
gagatacaac aaggctatac acccagagcc ataggaggca ccttgtggaa tttgttacat   17460
ggtccacacc ccaactatat cacattttag ctaagtccac agcactatct atgattgacc   17520
tggtaacaaa atttgagaag gaccatatga atgaaatttc agctctcata ggggatgacg   17580
atatcaatag tttcataact gagtttctgc tcatagagcc aagattattc actatctact   17640
tgggccagtg tgcggccatc aattgggcat ttgatgtaca ttatcataga ccatcaggga   17700
aatatcagat gggtgagctg ttgtcatcgt tcctttctag aatgagcaaa ggagtgttta   17760
aggtgcttgt caatgctcta agccacccaa agatctacaa gaaattctgg cattgtggta   17820
ttatagagcc tatccatggt ccttcacttg atgctcaaaa cttgcacaca actgtgtgca   17880
acatggttta cacatgctat atgacctacc tcgacctgtt gttgaatgaa gagttagaag   17940
agttcacatt tctcttgtgt gaaagcgacg aggatgtagt accggacaga ttcgacaaca   18000
tccaggcaaa acacttatgt gttctggcag atttgtactg tcaaccaggg acctgcccac   18060
caattcgagg tctaagaccg gtagagaaat gtgcagttct aaccgaccat atcaaggcag   18120
aggctaggtt atctccagca ggatcttcgt ggaacataaa tccaattatt gtagaccatt   18180
actcatgctc tctgacttat ctccggcgag gatcgatcaa acagataaga ttgagagttg   18240
atccaggatt cattttcgac gccctcgctg aggtaaatgt cagtcagcca aagatcggca   18300
gcaacaacat ctcaaatatg agcatcaagg ctttcagacc cccacacgat gatgttgcaa   18360
aattgctcaa agatatcaac acaagcaagc acaatcttcc catttcaggg ggcaatctcg   18420
ccaattatga aatccatgct ttccgcagaa tcgggttgaa ctcatctgct tgctacaaag   18480
ctgttgagat atcaacatta attaggagat gccttgagcc aggggaggac ggcttgttct   18540
tgggtgaggg atcgggttcc atgttgatca cttataagga gatacttaaa ctaaacaagt   18600
gcttctataa tagtgggggtt tccgccaatt ctagatctgg tcaaagggaa ttagcaccct   18660
atccctccga agttggcctt gtcgaacaca gaatgggagt aggtaatatt gtcaaagtgc   18720
tctttaacgg gaggcccgaa gtcacgtggg taggcagtgt agattgcttc aatttcatag   18780
ttagtaatat ccctacctct agtgtggggt ttatccattc agatatagag accttgccta   18840
acaaagatac tatagagaag ctagaggaat tggcagccat cttatcgatg gctctgctcc   18900
tgggcaaaat aggatcaata ctggtgatta agcttatgcc tttcagcggg gattttgttc   18960
agggatttat aagttatgta gggtcccatt atagagaagt gaaccttgta taccctagat   19020
acagcaactt catatctact gaatcttatt tggttatgac agatctcaag gctaaccggc   19080
taatgaatcc tgaaaagatt aagcagcaga taattgaatc atctgtgagg acttcacctg   19140
gacttatagg tcacatccta tccattaagc aactaagctg catacaagca attgtgggag   19200
acgcagttag tagaggtgat atcaatccta ctctgaaaaa acttacacct atagagcagg   19260
tgctgatcaa ttgcgggttg gcaattaacg gacctaagct gtgcaaagaa ttgatccacc   19320
```

-continued

```
atgatgttgc ctcagggcaa gatggattgc ttaattctat actcatcctc tacagggagt    19380
tggcaagatt caaagacaac caaagaagtc aacaagggat gttccacgct taccccgtat    19440
tggtaagtag caggcaacga gaacttatat ctaggatcac ccgcaaattt tgggggcaca    19500
ttcttcttta ctccgggaac agaaagttga taaataagtt tatccagaat ctcaagtccg    19560
gctatctgat actagactta caccagaata tcttcgttaa gaatctatcc aagtcagaga    19620
aacagattat tatgacgggg ggtttgaaac gtgagtgggt ttttaaggta acagtcaagg    19680
agaccaaaga atggtataag ttagtcggat acagtgccct gattaaggac taattggttg    19740
aactccggaa ccctaatcct gccctaggtg gttaggcatt atttgcaata gattaaagaa    19800
aactttgaaa atacgaagtt tctattccca gctttgtctg gtggccggca tggtcccagc    19860
ctcctcgctg gcgccggctg ggcaacattc cgaggggacc gtcccctcgg taatggcgaa    19920
tgggacgcgg ccgatccggc tgctaacaaa gcccgaaagg aagctgagtt ggctgctgcc    19980
accgctgagc aataactagc ataacccctt ggggcctcta aacgggtctt gaggggtttt    20040
ttgctgaaag gaggaactat atccggatgc ggccgatccg gctgctaaca aagcccgaaa    20100
ggaagctgag ttggctgctg ccaccgctga gcaataacta gcataacccc ttggggcctc    20160
taaacgggtc ttgagggggtt ttttgctgaa aggaggaact atatccggat ggccgccacc    20220
ggccggtggg ccttgcagca catcccctt tcgccagctg gcgtaatagc gaagaggccc    20280
gcaccgatcg cccttcccaa cagttgcgca gcctgaatgg cgaatgggac gcgccctgta    20340
gcggcgcatt aagcgcggcg ggtgtggtgg ttacgcgcag cgtgaccgct acacttgcca    20400
gcgccctagc gcccgctcct ttcgctttct tcccttcctt tctcgccacg ttcgccggct    20460
ttccccgtca agctctaaat cggggggctcc ctttagggtt ccgatttagt gctttacggc    20520
acctcgaccc caaaaaactt gattagggtg atggttcacg tgggccatcg ccctgataga    20580
cggtttttcg ccctttgacg ttggagtcca cgttctttaa tagtggactc ttgttccaaa    20640
ctggaacaac actcaaccct atctcggtct attcttttga tttataaggg attttgccga    20700
tttcggccta ttggttaaaa aatgagctga tttaacaaaa atttaacgcg aatttttaaca    20760 aaatattaac gcttacaatt taggtggcac ttttcgggga aatgtgcgcg gaaccccctat    20820 ttgtttattt ttctaaatac attcaaatat gtatccgctc atgagacaat aaccctgata    20880
aatgcttcaa taatattgaa aaaggaagag tatgagtatt caacatttcc gtgtcgccct    20940
tattcccttt tttgcggcat tttgccttcc tgttttttgct cacccagaaa cgctggtgaa    21000
agtaaaagat gctgaagatc agttgggtgc acgagtgggt tacatcgaac tggatctcaa    21060
cagcggtaag atccttgaga gttttcgccc cgaagaacgt tttccaatga tgagcacttt    21120
taaagttctg ctatgtggcg cggtattatc ccgtattgac gccgggcaag agcaactcgg    21180
tcgccgcata cactattctc agaatgactt ggttgagtac tcaccagtca cagaaaagca    21240
tcttacggat ggcatgacag taagagaatt atgcagtgct gccataacca tgagtgataa    21300
cactgcggcc aacttacttc tgacaacgat cggaggaccg aaggagctaa ccgctttttt    21360
gcacaacatg ggggatcatg taactcgcct tgatcgttgg gaaccggagc tgaatgaagc    21420
cataccaaac gacgagcgtg acaccacgat gcctgtagca atggcaacaa cgttgcgcaa    21480
actattaact ggcgaactac ttacactagc ttcccggcaa caattaatag actggatgga    21540
ggcggataaa gttgcaggac cacttctgcg ctcggccctt ccggctggct ggtttattgc    21600
tgataaatct ggagccggtg agcgtgggtc tcgcggtatc attgcagcac tggggccaga    21660
tggtaagccc tcccgtatcg tagttatcta cacgacgggg agtcaggcaa ctatggatga    21720
```

```
acgaaataga cagatcgctg agataggtgc ctcactgatt aagcattggt aactgtcaga    21780
ccaagtttac tcatatatac tttagattga tttaaaactt catttttaat ttaaaaggat    21840
ctaggtgaag atccttttg ataatctcat gaccaaaatc ccttaacgtg agttttcgtt     21900
ccactgagcg tcagacccg tagaaaagat caaaggatct tcttgagatc cttttttct      21960 gcgcgtaatc tgctgcttgc aaacaaaaaa accaccgcta ccagcggtgg tttgtttgcc    22020
ggatcaagag ctaccaactc ttttttccgaa ggtaactggc ttcagcagag cgcagatacc   22080
aaatactgtt cttctagtgt agccgtagtt aggccaccac ttcaagaact ctgtagcacc     22140
gcctacatac ctcgctctgc taatcctgtt accagtggct gctgccagtg gcgataagtc    22200
gtgtcttacc gggttggact caagacgata gttaccggat aaggcgcagc ggtcgggctg     22260 aacgggggt tcgtgcacac agcccagctt ggagcgaacg acctacaccg aactgagata      22320
cctacagcgt gagctatgag aaagcgccac gcttcccgaa gggagaaagg cggacaggta    22380
tccggtaagc ggcagggtcg aacaggaga gcgcacgagg gagcttccag ggggaaacgc      22440
ctggtatctt tatagtcctg tcgggtttcg ccacctctga cttgagcgtc gatttttgtg     22500
atgctcgtca ggggggcgga gcctatggaa aaacgccagc aacgcggcct ttttacggtt    22560
cctggccttt tgctggcctt ttgctcacat gttctttcct gcgttatccc ctgattctgt     22620
ggataaccgt attaccgcct ttgagtgagc tgataccgct cgccgcagcc gaacgaccga    22680
gcgcagcgag tcagtgagcg aggaagcgga agagcgccca atacgcaaac cgcctctccc    22740
cgcgcgttgg ccgattcatt aatgcagctg gcacgacagg tttcccgact ggaaagcggg     22800
cagtgagcgc aacgcaatta atgtgagtta gctcactcat taggcacccc aggctttaca    22860
ctttatgctt ccggctcgta tgttgtgtgg aattgtgagc ggacaacaat ttcacacagg     22920
aaacagctat gaccatgatt acgccaagct cgggcggccg cttgtaatac gactcactat    22980
a                                                                    22981

<210> SEQ ID NO 21
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA-fneg

<400> SEQUENCE: 21
accaaacaaa gttgggtaag gatagttcaa tcaatgatca ttttctagtg cacttaggat        60
tcaagatcct attatcaggg acaagagcag gattaaggat atccgagatg gccacacttt       120
taaggagctt agcattgttc aaaagaaaca aggacaaacc acccattaca tcaggatccg       180
gtggagccat cagaggaatc aaacacatta ttatagtacc aatccctgga gattcctcaa       240
ttaccactcg atccagactt ctggaccggt tggtcaggtt aattggaaac ccggatgtga       300
gcgggcccaa actaacaggg gcactaatag gtatattatc cttatttgtg gagtctccag       360
gtcaattgat tcagaggatc accgatgacc ctgacgttag cataaggctg ttagaggttg       420
tccagagtga ccagtcacaa tctggcctta ccttcgcatc aagaggtacc aacatggagg       480
atgaggcgga ccaatacttt tcacatgatg atccaattag tagtgatcaa tccaggttcg       540
gatggttcga gaacaaggaa atctcagata ttgaagtgca agaccctgag ggattcaaca       600
```

-continued

```
tgattctggg taccatccta gctcaaattt gggtcttgct cgcaaaggcg gttacggccc      660
cagacacggc agctgattcg gagctaagaa ggtggataaa gtacacccaa caaagaaggg      720
tagttggtga atttagattg gagagaaaat ggttggatgt ggtgaggaac aggattgccg      780
aggacctctc cttacgccga ttcatggtcg ctctaatcct ggatatcaag agaacacccg      840
gaaacaaacc caggattgct gaaatgatat gtgacattga tacatatatc gtagaggcag      900
gattagccag ttttatcctg actattaagt ttgggataga aactatgtat cctgctcttg      960
gactgcatga atttgctggt gagttatcca cacttgagtc cttgatgaac ctttaccagc     1020
aaatggggga aactgcaccc tacatggtaa tcctggagaa ctcaattcag aacaagttca     1080
gtgcaggatc ataccctctg ctctggagct atgccatggg agtaggagtg gaacttgaaa     1140
actccatggg aggtttgaac tttggccgat cttactttga tccagcatat tttagattag     1200
ggcaagagat ggtaaggagg tcagctggaa aggtcagttc cacattggca tctgaactcg     1260
gtatcactgc cgaggatgca aggcttgttt cagagattgc aatgcatact actgaggaca     1320
agatcagtag agcggttgga cccagacaag cccaagtatc atttctacac ggtgatcaaa     1380
gtgagaatga gctaccgaga ttggggggca aggaagatag gagggtcaaa cagagtcgag     1440
gagaagccag ggagagctac agagaaaccg ggcccagcag agcaagtgat gcgagagctg     1500
cccatcttcc aaccggcaca cccctagaca ttgacactgc atcggagtcc agccaagatc     1560
cgcaggacag tcgaaggtca gctgacgccc tgcttaggct gcaagccatg gcaggaatct     1620
cggaagaaca aggctcagac acggacaccc ctatagtgta caatgacaga aatcttctag     1680
actaggtgcg agaggccgag gaccagaaca acatccgcct accctccatc attgttataa     1740
aaaacttagg aaccaggtcc acacagccgc cagcccatca accatccact cccacgattg     1800
gagccgatgg cagaagagca ggcacgccat gtcaaaaacg gactggaatg catccgggct     1860
ctcaaggccg agcccatcgg ctcactggcc atcgaggaag ctatggcagc atggtcagaa     1920
atatcagaca acccaggaca ggagcgagcc acctgcaggg aagagaaggc aggcagttcg     1980
ggtctcagca aaccatgcct ctcagcaatt ggatcaactg aaggcggtgc acctcgcatc     2040
cgcggtcagg gacctggaga gagcgatgac gacgctgaaa cttttgggaat ccccccaaga    2100 aatctccagg catcaagcac tgggttacag tgttattatg tttatgatca cagcggtgaa     2160
gcggttaagg gaatccaaga tgctgactct atcatggttc aatcaggcct tgatggtgat     2220
agcaccctct caggaggaga caatgaatct gaaaacagcg atgtggatat tggcgaacct     2280
gataccgagg gatatgctat cactgaccgg ggatctgctc ccatctctat ggggttcagg     2340
gcttctgatg ttgaaactgc agaaggaggg gagatccacg agctcctgag actccaatcc     2400
agaggcaaca actttccgaa gcttgggaaa actctcaatg ttcctccgcc tccgacccc      2460 ggtagggcca gcacttccgg gacacccatt aaaaagggca cagacgcgag attagcctca     2520
tttggaacgg agatcgcgtc tttattgaca ggtggtgcaa cccaatgtgc tcgaaagtca     2580
ccctcggaac catcagggcc aggtgcacct gcggggaatg tccccgagtg tgtgagcaat     2640
gccgcactga tacaggagtg gacacccgaa tctggtacca caatctcccc gagatcccag     2700
aataatgaag aaggggggaga ctattatgat gatgagctgt tctctgatgt ccaagatatt    2760
aaaacagcct tggccaaaat acacgaggat aatcagaaga taatctccaa gctagaatca     2820
ctgctgttat tgaagggaga agttgagtca attaagaagc agatcaacag gcaaaatatc     2880
agcatatcca ccctgaagg acacctctca agcatcatga tcgccattcc tggacttggg     2940
aaggatccca acgaccccac tgcagatgtc gaaatcaatc ccgacttgaa acccatcata    3000
```

-continued

```
ggcagagatt caggccgagc actggccgaa gttctcaaga aacccgttgc cagccgacaa    3060
ctccaaggaa tgacaaatgg acggaccagt tccagaggac agctgctgaa ggaatttcag    3120
ctaaagccga tcgggaaaaa gatgagctca gccgtcgggt ttgttcctga caccggccct    3180
gcatcacgca gtgtaatccg ctccattata aaatccagcc ggctagagga ggatcggaag    3240
cgttacctga tgactctcct tgatgatatc aaaggagcca atgatcttgc caagttccac    3300
cagatgctga tgaagataat aatgaagtag ctacagctca acttacctgc caaccccatg    3360
ccagtcgacc caactagtac aacctaaatc cattataaaa aacttaggag caaagtgatt    3420
gcctcccaag ttccacaggc gcgccatgtt cgtcttcctg gtcctgctgc ctctggtctc    3480
ctcacagtgc gtcaatctga caactcggac tcagctgcca cctgcttata ctaatagctt    3540
caccagaggc gtgtactatc ctgacaaggt gtttagaagc tccgtgctgc actctacaca    3600
ggatctgttt ctgccattct ttagcaacgt gacctggttc cacgccatcc acgtgagcgg    3660
caccaatggc acaaagcggt tcgacaatcc cgtgctgcct tttaacgatg gcgtgtactt    3720
cgcctctacc gagaagagca acatcatcag aggctggatc tttggcacca cactggactc    3780
caagacacag tctctgctga tcgtgaacaa tgccaccaac gtggtcatca aggtgtgcga    3840
gttccagttt tgtaatgatc ccttcctggg cgtgtactat cacaagaaca ataagagctg    3900
gatggagtcc gagtttagag tgtattctag cgccaacaac tgcacatttg agtacgtgag    3960
ccagcctttc ctgatggacc tggagggcaa gcagggcaat ttcaagaacc tgagggagtt    4020
cgtgtttaag aatatcgacg gctacttcaa aatctactct aagcacaccc ccatcaacct    4080
ggtgcgcgac ctgcctcagg gcttcagcgc cctggagccc ctggtggatc tgcctatcgg    4140
catcaacatc acccggtttc agacactgct ggccctgcac agaagctacc tgacacccgg    4200
cgactcctct agcggatgga ccgccggcgc tgccgcctac tatgtgggct acctccagcc    4260
ccggaccttc ctgctgaagt acaacgagaa tggcaccatc acagacgcag tggattgcgc    4320
cctggacccc ctgagcgaga caaagtgtac actgaagtcc tttaccgtgg agaagggcat    4380
ctatcagaca tccaatttca gggtgcagcc aaccgagtct atcgtgcgct ttcctaatat    4440
cacaaacctg tgcccatttg gcgaggtgtt caacgcaacc cgcttcgcca gcgtgtacgc    4500
ctggaatagg aagcggatca gcaactgcgt ggccgactat agcgtgctgt acaactccgc    4560
ctctttcagc acctttaagt gctatggcgt gtcccccaca aagctgaatg acctgtgctt    4620
taccaacgtc tacgccgatt ctttcgtgat caggggcgac gaggtgcgcc agatcgcccc    4680
cggccagaca ggcaagatcg cagactacaa ttataagctg ccagacgatt tcaccggctg    4740
cgtgatcgcc tggaacagca caatctggga ttccaaagtg ggcggcaact acaattatct    4800
gtaccggctg tttagaaaga gcaatctgaa gcccttcgag agggacatct ctacagaaat    4860
ctaccaggcc ggcagcaccc cttgcaatgg cgtggagggc tttaactgtt atttcccact    4920
ccagtcctac ggcttccagc ccacaaacgg cgtgggctat cagccttacc gcgtggtggt    4980
gctgagcttt gagctgctgc acgccccagc aacagtgtgc ggccccaaga agtccaccaa    5040
tctggtgaag aacaagtgcg tgaacttcaa cttcaacggc ctgaccggca caggcgtgct    5100
gaccgagtcc aacaagaagt tcctgccatt tcagcagttc ggcagggaca tcgcagatac    5160
cacagacgcc gtgcgcgacc cacagaccct ggagatcctg gacatcacac cctgctcttt    5220
cggcggcgtg agcgtgatca cacccggcac caatacaagc aaccaggtgg ccgtgctgta    5280
tcaggacgtg aattgtaccg aggtgcccgt ggctatccac gccgatcagc tgaccccaac    5340
```

-continued

```
atggcgggtg tacagcaccg gctccaacgt cttccagaca agagccggat gcctgatcgg    5400
agcagagcac gtgaacaatt cctatgagtg cgacatccca atcggcgccg gcatctgtgc    5460
ctcttaccag acccagacaa actctcccgc atctgtgggc agcgtggcct cccagtctat    5520
catcgcctat accatgtccc tgggcgccga gaacagcgtg gcctactcta acaatagcat    5580
cgccatccca accaacttca caatctctgt gaccacagag atcctgcccg tgtccatgac    5640
caagacatct gtggactgca caatgtatat ctgtggcgat tctaccgagt gcagcaacct    5700
gctgctccag tacggcagct tttgtaccca gctgaataga gccctgacag gcatcgccgt    5760
ggagcaggat aagaacacac aggaggtgtt cgcccaggtg aagcaaatct acaagacccc    5820
ccctatcaag gactttggcg gcttcaattt ttcccagatc ctgcctgatc catccaagcc    5880
ttctaagcgg agctttatcg aggacctgct gttcaacaag gtgaccctgg ccgatgccgg    5940
cttcatcaag cagtatggcg attgcctggg cgacatcgca gccagggacc tgatctgcgc    6000
ccagaagttt aatggcctga ccgtgctgcc acccctgctg acagatgaga tgatcgcaca    6060
gtacacaagc gccctgctgg ccggcaccat cacatccgga tggaccttcg gcgcaggagc    6120
cgccctccag atcccctttg ccatgcagat ggcctatagg ttcaacggca tcggcgtgac    6180
ccagaatgtg ctgtacgaga accagaagct gatcgccaat cagtttaact ccgccatcgg    6240
caagatccag gacagcctgt cctctacagc cagcgccctg ggcaagctcc aggatgtggt    6300
gaatcagaac gcccaggccc tgaataccct ggtgaagcag ctgagcagca acttcggcgc    6360
catctctagc gtgctgaatg acatcctgag ccggctggac aaggtggagg cagaggtgca    6420
gatcgaccgg ctgatcaccg gccggctcca gagcctccag acctatgtga cacagcagct    6480
gatcagggcc gccgagatca gggccagcgc caatctggca gcaaccaaga gtgtccgagtg   6540 cgtgctgggc cagtctaaga gagtggactt ttgtggcaag ggctatcacc tgatgtcctt    6600
ccctcagtct gccccacacg gcgtggtgtt tctgcacgtg acctacgtgc ccgcccagga    6660
gaagaacttc accacagccc ctgccatctg ccacgatggc aaggcccact ttccaaggga    6720
gggcgtgttc gtgtccaacg gcacccactg gtttgtgaca cagcgcaatt tctacgagcc    6780
ccagatcatc accacagaca acaccttcgt gagcggcaac tgtgacgtgg tcatcggcat    6840
cgtgaacaat accgtgtatg atccactcca gcccgagctg gacagcttta aggaggagct    6900
ggataagtat ttcaagaatc acacctcccc tgacgtggat ctgggcgaca tcagcggcat    6960
caatgcctcc gtggtgaaca tccagaagga gatcgaccgc ctgaacgagg tggctaagaa    7020
tctgaacgag agcctgatcg acctccagga gctgggcaag tatgagcagt acatcaagtg    7080
gccctggtac atctggctgg gcttcatcgc cggcctgatc gccatcgtga tggtgaccat    7140
catgctgtgc tgtatgacat cctgctgttc ttgcctgaag ggctgctgta gctgtggctc    7200
ctgctgtaag tttgacgagg atgactctga acctgtgctg aagggcgtgg cgctggctta    7260
cacctaacgc gcgacgtcct acagctcaac ttacctgcca accccatgcc agtcgaccca    7320
actagtacaa cctaaatcca ttataaaaaa cttaggagca aagtgattgc ctcccaagtt    7380
ccacaatgac agagatctac gacttcgaca agtcggcatg gacatcaaa gggttgatcg     7440 ctccgataca acccaccacc tacagtgatg cgaggctggt gccccaggtc agagtcatag    7500
atcctggtct aggcgacagg aaggatgaat gctttatgta catgtttctg ctgggggttg    7560
ttgaggacag cgatccccta gggcctccaa tcgggcgagc atttgggtcc ctgcccttag    7620
gtgttggcag atccacagca aagcccgaaa aactcctcaa agaggccact gagcttgaca    7680
tagttgttag acgtacagca gggctcaatg aaaaactggt gttctacaac aacacccac    7740
```

-continued

```
taactctcct cacaccttgg agaaaggtcc taacaacagg gagtgtcttc aacgcaaacc    7800
aagtgtgcaa tgcggttaat ctgataccgc tcgataccccc gcagaggttc cgtgttgttt    7860
atatgagcat cacccgtctt tcggataacg ggtattacac cgttcctaga agaatgctgg    7920
aattcagatc ggtcaatgca gtggccttca acctgctggt gacccttagg attgacaagg    7980
cgataggccc tgggaagatc atcgacaata cagagcaact tcctgaggca acatttatgg    8040
tccacatcgg gaacttcagg agaaagaaga gtgaagtcta ctctgccgat tattgcaaaa    8100
tgaaaatcga aaagatgggc ctggtttttg cacttggtgg ataggggggc accagtcttc    8160
acattagaag cacaggcaaa atgagcaaga ctctccatgc acaactcggg ttcaagaaga    8220
ccttatgtta cccgctgata gatatcaatg aagaccttaa tcgattactc tggaggagca    8280
gatgcaagat agtaagaatc caggcagttt tgcagccatc agttcctcaa gaattccgca    8340
tttacgacga cgtgatcata aatgatgacc aaggactatt caaagttctg tagaccgtag    8400
tgcccagcaa tgcccgaaaa cgaccccccct cacaatgaca gccagaaggc ccggacaaaa    8460 aagcccccctc cgaaagactc cacggaccaa gcgagaggcc agccagcagc cgacggcaag    8520
cgcgaacacc aggcggcccc agcacagaac agccctgata caaggccacc accagccacc    8580
ccaatctgca tcctcctcgt gggaccccccg aggaccaacc cccaaggctg cccccgatcc    8640
aaaccaccaa ccgcatcccc accacccccg ggaaagaaac ccccagcaat tggaaggccc    8700
ctccccctct tcctcaacac aagaactcca caaccgaacc gcacaagcga ccgaggtgac    8760
ccaaccgcag gcatccgact ccctagacag atcctctctc cccggcaaac taaacaaaac    8820
ttagggccaa ggaacataca cacccaacag aacccagacc ccggcccacg gcgccgcgcc    8880 cccaacccccc gacaaccaga gggagcccccc aaccaatccc gccggctccc ccggtgccca    8940
caggcaggga caccaacccc cgaacagacc cagcacccaa ccatcgacaa tccaagacgg    9000 gggggcccccc ccaaaaaaag gcccccaggg gccgacagcc agcaccgcga ggaagcccac    9060 ccacccccaca cacgaccacg gcaaccaaac cagaacccag accaccctgg gccaccagct    9120
cccagactcg gccatcacccc cgcagaaagg aaaggccaca acccgcgcac cccagccccg    9180
atccggcggg gagccacccca acccgaacca gcacccaaga gcgatccccg aaggaccccc    9240
gaaccgcaaa ggacatcagt atcccacagc ctctccaagt ccccccggtct cctcccccttc    9300 tcgaagggac caaaagatca atccaccaca cccgacgaca ctcaactccc cacccctaaa    9360
ggagacaccg ggaatcccag aatcaagact catccaatgt ccatcatggg tctcaaggtg    9420
aacgtctctg ccatattcat ggcagtactg ttaactctcc aaacacccac cggtcaaatc    9480
cattggggca atctctctaa gatagggggtg gtaggaatag gaagtgcaag ctacaaagtt    9540
atgactcgtt ccagccatca atcattagtc ataaaattaa tgcccaatat aactctcctc    9600
aataactgca cgagggtaga gattgcagaa tacaggagac tactgagaac agttttggaa    9660
ccaattagag atgcacttaa tgcaatgacc cagaatataa gaccggttca gagtgtagct    9720
tcaagtagga gacacaagag atttgcggga gtagtcctgg caggtgcggc cctaggcgtc    9780
gccacagctg ctcagataac agccggcatt gcacttcacc agtccatgct gaactctcaa    9840
gccatcgaca atctgagagc gagcctggaa actactaatc aggcaattga ggcaatcaga    9900
caagcagggc aggagatgat attggctgtt caggtgtcc aagactacat caataatgag    9960 ctgatacccgt ctatgaacca actatcttgt gatttaatcg gccagaagct cgggctcaaa    10020
ttgctcagat actatacaga aatcctgtca ttatttggcc ccagcttacg ggacccccata    10080
```

-continued

```
tctgcggaga tatctatcca ggctttgagc tatgcgcttg gaggagacat caataaggtg   10140
ttagaaaagc tcggatacag tggaggtgat ttactgggca tcttagagag cagaggaata   10200
aaggcccgga taactcacgt cgacacagag tcctacttca ttgtcctcag tatagcctat   10260
ccgacgctgt ccgagattaa gggggtgatt gtccaccggc tagagggggt ctcgtacaac   10320
ataggctctc aagagtggta taccactgtg cccaagtatg ttgcaaccca agggtacctt   10380
atctcgaatt ttgatgagtc atcgtgtact ttcatgccag aggggactgt gtgcagccaa   10440
aatgccttgt acccgatgag tcctctgctc caagaatgcc tccgggggtc caccaagtcc   10500
tgtgctcgta cactcgtatc cgggtctttt gggaaccggt tcattttatc acaagggaac   10560
ctaatagcca attgtgcatc aatcctttgc aagtgttaca caacaggaac gatcattaat   10620
caagaccctg acaagatcct aacatacatt gctgccgatc actgcccggt agtcgaggtg   10680
aacggcgtga ccatccaagt cgggagcagg aggtatccag atgctgtgta cttgcacaga   10740
attgacctcg gtcctcccat atcattggag aggttggacg tagggacaaa tctgggggaat   10800 gcaattgcta agttggagga tgccaaggaa ttgttggagt catcggacca gatattgagg   10860
agtatgaaag gtttatcgag cactagcata gtctacatcc tgattgcagt gtgtcttgga   10920
gggttgatag ggatccccgc tttaatatgt tgctgcaggg ggcgttgtaa caaaaaggga   10980
gaacaagttg gtatgtcaag accaggccta aagcctgatc ttacgggaac atcaaaatcc   11040
tatgtaaggt cgctctgatc ctctacaact cttgaaacac aaatgtccca caagtctcct   11100
cttcgtcatc aagcaaccac cgcacccagc atcaagccca cctgaaatta tctccggctt   11160
ccctctggcc gaacaatatc ggtagttaat taaaacttag ggtgcaagat catccacaat   11220
gtcaccacaa cgagaccgga taaatgcctt ctacaaagat aacccccatc ccaagggaag   11280
taggatagtc attaacagag aacatcttat gattgataga ccttatgttt tgctggctgt   11340
tctgtttgtc atgtttctga gcttgatcgg gttgctagcc attgcaggca ttagacttca   11400
tcgggcagcc atctacaccg cagagatcca taaaagcctc agcaccaatc tagatgtaac   11460
taactcaatc gagcatcagg tcaaggacgt gctgacacca ctcttcaaaa tcatcggtga   11520
tgaagtgggc ctgaggacac ctcagagatt cactgaccta gtgaaattca tctctgacaa   11580
gattaaattc cttaatccgg atagggagta cgacttcaga gatctcactt ggtgtatcaa   11640
cccgccagag agaatcaaat tggattatga tcaatactgt gcagatgtgg ctgctgaaga   11700
gctcatgaat gcattggtga actcaactct actggagacc agaacaacca atcagttcct   11760
agctgtctca aagggaaact gctcagggcc cactacaatc agaggtcaat tctcaaacat   11820
gtcgctgtcc ctgttagact tgtatttagg tcgaggttac aatgtgtcat ctatagtcac   11880
tatgacatcc cagggaatgt atgggggaac ttacctagtg gaaaagccta atctgagcag   11940
caaaaggtca gagttgtcac aactgagcat gtaccgagtg tttgaagtag gtgttatcag   12000
aaatccgggt ttggggggctc cggtgttcca tatgacaaac tatcttgagc aaccagccag   12060
taatgatctc agcaactgta tggtggcttt ggggggagctc aaactcgcag ccctttgtca   12120
cggggaagat tctatcacaa ttccctatca gggatcaggg aaaggtgtca gcttccagct   12180
cgtcaagcta ggtgtctgga aatccccaac cgacatgcaa tcctgggtcc ccttatcaac   12240
ggatgatcca gtgatagaca ggctttacct ctcatctcac agaggtgtta tcgctgacaa   12300
tcaagcaaaa tgggctgtcc cgacaacacg aacagatgac aagttgcgaa tggagacatg   12360
cttccaacag gcgtgtaagg gtaaaatcca agcactctgc gagaatcccg agtgggcacc   12420
attgaaggat aacaggattc cttcatacgg ggtcttgtct gttgatctga gtctgacagt   12480
```

-continued

```
tgagcttaaa atcaaaattg cttcgggatt cgggccattg atcacacacg gttcagggat   12540
ggacctatac aaatccaacc acaacaatgt gtattggctg actatcccgc caatgaagaa   12600
cctagcctta ggtgtaatca acacattgga gtggataccg agattcaagg ttagtcccta   12660
cctcttcaat gtcccaatta aggaagcagg cgaagactgc catgccccaa catacctacc   12720
tgcggaggtg gatggtgatg tcaaactcag ttccaatctg gtgattctac ctggtcaaga   12780
tctccaatat gttttggcaa cctacgatac ttccagggtt gaacatgctg tggtttatta   12840
cgtttacagc ccaggccgct cattttctta cttttatcct tttaggttgc ctataaaggg   12900
ggtccccatc gaattacaag tggaatgctt cacatgggac caaaaactct ggtgccgtca   12960
cttctgtgtg cttgcggact cagaatctgg tggacatatc actcactctg ggatggtggg   13020
catgggagtc agctgcacag tcacccggga agatggaacc aatcgcagat agggctgcta   13080
gtgaaccaat ctcatgatgt cacccagaca tcaggcatac ccactagtgt gaaatagaca   13140
tcagaattaa gaaaaacgta gggtccaagt ggttccccgt tatggactcg ctatctgtca   13200
accagatctt ataccctgaa gttcacctag atagcccgat agttaccaat aagatagtag   13260
ccatcctgga gtatgctcga gtccctcacg cttacagcct ggaggaccct acactgtgtc   13320
agaacatcaa gcaccgccta aaaaacggat tttccaacca aatgattata aacaatgtgg   13380
aagttgggaa tgtcatcaag tccaagctta ggagttatcc ggcccactct catattccat   13440
atccaaattg taatcaggat ttatttaaca tagaagacaa agagtcaacg aggaagatcc   13500
gtgaactcct caaaaagggg aattcgctgt actccaaagt cagtgataag gtttccaat   13560 gcttaaggga cactaactca cggcttggcc taggctccga attgagggag gacatcaagg   13620
agaaagttat taacttggga gtttacatgc acagctccca gtggtttgag cccttctgt   13680 tttggtttac agtcaagact gagatgaggt cagtgattaa atcacaaacc catacttgcc   13740
ataggaggag acacacacct gtattcttca ctggtagttc agttgagttg ctaatctctc   13800
gtgaccttgt tgctataatc agtaaagagt ctcaacatgt atattacctg acatttgaac   13860 tggtttttgat gtattgtgat gtcatagagg ggaggttaat gacagagacc gctatgacta   13920
ttgatgctag gtatacagag cttctaggaa gagtcagata catgtggaaa ctgatagatg   13980
gtttcttccc tgcactcggg aatccaactt atcaaattgt agccatgctg gagcctcttt   14040
cacttgctta cctgcagctg agggatataa cagtagaact cagaggtgct ttccttaacc   14100
actgctttac tgaaatacat gatgttcttg accaaaacgg gttttctgat gaaggtactt   14160
atcatgagtt aattgaagct ctagattaca ttttcataac tgatgacata catctgacag   14220
gggagatttt ctcatttttc agaagtttcg gccaccccag acttgaagca gtaacggctg   14280
ctgaaaatgt taggaaatac atgaatcagc ctaaagtcat tgtgtatgag actctgatga   14340
aaggtcatgc catattttgt ggaatcataa tcaacggcta tcgtgacagg cacggaggca   14400
gttggccacc gctgacctc cccctgcatg ctgcagacac aatccggaat gctcaagctt   14460
caggtgaagg gttaacacat gagcagtgcg ttgataactg gagatctttt gctggagtga   14520
aatttggctg ctttatgcct cttagcctgg atagtgatct gacaatgtac ctaaaggaca   14580
aggcacttgc tgctctccaa agggaatggg attcagttta cccgaaagag ttcctgcgtt   14640
acgaccctcc caagggaacc gggtcacgga ggcttgtaga tgtttttctt aatgattcga   14700
gctttgaccc atatgatgtg ataatgtatg ttgtaagtgg agcttacctc catgaccctg   14760
agttcaacct gtcttacagc ctgaaagaaa aggagatcaa ggaaacaggt agacttttg    14820
```

-continued

```
ctaaaatgac ttacaaaatg agggcatgcc aagtgattgc tgaaaatcta atctcaaacg   14880
ggattggcaa atattttaag gacaatggga tggccaagga tgagcacgat ttgactaagg   14940
cactccacac tctagctgtc tcaggagtcc ccaaagatct caaagaaagt cacaggggg    15000 ggccagtctt aaaaacctac tcccgaagcc cagtccacac aagtaccagg aacgtgagag   15060
cagcaaaagg gtttataggg ttccctcaag taattcggca ggaccaagac actgatcatc   15120
cggagaatat ggaagcttac gagacagtca gtgcatttat cacgactgat ctcaagaagt   15180
actgccttaa ttggagatat gagaccatca gcttgtttgc acagaggcta aatgagattt   15240
acggattgcc ctcatttttc cagtggctgc ataagaggct tgagacctct gtcctgtatg   15300
taagtgaccc tcattgcccc cccgaccttg acgcccatat cccgttatat aaagtcccca   15360
atgatcaaat cttcattaag taccctatgg gaggtataga agggtattgt cagaagctgt   15420
ggaccatcag caccattccc tatctatacc tggctgctta tgagagcgga gtaaggattg   15480
cttcgttagt gcaaggggac aatcagacca tagccgtaac aaaaagggta cccagcacat   15540
ggccctacaa ccttaagaaa cgggaagctg ctagagtaac tagagattac tttgtaattc   15600
ttaggcaaag gctacatgat attggccatc acctcaaggc aaatgagaca attgtttcat   15660
cacatttttt tgtctattca aaaggaatat attatgatgg gctacttgtg tcccaatcac   15720
tcaagagcat cgcaagatgt gtattctggt cagagactat agttgatgaa acaagggcag   15780
catgcagtaa tattgctaca acaatggcta aaagcatcga gagaggttat gaccgttacc   15840
ttgcatattc cctgaacgtc ctaaaagtga tacagcaaat tctgatctct cttggcttca   15900
caatcaattc aaccatgacc cgggatgtag tcatacccct cctcacgaac aacgacctct   15960
taataaggat ggcactgttg cccgctccta ttgggggat gaattatctg aatatgagca    16020
ggctgtttgt cagaaacatc ggtgatccag taacatcatc aattgctgat ctcaagagaa   16080
tgattctcgc ctcactaatg cctgaagaga ccctccatca agtaatgaca caacaaccgg   16140
gggactcttc attcctagac tgggctagcg acccttactc agcaaatctt gtatgtgtcc   16200
agagcatcac tagactcctc aagaacataa ctgcaaggtt tgtcctgatc catagtccaa   16260
acccaatgtt aaaaggatta ttccatgatg acagtaaaga agaggacgag ggactggcgg   16320
cattcctcat ggacaggcat attatagtac ctagggcagc tcatgaaatc ctggatcata   16380
gtgtcacagg ggcaagagag tctattgcag gcatgctgga taccacaaaa ggcctgattc   16440
gagccagcat gaggaagggg gggttaacct ctcgagtgat aaccagattg tccaattatg   16500
actatgaaca attcagagca gggatggtgc tattgacagg aagaaagaga aatgtcctca   16560
ttgacaaaga gtcatgttca gtgcagctgg cgagagctct aagaagccat atgtgggcga   16620
ggctagctcg aggacggcct atttacggcc ttgaggtccc tgatgtacta gaatctatgc   16680
gaggccacct tattcggcgt catgagacat gtgtcatctg cgagtgtgga tcagtcaact   16740
acggatggtt ttttgtcccc cgcggttgcc aactggatga tattgacaag gaaacatcat   16800
ccttgagagt cccatatatt ggttctacca ctgatgagag aacagacatg aagcttgcct   16860
tcgtaagagc cccaagtcga tccttgcgat ctgctgttag aatagcaaca gtgtactcat   16920
gggcttacgg tgatgatgat agctcttgga acgaagcctg gttgttggct aggcaaaggg   16980
ccaatgtgag cctggaggag ctaagggtga tcactcccat ctcaacttcg actaatttag   17040
cgcataggtt gagggatcgt agcactcaag tgaaatactc aggtacatcc cttgtccgag   17100
tggcgaggta taccacaatc tccaacgaca atctctcatt tgtcatatca gataagaagg   17160
ttgatactaa ctttatatac caacaaggaa tgcttctagg gttgggtgtt ttagaaacat   17220
```

-continued

```
tgtttcgact cgagaaagat accggatcat ctaacacggt attacatctt cacgtcgaaa   17280
cagattgttg cgtgatcccg atgatagatc atcccaggat acccagctcc cgcaagctag   17340
agctgagggc agagctatgt accaacccat tgatatatga taatgcacct ttaattgaca   17400
gagatacaac aaggctatac acccagagcc ataggaggca ccttgtggaa tttgttacat   17460
ggtccacacc ccaactatat cacattttag ctaagtccac agcactatct atgattgacc   17520
tggtaacaaa atttgagaag gaccatatga atgaaatttc agctctcata ggggatgacg   17580
atatcaatag tttcataact gagtttctgc tcatagagcc aagattattc actatctact   17640
tgggccagtg tgcggccatc aattgggcat ttgatgtaca ttatcataga ccatcaggga   17700
aatatcagat gggtgagctg ttgtcatcgt tcctttctag aatgagcaaa ggagtgttta   17760
aggtgcttgt caatgctcta agccacccaa agatctacaa gaaattctgg cattgtggta   17820
ttatagagcc tatccatggt ccttcacttg atgctcaaaa cttgcacaca actgtgtgca   17880
acatggttta cacatgctat atgacctacc tcgacctgtt gttgaatgaa gagttagaag   17940
agttcacatt tctcttgtgt gaaagcgacg aggatgtagt accggacaga ttcgacaaca   18000
tccaggcaaa acacttatgt gttctggcag atttgtactg tcaaccaggg acctgcccac   18060
caattcgagg tctaagaccg gtagagaaat gtgcagttct aaccgaccat atcaaggcag   18120
aggctaggtt atctccagca ggatcttcgt ggaacataaa tccaattatt gtagaccatt   18180
actcatgctc tctgacttat ctccggcgag gatcgatcaa acagataaga ttgagagttg   18240
atccaggatt cattttcgac gccctcgctg aggtaaatgt cagtcagcca aagatcggca   18300
gcaacaacat ctcaaatatg agcatcaagg ctttcagacc cccacacgat gatgttgcaa   18360
aattgctcaa agatatcaac acaagcaagc acaatcttcc catttcaggg ggcaatctcg   18420
ccaattatga aatccatgct ttccgcagaa tcgggttgaa ctcatctgct tgctacaaag   18480
ctgttgagat atcaacatta attaggagat gccttgagcc aggggaggac ggcttgttct   18540
tgggtgaggg atcgggttcc atgttgatca cttataagga gatacttaaa ctaaacaagt   18600
gcttctataa tagtgggggtt tccgccaatt ctagatctgg tcaaagggaa ttagcaccct   18660
atccctccga agttggcctt gtcgaacaca gaatgggagt aggtaatatt gtcaaagtgc   18720
tctttaacgg gaggcccgaa gtcacgtggg taggcagtgt agattgcttc aatttcatag   18780
ttagtaatat ccctacctct agtgtggggt ttatccattc agatatagag accttgccta   18840
acaaagatac tatagagaag ctagaggaat tggcagccat cttatcgatg gctctgctcc   18900
tgggcaaaat aggatcaata ctggtgatta agcttatgcc tttcagcggg gattttgttc   18960
agggatttat aagttatgta gggtcccatt atagagaagt gaaccttgta taccctagat   19020
acagcaactt catatctact gaatcttatt tggttatgac agatctcaag gctaaccggc   19080
taatgaatcc tgaaaagatt aagcagcaga taattgaatc atctgtgagg acttcacctg   19140
gacttatagg tcacatccta tccattaagc aactaagctg catacaagca attgtgggag   19200
acgcagttag tagaggtgat atcaatccta ctctgaaaaa acttacacct atagagcagg   19260
tgctgatcaa ttgcgggttg gcaattaacg gacctaagct gtgcaaagaa ttgatccacc   19320
atgatgttgc ctcagggcaa gatggattgc ttaattctat actcatcctc tacagggagt   19380
tggcaagatt caaagacaac caaagaagtc aacaagggat gttccacgct taccccgtat   19440
tggtaagtag caggcaacga gaacttatat ctaggatcac ccgcaaattt tgggggcaca   19500 ttcttctttta ctccgggaac agaaagttga taaataagtt tatccagaat ctcaagtccg   19560
```

-continued

```
gctatctgat actagactta caccagaata tcttcgttaa gaatctatcc aagtcagaga   19620
aacagattat tatgacgggg ggtttgaaac gtgagtgggt tttaaggta acagtcaagg    19680 agaccaaaga atggtataag ttagtcggat acagtgccct gattaaggac taattggttg   19740
aactccggaa ccctaatcct gccctaggtg gttaggcatt atttgcaata gattaaagaa    19800
aactttgaaa atacgaagtt tctattccca gctttgtctg gtggccggca tggtcccagc    19860
ctcctcgctg gcgccggctg ggcaacattc cgaggggacc gtcccctcgg taatggcgaa   19920
tgggacgcgg ccgatccggc tgctaacaaa gcccgaaagg aagctgagtt ggctgctgcc    19980
accgctgagc aataactagc ataacccctt ggggcctcta aacgggtctt gaggggtttt   20040
ttgctgaaag gaggaactat atccggatgc ggccgatccg gctgctaaca aagcccgaaa    20100
ggaagctgag ttggctgctg ccaccgctga gcaataacta gcataacccc ttggggcctc    20160
taaacgggtc ttgaggggtt ttttgctgaa aggaggaact atatccggat ggccgccacc    20220
ggccggtggg ccttgcagca catccccctt tcgccagctg gcgtaatagc gaagaggccc    20280
gcaccgatcg cccttcccaa cagttgcgca gcctgaatgg cgaatgggac gcgccctgta    20340
gcggcgcatt aagcgcggcg ggtgtggtgg ttacgcgcag cgtgaccgct acacttgcca    20400
gcgccctagc gcccgctcct ttcgctttct tcccttcctt tctcgccacg ttcgccggct    20460
ttccccgtca agctctaaat cggggggctcc ctttagggtt ccgatttagt gctttacggc   20520
acctcgaccc caaaaaactt gattagggtg atggttcacg tgggccatcg ccctgataga    20580 cggttttttcg ccctttgacg ttggagtcca cgttctttaa tagtggactc ttgttccaaa   20640
ctggaacaac actcaaccct atctcggtct attcttttga tttataaggg attttgccga    20700
tttcggccta ttggttaaaa aatgagctga tttaacaaaa atttaacgcg aattttaaca   20760
aaatattaac gcttacaatt taggtggcac ttttcgggga aatgtgcgcg gaacccctat    20820
ttgtttattt ttctaaatac attcaaatat gtatccgctc atgagacaat aaccctgata    20880
aatgcttcaa taatattgaa aaaggaagag tatgagtatt caacatttcc gtgtcgccct    20940
tattcccttt tttgcggcat tttgccttcc tgttttttgct cacccagaaa cgctggtgaa    21000
agtaaaagat gctgaagatc agttgggtgc acgagtgggt tacatcgaac tggatctcaa   21060
cagcggtaag atccttgaga gttttcgccc cgaagaacgt tttccaatga tgagcacttt    21120
taaagttctg ctatgtggcg cggtattatc ccgtattgac gccgggcaag agcaactcgg    21180
tcgccgcata cactattctc agaatgactt ggttgagtac tcaccagtca cagaaaagca    21240
tcttacggat ggcatgacag taagagaatt atgcagtgct gccataacca tgagtgataa    21300
cactgcggcc aacttacttc tgacaacgat cggaggaccg aaggagctaa ccgcttttt    21360 gcacaacatg gggatcatg taactcgcct tgatcgttgg gaaccggagc tgaatgaagc    21420
cataccaaac gacgagcgtg acaccacgat gcctgtagca atggcaacaa cgttgcgcaa    21480
actattaact ggcgaactac ttacactagc ttcccggcaa caattaatag actggatgga    21540
ggcggataaa gttgcaggac cacttctgcg ctcggccctt ccggctggct ggtttattgc    21600
tgataaatct ggagccggtg agcgtgggtc tcgcggtatc attgcagcac tggggccaga    21660
tggtaagccc tcccgtatcg tagttatcta cacgacgggg agtcaggcaa ctatggatga    21720
acgaaataga cagatcgctg agataggtgc ctcactgatt aagcattggt aactgtcaga    21780
ccaagtttac tcatatatac tttagattga tttaaaactt catttttaat ttaaaaggat    21840
ctaggtgaag atcctttttg ataatctcat gaccaaaatc ccttaacgtg agttttcgtt    21900
ccactgagcg tcagacccccg tagaaaagat caaaggatct tcttgagatc cttttttttct   21960
```

-continued

```
gcgcgtaatc tgctgcttgc aaacaaaaaa accaccgcta ccagcggtgg tttgtttgcc   22020
ggatcaagag ctaccaactc tttttccgaa ggtaactggc ttcagcagag cgcagatacc   22080
aaatactgtt cttctagtgt agccgtagtt aggccaccac ttcaagaact ctgtagcacc   22140
gcctacatac ctcgctctgc taatcctgtt accagtggct gctgccagtg gcgataagtc   22200
gtgtcttacc gggttggact caagacgata gttaccggat aaggcgcagc ggtcgggctg   22260 aacgggggggt tcgtgcacac agcccagctt ggagcgaacg acctacaccg aactgagata   22320
cctacagcgt gagctatgag aaagcgccac gcttcccgaa gggagaaagg cggacaggta   22380
tccggtaagc ggcagggtcg aacaggaga gcgcacgagg gagcttccag ggggaaacgc   22440
ctggtatctt tatagtcctg tcgggtttcg ccacctctga cttgagcgtc gattttttgtg   22500 atgctcgtca ggggggcgga gcctatggaa aaacgccagc aacgcggcct ttttacggtt   22560
cctggccttt tgctggcctt ttgctcacat gttctttcct gcgttatccc ctgattctgt   22620
ggataaccgt attaccgcct ttgagtgagc tgataccgct cgccgcagcc gaacgaccga   22680
gcgcagcgag tcagtgagcg aggaagcgga agagcgccca atacgcaaac cgcctctccc   22740
cgcgcgttgg ccgattcatt aatgcagctg gcacgacagg tttcccgact ggaaagcggg   22800
cagtgagcgc aacgcaatta atgtgagtta gctcactcat taggcacccc aggctttaca   22860
ctttatgctt ccggctcgta tgttgtgtgg aattgtgagc ggacaacaat ttcacacagg   22920
aaacagctat gaccatgatt acgccaagct cgggcggccg cttgtaatac gactcactat   22980
a                                                                   22981
```

```
<210> SEQ ID NO 22
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: Non-codon optimized SARS-CoV-2 Spike from
      rMV-EZ-SARS-CoV-2-S clone 3
<220> FEATURE:
<221> NAME/KEY: misc_feature
<222> LOCATION: (3713)..(3713)
<223> OTHER INFORMATION: mutation that arose during cloning
<220> FEATURE:
<221> NAME/KEY: misc_feature
<222> LOCATION: (3805)..(3807)
<223> OTHER INFORMATION: mutation that disrupts ER retention signal
<220> FEATURE:
<221> NAME/KEY: misc_feature
<222> LOCATION: (3811)..(3813)
<223> OTHER INFORMATION: mutation that disrupts ER retention signal

<400> SEQUENCE: 22
atgtttgttt ttcttgtttt attgccacta gtctctagtc agtgtgttaa tcttacaacc       60
agaactcaat taccccctgc atacactaat tctttcacac gtggtgttta ttaccctgac      120
aaagttttca gatcctcagt tttacattca actcaggact tgttcttacc tttcttttcc      180
aatgttactt ggttccatgc tatacatgtc tctgggacca atggtactaa gaggtttgat      240
aaccctgtcc taccatttaa tgatggtgtt tattttgctt ccactgagaa gtctaacata      300
ataagaggct ggattttttgg tactacttta gattcgaaga cccagtccct acttattgtt      360
aataacgcta ctaatgttgt tattaaagtc tgtgaatttc aattttgtaa tgatccattt      420
ttgggtgttt attaccacaa aaacaacaaa agttggatgg aaagtgagtt cagagtttat      480
```

```
tctagtgcga ataattgcac ttttgaatat gtctctcagc cttttcttat ggaccttgaa      540
ggaaaacagg gtaatttcaa aaatcttagg gaatttgtgt ttaagaatat tgatggttat      600
tttaaaatat attctaagca cacgcctatt aatttagtgc gtgatctccc tcagggtttt      660
tcggctttag aaccattggt agatttgcca ataggtatta acatcactag gtttcaaact      720
ttacttgctt tacatagaag ttatttgact cctggtgatt cttcttcagg ttggacagct      780
ggtgctgcag cttattatgt gggttatctt caacctagga cttttctatt aaaatataat      840
gaaaatggaa ccattacaga tgctgtagac tgtgcacttg accctctctc agaaacaaag      900
tgtacgttga aatccttcac tgtagaaaaa ggaatctatc aaacttctaa ctttagagtc      960
caaccaacag aatctattgt tagatttcct aatattacaa acttgtgccc ttttggtgaa     1020 gttttttaacg ccaccagatt tgcatctgtt tatgcttgga acaggaagag aatcagcaac     1080
tgtgttgctg attattctgt cctatataat tccgcatcat tttccacttt taagtgttat     1140
ggagtgtctc ctactaaatt aaatgatctc tgctttacta atgtctatgc agattcattt     1200
gtaattagag gtgatgaagt cagacaaatc gctccagggc aaactggaaa gattgctgat     1260
tataattata aattaccaga tgattttaca ggctgcgtta tagcttggaa ttctaacaat     1320
cttgattcta aggttggtgg taattataat tacctgtata gattgtttag gaagtctaat     1380
ctcaaacctt ttgagagaga tatttcaact gaaatctatc aggccggtag cacaccttgt     1440
aatggtgttg aaggttttaa ttgttacttt cctttacaat catatggttt ccaacccact     1500
aatggtgttg gttaccaacc atacagagta gtagtacttt cttttgaact tctacatgca     1560
ccagcaactg tttgtggacc taaaaagtct actaatttgg ttaaaaacaa atgtgtcaat     1620
ttcaacttca atggtttaac aggcacaggt gttcttactg agtctaacaa aaagtttctg     1680
cctttccaac aatttggcag agacattgct gacactactg atgctgtccg tgatccacag     1740
acacttgaga ttcttgacat tacaccatgt tcttttggtg gtgtcagtgt tataacacca     1800
ggaacaaata cttctaacca ggttgctgtt ctttatcagg atgttaactg cacagaagtc     1860
cctgttgcta ttcatgcaga tcaacttact cctacttggc gtgtttattc tacaggttct     1920
aatgtttttc aaacacgtgc aggctgttta ataggggctg aacatgtcaa caactcatat     1980
gagtgtgaca tacccattgg tgcaggtata tgcgctagtt atcagactca gactaattct     2040
cctcggcggg cacgtagtgt agctagtcaa tccatcattg cctacactat gtcacttggt     2100
gcagaaaatt cagttgctta ctctaataac tctattgcca tacccacaaa ttttactatt     2160
agtgttacca cagaaattct accagtgtct atgaccaaga catcagtaga ttgtacaatg     2220
tacatttgtg gtgattcaac tgaatgcagc aatctttgt tgcaatatgg cagttttttgt     2280 acacaattaa accgtgcttt aactggaata gctgttgaac aagacaaaaa cacccaagaa     2340
gtttttgcac aagtcaaaca aatttacaaa acaccaccaa ttaaagattt tggtggtttt     2400 aattttttcac aaaatattacc agatccatca aaaccaagca agaggtcatt tattgaagat     2460
ctacttttca acaaagtgac acttgcagat gctggcttca tcaaacaata tggtgattgc     2520
cttggtgata ttgctgctag agacctcatt tgtgcacaaa agtttaacgg ccttactgtt     2580
ttgccacctt tgctcacaga tgaaatgatt gctcaataca cttctgcact gttagcgggt     2640
acaatcactt ctggttggac ctttggtgca ggtgctgcat tacaaatacc atttgctatg     2700
caaatggctt ataggtttaa tggtattgga gttacacaga atgttctcta tgagaaccaa     2760
aaattgattg ccaaccaatt taatagtgct attggcaaaa ttcaagactc actttcttcc     2820
```

```
acagcaagtg cacttggaaa acttcaagat gtggtcaacc aaaatgcaca agctttaaac    2880
acgcttgtta aacaacttag ctccaatttt ggtgcaattt caagtgtttt aaatgatatc    2940
ctttcacgtc ttgacaaagt tgaggctgaa gtgcaaattg ataggttgat cacaggcaga    3000
cttcaaagtt tgcagacata tgtgactcaa caattaatta gagctgcaga aatcagagct    3060
tctgctaatc ttgctgctac taaaatgtca gagtgtgtac ttggacaatc aaaaagagtt    3120
gatttttgtg gaaagggcta tcatcttatg tccttccctc agtcagcacc tcatggtgta    3180
gtcttcttgc atgtgactta tgtccctgca caagaaaaga acttcacaac tgctcctgcc    3240
atttgtcatg atggaaaagc acactttcct cgtgaaggtg tctttgtttc aaatggcaca    3300
cactggtttg taacacaaag gaatttttat gaaccacaaa tcattactac agacaacaca    3360
tttgtgtctg gtaactgtga tgttgtaata ggaattgtca acaacacagt ttatgatcct    3420
ttgcaacctg aattagactc attcaaggag gagttagata aatattttaa gaatcataca    3480
tcaccagatg ttgatttagg tgacatctct ggcattaatg cttcagttgt aaacattcaa    3540
aaagaaattg accgcctcaa tgaggttgcc aagaatttaa atgaatctct catcgatctc    3600
caagaacttg gaaagtatga gcagtatata aaatggccat ggtacatttg gctaggtttt    3660
atagctggct tgattgccat agtaatggtg acaattatgc tttgctgtat gaacagttgc    3720
tgtagttgtc tcaagggctg ttgttcttgt ggatcctgct gcaaatttga tgaagacgac    3780
tctgagccag tgctcaaagg agtcgcatta gcttacacat aa                       3822
```

```
<210> SEQ ID NO 23
<211> LENGTH: 4
<212> TYPE: PRT
<213> ORGANISM: Artificial Sequence
<220> FEATURE:
<223> OTHER INFORMATION: Synthetic

<400> SEQUENCE: 23

Ala Ser Val Gly
1

<210> SEQ ID NO 24
<211> LENGTH: 53
<212> TYPE: DNA
<213> ORGANISM: Artificial Sequence
<220> FEATURE:
<223> OTHER INFORMATION: Synthetic

<400> SEQUENCE: 24
caaagtgatt gcctcccaag ttccacaggc gcgccatgtt cgtcttcctg gtc          53

<210> SEQ ID NO 25
<211> LENGTH: 56
<212> TYPE: DNA
<213> ORGANISM: Artificial Sequence
<220> FEATURE:
<223> OTHER INFORMATION: Synthetic

<400> SEQUENCE: 25
gttggcaggt aagttgagct gtaggacgtc gcgcgttagg tgtaatgcag cttcac       56

<210> SEQ ID NO 26
<211> LENGTH: 60
<212> TYPE: DNA
<213> ORGANISM: Artificial Sequence
<220> FEATURE:
<223> OTHER INFORMATION: Synthetic
<220> FEATURE:
```

-continued

```
<221> NAME/KEY: misc_feature
<222> LOCATION: (47)..(48)
<223> OTHER INFORMATION: mutation that disrupts the ER retention signal
<220> FEATURE:
<221> NAME/KEY: misc_feature
<222> LOCATION: (53)..(54)
<223> OTHER INFORMATION: mutation that disrupts the ER retention signal

<400> SEQUENCE: 26
ggttggcagg taagttgagc tgtaggacgt cgcgcgttag gtgtaagcca gcgccacgcc      60
```